US012665053B2

(12) United States Patent
van Rooyen et al.

(10) Patent No.: US 12,665,053 B2
(45) Date of Patent: *Jun. 23, 2026

(54) GENOMIC INFRASTRUCTURE FOR ON-SITE OR CLOUD-BASED DNA AND RNA PROCESSING AND ANALYSIS

(71) Applicant: Illumina, Inc., San Diego, CA (US)

(72) Inventors: Pieter van Rooyen, San Diego, CA (US); Robert J. McMillen, San Diego, CA (US); Michael Ruehle, San Diego, CA (US); Rami Mehio, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 1036 days.

This patent is subject to a terminal disclaimer.

(21) Appl. No.: 17/032,117

(22) Filed: Sep. 25, 2020

(65) Prior Publication Data

US 2021/0193261 A1    Jun. 24, 2021

Related U.S. Application Data

(63) Continuation of application No. 15/404,146, filed on Jan. 11, 2017, now Pat. No. 10,847,251, which is a continuation-in-part of application No. 14/695,010, filed on Apr. 23, 2015, now Pat. No. 9,576,103, which is a continuation of application No. 14/279,063, filed on May 15, 2014, now Pat. No. 9,679,104, which is a continuation-in-part of application No. 14/180,248, filed on Feb. 13, 2014, now Pat. No. 9,014,989, and a continuation-in-part of application No. 14/179,513, filed on Feb. 12, 2014, now abandoned, and a continuation-in-part of application No. 14/158,758, filed on Jan. 17, 2014, now Pat. No. 9,483,610, said application No. 14/180,248 is a continuation of application No. 14/158,758, filed on Jan. 17, 2014, now Pat. No. 9,483,610, said application No. 14/179,513 is a continuation of application No. 14/158,758, filed on Jan. 17, 2014, now Pat. No. 9,483,610.

(60) Provisional application No. 62/277,445, filed on Jan. 11, 2016, provisional application No. 61/988,128, filed on May 2, 2014, provisional application No. 61/984,663, filed on Apr. 25, 2014, provisional application No. 61/943,870, filed on Feb. 24, 2014, provisional application No. 61/910,868, filed on Dec.

(Continued)

(51) Int. Cl.

| | |
|---|---|
| *G16B 30/10* | (2019.01) |
| *G16B 30/00* | (2019.01) |
| *G16B 50/00* | (2019.01) |
| *G16B 50/30* | (2019.01) |
| *G16B 50/40* | (2019.01) |
| *G16B 50/50* | (2019.01) |
| *H03K 19/17736* | (2020.01) |
| *H10D 1/00* | (2025.01) |
| *H10D 84/90* | (2025.01) |
| *H10D 89/10* | (2025.01) |

(52) U.S. Cl.
CPC ............. *G16B 30/10* (2019.02); *G16B 30/00* (2019.02); *G16B 50/00* (2019.02); *G16B 50/30* (2019.02); *G16B 50/40* (2019.02); *G16B 50/50* (2019.02); *H03K 19/17736* (2013.01); *H10D 1/00* (2025.01); *H10D 84/90* (2025.01); *H10D 84/907* (2025.01); *H10D 89/10* (2025.01); *H10D 84/938* (2025.01); *H10D 84/983* (2025.01)

(58) Field of Classification Search
CPC ........ G16B 30/10; G16B 50/30; G16B 50/50; G16B 50/40; G16B 30/00; G16B 50/00; H01L 27/0207; H01L 27/118; H01L 27/11807; H01L 28/00; H03K 19/17736
See application file for complete search history.

(56) References Cited

U.S. PATENT DOCUMENTS

| | | | |
|---|---|---|---|
| 5,629,147 A | 5/1997 | Asgari | |
| 5,859,972 A | 1/1999 | Subramaniam | |
| | (Continued) | | |

FOREIGN PATENT DOCUMENTS

| | | |
|---|---|---|
| CN | 102308206 A | 1/2012 |
| CN | 102521528 A | 6/2012 |
| | (Continued) | |

OTHER PUBLICATIONS

Abbas, N. et al., "Combining Executing Pipelines to Improve Parallel Implementation of HMMER on FPGA", Microprocessors and Microsystems 39(7), Jun. 25, 2015, 457-470.

(Continued)

*Primary Examiner* — Jerry Lin
(74) *Attorney, Agent, or Firm* — Heslin Rothenberg Farley & Mesiti P.C.

(57) ABSTRACT

A system, method and apparatus for executing a sequence analysis pipeline on genetic sequence data includes a integrated circuit formed of a set of hardwired digital logic circuits that are interconnected by physical electrical interconnects. One of the physical electrical interconnects forms an input to the integrated circuit connected with an electronic data source for receiving reads of genomic data. The hardwired digital logic circuits are arranged as a set of processing engines, each processing engine being formed of a subset of the hardwired digital logic circuits to perform one or more steps in the sequence analysis pipeline on the reads of genomic data. Each subset of the hardwired digital logic circuits is formed in a wired configuration to perform the one or more steps in the sequence analysis pipeline.

18 Claims, 19 Drawing Sheets

Related U.S. Application Data 2, 2013, provisional application No. 61/826,381, filed on May 22, 2013, provisional application No. 61/823, 824, filed on May 15, 2013, provisional application No. 61/822,101, filed on May 10, 2013, provisional application No. 61/753,775, filed on Jan. 17, 2013.

(56)　　　　　　　References Cited

U.S. PATENT DOCUMENTS

| | | | |
|---|---|---|---|
| 5,964,072 | A | 10/1999 | Rasissen |
| 5,964,860 | A | 10/1999 | Peterson |
| 6,112,288 | A | 8/2000 | Ullner |
| 6,253,529 | B1 | 7/2001 | De Boer et al. |
| 6,681,186 | B1 | 1/2004 | Denisov |
| 7,135,701 | B2 | 11/2006 | Amin et al. |
| 7,533,068 | B2 | 5/2009 | Maassen et al. |
| 7,680,790 | B2 | 3/2010 | Indeck |
| 7,917,299 | B2 | 3/2011 | Buhler |
| 7,917,302 | B2 | 3/2011 | Rognes |
| 7,945,668 | B1 | 5/2011 | Nucci |
| 7,948,015 | B2 | 5/2011 | Rothberg |
| 7,969,805 | B2 | 6/2011 | Thom et al. |
| 8,190,548 | B2 | 5/2012 | Choi |
| 8,195,596 | B2 | 6/2012 | Rose et al. |
| 8,209,130 | B1 | 6/2012 | Kennedy et al. |
| 8,217,433 | B1 | 7/2012 | Fife et al. |
| 8,280,640 | B2 | 10/2012 | Levin et al. |
| 8,445,945 | B2 | 5/2013 | Rothberg et al. |
| 8,524,487 | B2 | 9/2013 | Fife et al. |
| 8,558,288 | B2 | 10/2013 | Rothberg et al. |
| 8,560,282 | B2 | 10/2013 | Macready et al. |
| 8,594,951 | B2 | 11/2013 | Homer |
| 8,620,923 | B1 | 12/2013 | Wormley et al. |
| 8,700,689 | B2 | 4/2014 | Macready et al. |
| 8,738,105 | B2 | 5/2014 | Berkley et al. |
| 8,751,166 | B2 | 6/2014 | Friedlander et al. |
| 8,936,763 | B2 | 1/2015 | Rothberg et al. |
| 9,014,989 | B2 | 4/2015 | McMillen et al. |
| 9,026,574 | B2 | 5/2015 | Macready et al. |
| 9,235,680 | B2 | 1/2016 | Van Rooyen et al. |
| 9,355,365 | B2 | 5/2016 | Berkley et al. |
| 9,405,876 | B2 | 8/2016 | Macready et al. |
| 9,483,610 | B2 | 11/2016 | Mcmillen et al. |
| 9,576,103 | B2 | 2/2017 | Mcmillen et al. |
| 9,618,474 | B2 | 4/2017 | Van Rooyen et al. |
| 9,679,104 | B2 | 6/2017 | Van Rooyen et al. |
| 9,792,405 | B2 | 10/2017 | Van Rooyen et al. |
| 10,119,167 | B2 | 11/2018 | Srinivasan |
| 10,622,096 | B2 | 4/2020 | Van Rooyen |
| 2003/0033279 | A1 | 2/2003 | Gibson et al. |
| 2003/0033501 | A1 | 2/2003 | Cooke |
| 2003/0039362 | A1 | 2/2003 | Califano et al. |
| 2003/0104470 | A1 | 6/2003 | Fors et al. |
| 2004/0024536 | A1 | 2/2004 | Rognes et al. |
| 2004/0059721 | A1 | 3/2004 | Patzer |
| 2004/0098203 | A1 | 5/2004 | Rognes et al. |
| 2004/0126840 | A1 | 7/2004 | Cheng et al. |
| 2004/0142463 | A1 | 7/2004 | Walker |
| 2005/0060195 | A1 | 3/2005 | Bessette |
| 2005/0131649 | A1 | 6/2005 | Larsen et al. |
| 2005/0228595 | A1 | 10/2005 | Cooke et al. |
| 2006/0096324 | A1 | 5/2006 | Montani |
| 2006/0225165 | A1 | 10/2006 | Maassen et al. |
| 2007/0038381 | A1 | 2/2007 | Melchior et al. |
| 2007/0078897 | A1 | 4/2007 | Hayashi et al. |
| 2007/0088510 | A1 | 4/2007 | Li et al. |
| 2007/0196816 | A1 | 8/2007 | Schwartz |
| 2008/0005024 | A1 | 1/2008 | Kirkwood et al. |
| 2008/0022036 | A1 | 1/2008 | Diehl |
| 2008/0050782 | A1 | 2/2008 | Selifonov et al. |
| 2008/0086274 | A1 | 4/2008 | Chamberlain et al. |
| 2008/0176750 | A1 | 7/2008 | Rose et al. |
| 2008/0250016 | A1 | 10/2008 | Farrar et al. |
| 2009/0121215 | A1 | 5/2009 | Choi et al. |
| 2009/0125248 | A1 | 5/2009 | Shams et al. |
| 2009/0171647 | A1 | 7/2009 | Mannava et al. |
| 2009/0253130 | A1 | 10/2009 | Yoo |
| 2009/0270277 | A1 | 10/2009 | Glick |
| 2010/0077267 | A1 | 3/2010 | Perego et al. |
| 2010/0082805 | A1 | 4/2010 | Orton et al. |
| 2010/0085827 | A1 | 4/2010 | Thom |
| 2010/0169313 | A1 | 7/2010 | Kenedy et al. |
| 2010/0281401 | A1 | 11/2010 | Tebbs et al. |
| 2010/0327847 | A1 | 12/2010 | Leiber et al. |
| 2011/0004413 | A1 | 1/2011 | Carnevali |
| 2011/0093581 | A1 | 4/2011 | Ventatachalm |
| 2011/0184235 | A1 | 7/2011 | Schostek et al. |
| 2011/0227043 | A1 | 9/2011 | Guo |
| 2011/0231446 | A1 | 9/2011 | Buhler |
| 2012/0001615 | A1 | 1/2012 | Levine |
| 2012/0089339 | A1 | 4/2012 | Ganeshalingam et al. |
| 2012/0102041 | A1 | 4/2012 | Park et al. |
| 2012/0109849 | A1 | 5/2012 | Chamberlain |
| 2012/0149981 | A1 | 6/2012 | Khait et al. |
| 2012/0214172 | A1 | 8/2012 | Chen et al. |
| 2013/0018599 | A1 | 1/2013 | Peng et al. |
| 2013/0040583 | A1 | 2/2013 | Kim |
| 2013/0091121 | A1 | 4/2013 | Galinsky |
| 2013/0110407 | A1 | 5/2013 | Baccash et al. |
| 2013/0124100 | A1 | 5/2013 | Drmanac |
| 2013/0144925 | A1 | 6/2013 | Macready |
| 2013/0157870 | A1 | 6/2013 | Pushkarev et al. |
| 2013/0194882 | A1 | 8/2013 | Ishii et al. |
| 2013/0204851 | A1 | 8/2013 | Bhola et al. |
| 2013/0245958 | A1 | 9/2013 | Forster et al. |
| 2013/0246460 | A1 | 9/2013 | Maltbie |
| 2013/0254202 | A1 | 9/2013 | Friedlander |
| 2013/0267425 | A1 | 10/2013 | Liao |
| 2013/0275486 | A1 | 10/2013 | Dickinson et al. |
| 2013/0296175 | A1 | 11/2013 | Rafnar et al. |
| 2013/0297221 | A1 | 11/2013 | Johnson et al. |
| 2013/0307029 | A1 | 11/2013 | Xu et al. |
| 2013/0311106 | A1 | 11/2013 | White et al. |
| 2013/0316331 | A1 | 11/2013 | Isakov |
| 2013/0324417 | A1 | 12/2013 | Kennedy et al. |
| 2013/0332081 | A1 | 12/2013 | Reese et al. |
| 2013/0338012 | A1 | 12/2013 | Sulem et al. |
| 2013/0338934 | A1 | 12/2013 | Asadi et al. |
| 2014/0011458 | A1 | 1/2014 | Koga |
| 2014/0024537 | A1 | 1/2014 | Rigatti et al. |
| 2014/0033125 | A1 | 1/2014 | Merel et al. |
| 2014/0045705 | A1 | 2/2014 | Bustamante et al. |
| 2014/0046926 | A1 | 2/2014 | Walton |
| 2014/0051588 | A9 | 2/2014 | Drmanac et al. |
| 2014/0081665 | A1 | 3/2014 | Holmes |
| 2014/0093873 | A1 | 4/2014 | Tynan |
| 2014/0114582 | A1 | 4/2014 | Mittelman et al. |
| 2014/0121116 | A1 | 5/2014 | Richards |
| 2014/0164516 | A1 | 6/2014 | Maltbie |
| 2014/0200166 | A1 | 7/2014 | Van Rooyen et al. |
| 2014/0236490 | A1 | 8/2014 | Van Rooyen et al. |
| 2014/0297196 | A1 | 10/2014 | Olson |
| 2014/0304276 | A1 | 10/2014 | Boyce |
| 2014/0309944 | A1 | 10/2014 | Van Rooyen et al. |
| 2014/0310215 | A1 | 10/2014 | Trakadis |
| 2014/0316716 | A1 | 10/2014 | Jiang et al. |
| 2014/0337052 | A1 | 11/2014 | Pellini et al. |
| 2014/0350968 | A1 | 11/2014 | Hahn et al. |
| 2014/0371109 | A1 | 12/2014 | McMillen et al. |
| 2014/0371110 | A1 | 12/2014 | Van Rooyen et al. |
| 2015/0066824 | A1 | 3/2015 | Harris et al. |
| 2015/0123600 | A1 | 5/2015 | Graot et al. |
| 2015/0142334 | A1 | 5/2015 | Mishra et al. |
| 2015/0154406 | A1 | 6/2015 | Naehrig et al. |
| 2015/0211055 | A1 | 7/2015 | Apte et al. |
| 2015/0227697 | A1 | 8/2015 | Nelson et al. |
| 2015/0248525 | A1 | 9/2015 | Ury et al. |
| 2015/0286495 | A1 | 10/2015 | Lee et al. |
| 2015/0310163 | A1 | 10/2015 | Kingsmore et al. |
| 2015/0339437 | A1 | 11/2015 | McMillen et al. |
| 2015/0363550 | A1 | 12/2015 | Green, Jr. |
| 2016/0046986 | A1 | 2/2016 | Eltoukhy et al. |
| 2016/0057246 | A1 | 2/2016 | Krishnaiahsetty |
| 2016/0092631 | A1 | 3/2016 | Yandell et al. |

(56) References Cited

U.S. PATENT DOCUMENTS

| | | | |
|---|---|---|---|
| 2016/0140290 A1 | 5/2016 | Van Rooyen et al. |
| 2016/0171153 A1 | 6/2016 | Van Rooyen et al. |
| 2016/0178569 A1 | 6/2016 | Hoffman et al. |
| 2016/0283407 A1 | 9/2016 | Van Rooyen et al. |
| 2016/0306923 A1 | 10/2016 | Van Rooyen et al. |
| 2017/0270245 A1 | 9/2017 | Van Rooyen et al. |
| 2017/0308644 A1 | 10/2017 | Van Rooyen et al. |
| 2018/0121601 A1 | 5/2018 | Hahm |
| 2018/0189444 A1 | 7/2018 | Van Rooyen |
| 2018/0196916 A1 | 7/2018 | Van Rooyen et al. |
| 2018/0196917 A1 | 7/2018 | Van Rooyen et al. |
| 2018/0239865 A1 | 8/2018 | Van Rooyen et al. |
| 2021/0193261 A1 | 6/2021 | Van Rooyen et al. |
| 2021/0257052 A1 | 8/2021 | Van Rooyen et al. |

FOREIGN PATENT DOCUMENTS

| | | | |
|---|---|---|---|
| CN | 103080333 A | 5/2013 |
| CN | 103293209 A | 9/2013 |
| CN | 104428425 A | 3/2015 |
| CN | 105051741 B | 4/2018 |
| EP | 2313523 A2 | 4/2011 |
| EP | 2759952 A1 | 7/2014 |
| EP | 3317440 | 5/2018 |
| JP | 2007-108949 A | 4/2007 |
| JP | 2007-512808 A | 5/2007 |
| JP | 2016-514291 A | 5/2016 |
| JP | 2014146318 A | 8/2021 |
| KR | 1020130088512 A | 8/2013 |
| KR | 20140113053 A | 9/2014 |
| RU | 2015144109 A | 4/2017 |
| WO | 2011/149534 A2 | 12/2011 |
| WO | 2012/122546 A2 | 9/2012 |
| WO | 2013040583 A2 | 3/2013 |
| WO | 2013/128371 A2 | 9/2013 |
| WO | 2014/060305 A1 | 4/2014 |
| WO | 2014074246 A1 | 5/2014 |
| WO | 2014113736 A1 | 7/2014 |
| WO | 2014/121091 A1 | 8/2014 |
| WO | 2014/186604 A1 | 11/2014 |
| WO | 2015/051006 A2 | 4/2015 |
| WO | 2015089333 A1 | 6/2015 |
| WO | 2015/100427 A1 | 7/2015 |
| WO | 2015123600 A1 | 8/2015 |
| WO | WO 2015/166389 A1 | 11/2015 |
| WO | 2016051429 A1 | 4/2016 |

OTHER PUBLICATIONS

Alachiotis, N. et al., "Accelerating Phylogeny-Aware Short DNA Read Alignment with FPGAs", The Exelixis Lab, Scientific Computing Group, 2011, 8 pages.

Altera Corp, "Implementation of the Smith-Waterman Algorithm on a Reconfigurable Supercomputing Platform", White Paper, vol. 1, 2007, 18 pages.

Angiuoli, S. et al., "Mugsey; fast multiple alignment of closely related whole genomes", Bioinformatics (2011) 27(3); http://bioinformatics.oxfordjournals.org/content/27/3/334 URL retrieved May 25, 2016, Dec. 9, 2010, 334-342.

Anonymous, "FPGA-accelerated Bioinformatics at #ASHG—Dragen Aligner from Edico Genome", http://homolog.us/blogs/blog/2014/10/20/fpga-accelerated-bioinformatics-at-ashg-dragen-aligner-from-edico-genome/#, Oct. 20, 2014.

Benkrid, K. et al., "A Highly Parameterized and Efficient FPGA-Based Skeleton for Pairwise Biological Sequence Alignment", IEEE Transactions on VLSI Systems, Apr. 2009, 561-570.

Benkrid, K. et al., "High Performance Biological Pairwise Sequence Alignment: FPGA versus GPU versus Cell BE versus GPP", Hindawi Publishing Corporation, vol. 2012, 2012, 16 pages.

Buyukkurt, B. et al., "Compiler Generated Systolic Arrays For Wavefront Algorithm Acceleration on FPGAS", International Conference on Field Programmable Logic and Applications, 2008, 4 pages.

Carneiro, M., "Accelerating variant calling", Intel Genomic Sequencing Pipeline Workshop, Dec. 10, 2013, 26 pages.

Chang, M. et al., "The SMEM Seeding Acceleration for DNA Sequence Alignment", 2016 IEEE 24th Annual International Symposium on Filed-programmable Custom Computing Machines (FCCM), IEEE, CP032946099, May 2, 2016, 32-39.

Chang, X. et al., "Exploring Sequence Alignment Algorithms on FPGA-based Heterogeneous Architectures", IWBBIO, 2014, 330-341.

Chang, X. et al., "FPGA-based Heterogeneous Architecture for Sequence Alignment", Jan. 4, 2014.

Choi, Y. et al., "A Quantitative Analysis on Microarchitectures of modern CPU-FPGA platforms", Proceedings of the 53rd Annual Design Automation Conference On, DAC '16, Jun. 5, 2016, 1-6.

Chrysanthou, N. et al., "Parallel Accelerators For GlimmerHMM Bioinformatics Algorithm", Technical University of Crete, 2011, 6 pages.

Derrien, et al., "Fast Computation and Applications of Genome Mappability", PLoS One 7(1), doi: 10.1371/journal.pone.0030377, Jan. 19, 2012, e30377.

Derrien, S. et al., "Hardware Acceleration of HMMER on FPGAs", J Sign Process Syst 58, 2010, 53-67.

Deutsch, D., "Quantum theory, the Church-Turing principle and the universal quantum computer", Proceedings of the Royal Society of London, vol. A(400), 1985, 97-117.

Dydel, S. et al., "Large Scale Protein Sequence Alignment Using FPGA Reprogrammable Logic Devices", ECCV 2016 Conference, Springer International Publishing, Cham 032548; C. 3203, Aug. 30, 2004, 23-32.

Faes, P. et al., "Scalable Hardware Accelerator for Comparing DNA and Protein Sequences", INFOSCALE, 2006, 6 pages.

Fagin, B. et al., "FPGA and Rapid Prototyping Technology Use in a Special Purpose Computer for Molecular Genetics", Thayer School of Engineering, Dartmouth College, Jan. 11, 2017, 6 pages.

Fernandez, E. et al., "Exploration of Short Reads Genome Mapping in Hardware", Field Programmable Logic and Applications (FPL), Aug. 2010, 4 pages.

Fernandez, E. et al., "Multithreaded FPGA Acceleration of DNA Sequence Mapping", UC Riverside, Dept. of Computer Science and Engineering, 2012, 20 pages.

Fernandez, E. et al., "Multithreaded FPGA Acceleration of DNA Sequence Mapping", University of California, Riverside, 2012, 6 pages.

Ferraz, S. et al., "Evaluating Optimization Strategies for HMMer Acceleration on GPU", Federal University of Mato Grosso do Sul, Brazil, 2013, 59-68.

Feynman, R., "Simulating Physics with Computers", Department of Physics, California Institute of Technology, vol. 21(6/7), 1982, 467-488.

Giraldo, J. et al., "A HMMER Hardware Accelerator using Divergences", 2010 Design, Automation & Test in Europe Conference and Exhibition, Mar. 12, 2010, 405-410.

Guccione, S. et al., "Gene Matching Using JBits", Xilinx, Inc, 2002, 9 pages.

Guo, X. et al., "A Systolic Array-Based FPGA Parallel Architecture for the BLAST Algorithm", ISRN Bioinformatics, vol. 2012, 2012, 11 pages.

Hall, A., "Short-Read DNA Sequence Alignment with Custom Designed FPGA-based Hardware", The University of Cambridge, 2007, 186 pages.

Hardcastle, T. et al., "baySeq: Empirical Bayesian methods for identifying differential expression in sequence count data", BMC Bioinformatics 11:422 http://bmcbioinformatics.biomedcentral.com/rticles/10.1186/1471-2105-11-422, Aug. 10, 2010, 1-16.

Harris, B. et al., "A Banded Amith-Waterman FPGA Accelerator For Mercury BLASTP", BECS Technology, Inc, 2007, 5 pages.

Hasan, L. et al., "An Overview of Hardware-Based Acceleration of Biological Sequence Alignment", www.intechopen.com, Sep. 2011, 187-202.

Herbordt, M. et al., "Single Pass Streaming BLAST on FPGAs", NIH Public Access Manuscript, vol. 33 (10-11), Nov. 2007, 741-756.

(56) References Cited

OTHER PUBLICATIONS

Herbordt, M. et al., "Single Pass, BLAST-like, Approximate String Matching on FPGAs", Boston University, vol. 2006, 2007, 19 pages.

Hoang, D., "A Systolic Array for the Sequence Alignment Problem", Department of Computer Science, Brown University, Apr. 1992, 25 pages.

Hoang, D., "FPGA Implementation of Systolic Sequence Alignment", Department of Computer Science Brown University, 1991, 4 pages.

Hoang, D., "Searching Genetic Databases on Splash 2", Department of Computer Science, Brown University, 1993, 185-191.

Homer, N. et al., "BFAST: An Alignment Tool for Large Scale Genome Resequencing", PLOS One http://journals.plos.org/plosone/article?id=10.1371/journal.pone.0007767, Nov. 11, 2009.

Huang, S. et al., "Hardware Acceleration of the Pair-HMM Algorithm for DNA Variant Calling", Advanced Digital Sciences Center, Feb. 2017, 275-284.

Hughey, R., "Parallel hardware for sequence comparison and alignment", Cabios, vol. 12 (6), 1996, 473-479.

Isa, N. et al., "A Novel Efficient FPGA Architecture for HMMER Acceleration", System Level Integration Group, School of Engineering, University of Edinburgh, 2013, 6 pages.

Isaac, TS et al., "160-fold acceleration of the Smith-Waterman algorithm using a field programmable gate array (FPGA)", BMC Bioinformatics, Jun. 7, 2007, 7 pages.

Jacob, A. et al., "FPGA-accelerated seed generation in Mercury BLASTP", Washington University in St. Louis; BECS Technology, Inc, 2007, 10 pages.

Jacob, A. et al., "Preliminary results in accelerating profile HMM search on FPGAs", Dept. of Computer Science and Engineering, Mar. 2007, 9 pages.

Jiang, K. et al., "An Efficient Parallel Implementation of the Hidden Markov Methods for Genomic Sequence Search on a Massively Parallel System", IEEE Transaction on Parallel and Distributed Systems 19(1), Jan. 2008, 1-9.

Junid, A. et al., "Development of Novel Data Compression Technique for Accelerate DNA Sequence Alignment Based on Smith-Waterman Algorithm", University Technology MARA (UiTM), vol. 978, 2009, 181-186.

Junid, A. et al., "Optimization of DNA Sequences Data for Accelerate DNA Sequences Alignment on FPGA", University Technology Mara (UiTM), vol. 978, 2010, 231-236.

Kasap, S. et al., "Design and Implementation of an FPGA-based Core for Gapped BLAST Sequence Alignment with the Two-Hit Method", Engineering Letters, vol. 16:3, Aug. 20, 2012, 10 pages.

Lancaster, J. et al., "Acceleration of Ungapped Extension in Mercury BLAST", MSP-7th Workshop on Media and Streaming Processors, Nov. 2005, 9 pages.

Lancaster, J., "Design and Evaluation of a BLAST Ungapped Extension Accelerator, Master's Thesis", Washington University, vol. 2006 (21), Jan. 1, 2006, 79 pages.

Langmead, B. et al., "Searching for SNPs with cloud computing", Genome Biology 10 (11) R134, Nov. 20, 2009.

Lavenier, D., "SAMBA: Systolic Accelerator for Molecular Biological Applications", INRIA Research Report, Mar. 1996, 22 pages.

Lemoine, E. et al., "High Speed Pattern Matching in Genetic Data Base with Reconfigurable Hardware", ISMB-94 Proceedings, 1994, 269-275.

Liu, Y. et al., "An FPGA-Based Web Serv er for High Performance Biological Sequence Alignment", NASA/ESA Conference on Adaptive Hardware and Systems, 2009, 361-368.

Lloyd, S. et al., "Hardware Accelerated Sequence Alignment with Traceback", Department of Computer Science, BYU, vol. 2009 (762362), 2009, 10 pages.

Lopresti, D., "Department of Computer Science", Department of Computer Science, Brown University, 1991, 138-152.

Madhavan, A. et al., "Race Logic: A Hardware Acceleration for Dynamic Programming Algorithms", University of California, Santa Barbara, 2014, 12 pages.

Mahram, A., "FPGA Acceleration of Sequence Analysis Tools in Bioinformatics", Boston University College of Engineering, 2013, 180 pages.

Maxfield, C., "Impulse achieves 16X speed-up of genome analysis on $2,500 FPGA module", EE Times http://www.eetimes.com/document.asp?doc_id=1317288&print=yes, Jun. 5, 2012, 1-4.

Mckenna, et al., "The Genome Analysis Toolkit: A MapReduce framework for analyzing next-generation DNA sequencing data", Genome Research, 20, 2010, 1297-1303.

Mikami, S. et al., "Efficient FPGA-based Hardware Algorithms for Approximate String Matching", The 23rd International Technical Conference on Circuits/Systems, Computers and Communications, 2008, 4 pages.

Miller, N. et al., "A 26-hour system of highly sensitive whole genome sequencing for emergency management of genetic diseases", Genome Medicine 7(1000), Sep. 30, 2015, 1-16.

Moritz, G. et al., "Implementation of a Parallel Algorithm for Protein Pairwise Alignment Using Reconfigurable Computing", Bioinformatics Laboratory & Electronics Department, 2007, 7 pages.

Muriki, K. et al., "RC-BLAST: Towards a Portable, Cost-Effective Open Source Hardware Implementation", Supported in Part by the National Science Foundation, 2005, 8 pages.

Nawaz, Z. et al., "A Parallel FPGA design of the Smith-Waterman traceback", ACE Associated Compiler Expert, Jan. 6, 2011, 6 pages.

Nawaz, Z. et al., "Fast Smith-Waterman hardware implementation", Computer Engineering Lab, 2010, 4 pages.

Nelson, C. et al., "Shepard: A Fast Exact Match Short Read Aligner", Dept. of Electrical and Computer Engineering, 2012, 4 pages.

Oliver, T. et al., "Hyper Customized Processors for Bio-Sequence Database Scanning on FPGAs", Centre for High Performance Embedded Systems, Nanyang Technological University, 2005, 229-237.

Oliver, T. et al., "Multiple Sequence Alignment on an FPGA", Nanyang Technical University, 2005, 5 pages.

Oliver, T. et al., "Using reconfigurable hardware to accelerate multiple sequence alignment with ClustalW", Bioinformatics Applications Note, vol. 21 (16), 2005, 3431-3432.

Olson, C., "An FPGA Acceleration of Short Read Human Genome Mapping", University of Washington, 2011, 103 pages.

Olson, C. et al., "Hardware Acceleration of Short Read Mapping", University of Washington, 2012 IEEE 20th International Symposium on Field-Programmable Custom Computing Machines, 2012, 161-168.

PCT/US17/58890, "International Search Report", Feb. 23, 2018.

PCT/US2014/12144, "International Search Report", Jun. 18, 2014.

PCT/US2016/040842, "International Search Report", Oct. 4, 2016.

PCT/US2017/013057, "International Search Report", Apr. 11, 2017.

PCT/US2017/036424, "International Search Report", Sep. 12, 2017.

PCT/US2017/040385, "International Search Report", Oct. 27, 2017.

Peltenburg, J. et al., "Maximizing Systolic Array Efficiency to Accelerate the PairHMM Forward Algorithm", IEEE International Conference on Bioinformatic and Biomedicine, 2016, 758-762.

Ren, S. et al., "FPGA Acceleration of the Pair-HMMs Forward Algorithm for DNA Sequence Analysis", IEEE, 2015, 6 pages.

Ruffalo, M. et al., "Comparative analysis of algorithms for next-generation sequencing read alignment", Bioinformatics 27(20), Aug. 19, 2011, 2790-2796.

Sarkar, S. et al., "Network-on-Chip Hardware Accelerators for Biological Sequence Alignment", IEEE Transactions on Computers, vol. 59 (1), Jan. 2010, 29-41.

Schatz, M. et al., "Cloud Computing and the DNA Data Race", Nat Biotechnol 28(7), Jul. 2010, 691-693.

Schatz, M., "CloudBurst: highly sensitive read mapping with MapReduce", Bioinformatics 25(11), Apr. 8, 2009, 1363-1369.

Schatz, M. et al., "High-throughput sequence alignment using Graphics Processing Units", BMC Bioinformatics http://bmcbioinformatics.biomedcentral.com/articles/10.1186/1471-2105-8-474, Dec. 10, 2007.

(56)     References Cited

OTHER PUBLICATIONS

Settle, S., "High-performance Dynamic Programming on FPGAs with OpenCL", IEEE, 2013, 6 pages.

Sotiriades, E. et al., "FPGA based Architecture for DNA Sequence Comparison and Database Search", Technical University of Crete, vol. 1 (4244), 2006, 8 pages.

Sotiriades, E. et al., "Some Initial Results on Hardware BLAST Acceleration with a Reconfigurable Architecture", University of Crete, 2006, 8 pages.

Sun, Y. et al., "Accelerating HMMer on FPGAs Using Systolic Array Based Architecture", College of Computer Science and Technology, 2009, 8 pages.

Timelogic Division, "Accelerated BLAST Performance with Tera—BLAST ™: a comparison of FPGA versus GPU and CPU BLAST implementations", Technical Note, vol. 1, May 2013, 5 pages.

Van Court, T. et al., "Families of FPGA-Based Algorithms for Approximate String Matching", Boston University, 2004, 11 pages.

Van Der Auwera, G. et al., "From FastQ data to high confidence variant calls: the Genome Analysis Toolkit best practices pipeline", Curr rotoc Bioinformatics 11(1110) 11.10.1-11.10.33, Oct. 15, 2013, 1-27.

Wu, T. et al., "GMAP: a genomic mapping and alignment program for mRNA and EST sequences", Bioinformatics, vol. 21(9), Feb. 22, 2005, 1859-1875.

Yamaguchi, Y. et al., "High Speed Homology Search with FPGAs", Pacific Symposium of Biocomputing, vol. 7, 2002, 271-282.

Yu, C.W. et al., "A Smith-Waterman Systolic Cell", The Chinese University of Hong Kong, 2003, 10 pages.

Zhang, W. et al., "A Practical Comparison of De Novo Genome Assembly Software Tools for Next-Generation Sequencing Technologies", PLoS One 6(3), Mar. 14, 2011, e17915.

Benkrid, Khaled, et al. "A High Performance Reconfigurable Core for Motif Searching Using Profile HMM." NASA ESA Conference on Adaptive Hardware and Systems, IEEE, 2008. pp. 285-292.

Chrysos et al., "Reconfiguring the bioinformatics computational spectrum: Challenges and opportunities of fpga-based bioinformatics acceleration platforms," IEEE Design & Test, Oct. 2, 2013, 31(1):62-73.

EP Extended European Search Report in EP Appln. No. 19199685.9, dated Jan. 3, 2020, 13 pages.

EP Extended Search Report in European Appln. No. 21179125.5, dated Nov. 29, 2021, 9 pages.

Fromer et al., "Discovery and statistical genotyping of copy-number variation from whole-exome sequencing depth," The American Journal of Human Genetics, Oct. 5, 2012, 91(4):597-607.

JP Japanese Office Action in Japanese Appln. No. 2018-555440, dated Jan. 31, 2022, 4 pages (with English translation).

Mishra, "Gappy TotalReCaller for RNASeq Base-Calling and Mapping, " bioRxiv, Jan. 1, 2013, 000489, 10 pages.

Oliver, et al. "High performance database searching with HMMer on FPGAs," 2007 IEEE International Parallel and Distributed Processing Symposium, Mar. 7, 2007, 7 pages.

Rimmer et al., "Integrating mapping- , assembly-and haplotype-based approaches for calling variants in clinical sequencing applications," Nature Genetics, Aug. 2014, 46(8):912-8.

Russell, "TGAC Unleashes DRAGEN to Accelerate Genomics Workflows", HPC Wire, dated Oct. 28, 2015, retrieved Apr. 12, 2022 form URL <https://www.hpcwire.com/2015/10/28/tgac-unleashes-dragen-to-accelerate-genomics-workflows/>.

US Office Action in U.S. Appl. No. 15/048,935, dated Sep. 14, 2021, 21 pages.

AU Office Action in Australian Appln. No. 2017207317, dated Aug. 31, 2022, 6 pages.

AU Office Action in Australian Appln. No. 2022228089, mailed on Oct. 3, 2023, 5 pages.

CA Office Action in Canadian Appln. No. 3,008,176, dated Feb. 21, 2023, 5 pages.

JP Japanese Office Action in Japanese Appln. No. 2022-89149, dated Jun. 19, 2023, 9 pages (with English translation).

MX Office Action in Mexican Appln. No. MX/a/2018/008527, dated May 25, 2023, 9 pages (with English translation).

MY Malaysian Office Action in Malaysian Appln. No. PI 2018702376, dated Jun. 17, 2022, 3 pages.

NZ Office Action in New Zealand Appln. No. 784186, mailed on Jun. 29, 2023, 3 pages.

NZ Office Action in New Zealand Appln. No. 784189, mailed on Feb. 13, 2024, 7 pages.

NZ Office Action in New Zealand Appln. No. 784189, mailed on Jun. 27, 2023, 3 pages.

RU Office Action in Russian Appln. No. 2021134292, dated Nov. 23, 2022, 13 pages (with English translation).

AU Office Action in Australian Appln. No. 2022228089, mailed on Sep. 23, 2024, 3 pages.

Booth et al., "Bio-Linux as a tool for bioinformatics training," 2012 IEEE 12th International Conference on Bioinformatics & Bioengineering (BIBE), Nov. 11, 2012, 578-82.

BR Office Action in Brazilian Appln. No. 1220230005996, mailed on Sep. 16, 2024, 11 pages (with English translation).

CN Office Action in Chinese Appln. No. 202210534739.5, mailed on Jul. 11, 2024, 17 pages (with English translation).

Hwang et al., "The mechanism of personalized service recommendation for the academic field," 2017 4th International Conference on Computer Applications and Information Processing Technology (CAIPT), Aug. 8, 2017.

IN Office Action in Indian Appln. No. 202218018463, mailed on Sep. 26, 2024, 12 pages.

IN Office Action in Indian Appln. No. 202218018469, mailed on Sep. 26, 2024, 7 pages.

JP Office Action in Japanese Appln. No. 2023-196840, mailed on Sep. 9, 2024, 6 pages.

Luethy et al., "Hardware and software systems for accelerating common bioinformatics sequence analysis algorithms," Drug Discovery Today: BIOSILICO, Jan. 2004, 2(1):12-7.

Nagasaki et al., "DDBJ read annotation pipeline: a cloud computing-based pipeline for high-throughput analysis of next-generation sequencing data," DNA Research, Aug. 2013, 20(4):383-90.

Akita.com, "Science of Akita, RNA Sequence Manuals" Dec. 18, 2014, retrieved Sep. 4, 2024 from URL <https://www.dbp.akita-pu.ac.jp/esuzuki/RNASeq_manuals/30ddbjing_Pipeline.pdf>, 2-55 (no translation available).

EP Office Action in European Appln. No. 21179125.6, mailed on Dec. 10, 2024, 5 pages.

Batista, R. B., Boukerche, A and de Melo, A. C. M. A. A parallel strategy for biological sequence alignment in restricted memory space. Journal of Parallel and Distributed Computing, 68(4), pp. 548-561. (Year: 2008).

Cheever, E.A., Overton, G.C. and Searls, D.B., 1991. Fast Fourier transform-based correlation of DNA sequences using complex plane encoding. Bioinformatics, 7(2), pp. 143-154. (Year: 1991).

Wang, C. Heterogeneous Cloud Framework for Big Data Genome Sequencing, IEEE/ACM Transactions on Computational Biology and Bioinformatics, 12(1) (Sep. 12, 2014).

Cheever et al., "Fast Fourier transform-based correlation of DNA sequences using complex plane encoding", Bioinformatics, 1991, pp. 143-154.

Doddavula et al. "Implementation of a Scalable Next Generation Sequencing Business Cloud Platform-An 11 Experience Report", Presented at the 2011 IEEE 4th International Conference on Cloud Computing, Washington D.C, USA, 2011, pp. 598-605.

Iqbal et al., "De Novo Assembly And Genotyping Of Variants Using Colored De Bruijn Graphs", Nature Genetics, vol. 44, No. 2, 2012, pp. 226-232.

Lee et al., "Clinical exome sequencing for genetic identification of rare Mendelian disorders," Jama, Nov. 12, 2014, 312(18):1880-7.

Mandelker et al. "Navigating Highly Homologous Genes In A Molecular Diagnostic Setting: A Resource For Clinical Next-Generation Sequencing", Genetics in Medicine, vol. 18, No. 12, pp. 226-232. (Dec. 2016).

Oliver et al., "Integrating FPGA acceleration into HMMer", Parallel Computing, 2008, pp. 681-691.

(56) References Cited

OTHER PUBLICATIONS

Oliver, T.F., et al., "Reconfigurable architectures for bio-sequence database scanning on FPGAs", IEEE Transaction on Circuits and Systems—II: Express Briefs, 2005, pp. 851-855.

Vermij, Erik, "Genetic sequence alignment on a supercomputing platform", Thesis, Master of Science in Computer Engineering, Delft University of Technology, 2011, pp. 1-100.

Wang et al. "Heterogeneous cloud framework for big data genome sequencing", IEEE/ACM Transactions on Computational Biology and Bioinformatics, 2014, pp. 166-178.

Wilke et al., "A RESTful API for accessing microbial community data for MG-RAST," PLoS Computational Biology, Jan. 8, 2015, 11(1): e1004008, 9 pages.

Zhang et al., "Joint Haplotype Phasing and Genotype Calling of Multiple Individuals Using Haplotype Informative Reads", Bioinformatics, 2013, pp. 2427-2434.

100C

100B

100A

GENOMIC INFRASTRUCTURE FOR ON-SITE OR CLOUD-BASED DNA AND RNA PROCESSING AND ANALYSIS

CROSS REFERENCE TO RELATED APPLICATIONS

This application is a continuation of U.S. non-provisional patent application Ser. No. 15/404,146, filed on Jan. 11, 2017, which is a continuation-in-part of U.S. non-provisional patent application Ser. No. 14/695,010, filed on Apr. 23, 2015, now U.S. Pat. No. 9,576,103, issued on Feb. 21, 2017, which is a continuation of U.S. non-provisional patent application Ser. No. 14/279,063, filed on May 15, 2014, now U.S. Pat. No. 9,679,104, issued on Jun. 13, 2017, which is a continuation-in-part of U.S. non-provisional patent application Ser. No. 14/158,758, filed on Jan. 17, 2014, now U.S. Pat. No. 9,483,610, issued on Nov. 1, 2016, which claims the benefit of U.S. provisional application No. 61/753,775, filed on Jan. 17, 2013, U.S. provisional application No. 61/822, 101, filed on May 10, 2013, U.S. provisional application No. 61/823,824, filed on May 15, 2013, U.S. provisional application No. 61/826,381, filed on May 22, 2013, and U.S. provisional application No. 61/910,868, filed on Dec. 2, 2013, the contents of each of which are hereby incorporated by reference in their entireties.

U.S. patent application Ser. No. 14/279,063 is also a continuation-in-part of U.S. non-provisional patent application Ser. No. 14/180,248, filed on Feb. 13, 2014, now U.S. Pat. No. 9,014,989, issued on Apr. 21, 2015, which is a continuation of U.S. non-provisional patent application Ser. No. 14/158,758 filed on Jan. 17, 2014, now U.S. Pat. No. 9,483,610, issued on Nov. 1, 2016, the contents of each of which are hereby incorporated by reference in their entireties.

U.S. patent application Ser. No. 14/279,063 is also a continuation-in-part of U.S. provisional patent application Ser. No. 14/179,513, filed on Feb. 12, 2014, which is a continuation of U.S. non-provisional patent application Ser. No. 14/158,758, filed on Jan. 17, 2014, now U.S. Pat. No. 9,483,610, issued on Nov. 1, 2016, the contents of each of which are hereby incorporated by reference in their entireties.

U.S. patent application Ser. No. 14/279,063 also claims the benefit of provisional application No. 61/823,824, filed on May 15, 2013, U.S. provisional application No. 61/826, 381, filed on May 22, 2013, U.S. provisional application No. 61/910,868, filed on Dec. 2, 2013, U.S. provisional application No. 61/943,870, filed on Feb. 24, 2014, U.S. provisional application No. 61/984,663, filed on Apr. 25, 2014, and U.S. provisional application No. 61/988,128, filed on May 2, 2014, the contents of each of which are hereby incorporated by reference in their entireties.

U.S. non-provisional patent application Ser. No. 14/695, 010 is also a continuation of U.S. non-provisional patent application Ser. No. 15/436,435, filed on Feb. 17, 2017, now U.S. Pat. No. 10,216,898, issued on Feb. 26, 2019, which is hereby incorporated herein by reference in its entirety.

U.S. non-provisional patent application Ser. No. 15/404, 146, filed on Jan. 11, 2017, also claims the benefit of U.S. provisional application No. 62/277,445, filed on Jan. 11, 2016, which is hereby incorporated herein by reference in its entirety.

TECHNICAL FIELD

The subject matter described herein relates to bioinformatics, and more particularly to systems, apparatuses, and methods for implementing bioinformatic protocols, such as performing one or more functions for analyzing genomic data on an integrated circuit, such as on a hardware processing platform.

BACKGROUND

A goal for health care researchers and practitioners is to improve the safety, quality, and effectiveness of health care for every patient. Personalized health care is directed to achieving these goals on an individual level. For instance, "genomics" and/or "bioinformatics" are fields of study that aim to facilitate the safety, the quality, and the effectiveness of prophylactic and therapeutic treatments on a personalized, individual level. Accordingly, by employing genomics and/or bioinformatics techniques, the identity of an individual's genetic makeup, e.g., his or hers genes, may be determined and that knowledge may be used in the development of therapeutic and/or prophylactic regimens, including drug treatments, that are personalized to the individual, thus, enabling medicine to be tailored to meet each person's individual needs.

The desire to provide personalized care to individuals is transforming the health care system. This transformation of the health care system is likely to be powered by breakthrough innovations at the intersection of medical science and information technology such as is represented by the fields of genomics and bioinformatics. Accordingly, genomics and bioinformatics are key foundations upon which this future will be built. Science has evolved dramatically since the first human genome was fully sequenced in 2000 at a total cost of over $1 Billion. Today, we are on the verge of high resolution sequencing at a cost of less than $1K per genome, making it economically feasible for the first time to move out of the research lab and into widespread adoption for medical care. Genomic data, therefore, may become a vital input to diagnostic screening, therapeutic and/or prophylactic drug discovery, and/or disease treatment.

More particularly, genomics and bioinformatics are fields concerned with the application of information technology and computer science to the field of molecular biology. In particular, bioinformatics techniques can be applied to process and analyze various genomic data, such as from an individual so as to determine qualitative and quantitative information about that data that can then be used by various practitioners in the development of prophylactic and therapeutic methods for preventing or at least ameliorating diseased states, and thus, improving the safety, quality, and effectiveness of health care on an individualized level.

Because of its focus on advancing personalized healthcare, bioinformatics, therefore, promotes individualized healthcare that is proactive, instead of reactive, and this gives the patient the opportunity to become more involved in their own wellness. Typically, this can be achieved through two guiding principles. First, federal leadership can be provided to support research that addresses these individual aspects of disease and disease prevention, such as with the ultimate goal of shaping diagnostic and preventative care to match each person's unique genetic characteristics. Additionally, a "network of networks" may be created to aggregate health care data to help researchers establish patterns and identify genetic "definitions" to existing diseases.

An advantage of employing bioinformatics technologies in such instances is that the qualitative and/or quantitative analyses of molecular biological data can be performed on a broader range of sample sets at a much higher rate of speed and often times more accurately, thus expediting the emergence of a personalized healthcare system.

Accordingly, in various instances, the molecular data to be processed in a bioinformatics based platform typically concerns genomic data, such as Deoxyribonucleic acid (DNA) and/or Ribonucleic acid (RNA) data. For example, a well-known method for generating DNA and/or RNA data involves DNA/RNA sequencing. DNA/RNA sequencing can be performed manually, such as in a lab, or may be performed by an automated sequencer, such as at a core sequencing facility, for the purpose of determining the genetic makeup of a sample of an individual's genetic material, e.g., DNA and/or RNA. The person's genetic information may then be used in comparison to a referent, such as a reference sequence, haplotype, or theoretical haplotype, so as to determine its variance therefrom. Such variant information may then be subjected to further processing and used to determine or predict the occurrence of a diseased state in the individual.

For instance, manual or automated DNA/RNA sequencing may be employed to determine the sequence of nucleotide bases in a sample of DNA/RNA, such as a sample obtained from a subject. Using various different bioinformatics techniques these sequences may then be strung together to generate the genomic sequence of the subject. This sequence may then be compared to a reference genomic sequence to determine how the genomic sequence of the subject varies from that of the reference. Such a process involves determining the variants in the sampled sequence and presents a central challenge to bioinformatics methodologies.

For example, a central challenge in DNA sequencing is building full-length genomic sequences, e.g., chromosomal sequences, from a sample of genetic material that can be compared to a reference genomic sequence such as to determine the variants in the sampled full-length genomic sequences. In particular, the methods employed in sequencing protocols do not produce full-length chromosomal sequences of the sample DNA.

Rather, sequence fragments, typically from 100-1,000 nucleotides in length, are produced without any indication as to where in the genome they align. Therefore, in order to generate full length chromosomal genomic constructs, these fragments of DNA sequences need to be mapped, aligned, merged, and/or compared to a reference genomic sequence. Through such processes the variants of the sample genomic sequences from the reference genomic sequences may be determined.

However, as the human genome is comprised of approximately 3.1 billion base pairs, and as each sequence fragment is typically only from 100 to 500 nucleotides in length, the time and effort that goes into building such full length genomic sequences and determining the variants therein is quite extensive often requiring the use of several different computer resources applying several different algorithms over prolonged periods of time.

In a particular instance, thousands to millions of fragments of DNA sequences are generated, aligned, and merged in order to construct a genomic sequence that approximates a chromosome in length. A step in this process may include comparing the DNA fragments to a reference sequence to determine where in the genome the fragments align.

A number of such steps are involved in building chromosome length sequences and in determining the variants of the sampled sequence. Accordingly, a wide variety of methods have been developed for performing these steps. For instance, there exist commonly used software implementations for performing one or a series of such steps in a bioinformatics system. However, a common characteristic of such software based bioinformatics methods and systems is that they are labor intensive, take a long time to execute on general purpose processors, and are prone to errors.

A bioinformatics system, therefore, that could perform the algorithms implemented by such software in a less labor and/or processing intensive manner with a greater percentage accuracy would be useful. However, even as we approach the "$1000 Genome", the cost of analyzing, storing and sharing this raw digital data has far outpaced the cost of producing it. This data analysis bottleneck is a key obstacle standing between these ever-growing raw data and the real medical insight we seek from it.

Accordingly, presented herein are systems, apparatuses, and methods for implementing a genomics and/or bioinformatic protocols, such as for performing one or more functions for analyzing genomic data, for instance, via software implementations and/or on an integrated circuit, such as on a hardware processing platform. For example, as set forth herein below, in various implementations, a combination of software implementable and/or hardware accelerator solutions, such as including an integrated circuit and software for interacting with the same, may be employed in performing such bioinformatics related tasks where the integrated circuit may be formed of one or more hardwired digital logic circuits, which may be interconnected by a plurality of physical electrical interconnects, that can be arranged as a set of processing engines, wherein each processing engine is capable of being configured to perform one or more steps in a bioinformatics genetic analysis protocol. An advantage of this arrangement is that the bioinformatics related tasks may be performed in a manner that is faster than the software alone such as typically engaged for performing such tasks. Such hardware accelerator technology, however, is currently not typically employed in the genomics and/or bioinformatics space.

SUMMARY

This present disclosure is related to performing a task such as in a bioinformatics protocol. In various instances, a plurality of tasks are performed, and in some instances these tasks are performed in a manner so as to form a pipeline, wherein each task and/or its substantial completion acts as a building block for each subsequent task until a desired end result is achieved. Accordingly, in various embodiments, the present disclosure is directed to performing one or more methods on one or more apparatuses wherein the apparatus has been optimized for performing those methods. In certain embodiments, the one or more methods and/or one or more apparatuses are formulated into one or more systems.

For instance, in certain aspects, the present disclosure is directed to systems, apparatuses, and methods for implementing genomics and/or bioinformatic protocols such as, in various instances, for performing one or more functions for producing and/or analyzing genetic data employing innovative software and/or on an integrated circuit, such as implemented in a combination software and/or hardware processing platform. For example, in one aspect, a genomics and/or bioinformatics system is provided. The system may involve the performance of various bioanalytical production and/or analysis functions that have been optimized so as to be performed faster and/or with increased accuracy. The methods for performing these functions may be implemented in software or hardware solutions. Accordingly, in certain instances, methods are presented where the method involves the data production and/or acquisition and/or analysis that may include the performance of one or more algorithms where the algorithm(s) has been optimized in accordance with the manner, e.g., software, hardware, or a combination of both, in which it is to be implemented. In particular, where an algorithm is to be implemented in a software solution, the algorithm and/or its attendant processes, may be optimized so as to be performed faster and/or with better accuracy for execution by that media. Likewise, where the functions of an algorithm are to be implemented in a hardware solution, the hardware has been designed to perform these functions and/or their attendant processes in an optimized manner so as to be performed faster and/or with better accuracy for execution by that media. Further, where the functions involve a combination of software and/or hardware solutions, these functions and their attendant processes have been designed and configured to work seamlessly together to achieve heretofore unattainable speed while maintaining or enhancing accuracy.

Accordingly, in one aspect, presented herein are systems, apparatuses, and methods for implementing bioinformatic protocols, such as for performing one or more functions for generating and/or analyzing genetic data, for instance, via one or more developed and/or optimized algorithms and/or on one or more optimized integrated circuits, such as on one or more hardware processing platforms. Hence, in one instance, methods are provided for implementing one or more algorithms for the performance of one or more steps for generating and/or analyzing genomic data in a genomics and/or bioinformatics protocol. In another instance, methods are provided for implementing the functions of one or more algorithms for the performance of one or more steps for analyzing genomic data in a bioinformatics protocol, wherein the functions are at least partially implemented on an integrated circuit such as formed of one or more hard-wired digital logic circuits. In such an instance, the hard-wired digital logic circuits may be interconnected, such as by one or a plurality of physical electrical interconnects, and may be arranged to function as one or more processing engines. In various instances, a plurality of hardwired digital logic circuits are provided, which hardwired digital logic circuits are configured as a set of processing engines, wherein each processing engine is capable of performing one or more steps in a bioinformatics genetic analysis protocol, such as a bioinformatics processing pipeline.

More particularly, in one instance, a system for producing genetic sequence data, e.g., including devices and methods for nucleic acid sequencing, and/or for executing a sequence analysis pipeline on such genetic sequence data is provided. The system may include one or more of an electronic data source, such as associated with a DNA/RNA sequencing apparatus, such as herein described, a memory, and/or an integrated circuit. For instance, in one embodiment, an electronic data source is included, where in the electronic data source may be configured for generating and/or providing one or more digital signals, such as a digital signal representing one or more reads of genetic data, for example, where each read of genomic data includes a sequence of nucleotides. Further, the memory may be configured for storing one or more genetic reference sequences, and may further be configured for storing an index, such as an index of the one or more genetic reference sequences and/or annotated splice junction data.

Further still, a device and/or method for producing genetic sequence data is provided. For example, an approach to DNA/RNA analysis, such as for genetic diagnostics and/or sequencing, involving one or more of nucleic acid hybridization, detection, and/or sequencing reactions is provided. In various instances, the approach may include hybridization and/or detection devices and/or procedures for implementing one or more of the following steps. Particularly, for genetic analysis, an RNA or DNA sample of a subject to be analyzed may be isolated and immobilized, e.g., directly and/or indirectly, on a substrate, such as a substrate containing a chemically sensitive one-dimensional (1-D) and/or two-dimensional (2D) reaction layer, e.g., a graphene reaction layer, and/or a three-dimensional (3D) reaction layer and a probe of a known or to be detected genetic sequence, e.g., a disease marker, may be washed across the substrate, or vice versa. In various instances, one or more of the subject's RNA or DNA sample and/or the probe may be labeled.

In other instances, such as where the substrate includes a 1D or 2D, e.g., graphene, reaction layer, and/or other chemically sensitive reaction layer, a label or probe, such as a chemical or radioactive label may not be necessary and/or included. In either instance, if the disease marker is present, a binding event will occur, e.g., hybridization, and because the hybridization event is detectable, e.g., via a labeled analyte or probe and/or via the suitably configured reaction layer, as herein presented, the presence of the disease marker will be detected. If the disease marker is not present, there will be no reaction and therefore no detection. Of course, in some instances, the absence of a binding event may be the indicative event. Hence, the system may be configured such that the hybridization event may either be or not be detected thereby indicating the presence or absence of the disease marker in the subject's sample.

Likewise, for DNA and/or RNA sequencing, first, an unknown nucleic acid sequence the nucleotide identity of which is to be determined, e.g., a single-stranded sequence of DNA or RNA of a subject, is isolated, amplified, and immobilized on a substrate, which, as described herein may include a 1D, 2D, e.g., graphene layered, 3D, or other configured reaction layer thereon. Next, a known nucleic acid, e.g., a nucleotide base, which may be labeled with an identifiable tag is contacted with the unknown nucleic acid sequence in the presence of a polymerase. As noted, where the reaction event occurs proximate a suitably configured reaction layer, e.g., a graphene containing reaction layer, a labeled reactant need not be included.

Hence, when hybridization occurs, the nucleic acid binds to its complementary base in the unknown sequence, e.g., the sample DNA or RNA being sequenced, and is immobilized on the surface of the substrate, such as proximate the reaction layer. The binding event can then be detected, e.g., optically, electrically, and/or via a suitably detectable reaction occurring at the reaction layer. These steps are then repeated until the entire DNA or RNA sample has been completely sequenced. Typically, these steps are performed by a Next Gen Sequencer, as is known in the art, or they may be performed in accordance with the devices and methods herein described, such that thousands to millions of sequencing reactions may be performed and/or processed concurrently and digital data produced as a result thereof may be analyzed in conjunction with the innovative sequencing devices and processes disclosed herein such as in a multiplex bioinformatics processing pipeline.

For instance, in one aspect, such as with respect to the innovative sequencing devices herein presented, an appropriately configured sequencing platform may be provided as a field effect transistor (FET) containing a chemical reaction layer such as for use in performing a hybridization and/or sequencing reaction. Particularly, such a field effect transistor (FET) may be fabricated on a primary structure, such as a wafer, e.g., a silicon wafer. In various instances, the primary structure may include one or more additional structures, for instance, in a stacked configuration, such as an insulator material layer. For example, an insulator material may be included on top of the silicon wafer primary structure, and may be an inorganic material, such as a silicon oxide, e.g., a silicon dioxide, or a silicon nitride, or an organic material, such as a polyimide, BCB, or other like material.

The primary structure and/or insulator layer may include a further structure containing one or more of a conductive source and/or a conductive drain, such as separated one from another by a space, and embedded in the primary structure and/or insulator material layer and/or may be planar with a top and/or bottom surface of the insulator so as to form a top and/or bottom gate. In various instances, the structures, e.g., the silicon wafer structure, may further include or otherwise be associated with an integrated circuit, such as a processor, e.g., a microprocessor, for processing generated data, such as sensor derived data, e.g., data derived as a result of a sequencing reaction, e.g., proximate the gate region. Accordingly, the plurality of structures may be configured as, or otherwise include, an integrated circuit, and/or may be present as an ASIC, a structured ASIC, or an FPGA.

Particularly, these structures may be configured as a complementary metal-oxide semiconductor (CMOS), which in turn may be configured as a chemically-sensitive FET sensor containing one or more of a conductive source, a conductive drain, and/or a reaction region, such as a gate region, which itself may include a micro- or nano-channel, chamber, and/or well configuration, which sensor may be adapted so as to communicate with a processor. For instance, the FET may include a CMOS configuration having or otherwise being associated with an integrated circuit that is fabricated on a silicon wafer, which further includes an insulator layer, which insulator layer includes a conductive source and a conductive drain embedded in the insulator layer, which source and drain may be composed of metal, such as a damascene copper. In various instances, the CMOS and relevant structures may include a surface, e.g., a top surface, which surface may include a channel and/or a chamber so as to form a reaction well where the surface of the reaction well may be configured to extend from the conductive source to the conductive drain and be adapted to receive various reagents instrumental in performing a biochemical reaction, such as a DNA or RNA hybridization and/or sequencing reaction.

In certain instances, the surface and/or channel and/or chamber may include a one-dimensional transistor material, a two-dimensional transistor material, a three-dimensional transistor material, and/or the like. In various instances, a one-dimensional (1D) transistor material may be included, which 1D material may be composed of a carbon nanotube or a semiconductor nanowire, which in various instances may be formed as a sheet or a channel, and/or in various instances may include a nanopore, although in many instances, a nanopore is not included nor necessary. In various instances, a two-dimensional (2D) transistor material may be included, which 2D material may include a graphene layer, silicene, molybdenum disulfide, black phosphorous, and/or metal dichalcogenides. A three-dimensional (3D) configuration may also be present. In various instances, the surface and/or channel may include a dielectric layer. Additionally, in various instances, a reaction layer, e.g., an oxide layer, may be disposed on the surface and/or within the channel and/or chamber, such as layered or otherwise deposited on the 1D, 2D, e.g., graphene, or 3D layer(s). Such an oxide layer may be an aluminum oxide or a silicon oxide, such as silicon dioxide. In various instances, a passivation layer may be disposed on the surface and/or channel and/or within the chamber, such as layered or otherwise deposited on the 1D, 2D, e.g., graphene, or 3D layer(s) and/or on an associated reaction layer on the surface and/or channel and/or chamber.

In particular instances, the primary and/or secondary and/or tertiary structures may be fabricated or otherwise configured so as to include a chamber or well structure in and/or on the surface, e.g., in a manner so as to form the reaction region. For instance, a well structure may be positioned on a portion of a surface, e.g., an exterior surface, of the primary and/or secondary and/or tertiary structures. In some instances, the well structure may be configured as a micro- or nano-chamber and may be formed on top of, or may otherwise include, at least a portion of the 1D, 2D, e.g., graphene, and/or 3D material, and/or may additionally include the reaction, e.g., oxide, and/or passivation layers. In various instances, the chamber and/or well structure may define an opening, such as an opening that allows access to an interior of the chamber, such as allowing direct contact with the 1D, e.g., carbon nanotube or nanowire, 2D, e.g., graphene, or 3D surface and/or channel and/or chamber. In particular instances, the chamber and/or well may be dimensioned so as to be a micro- or nano-chamber.

Accordingly, a further aspect of the present disclosure is a bio-sensor such as for performing a nucleic acid sequencing reaction. The bio-sensor includes a CMOS structure that may be configured as a chemically sensitive FET sensor and may include a metal containing source and drain, e.g., a damascene copper source and/or drain, that further includes a surface, such as a reaction region that includes a 1D or 2D layered, e.g., a graphene layered, or 3D surface that extends from the source to the drain. Particularly, the reaction region may include or otherwise be configured as a well or chamber structure that may be positioned on a portion of an exterior surface of the 1D or 2D layered well. In such an instance, the well structure may be configured so as to define an opening that allows for direct contact with the nanotube, nanowire, and/or graphene well or chamber surface. In various instances, an oxide and/or passivation layer may be disposed in or on the chamber surfaces. Hence, in certain instances, a chemically-sensitive transistor, such as a field effect transistor (FET) including one or more nano- or micro-wells for performing a sequencing reaction may be provided.

In some embodiments, the chemically-sensitive field effect transistor may include a plurality of wells and may be configured as an array, e.g., a sensor array. Such an array or arrays may be employed such as to detect a presence and/or concentration change of various analyte types in a wide variety of chemical and/or biological processes, including DNA and/or RNA hybridization and/or DNA or RNA sequencing reactions. For instance, the devices herein described, and/or systems including the same, may be employed in a method for the analysis of biological or chemical materials, such as for whole genome sequencing and/or analysis, genome typing analysis, micro-array analysis, panels analysis, exome analysis, micro-biome analysis, and/or clinical analysis, such as cancer analysis, NIPT analysis, and/or UCS analysis, and the like.

Hence, in a particular embodiment, a graphene FET (gFET) array may be employed to facilitate DNA and/or RNA sequencing and processing techniques, such as in a genetic analysis pipeline, as herein described. For example, a CMOS FET, e.g., a graphene FET (gFET) array, may be configured to include a reaction well that includes a reaction layer that is adapted to detect changes in hydrogen ion concentration (pH), changes in other analyte concentrations, and/or binding events associated with chemical processes such as related to DNA or RNA synthesis, such as within a gated reaction chamber or well of the gFET based sensor. Such a chemically-sensitive field effect transistor may include or be adapted to associate with one or more integrated circuits and/or be adapted to increase the measurement sensitivity and/or accuracy of the sensor and/or associated array(s), such as by including one or more surfaces within the reaction chamber or well having at least one surface layered with a 1D and/or 2D and/or 3D material, a dielectric or reaction layer, a passivation layer, and/or the like.

Accordingly, an aspect of the present disclosure may include one or more integrated circuits that may be formed of one or more sets of hardwired digital logic circuits, such as where a set of the hardwired digital logic circuits are interconnected, e.g., by a plurality of physical electrical interconnects, and may be adapted so as to participate in the performance and/or detection of a DNA or RNA hybridization and/or sequencing reaction, e.g., primary processing, and/or may further be adapted for processing the results thereof, e.g., such as in one or more secondary and/or tertiary processing steps. In such instances, the integrated circuit may include an input, such as via one or more of the plurality of physical electrical interconnects, so as to be connected with an electronic data generating source, such as a sequencing CMOS FET of the disclosure and/or a Next Gen Sequencer, which is configured for generating such data, e.g., in the form of a plurality of sequenced segments, e.g., reads, of genomic data. In particular instances, the one or more integrated circuits may include a set of hardwired digital logic circuits that are configured for performing a secondary and/or tertiary processing analysis pipeline on the generated reads of genomic data, and may therefore be connected to the electronic data generating source such as through the one or more of the associated interconnects.

In such an instance, the hardwired digital logic circuits of the integrated circuit and/or associated interconnects may be configured so as to be able to receive the one or more reads of genomic data, e.g., from the electronic data source. In particular instances, one or more of the hardwired digital logic circuits may be arranged as a set of processing engines, such as where each processing engine is formed of a subset of the hardwired digital logic circuits, and is configured so as to perform one or more steps in the sequencing and/or analysis pipeline, such as on the plurality of reads of genomic data. In such instances, each subset of the hardwired digital logic circuits may, in certain instances, be in a wired configuration so as to perform the one or more steps in the sequence and/or analysis pipeline. However, as indicated above, one or more of the steps in the sequence and/or analysis pipeline may be configured so as to be implemented in software, such as where the software and/or hardware have been adapted to operate in an optimized manner with respect to each other.

Accordingly, in various instances, a plurality of hardwired digital logic circuits are provided wherein the hardwired digital logic circuits are arranged as a set of processing engines, wherein one or more of the processing engines may include one or more of a sequencing module and/or a mapping module and/or an alignment module and/or a sorting module and/or variant call module and/or one or more tertiary processing modules as herein described. For instance, in various embodiments, the one or more of the processing engines may include a mapping module, which mapping module may be in a wired configuration and further be configured for communicating with a memory, on the device or otherwise associated therewith, e.g., via a suitably configured interconnect, so as to access an index containing one or more of a genetic reference sequence(s), one or more reads of generated sequencing data, and/or a splice junction index (e.g., in the case of RNA sequencing), and employing the same so as to perform one or more mapping operations.

Particularly, a suitably configured processing engine(s) may include or may otherwise be adapted as a mapping module for performing one or more mapping operations, such as including accessing an index of the one or more genetic reference sequences from the memory, such as by one or more of the plurality of physical electronic interconnects, for example, so as to map the plurality of reads to one or more segments of the one or more genetic reference sequences. Additionally, in various embodiments, the one or more of the processing engines may include an alignment module, which alignment module may be in the wired configuration and may be configured for accessing the one or more genetic reference sequences from the memory, such as by one or more of the plurality of physical electronic interconnects, for example, so as to align the plurality of reads to the one or more segments of the one or more genetic reference sequences.

Further, in various embodiments, the one or more of the processing engines may include a sorting module, which sorting module may be in the wired configuration and may be configured for accessing the one or more aligned reads from the memory, such as by one or more of the plurality of physical electronic interconnects, for example, so as to sort each aligned read, such as according to its one or more positions in the one or more genetic reference sequences. In such instances, the one or more of the plurality of physical electrical interconnects may include an output from the integrated circuit, such as for communicating result data from the mapping module and/or the alignment module and/or the sorting module. Furthermore, in particular embodiments, as indicated above, one or more of the processing engines may be configured for interacting with various software implemented processing functions, such as via one or more interconnects, e.g., a plurality of physical electronic interconnects, for performing one or more steps in the analysis pipeline including implementing one or more of RNA and/or DNA sequencing protocols and/or a variant call protocol.

In various instances, the one or more integrated circuit(s) may include a master controller so as to establish the wired configuration for each subset of the hardwired digital logic circuits, for instance, for performing the one or more of mapping, aligning, and/or sorting functions, which functions may be configured as one or more steps in a sequence analysis pipeline and/or may include the performance of one or more aspects of a sequencing and/or variant call function. Further, in various embodiments, the one or more integrated circuits herein disclosed may be configured as a field programmable gate array (FPGA) having hardwired digital logic circuits, such as where the wired configuration may be established upon manufacture of the integrated circuit, and thus may be non-volatile. In other various embodiments, the integrated circuit may be configured as an application specific integrated circuit (ASIC) having hardwired digital logic circuits. In other various embodiments, the integrated circuit may be configured as a structured application specific integrated circuit (Structured ASIC) having hardwired digital logic circuits.

In certain instances, the one or more integrated circuits, e.g., the CMOS FET sequencing and/or biosensor, and/or one or more associated memories may be housed on an expansion card, such as a peripheral component interconnect (PCI) card, for instance, in various embodiments, an integrated circuit(s) of the disclosure may be a chip having a PCIe card. In various instances, the integrated circuit and/or chip may be a component within a sequencer, such as an automated sequencer employing a FET sensor and/or an NGS, and/or in other embodiments, the integrated circuit and/or expansion card may be accessible via the internet, e.g., via the cloud. Further, in some instances, the memory may be a volatile random access memory (RAM) or DRAM.

Accordingly, in one aspect, an apparatus for executing one or more steps of a sequence analysis pipeline, such as on genetic data, is provided wherein the genetic data includes one or more of a genetic reference sequence(s), an index of the one or more genetic reference sequence(s), an index of one or more splice junctions, e.g., an annotated splice junction index or table, and/or a plurality of reads, such as of genetic data, e.g., DNA or RNA. In various instances, the apparatus may include an integrated circuit, which integrated circuit may include one or more, e.g., a set, of hardwired digital logic circuits, wherein the set of hardwired digital logic circuits may be interconnected, such as by one or a plurality of physical electrical interconnects. In certain instances, the one or more of the plurality of physical electrical interconnects may include an input, such as for receiving the plurality of reads of genomic data, such as from a sequencing device as disclosed herein. Additionally, the set of hardwired digital logic circuits may further be in a wired configuration, so as to access the index of the one or more genetic reference sequences and/or annotative splice junctions, via one of the plurality of physical electrical interconnects, and to map the plurality of reads of DNA and/or RNA to one or more segments of the one or more genetic reference sequences, such as according to the index or indexes.

In various embodiments, the index may include one or more hash tables, such as a primary and/or secondary hash table and/or a splice junction table. For instance, a primary hash table may be included, wherein in such an instance, the set of hardwired digital logic circuits may be configured to do one or more of: extracting one or more seeds of genetic data from the plurality of reads of genetic data; executing a primary hash function, such as on the one or more seeds of genetic data so as to generate a lookup address for each of the one or more seeds; and accessing the primary hash table using the lookup address so as to provide a location in the one or more genetic reference sequences for each of the one or more seeds of genetic data. In various instances, the one or more seeds of genetic data may have a fixed number of nucleotides.

Further, in various embodiments, the index may include a secondary hash table, such as where the set of hardwired digital logic circuits is configured for at least one of extending at least one of the one or more seeds with additional neighboring nucleotides, so as to produce at least one extended seed of genetic data; executing a hash function, e.g., a secondary hash function, on the at least one extended seed of genetic data, so as to generate a second lookup address for the at least one extended seed; and accessing the secondary hash table, e.g., using the second lookup address, so as to provide a location in the one or more genetic reference sequences for each of the at least one extended seed of genetic data. In various instances, the secondary hash function may be executed by the set of hardwired digital logic circuits, such as when the primary hash table returns an extend record instructing the set of hardwired digital logic circuits to extend the at least one of the one or more seeds with the additional neighboring nucleotides. In certain instances, the extend record may specify the number of additional neighboring nucleotides by which the at least one or more seeds is extended, and/or the manner in which the seed is to be extended, e.g., equally by an even number of "x" nucleotides to each end of the seed.

Furthermore, as is known, DNA codes for genes. However, in order for a gene to be expressed, its genetic code needs to be transcribed and translated into proteins. Specifically, a gene may be transcribed within the nucleus of a cell by RNA polymerase enzymes into a messenger RNA (mRNA) transcript or other types of RNA (e.g., a transfer RNA). The immediate RNA transcript is a single-stranded copy of the gene, except that DNA thymine (T) bases are transcribed into RNA Uracil (U) bases. But immediately after this copy is produced, its sequence includes both various intron- and exon copies, where the various intron-copies usually need to be spliced out, e.g., by spliceosomes, leaving only the exon-copies that are to be concatenated together at "splice junctions" (which are not thereafter directly evident), so as to form codon regions. Spliced mRNA containing the codon regions is then transported out of the cellular nucleus to a ribosome, which decodes it into a protein, where each group of three RNA nucleotides form the codon that codes for one amino acid. During the decoding process, a string of amino acids are strung together, and when strung together and glycosylated form the proteins, of which the cells, tissues, and organs of the body are composed. In this manner, genes in DNA serve as original instructions for the manufacture of proteins.

Accordingly, because the DNA includes both coding regions, e.g., exons, and non-coding regions, e.g., introns, the mapping and/or aligning and/or sorting of RNA back to its genetic precursor in the genomic DNA, may be complicated. Particularly, each gene exists on a single strand of the double-stranded DNA double-helix, often as a series of exons (coding segments) separated by introns (non-coding segments). Some genes have only a single exon, but most have several exons (separated by introns), and some have hundreds of exons or thousands of exons. Exons are commonly a few hundred nucleotides long, but may be as short as a single nucleotide or as long as tens or hundreds of thousands. Introns are commonly thousands of nucleotides long, and some exceed a million nucleotides. Hence, when mapping, aligning, and/or sorting from RNA, e.g., spliced mRNA, portions of the spliced mRNA may come from different regions of the DNA that may be separated from each other by one or two or even a million or more nucleotides. This makes the processing of RNA very complicated.

However, an aspect of the present disclosure overcomes these challenges, by the methods herein described, and therefore allows for the rapid and accurate whole-transcriptome RNA sequencing, mapping, aligning, and/or sorting. More particularly, where RNA processing is involved, the aforementioned index may include one or more tables, e.g., a hash table or other index, which includes or is otherwise associated with a table that allows for the ready lookup of various known or determined splice junctions employed by biological systems in transcribing RNA from DNA, as described in detail herein below. In such instances, therefore, an RNA-capable mapper/aligner may be configured to process such splice junctions and account for RNA-sequence reads that correspond to segments of transcribed and spliced RNA, such as where the read crosses one or more splice junctions; which, with respect to the DNA-oriented reference genome, means a first portion of the read came from, and should map to, a first exon, and a second portion of the read should map to a second exon, and so forth. Accordingly, the index may include or otherwise be associated with one or more splice junction tables and the set of hardwired digital logic circuits may be configured to do one or more of: employing said splice junction data to determine and/or extract one or more seeds of genetic, e.g., RNA, data from the plurality of reads of genetic RNA data; executing a function, e.g., a hash function, such as on the one or more seeds of genetic RNA data so as to generate a lookup address for each of the one or more seeds; and accessing the hash table using the lookup address so as to provide a location in the one or more genetic reference sequences for each of the one or more seeds of genetic RNA data.

Additionally, in one aspect, an apparatus for executing one or more steps of a sequence analysis pipeline on genetic sequence data, e.g., either DNA or RNA, is provided, wherein the genetic sequence data includes one or more of one or a plurality of genetic reference sequences, which may include both exons and introns, an index of the one or more genetic reference sequences and/or an index of annotated splice junctions, and a plurality of reads of genomic data. In various instances, the apparatus may include an integrated circuit, which integrated circuit may include one or more, e.g., a set, of hardwired digital logic circuits, wherein the set of hardwired digital logic circuits may be interconnected, such as by one or a plurality of physical electrical interconnects. In certain instances, the one or more of the plurality of physical electrical interconnects may include an input, such as for receiving the plurality of reads of genomic data, which reads may have previously been processed, as herein described so as to be mapped. Additionally, the set of hardwired digital logic circuits may further be in a wired configuration, so as to access the one or more genetic reference sequences, via one of the plurality of physical electrical interconnects, to receive location information, e.g. such as from a mapper, specifying one or more segments of the one or more reference sequences, and to align the plurality of reads to the one or more segments of the one or more genetic reference sequences.

Accordingly, in various instances, the wired configuration of the set of hardwired digital logic circuits, are configured to align the plurality of reads of DNA or RNA genetic data to the one or more segments of the one or more genetic reference sequences, and further include a wave front processor that me be formed of the wired configuration of the set of hardwired digital logic circuits. In certain embodiments, the wave front processor may be configured to process an array of cells of an alignment matrix, such as a matrix defined by a subset of the set of hardwired digital logic circuits. For instance, in certain instances, the alignment matrix may define a first axis, e.g., representing one of the plurality of reads, and a second axis, e.g., representing one or more of the segments of the one or more genetic reference sequences. In such an instance, the wave front processor may be configured to generate a wave front pattern of cells that extend across the array of cells from the first axis to the second axis; and may further be configured to generate a score, such as for each cell in the wave front pattern of cells, which score may represent the degree of matching of the one of the plurality of reads and the one of the segments of the one or more genetic reference sequences.

In such an instance, the wave front processor may further be configured so as to steer the wave front pattern of cells over the alignment matrix such that the highest score may be centered on the wave front pattern of cells. Additionally, in various embodiments, the wave front processor may further be configured to backtrace one or more, e.g., all, the positions in the scored wave front pattern of cells through previous positions in the alignment matrix; track one or more, e.g., all, of the backtraced paths until a convergence is generated; and generate a CIGAR string based on the backtrace from the convergence.

In certain embodiments, the wired configuration of the set of hardwired digital logic circuits to align the plurality of reads to the one or more segments of the one or more genetic reference sequences may include a wired configuration to implement a Burrows-Wheeler algorithm, as described above, e.g., for mapping prior to aligning, and/or to implement a Smith-Waterman and/or Needleman-Wunsch scoring algorithm. In such an instance, the Smith-Waterman and/or Needleman-Wunsch scoring algorithm may be configured to implement a scoring parameter that is sensitive to base quality scores. Further, in certain embodiments, the Smith-Waterman scoring algorithm may be an affine Smith-Waterman scoring algorithm.

In particular embodiments, the apparatus may include an integrated circuit, which integrated circuit may include one or more, e.g., a set, of hardwired digital logic circuits, wherein the set of hardwired digital logic circuits may be interconnected, such as by one or a plurality of physical electrical interconnects. In certain of these instances, the one or more of the plurality of physical electrical interconnects may include an input, such as for receiving the plurality of reads of genomic data, which reads may have previously been processed, as herein described so as to be mapped and/or aligned. Additionally, the set of hardwired digital logic circuits may further be in a wired configuration, so as to access the one or more genetic reference sequences, via one of the plurality of physical electrical interconnects, to receive location information, e.g. such as from a mapper and/or aligner, specifying one or more segments of the one or more reference sequences, and to sort the plurality of reads to the one or more segments of the one or more genetic reference sequences.

Accordingly, in one aspect, a method for sequencing genetic material, e.g., so as to produce electronic genetic data, may be provided. In particular instances, the method involves the use of a Next Gen Sequencer for sequencing of genomic DNA and/or RNA derived therefrom, as described generally herein and known in the art. In other instances, the method involves the use of a Next Gen Sequencer, modified as described herein, for sequencing of genomic DNA and/or RNA derived therefrom. In further instances, the method involves the use of a Field Effect Transistor and/or CMOS Sequencer, e.g., a sequencer on a chip, as described herein in detail below, for the sequencing of genomic DNA and/or RNA derived therefrom. In various instance, the genetic material once produced may be converted into an electronic form, e.g., a digital form, that may be streamed or otherwise transferred to one or more of the pipeline modules herein described.

Additionally, once the electronic, e.g., analog or digital, genetic data, such as sequencing data, is received, another aspect of the disclosure is directed to executing a sequence analysis pipeline on such genetic sequence data. The genetic data may include one or more genetic reference sequences, one or more indexes of the one or more genetic reference sequences and/or a list of one or more annotated splice junctions (e.g., in the case of RNA sequencing) pertaining thereto, and/or a plurality of reads of genomic data (e.g., DNA and/or RNA). The method may include one or more of receiving, accessing, mapping, aligning, and/or sorting various iterations of the genetic sequence data. For instance, in certain embodiments, the method may include receiving, on an input to an integrated circuit from an electronic data source, one or more of a plurality of reads of genomic data, wherein each read of genomic data may include a sequence of nucleotides. In such an instance, the integrated circuit may be formed of a set of hardwired digital logic circuits such as are interconnected by a plurality of physical electrical interconnects, which physical electrical interconnects may include one or more of the plurality of physical electrical interconnects comprising the input.

The method may further include accessing, by the integrated circuit on one or more of the plurality of physical electrical interconnects from a memory, the index of the one or more genetic reference sequences and/or, in the case of RNA sequencing, the annotated splice junctions. Particularly, if annotated splice junctions are provided to the mapper engine, they can be leveraged to improve mapping sensitivity. In such an instance, the list of annotated junctions may be loaded into the memory so as to be accessible by the mapper engine so as to assist with the mapping of RNA genetic material. Advantageously, the annotated junctions may be formatted into a table, e.g., a hash table or index that may be associated therewith, so as to be easily accessed by the mapper engine. Accordingly, the method may include mapping, by a first subset of the hardwired digital logic circuits of the integrated circuit, the plurality of genetic reads, e.g., DNA or RNA reads, to one or more segments of the one or more genetic reference sequences. Additionally, the method may include accessing, by the integrated circuit on one or more of the plurality of physical electrical interconnects from the memory, the one or more mapped reads and/or genetic reference sequences; and aligning, by a second subset of the hardwired digital logic circuits of the integrated circuit, the plurality of reads, e.g., mapped reads, to the one or more segments of the one or more genetic reference sequences.

In various embodiments, the method may additionally include accessing, by the integrated circuit on one or more of the plurality of physical electrical interconnects from a memory, the aligned plurality of reads. In such an instance the method may include sorting, by a third subset of the hardwired digital logic circuits of the integrated circuit, the aligned plurality of reads according to their positions in the one or more genetic reference sequences. In certain instances, the method may further include outputting, such as on one or more of the plurality of physical electrical interconnects of the integrated circuit, result data from the mapping and/or the aligning and/or the sorting, such as where the result data includes positions of the mapped and/or aligned and/or sorted plurality of reads.

Further, once the genetic data has been generated and/or processed, e.g., in one or more secondary processing protocols, such as by being mapped, aligned, and/or sorted, such as to produce one or more variant call files, for instance, to determine how the genetic sequence data from a subject differs from one or more reference sequences, a further aspect of the disclosure may be directed to performing one or more other analytical functions on the generated and/or processed genetic data such as for further, e.g., tertiary, processing. For example, the system may be configured for further processing of the generated and/or secondarily processed data, such as by running it through one or more tertiary processing pipelines, such as one or more of a genome pipeline, an epigenome pipeline, metagenome pipeline, joint genotyping, a MuTect2 pipeline, or other tertiary processing pipeline, such as by the devices and methods disclosed herein. Particularly, in various instances, an additional layer of processing may be provided, such as for disease diagnostics, therapeutic treatment, and/or prophylactic prevention, such as including NIPT, NICU, Cancer, LDT, AgBio, and other such disease diagnostics, prophylaxis, and/or treatments employing the data generated by one or more of the present primary and/or secondary and/or tertiary pipelines. Hence, the devices and methods herein disclosed may be used to generate genetic sequence data, which data may then be used to generate one or more variant call files and/or other associated data that may further be subject to the execution of other tertiary processing pipelines in accordance with the devices and methods disclosed herein, such as for particular and/or general disease diagnostics as well as for prophylactic and/or therapeutic treatment and/or developmental modalities.

Hence, in various instances, implementations of various aspects of the disclosure may include, but are not limited to: apparatuses, systems, and methods including one or more features as described in detail herein, as well as articles that comprise a tangibly embodied machine-readable medium operable to cause one or more machines (e.g., computers, etc.) to result in operations described herein. Similarly, computer systems and/or networks are also described that may include one or more processors and/or one or more memories coupled to the one or more processors, either directly or remotely. Accordingly, computer implemented methods consistent with one or more implementations of the current subject matter can be implemented by one or more data processors residing in a single computing system or multiple computing systems, such as one or more computer clusters. Such multiple computing systems can be connected and can exchange data and/or commands or other instructions or the like via one or more connections, including but not limited to a connection over a network (e.g. the Internet, a wireless wide area network, a local area network, a wide area network, a wired network, or the like), via a direct connection between one or more of the multiple computing systems, etc. A memory, which can include a computer-readable storage medium, may include, encode, store, or the like one or more programs that cause one or more processors to perform one or more of the operations described herein.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to an enterprise resource software system or other business software solution or architecture, it should be readily understood that such features are not intended to be limiting. The claims that follow this disclosure are intended to define the scope of the protected subject matter.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

When practical, similar reference numbers denote similar structures, features, or elements.

DETAILED DESCRIPTION

Figure 1:
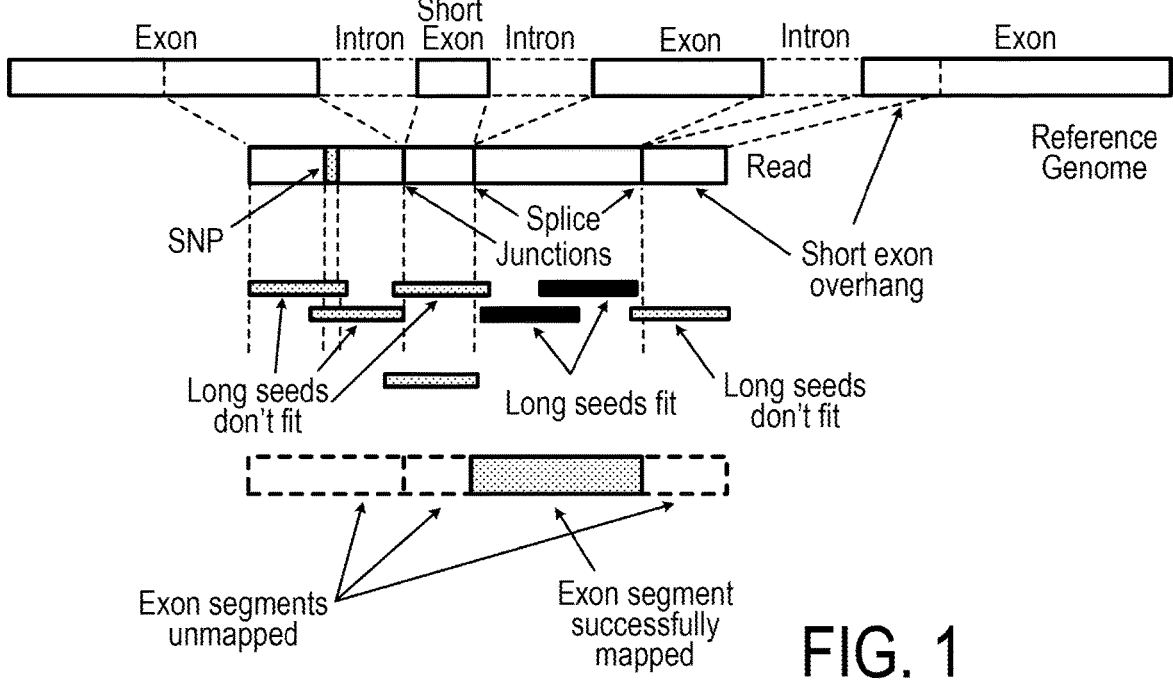
FIG. 1 depicts an RNA read, illustrating the crossover between one or more splice junctions, and a seed crossing the read's splice junction

To address these and potentially other issues with currently available solutions, methods, systems, articles of manufacture, and the like consistent with one or more implementations of the current subject matter can, among other possible advantages, provide a sequence analysis apparatus for executing a sequence analysis pipeline on genetic sequence data.

The following provides details of various implementations of a sequencing platform, a sequence analysis pipeline, as well as a system for performing one or more tertiary processing protocols.

In its most basic form, the body is comprised of cells, the cells form tissues, tissues form organs, organs form systems, and these systems function together to ensure the body operates to sustain the life of the individual. The cells of the body, therefore, are the building blocks of life. More particularly, each cell has a nucleus, and within the nucleus of every cell reside chromosomes. Chromosomes are formed from Deoxyribonucleic Acid, which has an organized but winding double helix structure. The DNA itself is comprised of two opposed, but complementary strands of nucleotides, which nucleotides comprise the genes that code for the proteins that give the cells their structures and mediate the functions and regulations of the body's tissues and organs. Basically, proteins do most of the work of cells in maintaining the body's normal processes and functions.

Given the multiplicity of components of the body and the complexity involved in how they interact with one another to maintain the body's various processes and functions, there are a multiplicity of ways that the body may malfunction on any one of these different levels. For instance, in one such instance, there may be a malfunction in the way a particular gene codes for a given protein, which dependent on the protein and the nature of its malfunctioning can result in the onset of a diseased state.

Accordingly, in diagnosing, preventing, and/or curing such diseased states, determining the genetic makeup of a subject may be extremely useful. For instance, once known, a person's genetic makeup, e.g., his or her genomic composition, can be used for purposes of diagnostics and/or for determining whether a person has or has the potential for a diseased state, and therefore, may be used for prophylaxis. Likewise, the knowledge of a person's genome may be useful in determining various potential therapeutic modalities, such as drugs, that can or cannot be used in a prophylactic or therapeutic regimen without causing harm to the user. In various instances, knowledge of a person's genome may also be employed to determine drug efficacy and/or problematic side effects of such drug use may be predicted and/or identified. Potentially, the knowledge of a person's genome can be used to produce designer drugs, such as drugs tailor made and optimized in accordance with a person's specific genetic makeup. In particular, in one instance, an engineered protein or nucleotide sequence can be fabricated to an individual's unique genetic characteristics so as to turn off or turn on the transcription of genes that either over or under produce proteins and thereby ameliorate diseased states.

Hence, in some instances, it is a goal of bioinformatics processing to determine individual genomes of people, which determinations may be used in gene discovery protocols as well as for prophylaxis and/or therapeutic regimes to better enhance the livelihood of each particular person and human kind as a whole. Further, knowledge of an individual's genome may be used such as in drug discovery and/or FDA trials to better predict with particularity which, if any, drugs will be likely to work on an individual and/or which would be likely to have deleterious side effects, such as by analyzing the individual's genome and/or a protein profile derived therefrom and comparing the same with a predicted biological response from such drug administration.

Such genomics and bioinformatics processing usually involves three well defined, but typically separate phases of information processing. The first phase involves DNA/RNA sequencing, where a subject's DNA/RNA is obtained and subjected to various processes whereby the subject's genetic code is converted to a machine-readable digital code, e.g., a FASTQ file. The second phase involves using the subject's generated digital genetic code for the determination of the individual's genetic makeup, e.g., determining the individual's genomic nucleotide sequence and/or variant call file, e.g., how the individual's genome differs from that of one or more reference genomes. And the third phase involves performing one or more analyses on the subject's genetic makeup so as to determine therapeutically useful information therefrom. Sequentially, these may be termed: primary, secondary, and tertiary processing, respectively.

Preliminarily, e.g., in Phase I, or primary processing, the genetic material must be pre-processed, e.g., via nucleotide sequencing, so as to derive usable genetic sequence data. The sequencing of nucleic acids, such as deoxyribonucleic acid (DNA) and ribonucleic acid (RNA), is a fundamental part of biological discovery. Such detection is useful for a variety of purposes and is often used in scientific research as well as medical advancement. For instance, the genomics and bioinformatics fields are concerned with the application of information technology and computer science to the fields of genetics and/or molecular biology. In particular, bioinformatics techniques, such as those described herein, can be applied to generate, process, and analyze various genomic data, such as from an individual so as to determine qualitative and quantitative information about that data that can then be used by various practitioners in the development of individual and/or global diagnostic, prophylactic, and/or therapeutic methods for detecting, preventing and/or at least ameliorating diseased states, and thus, improving the safety, quality, and effectiveness of health care for the individual and/or the community.

Generally, the approach to DNA/RNA analysis, such as for genetic diagnostics, involves nucleic acid hybridization and detection. For example, various typical hybridization and detection approaches include the following steps. For genetic analysis, an RNA or DNA sample of a subject to be analyzed may be isolated and immobilized on a substrate, a probe of a known genetic sequence, e.g., a disease marker, may be labeled and washed across the substrate. If the disease marker is present, a binding event will occur, e.g., hybridization, and because the probe has been labeled the hybridization event may either be or not be detected thereby indicating the presence or absence of the disease marker in the subject's sample. Alternatively, as indicated above, where the hybridization reaction takes place next to a reaction layer, e.g., configured to detect a reactant and/or a by product of the reaction, such as in a suitably configured FET device, a labeled probe need not be employed.

Typically, for nucleotide sequencing, first, an unknown nucleic acid sequence to be identified, e.g., a single-stranded sequence of DNA and/or RNA of a subject, is isolated, amplified, and immobilized on a substrate. Next, a known nucleic acid labeled with an identifiable tag is contacted with the unknown nucleic acid sequence in the presence of a polymerase. When hybridization occurs, the labeled nucleic acid binds to its complementary base in the unknown sequence immobilized on the surface of the substrate. The binding event can then be detected, e.g., optically or electrically. These steps are then repeated until the entire DNA sample has been completely sequenced.

Generally, these steps are performed manually or via an automated sequencer, such as a Next Gen Sequencer (NGS), wherein thousands to millions of sequences may concurrently be produced in the next-generation sequencing process. However, as presented herein, a direct, label-free system for the sequencing of DNA and/or RNA such as on a computer chip, such as a complementary metal oxide semiconductor (CMOS) chip, is presented, such as where various components or the entire sensory apparatus of the sequencer may be embodied within or otherwise associated with the semiconductor chip. Such a system, as herein provided, allows for the seamless integration of primary, secondary, and/or tertiary processing, such as within the same semiconductor chip set.

More particularly, a typical sequencing procedure, regardless of the type of sequencing apparatus employed, involves obtaining a biological sample from a subject, such as through venipuncture, hair, etc. and treating the sample to isolate the genetic content therefrom. Once isolated, where the genetic sample is DNA, the DNA may be denatured and strand separated. As RNA is already single stranded this step may not be necessary when processing RNA. The isolated DNA and/or RNA or portions thereof may then be multiplied, e.g., via polymerase chain reaction (PCR), so as to build a library of replicated strands that are now ready to be sequenced and read, such as by an automated sequencer, which sequencer is configured to read the replicated strands, e.g., by synthesis, and thereby determine the nucleotide sequences that makes up the DNA and/or RNA. Further, in various instances, such as in building the library of replicated and multiplies strands, it may be useful to provide for over-coverage when preprocessing a given portion of the DNA and/or RNA. To perform this over-coverage, e.g., using PCR, may require increased sample preparation resources and time, and therefore be more expensive, but it often gives an enhanced probability of the end result being more accurate.

Once the library of replicated DNA/RNA strands has been generated they may be injected into an automated sequencer, e.g., NGS, which may then read the strands, such as by synthesis, so as to determine the nucleotide sequences thereof. For instance, the replicated single stranded DNA or RNA may be attached to a glass bead and inserted into a test vessel, e.g., an array. All the necessary components for replicating its complementary strand, including labeled nucleotides, are also added to the vessel but in a sequential fashion. For example, all "A", "C", "G", and "T's," which may be labeled, are added, either one at a time, or all together, if labeled, to see which of the nucleotides is going to bind at position one of the single stranded DNA or RNA.

After each addition, in the labeled model, a light, e.g., a laser, is shone on the array. If the composition fluoresces then an image is produced indicating which nucleotide bound to the subject location. In the unlabeled model, a binding event can be detected such as by a change in resistance at a gate, e.g., a solution gate, proximate a reaction layer where the replicated single stranded DNA or RNA containing glass bead is positioned. More particularly, where the nucleotides are added one at a time, if a binding event occurs, then its indicative fluorescence or change in resistance will be observed. If a binding event does not occur, the test vessel may be washed and the procedure repeated until the appropriate one of the four nucleotides binds to its complement at the subject location, and its indicative change in conditions is observed. Where all four nucleotides are added at the same time, each may be labeled with a different fluorescent indicator, and the nucleotide that binds to its complement at the subject position may be determined, such as by the color of its fluorescence. This greatly accelerates the synthesis process.

Once a binding event has occurred, the complex is then washed and the synthesis steps are repeated for position two. For example, a labeled or otherwise marked nucleotide "A" may be added to the reaction mixture to determine if the complement at position one in the bound template molecule being sequenced is an "A", and if so, the labeled "A" reactant will bind to the template sequence having that complement and will therefore fluoresce, after which the samples will all be washed so as to clear away any excess nucleotide reactants. Where a binding event happened the bound nucleotide is not washed away. This process will be repeated for all nucleotides for all positions until all the over-sampled nucleic acid segments, e.g., reads, have been sequenced and the data collected. Alternatively, where all four nucleotides are added at the same time, each labeled with a different fluorescent indicator, only one nucleotide will bind to its complement at the subject position, and the others will be washed away, such that after the vessel has been washed, a laser may be shone on the vessel and which nucleotide bound to its complement may be determined, such as by the color of its fluorescence. However, where a CMOS FET sensor is employed, as described below, the binding event may be detected by a change in conductance that takes place proximate a suitably configured gate or other reaction region.

Particularly, in part, due to the need for the use of optically detectable, e.g., fluorescent, labels in the sequencing reactions being performed, the required instrumentation for performing such high throughput sequencing may have a tendency to be bulky, costly, time-consuming, and non-portable. For this reason, a new approach for direct, label-free detection of DNA and/or RNA sequencing are herein proposed. For instance, although in various embodiments, improved methods for performing NGS processing is provided, in other embodiments, improved methods and devices for nucleic acid sequencing and/or processing not necessarily involving an NGS are provided. For example, in particular instances, a detection method is herein proposed that is based on the use of various electronic analytical devices. Such direct electronic detection methods have several advantages over a typical NGS platform.

More particularly, the sensor and/or detection apparatus, as herein disclosed, may be incorporated in the substrate itself, such as employing a biosystem-on-a-chip device, such as a complementary metal oxide semiconductor device, "CMOS". Specifically, in using a CMOS device in genetic detection, the output signal representative of a hybridization event, e.g., either for hybridization and/or nucleic acid sequencing, can be directly acquired and processed on the microchip itself. In such an instance, automatic recognition is achievable in real time and at a lower cost than is currently achievable using typical NGS processing. Moreover, standard CMOS substrate devices may be employed for such electronic detection making the process simple, inexpensive, rapid, and portable.

For instance, in order for next-generation sequencing to become widely used as a diagnostic in the healthcare industry, sequencing instrumentation will need to be mass produced with a high degree of quality, mobility, and economy. One way to achieve this is to recast DNA/RNA sequencing in a format that fully leverages the manufacturing base created for computer chips, such as complementary metal oxide semiconductor (CMOS) chip fabrication, which is the current pinnacle of large scale, high quality, low-cost manufacturing of high technology. To achieve this, ideally the entire sensory apparatus of the sequencer may be embodied in a standard semiconductor chip, such as manufactured in the same fab facilities used for logic and memory chips.

Accordingly, in another aspect of the disclosure, herein presented is a field effect transistor (FET) that may be fabricated on or otherwise associated with a CMOS chip that is configured for use in performing one or more of a DNA/RNA sequencing and/or hybridization reactions. Such a FET may include a gate, a channel region connecting a source and a drain terminals, and an insulating barrier that may be configured to separate the gate from the channel. The optimal operation of such a FET relies on the control of the channel conductivity, and thus the control of the drain current, such as by a voltage that may be applied between the gate and source terminals.

For high-speed applications, and for the purposes of increasing sensor sensitivity, the FETs herein provided can be operated in a manner to respond quickly to variations in the gate voltage ($V_{GS}$). However, this requires short gates and fast carriers in the channel. In view of this, the present FET sensors, such as for use in nucleic acid hybridization and/or sequencing reactions, are configured so as to have channels that may be very thin in the vertical and/or horizontal dimensions so as to allow for high-speed transmission of carriers as well as for increased sensor sensitivity and accuracy, thereby giving the present sensors particular advantages for nucleic acid sequencing reactions. Therefore, the devices, systems, and methods of employing the same provided herein are ideal for the performance of genomics analysis and applications, such as for nucleic acid sequencing and/or genetic diagnostics.

Hence, one aspect of the present disclosure is a chemically-sensitive transistor, such as a field effect transistor (FET) that is designed for analysis of biological or chemical materials that solves many of the current problems associated with nucleic acid sequencing and genetic diagnostics. Such FETs may be fabricated on a primary structure, such as a wafer, e.g., a silicon wafer. In various instances, the primary structure may include one or more additional structures, for instance, in a stacked configuration, such as an insulator material layer. For example, an insulator material may be included on top of the primary structure, and may be an inorganic material, such as a silicon oxide, e.g., a silicon dioxide, or a silicon nitride, or an organic material, such as a polyimide, BCB, or other like material.

The primary and secondary structures, e.g., including an insulator layer, may include a further structure containing one or more of a conductive source and/or a conductive drain, such as separated one from another by a space, and embedded in the primary structure and/or insulator material and/or may be planar with a top surface of the insulator. In various instances, the structures may further include or may be otherwise associated with a processor, such as for processing generated data, such as sensor derived data. Accordingly, the structures may be configured as, or otherwise include, an integrated circuit, such as herein described, and/or may be an ASIC, a structured ASIC, or an FPGA.

In particular instances, the structures may be configured as a complementary metal-oxide semiconductor (CMOS), which in turn may be configured as a chemically-sensitive FET containing one or more of a conductive source, a conductive drain, a channel or well, and/or a processor. For instance, the FET may include a CMOS structure having an integrated circuit that is fabricated on a silicon wafer, which further includes an insulator layer, which insulator layer includes the conductive source and the conductive drain, such as embedded therein, which source and drain terminals may be composed of metal, such as a damascene copper source and a damascene copper drain. In various instances, the structures may include a surface, e.g., a top surface, which surface may include a channel, such as where the surface and/or channel may be configured to extend from the conductive source to the conductive drain and form a reaction zone thereby.

In certain instances, the surface and/or channel may include a one-dimensional transistor material, a two-dimensional transistor material, a three-dimensional transistor material, and/or the like. In various instances, a one-dimensional (1D) transistor material may be included, which 1D material may be composed of a carbon nanotube or a semiconductor nanowire. In other instances, the chamber and/or channel is composed of a one-dimensional transistor material such as containing one or more carbon nanotube(s) and/or a semiconductor nanowire(s), such as a sheet of semiconductor nanowire.

In particular instances, a two-dimensional (2D) transistor material may be included, such as where the 2D material may be one or two atoms thick and may stretch out in a plane. In such instances, the 2D material may include or otherwise be composed of as elemental 2D materials like graphene, graphyne (a carbon allotrope comprised of a lattice of benzene rings connected by acetylene bonds), borophene (a boron allotrope), germanene (a germanium allotrope), germanane (another germanium allotrope), silicene (a silicon allotrope) stanene (a tin allotrope), phosphorene (a phosphorous allotrope sometimes referred to as black phosphorous) or single atom layers of metals such as palladium or rhodium; a transition metal dichalcogenides (that contain one transition metal atom for every two chalcogen atoms) such as molybdenum disulfide (MoS2 sometimes referred to as molybdenite), tungsten diselenide (WSe2), tungsten disulfide (WS2), or others; MXenes (transition metal carbides and/or nitrides typically of a formula of $M_{n+1}X_n$ where M is a transition metal and X is carbon and/or nitrogen) such as Ti2C, V2C, Nb2C, Ti3C2, Ti3CN, Nb4C3 or Ta4C3 (furthermore MXenes may be terminated by O, OH or F to produce semiconductors with a small band gap.); or organo-metallic compounds such as Ni HITP (Ni3(2,3,6,7,10,11-hexaiminotriphenylene)2; or 2D supracrystals (the supracrystals are defined as the supra atomic periodic structures where the atoms typically found in the nodes of a structure are replaced by their symmetric complexes. It should be noted that transition metal dichalcogenides may comprise in ratio one atom of any transition metal (Sc, Ti, V, Cr, Mn, Fe, Co, Ni, Cu, Zn, Y, Zr, Nb, Mo, Tc, Ru, Rh, Pd, Ag, Cd, Hf, Ta, W, Re, Os, Ir, Pt, Au, Hg, Rt, Db, Sg, Bh, Mt, Ds or Rg) paired with two atoms of any of the chalcogenides (S, Se or Te). In particular instances, the 2D material may include one or more of a graphene layer, silicene, molybdenum disulfide, black phosphorous, and/or metal dichalcogenides. In various instances, a three-dimensional (3D) material may be included on the surface and/or channel may include a dielectric layer.

Additionally, in various instances, a reaction layer, e.g., an oxide layer, may be disposed on the surface and/or channel, such as layered or otherwise deposited on the 1D, 2D, e.g., graphene, or 3D layer. Such an oxide layer may be an aluminum oxide or a silicon oxide, such as silicon dioxide. In various instances, a passivation layer may be disposed on the surface and/or channel, such as layered or otherwise deposited on the 1D, 2D, e.g., graphene, or 3D layer and/or on an associated reaction layer on the surface and/or channel.

In particular instances, the primary and/or secondary structures may be fabricated or otherwise configured so as to include a chamber or well structure in and/or on the surface. For instance, a well structure may be positioned on a portion of a surface, e.g., an exterior surface, of the primary and/or secondary structures. In some instances, the well structure may be formed on top of, or may otherwise include, at least a portion of the 1D, 2D, e.g., graphene, and/or 3D material, and/or may additionally include the reaction, e.g., oxide, and/or passivation layers. In various instances, the chamber and/or well structure may define an opening, such as an opening that allows access to an interior of the chamber, such as allowing direct contact with the 1D, e.g., carbon nanotube or nanowire, 2D, e.g., graphene, surface and/or channel.

Accordingly, in various embodiments the present disclosure is directed to a bio-sensor. The bio-sensor includes a CMOS structure that may include a metal containing source, e.g., a damascene copper source, as well as a metal containing drain, e.g., a damascene copper drain, a 1D or 2D layered, e.g., a graphene layered, surface or channel extending from the source to the drain terminals, and a well or chamber structure that may be positioned on a portion of an exterior surface of the 1D or 2D or 3D layered well structure. In such an instance, the well structure may be configured so as to define an opening that allows for direct contact with the nanotube, nanowire, and/or graphene well or chamber surface. In various instances, an oxide and/or passivation layer may be disposed in or on the chamber surfaces. Hence, in certain instances, a chemically-sensitive transistor, such as a field effect transistor (FET) including one or more nano- or micro-wells may be provided.

In some embodiments, the chemically-sensitive field effect transistor may include a plurality of wells and may be configured as an array, e.g., a sensor array. As such, the system may include an array of wells including one or more, e.g., a plurality of, sensors, such as where each of the sensors includes a chemically-sensitive field-effect transistor having a conductive source, a conductive drain, and a reaction surface or channel extending from the conductive source to the conductive drain. Such an array or arrays may be employed such as to detect a presence and/or concentration change of various analyte types in a wide variety of chemical and/or biological processes, including DNA/RNA hybridization and/or sequencing reactions. For instance, the devices herein described and/or systems including the same may be employed in a method for the diagnosis of disease and/or analysis of biological or chemical materials, such as for whole genome analysis, genome typing analysis, microarray analysis, panels analysis, exome analysis, micro-biome analysis, and/or clinical analysis, such as cancer analysis, NIPT analysis, and/or UCS analysis.

In a particular embodiment, the FET may be a graphene FET (gFET) array, as herein described, and may be employed to facilitate DNA/RNA sequencing and/or hybridization techniques, such as based on monitoring changes in hydrogen ion concentration (pH), changes in other analyte concentrations, and/or binding events associated with chemical processes relating to DNA/RNA synthesis, such as within a gated reaction chamber or well of the gFET based sensor. For example, the chemically-sensitive field effect transistor may be configured as a CMOS biosensor and/or may be adapted to increase the measurement sensitivity and/or accuracy of the sensor and/or associated array(s), such as by including one or more surfaces or wells having a surface layered with a 1D and/or 2D and/or 3D material, a dielectric or reaction layer, a passivation layer and/or the like. For instance, in a particular embodiment, a chemically-sensitive graphene field effect transistor (gFET), such as a gFET having a CMOS structure is provided, where the gFET sensor, e.g., biosensor, may include an oxide and/or passivation layer, such as a layer that is disposed on the surface of the well or chamber so as to increase the measurement sensitivity and/or accuracy of the sensor and/or associated array(s). The oxide layer, when present, may be composed of an aluminum oxide, a silicon oxide, a silicon dioxide, and the like.

The system may further include one or more of a fluidic component, such as for performing the reaction, a circuitry component, such as for running the reaction processes, and/or a computing component, such as for controlling and/or processing the same. For instance, a fluidics component may be included where the fluidic component is configured to control one or more flows of reagents over the array and/or one or more chambers thereof. Particularly, in various embodiments, the system includes a plurality of reaction locations, such as surfaces or wells, which in turn includes a plurality of sensors and/or a plurality of channels, and further includes one or more fluid sources containing a fluid having a plurality of reagents and/or analytes for delivery to the one or more surfaces and/or wells for the performance of one or more reactions therein. In certain instances, a mechanism for generating one or more electric and/or magnetic fields may also included.

The system may additionally include a circuitry component, such as where the circuitry component may include a sample and hold circuit, an address decoder, a bias circuitry, and/or at least one analog-to-digital converter. For instance, the sample and hold circuit may be configured to hold an analog value of a voltage to be applied to or on a selected column and/or row line of an array of a device of the disclosure, such as during a read interval. Additionally, the address decoder may be configured to create column and/or row select signals for a column and/or row of the array, so as to access a sensor with a given address within the array. The bias circuitry may be coupled to one or more surfaces and/or chambers of the array and include a biasing component such as may be adapted to apply a read and/or bias voltage to selected chemically-sensitive field-effect transistors of the array, e.g., to a gate terminal of the transistor. The analog to digital converter may be configured to convert an analog value to a digital value.

A computing component may also be included, such as where the computing component may include one or more processors, such as a signal processor; a base calling module, configured for determining one or more bases of one or more reads of a sequenced nucleic acid; a mapping module, configured for generating one or more seeds from the one or more reads of sequenced data and for performing a mapping function on the one or more seeds and/or reads; an alignment module, configured for performing an alignment function on the one or more mapped reads; a sorting module, configured for performing a sorting function on the one or more mapped and/or aligned reads; and/or an variant calling module, configured for performing a variant call function on the one or more mapped, aligned, and/or sorted reads. In particular instances, the base caller of the base calling module may be configured to correct a plurality of signals, such as for phase and signal loss, to normalize to a key, and/or to a generate a plurality of corrected base calls for each flow in each sensor to produce a plurality of sequencing reads. In various embodiments, the device and/or system may include at least one reference electrode.

Particularly, the system may be configured for performing a sequencing reaction. In such an instance, the FET sequencing device may include an array of sensors having one or more chemically-sensitive field-effect transistors associated therewith. Such transistors may include a cascode transistor having one or more of a source terminal, a drain terminal, and or a gate terminal. In such an instance, the source terminal of the transistor may be directly or indirectly connected to the drain terminal of the chemically-sensitive field-effect transistor. In some instances, a one or two dimensional channel may be included and may extend from the source terminal to the drain terminal, such as where the 1D channel material may be a carbon nanotube or nanowire, and the two-dimensional channel material may be composed of graphene, silicene, a phosphorene, a molybdenum disulfide, and a metal dichalcogenide. The device may further be configured to include a plurality of column and row lines coupled to the sensors in the array of sensors. In such an instance, each column line in the plurality of column lines may be directly or indirectly connected to or otherwise coupled to the drain terminals of the transistors, e.g., cascode transistors, of a corresponding plurality of pixels in the array, and likewise each row line in the plurality of row lines may be directly or indirectly connected to or otherwise coupled with the source terminals of the transistors, e.g., cascode transistors, of a corresponding plurality of sensors in the array.

In some instances, a plurality of source and drain terminals having a plurality of reaction surfaces, e.g., channel members, extended there between may be included, such as where each channel member includes a one or two or three dimensional material. In such an instance, a plurality of first and/or second conductive layers may be coupled to the first and second source/drain terminals of the chemically-sensitive field-effect transistors in respective columns and rows in the array. Additionally, control circuitry may be provided and coupled to the plurality of column and row lines such as for reading a selected sensor connected to a selected column line and/or a selected row line. The circuitry may also include a biasing component such as may be configured for applying a read voltage to the selected row line, and/or to apply a bias voltage such as to the gate terminal of a transistor, such as FET and/or cascode transistor of the selected sensor. In a particular embodiment, the bias circuitry may be coupled to one or more chambers of the array and be configured to apply a read bias to selected chemically-sensitive field-effect transistors via the conductive column and/or row lines. Particularly, the bias circuitry may be configured to apply a read voltage to the selected row line, and/or to apply a bias voltage to the gate terminal of the transistor, e.g., cascode transistor, such as during a read interval.

A sense circuitry may be included and coupled to the array so as to sense a charge coupled to one or more of the gate configurations of a selected chemically-sensitive field-effect transistor. Sense circuitry may also be configured to read the selected sensor based on a sampled voltage level on the selected row and/or column line. In such an instance, the sense circuitry may include one or more of a pre-charge circuit, such as to pre-charge the selected column line to a pre-charge voltage level prior to the read interval; and a sample circuit such as to sample a voltage level at the drain terminal of the selected transistor, e.g., cascode transistor, such as during the read interval. The sample circuit may also be included and contain a sample and hold circuit configured to hold an analog value of a voltage on the selected column line during the read interval, and may further include an analog to digital converter to convert the analog value to a digital value.

In another aspect, the present 1D, 2D, or 3D FET integrated circuits, e.g., a gFET, sensors, and/or arrays of the disclosure may be fabricated such as using any suitable complementary metal-oxide semiconductor (CMOS) processing techniques known in the art. In certain instances, such a CMOS processing technique may be configured to increase the measurement sensitivity and/or accuracy of the sensor and/or array, and at the same time facilitate significantly small sensor sizes and dense gFET chamber sensor regions. Particularly, the improved fabrication techniques herein described employing a 1D, 2D, 3D, and/or oxide as a reaction layer provide for rapid data acquisition from small sensors to large and dense arrays of sensors. In particular embodiments, where an ion-selective permeable membrane is included, the membrane layer may include a polymer, such as a perfluorosulphonic material, a perfluorocarboxylic material, PEEK, PBI, Nafion, and/or PTFE. In some embodiments, the ion-selective permeable membrane may include an inorganic material, such as an oxide or a glass. One or more of the various layers, e.g., the reaction, passivation, and/or permeable membrane layers may be fabricated or otherwise applied by a spin-coating, anodization, PVD, and/or sol gel method.

Accordingly, the CMOS FET device described herein may be employed for sequencing a nucleic acid sample, in such an instance the nucleic acid sample serves as a template for DNA/RNA synthesis and sequencing that may be coupled to or in proximity with the surface, e.g., a graphene coated surface, of the reaction zone. Once immobilized the template sequence may then be sequenced and/or analyzed by performing one or more of the following steps. For example, a primer, and/or a polymerase, e.g., an DNA and/or RNA polymerase, and/or one or more substrates, e.g. deoxynucleotide triphosphates dATP, dGTP, dCTP, and dTTP, may be added, e.g., sequentially, to the reaction chamber, such as after the hybridization reaction begins so as to induce an elongation reaction. Once the appropriate, e.g., corresponding, substrate hybridizes to its complement in the template sequence, there will be a concomitant change in the individual electrical characteristic voltage, e.g., the source-drain voltage (Vsd), measured as a result of the new local gating effect. Where a reaction layer is included, such as an oxide layer deposited upon the 1D, 2-D, or 3-D surface, the sensitivity with which a binding event occurs can be amplified, such as where the reaction layer is configured for producing and/or monitoring changes in hydrogen ion concentration (pH), changes in other analyte concentrations.

Hence, for every elongation reaction with the appropriate, e.g., complementary, substrate there will be a change in the characteristic voltage and/or pH concentration. For instance, as described herein, a field-effect device for nucleic acid sequencing and/or gene detection may disposed in a sample chamber or well of a flow cell, and a sample solution, e.g., containing a polymerase and one or more substrates, e.g., nucleic acids, may be introduced to the sample solution chamber, such as via one or more of the fluidics components of the system. In various embodiments, a reference electrode may be disposed upstream, downstream or in fluid contact with the field effect device and/or the source and/or drain terminals may themselves serve as electrodes, such as for hybridization detection, and gate voltage may be applied whenever needed.

Particularly, in an exemplary elongation reaction, such as described above, polynucleotides are synthesized if the added substrate is complementary to the base sequence of the target DNA/RNA primer and/or template. If the added substrate is not complementary to the next available base sequence in the template, hybridization does not occur and there is no elongation. Since nucleic acids, such as DNAs and RNAs, have a negative charge in aqueous solutions, hybridization resulting in elongation can be incrementally determined by the change in the charge density on the reaction surface and/or in the reaction chamber. Such detection may be enhanced by being able to detect increases in ion concentration, such as by detecting a change in the pH. Because the substrates are added sequentially, it can readily be determined which nucleotide bound to the template thereby facilitating the elongation reaction. Accordingly, as a result of elongation, the negative charge on the graphene layered gate surface, insulating film surface, and/or the sidewall surface of the reaction chamber will be increased. This increase may then be detected, such as a change in the gate source voltage and/or ion concentration, as described in detail herein. By determining the addition of which substrate resulted in a signal or pH change in gate-source voltage, the base sequence identity of the target nucleic acid can be determined and/or analyzed.

Particularly, regardless of the sequencing device employed, such as an NGS and/or a FET based sequencing device, as herein described, this iterative synthesis process continues until the entire DNA/RNA template strand has been replicated in the vessel. Usually a typical length of a sequence replicated in this manner is from about 100 to about 500 base pairs, such as between 150 to about 400 base pairs, including from about 200 to about 350 base pairs, such as about 250 base pairs to about 300 base pairs dependent on the sequencing protocol being employed. Further, the nucleotide length of these template segments may be predetermined, e.g., engineered, to accord with any particular sequencing machinery and/or protocol by which it is run.

The end result is a readout, or read, that is comprised of a replicated DNA/RNA segment, e.g., from about 100 to about 1,000 nucleotides or more in length, that has either been labeled in such a manner that every nucleotide in the sequence, e.g., read, is known because of its label or is determined and known by a change in a gate characteristic, such as a change in voltage and/or pH. Hence, since the human genome is comprised of about 3.2 billion base pairs, and various known sequencing protocols usually result in labeled replicated sequences, e.g., reads, from about 100 or 101 bases to about 250 or about 300 or about 400 bases, the total amount of segments that need to be sequenced, and consequently the total number of reads generated, can be anywhere from about 10,000,000 to about 40,000,000, such as about 15,000,000 to about 30,000,000, dependent on how long the label replicated sequences are. Therefore, the sequencer may typically generate about 30,000,000 reads, such as where the read length is 100 nucleotides in length, so as to cover the genome once. However, as indicated herein, due to the condensed nature of the present sequencing on a chip format presented herein, much more substantial read lengths, such as 800 bases, 1,000 bases, 2,500 bases, 5,000 bases, up to 10,000 bases may be achievable.

Further, as indicated above, in such procedures, it may be useful to oversample the DNA/RNA such by about 5×, or about 10×, or about 20×, or about 25×, or about 30×, or about 40×, or about 50×, or about 100×, or about 200×, or about 250×, or about 500×, or about 1,000×, or about 5,000×, or even about 10,000× or more, and as such the amount of primary processing needed to be done and the time taken to do this can be quite extensive. For instance, with 40× oversampling, wherein the various synthesized reads are designed to overlap to some extent, up to about 1.2 billion reads may need to be synthesized. Typically, a large majority if not all of these labeled sequences can be generated in parallel. The end result is that the initial biological genetic material is processed, e.g., by sequencing protocols such as those summarized herein, and a digital representation of that data is generated, which digital representation of data may be subjected to a primary processing protocol.

Particularly, the genetic material of a subject may be replicated and sequenced in such a manner that a measurable electrical, chemical, radioactive, and/or optical signal is generated, which signal is then converted, e.g., by the sequencer and/or a processing apparatus associated therewith, into a digital representation of the subject's genetic code. More particularly, primary processing may include the conversion of images, such as recorded flashes of light or other electrical or chemical signal data, into FASTQ file data. Accordingly, this information is stored as a FASTQ file, which may then be sent for further, e.g., secondary processing. A typical FASTQ file includes a large collection of reads representing digitally encoded nucleotide sequences wherein each predicted base in the sequence has been called and given a probability score that the called base at the indicated position is incorrect.

In many instances, it may be useful to further process the digitally encoded sequence data obtained from the sequencer and/or sequencing protocol, such as by subjecting the digitally represented data to secondary processing. This secondary processing, for instance, can be used to assemble an entire genomic profile of an individual, such as where the individual's entire genetic makeup is determined, for instance, where each and every nucleotide of each and every chromosome is determined in sequential order such that the composition of the individual's entire genome has been identified. In such processing, the genome of the individual may be assembled such as by comparison to a reference genome, such as a standard, e.g., one or more genomes obtained from the human genome project, so as to determine how the individual's genetic makeup differs from that of the referent(s). This process is commonly known as variant calling. As the difference between the DNA/RNA of any one person to another is 1 in 1,000 base pairs, such a variant calling process can be very labor and time intensive.

Accordingly, in a typical secondary processing protocol, a subject's genetic makeup is assembled by comparison to a reference genome. This comparison involves the reconstruction of the individual's genome from millions upon millions of short read sequences and/or the comparison of the whole of the individual's DNA and/or RNA to an exemplary DNA and/or RNA sequence model. In a typical secondary processing protocol a FASTQ file is received from the sequencer containing the raw sequenced read data. For instance, in certain instances, there can be up to 30,000,000 reads or more covering the subject's genome, assuming no oversampling, such as where each read is about 100 nucleotides in length. Hence, in such an instance, in order to compare the subject's DNA/RNA genome to that of the standard reference genome, it needs to be determined where each of these reads map to the reference genome, such as how each is aligned with respect to one another, and/or how each read can also be sorted by chromosome order so as to determine at what position and in which chromosome each read belongs. One or more of these functions may take place prior to performing a variant call function on the entire full-length sequence. Once it is determined where in the genome each read belongs, the full length genetic sequence may be determined, and then the differences between the subject's genetic code and that of the referent can be assessed.

As the human genome is over 3 billion base pairs in length, efficient automated sequencing protocols and machinery have been developed so as to effectuate the sequencing of such DNA/RNA genomes within a time period that could be clinically useful. Such innovations in automated sequencing have resulted in the capabilities of sequencing an entire genome in a matter of hours to days dependent on the number of genomes being sequenced, the amount of oversampling involved, and the number of processing resources being dedicated to the job. Hence, given these advancements in sequencing, a large amount of sequencing data is capable of being generated in a relatively short period of time. A result of these advancements, however, is the development of a bottleneck at the secondary processing stage. In efforts to help overcome this bottleneck various software-based algorithms, such as those described herein, have been developed to help expedite the process of assembling a subject's sequenced DNA and/or RNA such as by a reference based assembly process.

For instance, reference based assembly is a typical secondary processing assembly protocol involving the comparison of sequenced genomic DNA and/or RNA of a subject to that of one or more standards, e.g., known reference sequences. Various algorithms have been developed to help expedite this process. These algorithms typically include some variation of one or more of: mapping, aligning, and/or sorting the millions of reads received from the digital, e.g., FASTQ, files communicated by the sequencer, to determine where on each chromosome each particular read corresponds or is otherwise located. Often a common feature behind the functioning of these various algorithms is their use of an index and/or an array to expedite their processing function.

For instance, with respect to mapping, a large quantity, e.g., all, of the sequenced reads may be processed to determine the possible locations in the reference genome to which those reads could possibly align. One methodology that can be used for this purpose is to do a direct comparison of the read to the reference genome so as to find all the positions of matching. Another methodology is to employ a prefix or suffix array, or to build out a prefix or suffix tree, for the purpose of mapping the reads to various positions in the reference DNA/RNA genome. A typical algorithm useful in performing such a function is a Burrows-Wheeler transform, which is used to map a selection of reads to a reference using a compression formula that compresses repeating sequences of data.

A further methodology is to employ a hash table, such as where a selected subset of the reads, a k-mer of a selected length "k", e.g., a seed, are placed in a hash table as keys and the reference sequence is broken into equivalent k-mer portions and those portions and their location are inserted by an algorithm into the hash table at those locations in the table to which they map according to a hashing function. A typical algorithm for performing this function is "BLAST", a Basic Local Alignment Search Tool. Such hash table based programs compare query nucleotide or protein sequences to one or more standard reference sequence databases and calculates the statistical significance of matches. In such manners as these, it may be determined where any given read is possibly located with respect to a reference genome. These algorithms are useful because they require less memory, fewer look ups, and therefore require fewer processing resources and time in the performance of their functions, than would otherwise be the case, such as if the subject's genome were being assembled by direct comparison, such as without the use of these algorithms.

Additionally, an aligning function may be performed to determine out of all the possible locations a given read may map to on a genome, such as in those instances where a read may map to multiple positions in the genome, which is in fact the location to which it actually was derived, such as by being sequenced therefrom by the original sequencing protocol. This function may be performed on a number of the reads of the genome and a string of ordered nucleotide bases representing a portion or the entire genetic sequence of the subject's DNA and/or RNA may be obtained. Along with the ordered genetic sequence a score may be given for each nucleotide position, representing the likelihood that for any given nucleotide position, the nucleotide, e.g., "A", "C", "G", "T" (or "U"), predicted to be in that position is in fact the nucleotide that belongs in that assigned position. Typical algorithms for performing alignment functions are Needle-man-Wunsch and Smith-Waterman. In either case, these algorithms perform sequence alignments between a string of the subject's query genomic DNA and/or RNA sequence and a string of the reference genomic sequence whereby instead of comparing the entire genomic sequences, one with the other, segments of a selection of possible lengths are compared.

Once the reads have been assigned a position, such as relative to the reference genome, which may include identifying to which chromosome the read belongs and/or its offset from the beginning of that chromosome, the reads may be sorted by position. This may enable downstream analyses to take advantage of the oversampling described above. All of the reads that overlap a given position in the genome will be adjacent to each other after sorting and they can be organized into a pileup and readily examined to determine if the majority of them agree with the reference value or not. If they do not, a variant can be flagged.

Although these algorithms and the others like them go a ways to resolving the bottlenecks inherent in secondary processing, faster performance time and better accuracy are still desirable. More particularly, although there has been advancement in the generation of raw data, such as generated DNA/RNA sequence data, the advancements in information technologies have not kept up pace, leading to a data analysis bottleneck. This bottleneck is somewhat lessened by the development of various algorithms, such as those described above, which help accelerate these analyses, but there still exists a need for new technologies to handle the data generation and acquisition, computation, storage, and/or analysis of such data, especially as it relates to genomic sequence analysis, such as in a secondary processing stage.

For instance, employing standard NGS technologies it can take several hours, up to about a day, to sequence a human genome, and using standard protocols for performing secondary processing on such obtained genomic sequencing data, can take up to three (3) days or even up to a week or more to process the sequenced data so as to generate clinically relevant genomic sequence information of an individual. Employing various different optimized devices, algorithms, methods, and/or systems the time expended for primary to secondary processing can be brought down to a mere 27 to 48 hours. However, in order to achieve such rapid results typically requires virtually all the generated reads, e.g., 30 million reads of 100 nucleotides each, to be processed in parallel and at the same time. Such parallel processing requires extensive processing power involving massive CPU resources and still takes a relatively long time.

Further, in various instances, enhanced accuracy of results is desired. Such enhanced accuracy can be achieved through providing some amount of oversampling of the sequenced genome. For example, as described above, it may be desirable to process the subject's DNA in such a manner that at any given location of a sequence of nucleotides, there is an oversampling of that region. As indicated above, it may be desired to oversample any given region of the genome up to 10×, or 15×, or 20×, or 25×, or 30×, or 40×, 50×, 100×, 250× or even 500× or 1,000 times or more. However, where the genome is oversampled, such as by 40×, the amount of reads to be processed is roughly 30 Million×40 (dependent on the length of the reads), which amounts to about 1.2 billion reads that need to be processed, when the entire genome is oversampled by 40×. Hence, although such oversampling typically results in greater accuracy, it is at a cost of taking more time and requiring more extensive processing resources as each section of the genome is covered by anywhere from 1 to 40 times. Moreover, for certain oncology applications in which a clinician is trying to distinguish between the mutated genome of cancer cells in the blood stream as distinct from the genome of healthy cells, oversampling of as much as 500×, or 1,000×, or 5,000×, or even 10,000× may be employed.

The present disclosure, therefore, is directed to such new technologies that may be implemented in one or a series of genomics and/or bioinformatics protocols, e.g., pipelines, for performing genetic acquisition and/or analysis, such as primary and/or secondary processing, on obtained genomic sequencing data or a portion thereof. The sequencing data may be obtained directly from an automated high throughput sequencer system, such as by a "Sequencing by Synthesis" 454 automated sequencer from ROCHE, a HiSeqxTen or a Solexia automated sequencer from ILLUMINA, a "Sequencing by Oligonucleotide Ligation and Detection" (SOLID) or Ion Torrent sequencer by LIFE TECHNOLO-GIES, and/or a "Single Molecule Fluorescent Sequencing" sequencer by HELICOS GENETIC ANALYSIS SYS-TEMS, or the like, such as by a direct linkage with the sequencing processing unit, or the sequencing data may be obtained directly such as in a sequencing on a chip configuration, such as a graphene layered FET sensor containing CMOS sequencing chip, as herein described. Such sequencing data may also be obtained remotely, such as from a database, for instance, accessible via the internet or other remote location accessible through a wireless communications protocol, such as Wi-Fi, Bluetooth, or the like.

In certain aspects, these genetic acquisition and/or analysis technologies may employ improved algorithms that may be implemented by software that is run in a less processing intensive and/or less time consuming manner and/or with greater percentage accuracy. For instance, in certain embodiments, improved devices and methods for producing genetic sequence information, such as in a primary processing protocol, as disclosed herein, and/or improved algorithms for performing secondary processing thereon, as disclosed herein, is provided. In various particular embodiments, the improved devices, systems, their methods of use, and the algorithms employed are directed to more efficiently and/or more accurately performing one or more of sequencing, mapping, aligning, and/or sorting functions, such as to generate and/or analyze a digital representation of DNA/RNA sequence data obtained from a sequencing platform, such as in a FASTQ file format obtained from an automated sequencer and/or sequencer on a chip, such as one of those set forth above.

Additionally, in certain embodiments, improved algorithms directed to more efficiently and/or more accurately performing one or more of local realignment, duplicate marking, base quality score recalibration, variant calling, compression, and/or decompression functions are provided. Further, as described in greater detail herein below, in certain aspects, these genetic production and/or analysis technologies may employ on or more algorithms, such as improved algorithms, that may be implemented by hardware that is run in a less processing intensive and/or less time consuming manner and/or with greater percentage accuracy than various software implementations for doing the same.

In particular embodiments, a platform of technologies for sequencing DNA/RNA so as to produce genetic sequence data and/or performing genetic analyses are provided where the platform may include the performance of one or more of: sequencing, mapping, aligning, sorting, local realignment, duplicate marking, base quality score recalibration, variant calling, compression, and/or decompression functions, and/or may further include tertiary processing protocols, as herein described. In certain instances, the implementation of one or more of these platform functions is for the purpose of generating and/or performing one or more of determining and/or reconstructing a subject's consensus genomic sequence, comparing a subject's genomic sequence to a referent sequence, e.g., a reference or model genetic sequence, determining the manner in which the subject's genomic DNA and/or RNA differs from a referent, e.g., variant calling, and/or for performing a tertiary analysis on the subject's genomic sequence, such as for whole genome analysis, such as genome-wide variation analysis and/or genome typing analysis, gene function analysis, protein function analysis, e.g., protein binding analysis, quantitative and/or assembly analysis of genomes and/or transcriptomes, micro-array analysis, panels analysis, exome analysis, micro-biome analysis, and/or clinical analysis, such as cancer analysis, NIPT analysis, and/or UCS analysis, as well as for various diagnostic, and/or a prophylactic and/or therapeutic evaluation analyses.

Particularly, once the genetic data has been generated and/or processed, e.g., in one or more primary and/or secondary processing protocols, such as by being mapped, aligned, and/or sorted, such as to produce one or more variant call files, for instance, to determine how the genetic sequence data from a subject differs from one or more reference sequences, a further aspect of the disclosure may be directed to performing one or more other analytical functions on the generated and/or processed genetic data such as for further, e.g., tertiary, processing. For example, the system may be configured for further processing of the generated and/or secondarily processed data, such as by running it through one or more tertiary processing pipelines, such as one or more of a genome pipeline, an epigenome pipeline, metagenome pipeline, joint genotyping, a MuTect2 pipeline, or other tertiary processing pipeline, such as by the devices and methods disclosed herein. For instance, in various instances, an additional layer of processing may be provided, such as for disease diagnostics, therapeutic treatment, and/or prophylactic prevention, such as including NIPT, NICU, Cancer, LDT, AgBio, and other such disease diagnostics, prophylaxis, and/or treatments employing the data generated by one or more of the present primary and/or secondary and/or tertiary pipelines. Hence, the devices and methods herein disclosed may be used to generate genetic sequence data, which data may then be used to generate one or more variant call files and/or other associated data that may further be subject to the execution of other tertiary processing pipelines in accordance with the devices and methods disclosed herein, such as for particular and/or general disease diagnostics as well as for prophylactic and/or therapeutic treatment and/or developmental modalities.

Further, in various embodiments, a bioinformatics processing regime, as disclosed herein, may be employed for the purpose of creating one or more masks, such as a genome reference mask, a default mask, a disease mask, and/or an iterative feed back mask, which may be added to the mapper and/or aligner, e.g., along with a reference, wherein the mask set is configured so as to identify a particular area or object of interest. For instance, in one embodiment, the methods and apparatuses described herein may be employed so as to create genome reference mask, such as by creating a mask-set that can be loaded into the mapper and/or aligner along with a reference, wherein the mask set is configured so as to identify areas of high importance and/or relevance, e.g., to the practitioner or subject, and/or so as to identify areas having increased susceptibility to errors. In various embodiments, the mask-set may provide intelligent guidance to the mapper and/or aligner such as on which areas of the genome to focus on to improve quality. Masks, therefore, can be created in a layered manner to provide varying levels or iterations of guidance based on various specific applications. Each mask accordingly could identify the areas of interest and provide a minimum quality target for the area. Additionally, a default mask may be employed to provide guidance, such as on an identified, e.g., typical, "high value" areas of the genome. Such areas could include known coding areas, control areas, etc. as well as areas that are well known to produce errors. Further, a disease mask, or application specific mask, may be employed to the mask-set that identifies areas of high importance, such as areas that require very high levels of accuracy based on known markers, e.g., Cancer. Further still, iterative feedback masking may be employed, such as by adding a new, ad-hoc mask, that may be specifically designed by using feedback from a tertiary analysis system (like Cypher Genomics) that has identified areas of concern based on observed errors or inconsistencies.

As indicated above, in one aspect one or more of these platform functions, e.g., mapping, aligning, sorting, realignment, duplicate marking, base quality score recalibration, variant calling, one or more tertiary processing modules, compression, and/or decompression functions is configured for implementation in software. In another embodiment, one or more of these platform functions, e.g., mapping, aligning, sorting, local realignment, duplicate marking, base quality score recalibration, decompression, variant calling, tertiary processing, compression, and/or decompression functions is configured for implementation in hardware.

Accordingly, in certain instances, methods are presented herein where the method involves the performance of an algorithm, such as an algorithm for performing one or more genetic analysis functions such as mapping, aligning, sorting, realignment, duplicate marking, base quality score recalibration, variant calling, compression, and/or decompression where the algorithm has been optimized in accordance with the manner in which it is to be implemented. In particular, where the algorithm is to be implemented in a software solution, the algorithm and/or its attendant processes, has been optimized so as to be performed faster and/or with better accuracy for execution by that media. Likewise, where the functions of the algorithm are to be implemented in a hardware solution, the hardware has been designed to perform these functions and/or their attendant processes in an optimized manner so as to be performed faster and/or with better accuracy for execution by that media. These methods, for instance, can be employed such as in an iterative variant calling procedure.

Hence, in one aspect, presented herein are systems, apparatuses, and methods for implementing bioinformatic protocols, such as for performing one or more functions for analyzing genetic data, such as genomic data, for instance, via one or more optimized algorithms and/or on one or more optimized integrated circuits, such as on one or more hardware processing platforms. Hence, in one instance, systems and methods are provided for implementing one or more algorithms for the performance of one or more steps for analyzing genomic data in a bioinformatics protocol, such as where the steps may include the performance of one or more of: mapping, aligning, sorting, local realignment, duplicate marking, base quality score recalibration, variant calling, compression, and/or decompression. In another instance, systems and methods are provided for implementing the functions of one or more algorithms for the performance of one or more steps for analyzing genomic data in a bioinformatics protocol, as set forth herein, wherein the functions are implemented on a hardware accelerator, which may or may not be coupled with one or more general purpose processors and/or super computers.

More specifically, in some instances, methods for performing secondary analytics on data pertaining to the genetic composition of a subject are provided. In one instance, the analytics to be performed may involve reference based reconstruction of the subject genome. For instance, referenced based mapping involves the use of a reference genome, which may be generated from sequencing the genome of a single or multiple individuals, or it may be an amalgamation of various people's DNA that have been combined in such a manner so as to produce a prototypical, standard reference genome to which any individual's DNA may be compared, for example, so as to determine and reconstruct the individual's genetic sequence and/or for determining the difference between their genetic makeup and that of the standard reference, e.g., variant calling.

More particularly, a reason for performing a secondary analysis on a subject's sequenced DNA is to determine how the subject's DNA varies from that of the reference. More specifically, to determine one, a multiplicity, or all the differences in the nucleotide sequence of the subject from that of the reference. For instance, the differences between the genetic sequences of any two random persons is 1 in 1,000 base pairs, which when taken in view of the entire genome of over 3 billion base pairs amounts to a variation of up to 3,000,000 divergent base pairs per person. Determining these differences may be useful such as in a tertiary analysis protocol, for instance, so as to predict the potential for the occurrence of a diseased state, such as because of a genetic abnormality, and/or the likelihood of success of a prophylactic or therapeutic modality, such as based on how a prophylactic or therapeutic is expected to interact with the subject's DNA or the proteins generated therefrom. In various instances, it may be useful to perform both a de novo and a reference based reconstruction of the subject's genome so as to confirm the results of one against the other, and to, where desirable, enhance the accuracy of a variant calling protocol.

In various instances, as set forth above, it may be useful in performing a primary sequencing protocol to produce oversampling for one or more regions of the subject's genome. These regions may be selected based on known areas of increased variability, suspected regions of variability, such as based on the condition of the subject, and/or on the entire genome generally. In its basic form, as indicated above, based on the type of sequencing protocols performed, sequencing produces readouts, e.g., reads, that are digital representations of the subject's genetic sequence code. These read lengths are typically designed based on the type of sequencing machinery being employed. For instance, the 454 automated sequencer from ROCHE, typically produces read lengths from 100 or 150 base pairs in length to about 1,000 base pairs; for ILLUMINA the read lengths are typically engineered to be from about 100 or 101 to about 150 base pairs in length for some of their technology, and 250 base pairs in length for other of their technology; for LIFE TECHNOLOGIES the read lengths are typically engineered to be from about 50 to about 60 base pairs in length for their SOLID technology and from 35 to 450 base pairs in length for their Ion Torrent technology; and for the HELICOS GENETIC ANALYSIS SYSTEMS the read lengths may vary but may typically be less than 1,000 nucleotides in length.

However, because the processing of the DNA sample required to produce engineered read lengths of a specific size is both labor and chemistry intensive, and because the sequencing itself often depends on the functioning of the sequencing machinery, there is some possibility that errors may be made throughout the sequencing process thereby introducing an abnormality into that portion of the sequenced genome where the error occurred. Such errors can be problematic especially where a purpose for reconstructing the subject's genome is to determine how it or at least a portion of the genome varies from a standard or model reference. For instance, a machine or chemistry error resulting in the change of one nucleotide, e.g., in a read, for another will give a false indication of a variation that is not really there. This can result in an incorrect variant call and may further result in the false indication of a diseased state and the like. Accordingly, because of the possibility of machine, chemistry, and/or even human error in the execution of a sequencing protocol, in many instances, it is desirable to build redundancy into an analysis system, such as by oversampling portions of or the entire genome. More particularly, as an automated sequencer produces a FASTQ file calling out a sequence of reads having nucleotides at a given position along with the probability that the call for a given nucleotide being at the called position is actually incorrect, e.g., a base call, it is often desirable to employ methods, such as oversampling, for ensuring that base calls made by the sequencing processes can be detected and corrected.

Hence, in performing the methods herein described, in certain instances, a primary sequencing protocol is performed in such a manner so as to produce a sequenced genome where a portion or the entire genome is oversampled by about 10×, about 15×, about 20×, about 25×, about 30× about 40×, such as about 50× or more. Accordingly, where the read lengths are engineered to be about 50-60 base pairs in length, this oversampling can result in about 2 to about 2.5 billion reads, or where the read lengths are about 100 or 101 base pairs in length, oversampling may result in about 1 to about 1.2 billion reads, and where the read lengths are about 1,000 base pairs in length, about 50 to about 100 million reads may be generated by the sequencer, such as where the oversampling is about 40×. More particularly, in such an instance, because of the 40× oversampling, at any given point in the genome it is expected that there will be 40 reads to cover any one position albeit, the given position might be at the beginning of one read, the middle of another, and the end of another, but it is expected to be covered about 40 times.

Therefore, such oversampling produces regions of the sequenced genome that are covered by a multiplicity of reads, e.g., duplications, such as up to about 40 reads, for instance, where the oversampling is about 40×. These at least partial duplications are useful in determining whether any given variation in any particular read is in fact an actual genomic variation or rather a machine or chemistry artifact. Hence, oversampling can be employed to improve the accuracy in reconstructing the subject's genome, especially in instances where the subject's genome is to be compared against a reference genome so as to determine those instances where the subject's genetic sequence differs from that of the reference genetic sequence. In a manner such as this, as described in greater detail herein below, it can be confirmed that any given variation between the reconstructed sequence and the model is in fact due to the presence of an actual variant and not an error in the initial processing of sample DNA, or read alignment software, etc.

For instance, in building the genetic sequence of the individual's sequenced DNA, it must be determined what nucleotide goes where in the growing string of nucleotides. In order to determine what nucleotide goes where, the various reads can be organized and a pile up of reads covering duplicate locations can be built up. This allows for a comparison to be made of all the reads covering the same locations so as to more accurately determine if there is an actual variation at any given position or if there may be an error in any one read at the position in question in the pileup. For example, if there is only one or two of the reads out of the 40 that has a particular nucleotide at position X, and all 38 or 39 other reads agree on a different nucleotide being at that position, then the two outlying reads may be excluded as being in error, at least at this specific location.

More particularly, where there are a multiplicity of reads generated for any one location of the subject's genome, there are likely to be multiple overlaps or pile-ups for any given nucleotide position. These pile-ups represent the coverage for any particular location and may be useful for determining with better accuracy the correct sequence of the subject's genome.

For instance, as indicated, sequencing results in the production of reads, and in various instances, the reads produced are over sampled, and so at various positions various particular reads will overlap. This overlapping is useful for determining the actual sample genome such as with a high probability of correctness.

The purpose, therefore, may be to scan over the reference genome incrementally multiple times, as described in greater detail herein below, so as to more accurately reconstruct the subject's genome, and where it is desirable to determine how the subject's genome differs from a different genome, e.g., a model genome, the use of pile-ups can more accurately identify errors, such as chemical, machine, or read errors, and distinguish them from actual variants. More specifically, where the subject has an actual variation at position X, the majority of reads in the pile up should verify, e.g., include, that variation. Statistical analysis procedures, such as those described herein, may then performed to determine the actual genetic sequence of the subject with all its variants from a reference genome.

For instance, where the subject's genetic sequence is to be rebuilt with respect to the use of a reference genome, once the reads, e.g., a pile-up of reads, have been generated, the next steps may be to map and/or align and/or sort the reads to one or more reference genomes (e.g., the more exemplary reference genomes available as models the better the analysis is likely to be) and thereby rebuild the genome of the subject, this results in a series of reads that have been mapped and/or aligned with the reference genome(s) at all possible positions along the chain where there is a match, and at each such position they are given a probability score as to the probability that they actually belong in that position.

Accordingly, in various instances, once the reads have been generated, their positions mapped, e.g., the potential locations in the reference genome to which the reads may map have been determined, and their sequential order aligned, the actual genetic sequence of the subject's genome may be determined, such as by performing a sorting function on the aligned data. Further, once the actual sample genome is known and compared to the reference genome, the variations between the two can be determined, a list of all the variations/deviations between the reference genome and the sample genome are determined and called out. Such variations between the two genetic sequences may be due to a number of reasons.

For instance, there may be a single nucleotide polymorphism (SNP), such as wherein one base in the subject's genetic sequence has been substituted for another; there may be more extensive substitutions of a plurality of nucleotides; there may be an insertion or a deletion, such as where one or a multiplicity of bases have been added to or deleted from the subject's genetic sequence, and/or there may be a structural variant, e.g., such as caused by the crossing of legs of two chromosomes, and/or there may simply be an offset causing a shift in the sequence. In various instances, a variant call file containing all the variations of the subject's genetic sequence to the reference sequence is generated. More particularly, in various embodiments, the methods of the disclosure include generating a variant call file (VCF) identifying one or more, e.g., all of the genetic variants in the individual whose DNA was sequenced, e.g., relevant to one or more reference genomes. The VCF in its basic form is a list of locations of variants and their type: e.g., chromosome 3, at position X, an "A" is substituted for a "T", etc.

However, as indicated above, in order to generate such a file, the genome of the subject must be sequenced and rebuilt prior to determining its variants. There are, however, several problems that may occur when attempting to generate such an assembly. As noted above, there may be problems with the chemistry, the sequencing machine, and/or human error that occur in the sequencing process. Additionally, there may be genetic artifacts that make such reconstructions problematic. For instance, a problem with performing such assemblies is that there are sometimes huge portions of the genome that repeat themselves, such as long sections of the genome that include the same strings of nucleotides. Hence, because any genetic sequence is not unique everywhere, it may be difficult to determine where in the genome an identified read actually maps and aligns.

For instance, dependent on the sequencing protocol employed shorter or longer reads may be produced. Longer reads are useful in that the longer the read the less likely it is to show up in multiple locations in the genome. Having fewer possible locations to evaluate can also speed up the system. However, the longer the reads the more problematic they may be because the more likely they are to include a real or false variation, e.g., caused by an SNP, InDel (insertion or deletion), or a machine error, or the like, resulting in a no match between the read and the reference genome. On the other hand, shorter reads are useful because the shorter the read the less likely it is to cover a position that codes for a variant. A problem with shorter reads however is that the shorter the read the more likely it is to show up at multiple positions in the genome, thus requiring additional processing time and resources so as to determine which out of all possible positions is the most likely actual position to where it aligns. Ideally what may be achieved, such as by practicing the methods herein disclosed, is that a variant call file may be produced wherein a list of the sequenced genome (the query sequence) is generated that shows where all the variant base pairs are, making sure each variant called is an actual variant and not simply a chemistry or machine read or other human based error.

There are, therefore, two main possibilities for variation. For one, there is an actual variation at the particular location in question, for instance, where the person's genome is in fact different at a particular location than that of the reference, e.g., there is a natural variation due to an SNP (one base substitution), an Insertion or Deletion (of one or more nucleotides in length), and/or there is a structural variant, such as where the DNA material from one chromosome gets crossed onto a different chromosome or leg, or where a certain region gets copied twice in the DNA. Alternatively, a variation may be caused by there being a problem in the read data, either through chemistry or the machine, sequencer or aligner, or other human error. Accordingly, the methods disclosed herein may be employed in a manner so as to compensate for these types of errors, and more particularly so as to distinguish errors in variation due to chemistry, machine or human, and real variations in the sequenced genome. More specifically, the methods, apparatuses, and systems for employing the same, as here in described, have been developed so as to clearly distinguish between these two different types of variations and therefore to better ensure the accuracy of any call files generated so as to correctly identify true variants.

Further, in various embodiments, once the subject's genome has been reconstructed and/or a VCF has been generated, such data may then be subjected to tertiary processing so as to interpret it, such as for determining what the data means with respect to identifying what diseases this person may or may have the potential for suffer from and/or for determining what treatments or lifestyle changes this subject may want to employ so as to ameliorate and/or prevent a diseased state. For example, the subject's genetic sequence and/or their variant call file may be analyzed to determine clinically relevant genetic markers that indicate the existence or potential for a diseased state and/or the efficacy of a proposed therapeutic or prophylactic regimen may have on the subject. This data may then be used to provide the subject with one or more therapeutic or prophylactic regimens so as to better the subject's quality of life, such as treating and/or preventing a diseased state.

More particularly, medical science technologies have advanced in conjunction with the advancement of information technologies, which advancement has enhanced our ability to store and analyze medical data. Hence, once one or more of an individual's genetic variations are determined, such variant call file information can be used to develop medically useful information, which in turn can be used to determine, e.g., using various known statistical analysis models, health related data and/or medical useful information, e.g., for diagnostic purposes, e.g., diagnosing a disease or potential therefore, clinical interpretation (e.g., looking for markers that represent a disease variant), whether the subject should be included or excluded in various clinical trials, and other such purposes. As there are a finite number of diseased states that are caused by genetic malformations, in tertiary processing variants of a certain type, e.g., those known to be related to the onset of diseased states, can be queried for, such as by determining if one or more genetic based diseased markers are included in the variant call file of the subject.

Consequently, in various instances, the methods herein disclosed may involve analyzing, e.g., scanning, the VCF and/or the generated sequence, against a known disease sequence variant, such as in a data base of genomic markers therefore, so as to identify the presence of the genetic marker in the VCF and/or the generated sequence, and if present to make a call as to the presence or potential for a genetically induced diseased state. As there are a large number of known genetic variations and a large number of individual's suffering from diseases caused by such variations, in some embodiments, the methods disclosed herein may entail the generation of one or more databases linking sequenced data for an entire genome and/or a variant call file pertaining thereto, e.g., such as from an individual or a plurality of individuals, and a diseased state and/or searching the generated databases to determine if a particular subject has a genetic composition that would predispose them to having such diseased state. Such searching may involve a comparison of one entire genome with one or more others, or a fragment of a genome, such as a fragment containing only the variations, to one or more fragments of one or more other genomes such as in a database of reference genomes or fragments thereof.

Further, it is understood that the genetic sequences to be employed in these manners may be DNA, ssDNA, RNA, mRNA, tRNA, tRNA, or the like. Hence, although throughout the present disclosure various mention is made to various methods and apparatuses for analyzing genomic DNA, in various instances, the systems, apparatuses and methods disclosed herein are equally suitable for performing their respective functions, e.g., analysis, on all types of genetic material including DNA, ssDNA, RNA, mRNA, tRNA, tRNA, and the like. Additionally, in various instances, the methods of the disclosure may include analyzing the generated genetic sequence, e.g., DNA, ssDNA, RNA, mRNA, tRNA, tRNA, and the like, from the subject and determining therefrom the protein variations which are likely to be caused by the genetic sequence and/or determining and/or predicting the potential for a diseased state therefrom, such as due to an error in protein expression. It is to be noted that the genetic sequence obtained can represent an intron or an exon, for instance, the genetic sequence can be for a coding portion of the DNA only, such as where an exome is obtained and using known processing techniques only the coding regions, or non-coding regions, may be sequenced, which can lead to faster sequencing and/or faster processing times, albeit involving a more difficult sample preparation procedure.

Currently, such steps and analyses herein described are typically performed in various distinct and unrelated steps often employing different analytic machines at different locations. Accordingly, in various aspects the methods and systems of the disclosure are performed by a single apparatus and/or at one location, such as in conjunction with an automated sequencer or other apparatus configured to generate genetic sequence data. In various instances, a plurality of apparatuses may be employed at the same location, or a multiplicity of remote locations, and in some instances, the methods may involve two or more processing units being deployed at two or more locations.

For instance, in various aspects a pipeline may be provided wherein the pipeline includes performing one or more analytic functions, as described herein, on a genomic genetic sequence of one or more individuals, such as data obtained in a digital, e.g., FASTQ, file format from an automated sequencer. A typical pipeline to be executed may include one or more of sequencing genetic material, such as a portion or an entire genome, of one or more subjects, which genetic material may include DNA, ssDNA, RNA, rRNA, tRNA, and the like, and/or in some instances the genetic material may represent coding or non-coding regions, such as exomes, episomes of the DNA. The pipeline may include one or more of performing a base calling and/or error correction operation, such as on the digitized genetic data, and/or may include one or more of performing a mapping, an alignment, and/or a sorting function on the genetic data. In certain instances, the pipeline may include performing one or more of a realignment, a deduplication, a base quality or score recalibration, a reduction and/or compression, and/or a decompression on the digitized genetic data. In certain instances the pipeline may include performing a variant calling operation on the genetic data.

Therefore, in various instances, a pipeline of the disclosure may include one or more modules, wherein the modules are configured for performing one or more functions, such as a base calling and/or error correction operation and/or a mapping and/or an alignment and/or a sorting function on genetic data, e.g., sequenced genetic data. And in various instances, the pipeline may include one or more modules, wherein the modules are configured for performing one more of a local realignment, a deduplication, a base quality score recalibration, a variant calling, a reduction and/or compression, and/or a decompression on the genetic data. Many of these modules may either be performed by software or on hardware or remotely, e.g., via software or hardware, such as on the cloud or a remote server and/or server bank.

Additionally, many of these steps and/or modules of the pipeline are optional and/or can be arranged in any logical order and/or omitted entirely. For instance, the software and/or hardware disclosed herein may or may not include a base calling or sequence correction algorithm, such as where there may be concern that such functions may result in a statistical bias. Consequently the system will include or will not include the base calling and/or sequence correction function, respectively, dependent on the level of accuracy and/or efficiency desired. And as indicated above, one or more of the pipeline functions may be employed in the generation of a genomic sequence of a subject such as through a reference based genomic reconstruction. Also as indicated above, in certain instances, the output from the pipeline is a variant call file indicating a portion or all the variants in a genome or a portion thereof.

Accordingly, as indicated above, the output of performing a sequencing protocol, such as one or more of those set forth above, is typically a digital representation of the subject's genetic material, such as in a FASTQ file format. However, an autorad that has been digitally transcribed may also be employed. More particularly, the output from a sequencing protocol may include a plurality of reads, where each read includes a sequence, e.g., a string, of nucleotides where the position of every nucleotide has been called, and a quality score representing the probability that the called nucleotide is wrong. However, the quality of these outputs may be improved by various pre-processing protocols so as to achieve higher quality of scores, which one or more of such protocols may be employed in the methods disclosed herein.

For instance, in certain instances, the raw FASTQ file data may be processed to clean up the initial base calls obtained from the sequencer/reader, such as in a primary processing stage, e.g., prior to the secondary processing described herein above. Specifically, the sequencer/reader typically analyzes the sequencing data, such as the fluorescent data indicating which nucleotide is at what position, and converts the image data into a base call with a quality score, such as where the quality score is based on the comparative brightness of the fluorescence at each position. A specialized algorithm may be employed, such as in a primary processing stage, to correctly analyze these distinctions in fluorescence so as to more accurately make the appropriate base call. As indicated above, this step may be included in a pipeline of steps and may be implemented via software or hardware or both, however, in this instance would be part of a primary processing platform.

An additional preprocessing step may include an error correction function, which may include an attempt to take the millions to billions of reads in the FASTQ file and correct some proportion of any mechanical sequencing error with the information pertaining to the base call and quality score available prior to any further processing such as mapping, alignment, and/or sorting functions, etc. For instance, the reads within the FASTQ file may be analyzed to determine if there are any sub-sequences in any of the reads that appear in other reads, which because of the duplicate coverage can increase confidence that the subsequences in the reads may be correct. This may be implemented by building a hash table containing all possible k-mers of a selected length, k, from every read, and storing with each one its frequency and also which bases immediately follow it and with what probability. Then, using the hash table each read can be rescanned. As each k-mer in a particular read is looked up in the hash table, and evaluation can be made as to whether the base immediately following that k-mer is likely to be correct or not. If it is unlikely, then it can be replaced with the most likely one to follow from the table. Subsequent k-mers for that read will then include the corrected base as the value at that position and the process is repeated. This can be highly effective in correcting errors because oversampling enables gathering accurate statistics for predicting what comes next after each k-mer. However, as indicated above, such corrections could add statistical biasing to the system, such as due to false corrections, to the data, and so these procedures can be skipped if desired.

Accordingly, in accordance with the aspects of the disclosure, in various instances, the methods, apparatuses, and/or systems of the disclosure, may include obtaining read data, that either have or have not been preprocessed, such as by being obtained directly from a FASTQ file of an automated sequencer, and subjecting the obtained data to one or more of a mapping, aligning, and/or sorting function. The performance of such functions may be useful, for instance, because, as set forth above, in various instances, the sequencing data typically generated by various automated sequencers, e.g., reads, have lengths that are substantially shorter than the entire genomic sequence being analyzed, and since the human genome typically has a multiplicity of repetitive sections, and is known to have various repeating patterns in it, there may be therefore a multiplicity of locations that any given read sequence may correspond to a segment in the human genome. Consequently, given all the possibilities a given read may match to the sequence of the genome, such as because of various repeating sequences in the genome, etc. the raw read data may not clearly indicate which one of the possibilities is in fact the correct location from which it was derived. Hence, for each read it will need to be determined to where in the genome the reads actually map. Additionally, it may also be useful to determine the sequential alignment of the reads, so as to determine the actual sequence identity of the subject, and/or it may also be useful to determine the chromosomal location for each portion of the sequence.

In various instances, the methods of the disclosure may be directed to mapping, aligning, and/or sorting the raw read data of the FASTQ files so as to find all the likely places that a given read may be aligned, and/or to determine the actual sequence identify of a subject, and/or to determine the chromosome location for each portion of the sequence. For example, mapping may be employed so as to map the generated reads to the reference genome and thereby find the location where each read appears to match well to the genome, e.g., finding all the places where there might be a good score for aligning any given read to the reference genome. Mapping therefore may involve taking one or more, e.g., all, of the raw or preprocessed reads received from the FASTQ file and comparing the reads with one or more reference genomes and determining where the read may match with the reference genome(s). In its basic from, mapping involves finding the location(s) in the reference genome where one or more of the FASTQ reads obtained from the sequencer appears to match.

Likewise, alignment may be employed so as to evaluate all the candidate locations of the individual reads against a window of the reference genome to determine where and how the read sequences best align to the genome. However, performing an alignment may be difficult due to substitutions, insertions, deletions, structural variations, and the like which may prevent the read from aligning exactly. There are, therefore, several different ways to get an alignment, but to do so may require making changes in the read, where each change that needs to be made to get the appropriate alignment results in a lower confidence score. For instance, any given read may have substitutions, insertions, and/or deletions as compared to the reference genome, and these variations need to be accounted for in performing an alignment.

Accordingly, along with the predicted alignment a probability score that the predicted alignment is correct may also be given. This score indicates the best alignment for any given read amongst multiple locations where that read may align. For example, the alignment score is predicated upon how well a given read matches a potential map location and may include stretching, condensing, and changing bits and pieces of the read so as to get the best alignment.

The score will reflect all the ways the read was changed so as to accommodate the reference. For instance, in order to generate an alignment between the read and the reference one or more gaps in the read may need to be inserted, wherein the insertion of each gap represents a deletion in the read over the reference. Likewise, deletions may need to be made in the read, wherein each deletion represents an insertion in the read over the reference. Additionally, various bases may need to be changed such as due to one or more substitutions. Each of these changes are made to make the read(s) more exactly align to the reference, but each change comes with a cost to the quality score, which score is a measure as to how well the entire read matches to some region of the reference. The confidence in such quality scores is then determined by looking at all the locations the read can be made to map to the genome and comparing the scores at each location, and choosing the one with the highest score. More particularly, where there are multiple positions with high quality scores, then confidence is low, but where the difference between the first and second best scores is large, then confidence is high. At the end, all the proposed reads and confidence scores are evaluated and the best fit is selected.

Once the reads are assigned a position relative to the reference genome, which consists of identifying to which chromosome the read belongs and its offset from the beginning of that chromosome, they may be sorted, such as by position. This enables downstream analyses to take advantage of the various oversampling protocols described herein. All of the reads that overlap a given position in the genome maybe be adjacent to each other after sorting and they can be piled up and readily examined to determine if the majority of them agree with the reference value or not. If they do not, as indicated above, a variant can be flagged.

As indicated above, the FASTQ file obtained from the sequencer is comprised of a plurality, e.g., millions to a billion or more, of reads consisting of short strings of nucleotide sequence data representing a portion or the entire genome of an individual. Mapping, in general, involves plotting the reads to all the locations in the reference genome to where there is a match. For example, dependent on the size of the read there may be one or a plurality of locations where the read substantially matches a corresponding sequence on the reference genome. Accordingly, the mapping and/or other functions disclosed herein may be configured for determining where out of all the possible locations one or more reads may match to in the reference genome is actually the true location to where they map.

It is possible to compare every read with every position in the 3.2 billion reference genome to determine where, if any, the reads match to the reference genome. This may be done, for instance, where the read lengths approach about 100,000 nucleotides, about 200,000 nucleotides, about 400,000 nucleotides, about 500,000 nucleotides, even about 1,000, 000 or more nucleotides in length. However, where the reads are substantially shorter in length, such as where there are 50 million reads or more, e.g., 1 billion reads, this process could take a very long time and require a large amount of computing resources. Accordingly, there are several methods, such as described herein, that have been developed for aligning the FASTQ reads to the reference genome in a much quicker manner. For instance, as disclosed above, one or more algorithms may be employed so as to map one or more of the reads generated by the sequencer, e.g., in a FASTQ file, and match them to the reference genome, so as to determine where in the reference genome the subject reads potentially map.

For instance, in various methods, an index of the reference is generated, so that the reads or portions of the reads may be looked up in the index, retrieving indications of locations in the reference, so as to map the reads to the reference. Such an index of the reference can be constructed in various forms and queried in various manners. In some methods, the index may include a prefix and/or a suffix tree. In other various methods, the index may include a Burrows/Wheeler transform of the reference. In further methods, the index may include one or more hash tables, and a hash function may be performed on one or more portions of the reads in an effort to map the reads to the reference. In various instances, one or more of these algorithms may be performed sequentially or at the same time so as to accurately determine where one or more, e.g., a substantial portion or every, read correctly matches with the reference genome.

Each of these algorithms may have advantages and/or disadvantages. For example, a prefix and/or suffix Tree and/or a Burrows/Wheeler transformation may be performed on the sequence data in such a manner that the index of the reference genome is constructed and/or queried as a tree-like data structure, where starting from a single-base or short subsequence of a read, the subsequence is incrementally extended within the read, each incremental extension stimulating accesses to the index, tracing a path through the tree-like data structure, until the subsequence becomes unique enough, e.g., an optimal length has been attained, and/or a leaf node is reached in the tree-like data structure, the leaf or last-accessed tree node indicating one or more positions in the reference genome from which the read may have originated. These algorithms, therefore, typically do not have a fixed length for the read subsequences that may be mapped by querying the index. A hash function, however, often employs a fixed length comparison unit that may be the entire length of the read, but is often times a length that is some sub-portion thereof, which sub-portion is termed a seed. Such seeds can be shorter or longer, but unlike with the prefix and/or suffix trees and/or the Burrows/Wheeler transformations, the seeds of the reads employed in a hash function are typically of a preselected, fixed length.

A prefix and/or suffix tree is a data structure that is built up from the reference genome, such that each link from a parent node to a child node is labeled or associated with a nucleotide or sequence of nucleotides, and each path from a root node through various links and nodes traces a path whose associated aggregate nucleotide sequence matches some continuous subsequence of the reference genome. The node reached by such a path is implicitly associated with the reference subsequence traced by its path from the root. Proceeding from the root node, subsequences in a prefix tree grow forward in the reference genome, whereas subsequences in a suffix tree grow backward in the reference genome. Both a prefix tree and a suffix tree may be used in a hybrid prefix/suffix algorithm, so that subsequences may grow in either direction. Prefix and suffix trees may also contain additional links, such as jumping from a node associated with one reference subsequence to another node associated with a shorter reference subsequence.

For instance, a tree-like data structure serving as an index of the reference genome may be queried by tracing a path through the tree, corresponding to a subsequence of a read being mapped, that is built up by adding nucleotides to the subsequence, using the added nucleotides to select next links to traverse in the tree, and going as deep as necessary until a unique sequence has been generated. This unique sequence may also be termed a seed, and may represent a branch and/or root of the sequence tree data structure. Alternatively, the tree descent may be terminated before the accumulated subsequence is fully unique, so that a seed may map to multiple locations in the reference genome. Particularly, the tree may be built out for every starting position for the reference genome, then the generated reads may be compared against the branches and/or roots of the tree and these sequences may be walked through the tree to find where in the reference genome the read fits. More particularly, the reads of the FASTQ file may be compared to the branches and roots of the reference tree and once matched therewith the location of the reads in the reference genome may be determined. For example, a sample read may be walked along the tree until a position is reached whereby it is determined that the accumulated subsequence is unique enough so as to identify that the read really does align to a particular position in the reference, such as walking through the tree until a leaf node is reached.

A disadvantage, however, of such a prefix and/or suffix tree is that it is a huge data structure that must be accessed a multiplicity of times as the tree is walked so as to map the reads to the reference genome. An advantage of a hash table function, on the other hand, as described in greater detail herein below, is that once built, it typically only takes one look up to determine where, if anywhere, there may be a match between a seed and the reference. A prefix and/or suffix tree will typically take a plurality of look ups, e.g., 5, 10, 15, 20, 25, 50, 100, 1,000, or more, etc., in determining if and where there is a match. Further, due to the double helix structure of DNA, a reverse complement tree may also need to be built and searched, as the reverse complement to the reference genome may also need to be found. With respect to the above, the data tree is described as being built from the reference genome which is then compared with the reads from the subject's sequenced DNA, however, it is to be understood that the data tree may initially be built from either the reference sequence or the sample reads, or both, and compared one to the other as described above.

Alternatively, or in addition to employing a prefix or a suffix tree, a Burrows/Wheeler transform can be performed on the data. For instance, a Burrows/Wheeler transform may be used to store a tree-like data structure abstractly equivalent to a prefix and/or suffix tree, in a compact format, such as in the space allocated for storing the reference genome. In various instances, the data stored is not in a tree-like structure, but rather the reference sequence data is in a linear list that may have been scrambled into a different order so as to transform it in a very particular way such that the accompanying algorithm allows the reference to be searched with reference to the sample reads so as to effectively walk the "tree". An advantage of the Burrows/Wheeler transform, such as over a prefix and/or suffix tree, is that it typically requires less memory to store, and an advantage over a hash function is that it supports a variable seed length, and hence it can be searched until a unique sequence is determined and a match found. For instance, as with the prefix/suffix tree, however many nucleotides it takes for a given sequence to be unique, or to map to a sufficiently small number of reference positions, determines the length of the seed. Whereas for a hash table, the seeds are all of the same predetermined length. A disadvantage, however, for the Burrows/Wheeler transform is that it typically requires a multiplicity of lookups, such as two or more look ups, such as for every step down the tree.

Alternatively, or in addition to utilizing one or both a prefix/suffix tree and/or a Burrows/Wheeler transform on the reference genome and subject sequence data, so as to find where the one maps against the other, another such method involves the production of a hash table index and/or the performance of a hash function. The hash table index may be a large reference structure that is built up from sequences of the reference genome that may then be compared to one or more portions of the read to determine where the one may match to the other. Likewise, the hash table index may be built up from portions of the read that may then be compared to one or more sequences of the reference genome and thereby used to determine where the one may match to the other.

More particularly, in any of the mapping algorithms described herein, such as for implementation in any of the method steps herein disclosed, one or all three mapping algorithms, or others known in the art, may be employed, in software or hardware, so as to map one or more sequences of a sample of sequenced DNA with one or more sequences of one or more reference genomes. As described herein in greater detail below, all of these operations may be performed via software or by being hardwired, such as into an integrated circuit, such as on a chip, for instance as part of a circuit board. For instance, the functioning of one or more of these algorithms may be embedded onto a chip, such as into a FPGA (field programmable gate array) ASIC (application specific integrated circuit) chip, or Structured ASIC (application specific integrated circuit) chip, and may be optimized so as to perform more efficiently because of their implementation in such hardware.

Additionally, one or more, e.g., two or all three, of these mapping functions may form a module, such as a mapping module, that may form part of a system, e.g., a pipeline, that is used in a process for determining an actual entire genomic sequence, or a portion thereof, of an individual. The output returned from the performance of a mapping function may be a list of possibilities as to where one or more, e.g., each, read maps to one or more reference genomes. For instance, the output for each mapped read may be a list of possible locations the read may be mapped to a matching sequence in the reference genome. In various embodiments, an exact match to the reference for at least a piece, e.g., a seed of the read, if not all of the read may be sought. Accordingly, in various instances, it is not necessary for all portions of all the reads to match exactly to all the portions of the reference genome.

Further, one or all of these functions may be programmed in such a manner that exact or approximate matching and/or editing, such as editing of the results, may be performed. Hence, all of these processes can be configured to do inexact matching as well, where desired, such as in accordance with a preselected variance, such as 80% matching, 85% matching, 90% matching, 95% matching, 99% matching, or more. However, as described in greater detail herein below, inexact matching may be a lot more expensive such as in time and processing power requirements, because it may require any number of edits, e.g., where the edit may be a SNP or insertion or deletion of one or more bases, e.g., 1 or 2 or 3 or 5 or more edits, to be performed so as to achieve an acceptable match. Such editing is likely to be used more extensively in implementing hashing protocols or when implementing prefix and/or suffix trees and/or performing a Burrows/Wheeler transform.

With respect to hash tables, a hash table may be produced in many different ways. In one instance, a hash table may be built by breaking the reference genome into segments of standard length, e.g., seeds of about 16 to about 30 nucleotides or more in length, such as about 18 to about 28 nucleotides, formatting them into a searchable table, and making an index of all the reference segments from which sequenced DNA, e.g., one or more reads, or a portion thereof, may be compared to determine matching. More particularly, a hash table index may be generated by breaking down the reference genome into segments of nucleotide sequences of known, uniform length, e.g., seeds, and storing them in random order into individual cubicles in the reference table. This may be done for a portion or the entire reference genome so as to build an actual reference index table that may be used to compare portions of the reference genome with portions of one or more reads, such as from a FASTQ file, for the purpose of determining matching.

This method may then be repeated in approximately the same manner for a portion, e.g., a majority or all, of the reads in the FASTQ file, so as to generate seeds of the appropriate, e.g., selected, length. For instance, the reads of the FASTQ file may be used to produce seeds of a predetermined length, which seeds may be converted into binary form and fed through a hash function and fit into a hash table index where the binary form of the seeds may match up with the binary segments of the reference genome, so as to give the location as to where in the genome the sample seeds match with the position in the reference genome.

For example, where the read is approximately 100 bases long, a typical seed may be about half or a about a third, e.g., about 27 to about 30 bases, as long. Hence, in such an instance, for each read a multiplicity of seeds, e.g., approximately 3 or 4 seeds dependent on the length of the read and/or the lengths of the seeds, may be generated to cover the read. Each seed may then be converted into a binary form and/or then be fed into the hash table and a possible result as to its position with respect to the reference genome may be obtained. In such instances, the entire read need not be compared to every possible position in the entire reference genome, rather only a portion of the reads, e.g., one or more of the generated sample seeds per read, need only be compared such as to an index containing equivalent seed portions of the reference genome. Hence, in various instances, a hash table may be configured such that by only one memory look up it can typically be determined where the sample seed and therefore read is positioned relative to the reference genome. However, in certain instances, it may be desirable to perform a hash function and look up on one or more overlapping sections of seeds from one read. In such instances, the seeds to be generated may be formed in such a manner that at least a portion of their sequence overlaps one another. This may be useful for instance in getting around machine and/or human errors or differences between the subject and the reference genome and may promote exact matching.

In certain instances, the building of the hash table as well as the performance of one or more of the various comparisons is executed by the hash function. The hash function is in part a scrambler. It takes an input and gives what appears to be a random order to it. In this instance, the hash function scrambler breaks down the reference genome into segments of a preselected length and places them randomly in the hash table. The data may then be stored evenly across the whole storage space. Alternatively, the storage space may be segmented and/or storage therein may be weighted differently. More particularly, the hash function is a function that takes any input and gives a number, such as a binary pattern out, which number may typically random except that for any one given input the same output is always returned. Hence, even if two inputs that are fed into the hash table are almost the same, because they are not an exact match, two completely, randomly different outputs will be returned.

Further, since genetic material may be composed of four basic nucleotides, e.g., "A", "C", "G", and "T" (or "U" in the case of RNA), the individual nucleotides of the sequences, e.g., the reference segments and or reads, or portions thereof, to be fed into the hash table may be digitized and represented in binary format, such as where each of the four bases represents a two bit digital code, e.g., "A"=00, "C"=01, "G"=11, and "T"/"U"=10. In certain instances, it is this binary "seed" value that is then randomly placed in the hash table at a known location having a value equal to its binary representation. The hash function, therefore, works to break down the reference genome into binary representations of reference seeds and inserts each binary seed data into a random space, e.g., cubicle, in the hash table based on its numeric value. Along with this digital binary code, e.g., access key, each cubicle may also include the actual entry points to where the segment originated from in the actual reference genome, e.g., the reference position. The reference position therefore may be a number indicating the position of the original reference seed in the genome. This may also be done for overlapping positions, which are put into the table in random order but at known location, such as by the hash function. In a manner such as this, a hash table index may be generated, wherein the index includes the digital binary code for a portion or all of a plurality of segments of one or more reference genomes, which may then be referenced by one or more sequences of genetic material, e.g., one or more reads, or portions thereof, from one or more individuals.

When implementing the hash table and/or function as a module, such as a module in a pipeline of modules, on software (such as where the bit width is 2×the number of bases in the seed described above) and/or hardware, as referenced above, the hash table can be built so that the binary representation of the reference seeds can be any bit width desired. As the seeds can be long or short, the binary representations can be greater or lesser, but typically the seed length should be chosen so as to be long enough to be unique, but not too long that it is too hard to find matches between the seeds of the genome reference and the seeds of the sample reads, such as because of errors or variants. For instance, as indicated above, the human genome is made up of about 3.1 billion base pairs, and a typical read may be about 100 nucleotides in length. Hence, a useful seed length may be between about 16 or about 18 nucleotides or less in length to about 28 or about 30 nucleotides or more in length. For example, in certain instances, the seed length may be a segment of 20 nucleotides in length. In other instances, the seed length may be a segment of 28 nucleotides in length.

Consequently, where the seed length is a segment of 20 nucleotides, each segment may be represented digitally by a 40 bit output, e.g., a 40 bit binary representation of the seed. For example, where 2 bits are selected to represent each nucleotide, e.g., such as where A=00, C=01, G=10, and T=11, a seed of 20 nucleotides×2 bits per nucleotide=a 40 bit (5 byte) vector, e.g., number. Where the seed length may be 28 nucleotides in length, the digital, e.g., binary, representation of the seed may be a 56 bit vector. Hence, where the seed length is approximately 28 nucleotides in length, 56 bits can be employed to handle a 28 nucleotide seed length. More particularly, where the 56 bits represents the binary form of the seeds of the reference genome that have been randomly positioned in the hash table, a further 56 bits can be used to digitally represent the seeds of the read that are to be matched against the seeds of the reference. These 56 bits may be run through a polynomial that converts the 56 bits in to 56 bits out in a 1:1 correspondence. Without increasing or decreasing the number of bits of output, performing this operation randomizes the storage location of adjacent input values so that the various seed values will be uniformly distributed among all possible storage locations. This also serves to minimize collisions among values that hash to the same location. In particular, in a typical hash table implementation described herein, only a portion of the 56 bits is used as a lookup address to select a storage location and the remaining bits are stored in that location for confirmation of a match. If a hashing function were not used, a great many patterns having the same address bits, but different stored bits would have to share the same hash location.

More specifically, there is similarity between the way the hash table is constructed, e.g., by software and/or hardware placing the reference genome seeds randomly in the hash table, and the way the hash table is accessed by the seeds of the reads being hashed such that they both access the table in the same way. Hence, seeds of the reference and seeds of the sample read that are the same, e.g., have the same binary code, will end up in the same location, e.g., address, in the table because they access the hash table in the same manner, e.g., for the same input pattern. This is the fastest known method for performing a pattern match. Each lookup takes a nearly constant amount of time to perform. This may be contrasted with a Burrows-Wheeler method which may require many probes (the number may vary depending on how many bits are required to find a unique pattern) per query to find a match, or a binary search method that takes $\log_2(N)$ probes where N is the number of seed patterns in the table.

Further, even though the hash function can break the reference genome down into segments of seeds of any given length, e.g., 28 base pairs, and can then convert the seeds into a digital, e.g., binary, representation of 56 bits, not all 56 bits need be accessed entirely at the same time or in the same way. For instance, the hash function can be implemented in such a manner that the address for each seed is designated by a number less than 56 bits, such as about 20 to about 45 bits, such as about 25 to about 40 bits, such as about 28 to about 35 bits, including about 28 to about 30 bits may be used as an initial key or address so as to access the hash table.

For example, in certain instances, about 26 to about 29 bits may be used as a primary access key for the hash table, leaving about 27 to about 30 bits left over, which may be employed as a means for double checking the first key, e.g., if both the first and second keys arrive at the same cell in the hash table, then it is relatively clear that said location is where they belong. Specifically, in order to save space and reduce the memory requirements and/or processing time of the hash module, such as when the hash table and/or hash function are implemented in hardware, the about 26 to about 29 bits representing the primary access key derived from the original 56 bits representing the digitized seed of a particular sequenced read may be employed by the hashing function to comprise the primary address, leaving about 27 to about 30 bits that can be used in a double checking method.

More particularly, in various instances, about 26 to about 29 bits from the 56 bits representing the binary form of a reference seed may be employed to comprise a primary address, which designated 26 to 29 bits may then be given a randomized location in the hash table, which in turn may then be populated with the location of where the reference seed originally came from along with the remaining 27 to 30 bits of the seed so that an exact match may be ascertained. The query seeds representing the reads of the subject genome converted into binary form may also be hashed by the same function in such a manner that they as well are represented by 29 bits comprising a primary access key. If the 29 bits representing the reference seed are an exact match to the 29 bits representing the query seeds, they both will be directed to the same position in the hash table. If there was an exact match to the reference seed, then we expect to find an entry at that location containing the same remaining 27 to 30 bits. In such an instance, the 29 designated address bits of the reference sequence may then be looked up to identify the position in the reference to where the query read from which the query seed was derived, aligns.

However, with respect to the left over 27 to 30 bits, these bits may represent a secondary access key that may also be imported into the hash table as well, such as for the purpose of ensuring the results of the first 26 to 29 bits of the primary access key. Because the hash table represents a perfect 1:1 scrambling of the 28 nucleotide/56 bit sequence, and only about 26 to about 29 of the bits are used to determine the address, these 26 to about 29 bits of the primary access key have basically been checked, thereby determining the correct address in a first go around. This data, therefore, does not need to be confirmed. However, the remaining about 27 to about 30 bits of the secondary access key must be checked. Accordingly, the remaining about 27 to 30 bits of the query seeds are inserted into the hash table as a means for completing the match. Such an implementation may be shorter than storing the 56 bit whole key, and thus, saves space and reduces over all memory requirements and processing time of the module.

The hash table, therefore, can be configured as an index where known sequences of one or more reference genomes that have been broken down into sequences of predetermined lengths, e.g., seeds, such as of 28 nucleotides in length, are organized into a table randomly, and one or more sequenced reads, or "seed" portions thereof, derived from the sequencing of a subject's genomic DNA or RNA, may be passed through the hash table index, such as in accordance with a hash function, so as to look up the seed in the index, and one or more positions, e.g., locations in the reference genome, may be obtained from the table where the sample seed matches positions in the reference genome. Using a brute force linear search to scan the reference genome for locations where a seed matches, over 3 billion locations would have to be checked. However, by using a hashing approach, each seed lookup can occur in approximately a constant amount of time. Often, the location can be ascertained in a single access. In cases where multiple seeds map to the same location in the table, a few additional accesses may be made to find the seed being currently looked up. Hence, even though there can be 30M or more possible locations for a given 100 nucleotide length read to match up to, with respect to a reference genome, the hash table and hash function can quickly determine where that read is going to show up in the reference genome. By using a hash table index, therefore, it is not necessary to search the whole reference genome to determine where the read aligns.

As indicted above, chromosomes have a double helix structure that is comprised of two opposed, complementary strands of nucleic acid sequences that are bound together so as to form the double helix. For instance, when the double helix structure is formed these complementary base pairs bind one with the other in accordance with the following formula: "A" binds to "T", and "G" binds to "C". Accordingly, this results in two equal and opposite strands of nucleic acid sequences that are the complement of each other. More particularly, the bases of a nucleotide sequence of one strand will be mirrored by their complementary bases on the opposed strand resulting in two complementary strands. However, transcription of DNA takes place in one direction only, starting from one end of the DNA and moving towards the other. Hence, as it turns out, for one strand of the DNA, transcription takes place in one direction, and for its complement strand, transcription takes place in the opposite direction. Consequently, the two strands of DNA sequences turn out to be reverse complemented, that is if the sequence order of one strand of the DNA is compared to the other what can be seen is two strands where the nucleotide letters of one strand are switched for their complement in the other strand, e.g., "As" for "Ts" and "Gs" for "Cs" and vice versa, and their order is reversed.

Because of the double helix structure of the DNA, during the sample prep step prior to sequencing the DNA, the chromosomes are pulled apart, e.g., de natured, separated into separate strands, and then lysed into smaller segments of a predetermined length, e.g., of 100-300 bases long, which are then sequenced. It is possible to separate the strands prior to sequencing so that only one strand is sequenced, but typically the strands of DNA are not separated and so both strands of DNA are sequenced. Accordingly, in such an instance, about half of the reads in the FASTQ file may be reverse complemented.

Of course, both strands of the reference genome, e.g., the complement and the reverse complement, may be processed and hashed as described above, however this would make the hash table twice as big, and make the performance of the hash function take twice as long, e.g., it could require about twice the amount of processing to compare both complement and reverse complemented sequences of the two genomic sequences. Accordingly, to save memory space, reduce processing power, and/or decrease the time of processing, in various instances, only one strand of the model genomic DNA need be stored in the hash table as a reference.

However, because in accordance with typical sequencing protocols, such as where the two strands of the subject DNA have not been isolated from one another, any read generated from the sequenced DNA can be from either strand, the complement or its reverse complement, it may be difficult to determine which strand is being processed, the complement of the reverse complement. More specifically, in various instances, since only one strand of the reference genome need be used to generate the hash table, half of the reads generated by the sequencing protocol may not match the particular strand, e.g., either the complement or its reverse complement, of the model genome reference, e.g., because half the time the read being processed is a reverse complement with respect to the hashed segments of the reference genome. Hence, only the reads generated from one strand of the DNA will match the indexed sequences of the reference genome, while the reads generated from the other strand will theoretically be their reverse complements and will not match anywhere in the reference genome. Further, an additional complication can be that for any given read that is reverse complemented to the stored reference genome strand, the read may still, erroneously, match to a portion of the reference genome, such as by mere chance. In view of the above, in order for mapping to proceed efficiently, in various instances, it not only must be determined where the read matches in the reference genome it must also be determined if the read is reverse complemented. Therefore, the hash table and/or function module should be constructed so as to be able to minimize these complications and/or the types of errors that may result therefrom.

For instance, as indicated above, in one instance, the hash table could be populated with both the complement and the reverse complement for the reference genome so that every read or its reverse complement of the subject's sequenced DNA can be matched to its respective strand in the genomic reference DNA. In such an instance, for any given seed in a read, the seed should theoretically match with one strand or the other, the complement or the reverse complement of the reference, assuming no errors or variations. However, storing both strands of the reference genome in the hash index can require about twice as much storage space (e.g., instead of 32 gigabytes 64 gigabytes may be necessary), and may require twice the amount of processing resources and/or twice as much time for processing. Further, such a solution doesn't solve the problem of palindromes that can match in both directions, e.g., the complement and reverse complement strands.

Accordingly, although the hash table index may be constructed to include both strands of the genomic reference sequence. In various instances, the hash table may be constructed so as to only include one strand of the model genome as a reference. This may be useful because storing the hash table in memory will require half of the storage and/or processing resources than would be required if both strands were to be stored and processed, and thus, the time required for a look up should also require less time. However, storing only one strand of the genome as a reference could cause complications because, as indicated above, where the sequenced subject DNA is double stranded, it is not typically known from which strand any given read was generated. In such an instance, therefore, the hash table should be constructed to account for the fact the read being mapped may be from either strand and thus can be the complement or reverse complement of the stored segments of the reference genome.

Accordingly, in various instances, such as where only one orientation of seeds from the reference are populated into the hash table, when performing the hash function on the seeds generated from the reads of the FASTQ file, the seed may first be looked up in its present orientation, and/or may then be reverse complemented and the reverse complement may be looked up. This may require two looks up in the hash index, e.g., twice as many, but one of the seed or its reverse complement should match its complementary segment in the reference genome, assuming no errors or variations, and it should reduce the overall processing resources, e.g., less memory is used, as well as reducing time, e.g., not as many sequences need to be compared.

More particularly, such as where a seed in one particular orientation is comprised of 28 nucleotides, e.g., digitally represented in a 56 bit binary format, as described above, the seed can be reverse complemented and the reverse complement can also be represented digitally in a 56 bit binary format. The binary format for each representation of the seed sequence and its complement results in a number, e.g., an integer, having a value represented by that number. These two values, e.g., the two integers, may be compared and the number with the higher or lower value, e.g., higher or lower absolute value, may be selected as the canonical choice of orientation and that is the one that can be stored in the hash table and/or subjected to the hash function. For instance, in certain instances, the number with the higher value may be selected for being processed by the hash function.

Another method that may be employed is to construct seeds wherein each seed is comprised of an odd number of bases. The canonical orientation to be selected then may be those strands having a middle base being an "A" or a "G", but not a "T" or a "C", or vice versa. The hash function then will be performed on the seeds meeting the requirements of the canonical orientation. In such a manner, it is only the two bits representing the middle base that needs to be compared to see which has the higher value and it is only the 2 bits of that sequence that are looked up. Hence, you only have to look at the bits representing the middle two bases. Typically, this can work well because if the seed is an odd length, then it always reverse complements the center base. However, although this may work for odd seed lengths, hashing those seeds having a higher, or lower, value, as described above, should work for all seed lengths, albeit such a method may require having to process, e.g., look up, more bits of data.

These methods may be performed for any number of seeds, e.g., all seeds of the reference and/or any number of seeds, e.g., all, derived from all or a portion of the reads of the FASTQ file. Approximately half of the time the binary representation of the seeds of a given orientation, e.g., the complement, will have a higher value, and approximately half the time the binary representation of the seeds of the opposite orientation, e.g., the reverse complement, will have the higher value. But, when looking at the binary numbers, whichever one has the higher value, that is the one that gets fed into the hash table. For instance, the binary integers for each read and its complement may be compared, and the sequence having the first 1 encountered is the one of the two strands selected to be stored as the strand in the hash table and/or be subjected to the hash function. If both strands have a first 1 in the same position, then the strand having the second 1 that comes first is selected, and so on. Of course, the read with the lower value may also be selected, in which case the strand having the first and/or larger number of initial 0's will be selected. An indication, e.g., a flag, may also be inserted into the hash table where the flag indicates which orientation, complement or reverse complement, the stored and/or hashed strand represents, e.g., a 1RC flag, if reverse complemented.

More particularly, when performing the hash function and accessing the hash table, seeds from the genomic reference DNA and seeds derived from the reads of the sequence data are subjected to these same operations, such as converted into binary form and compared with its reverse complement where the integers having the higher, or lower, values are selected as the canonical orientations and subjected to the hash function and fed into the hash table to be looked up and matched against each other. However, because it is the same operation being performed in substantially the same manner on the reference sequences and the read sequences, the same record will be derived, if the two sequences, the reference and the subject seeds, have the same sequence to begin with, even if one was reverse complemented, they will all be directed to the same cell in the hash table.

Consequently, if a certain seed in the reference having a given sequence in a particular orientation is converted to binary form and hashed, and then a seed derived from a sample read having the same sequence, but in its reverse orientation, e.g., reverse complemented, and it is subjected to the above protocols, because of the above disclosed methods, when the binary value is determined and the hash function performed, the look up will be directed to the very same address in the hash table as if the hash function were performed on the complimentary seed to begin with. Hence, in this manner it doesn't matter which orientation the seed being processed is in because it will always be directed to the same address.

Therefore, in a manner such as this, the methods herein disclosed are able to hash and thereby determine the location of the seed within the table despite its orientation, and because of the flag in the record it will also be known if any given seeds is reverse complemented. For instance, it will be known if the seed was flipped from the reference and it will also be known if the seed derived from the subject read had to be flipped as well. Consequently, if the decision was the same on both sides then the orientation is the same between the read and the reference. However, if one side is flipped and the other is not, then it can be concluded that the read maps reverse complemented to the reference. Hence, by using a hash table it may be determined where in the genome a given read, or portion thereof, e.g., a seed, matches and/or if it is reverse complimented. Further, it is to be understood that although the above is described with respect to generating the hash table from the reference genome and performing various ancillary hash function processes on the seeds generated from the reads, e.g., from a FASTQ file, the system can also be structured such that the hash table index is generated from seeds derived from the reads of the subject's sequenced DNA, and the various ancillary hash function processes, as herein described, are performed on seeds generated from the reference genome.

As set forth above, an advantage of employing a hash table and/or a hash function is that by employing the use of seeds, a majority of the reads of the sequenced DNA can be matched to the reference genome often by employing single hash lookups, and in various instances, not all seeds derived from a read need be hashed and/or looked up. Seeds may be of any suitable length, such as relatively short, e.g., 16 nucleotides or less, such as about 20 nucleotides, such as about 24 nucleotides, such as about 28 nucleotides, such as about 30 or about 40 or about 50, or 75 or about 100 nucleotides, or even up to 250 or 500, or 750, or even 999 or even about 1,000 nucleotides in length; or relatively long such as over about 1,000 nucleotides or over about 10,000, or over about 100,000 or over 1,000,000 or more nucleotides in length. However, as described above, there are some disadvantages to using seeds, such as in a hash table, in particular with respect to selecting seeds of the appropriate length.

For instance, any suitable seed length may be employed in a mapping function, however there are advantages and disadvantages of using relatively short or relatively long seed lengths. For example, the shorter the seed length the less likely it is to incorporate an error or a variation that can prevent finding a match within the hash table. However, the shorter the seed length, the less unique it is, and the more matching is to be expected between the seeds of the reference genome and the seeds derived from the reads of the subject's sequenced DNA. Further, the shorter the seed length the more lookups will have to be performed by the hash function, taking more time and increased processing power.

On the other hand, the longer the seed length the more unique it is and the less likely there is to be multiple matching positions between the seeds between the seeds of the reference and the query. Also, with a longer seed, there need be fewer seeds within the read, so fewer look ups, thereby taking less time and requiring less processing power. The longer the seed, however, the more likely it is that the seeds derived from the sequenced DNA may include an error, such as a sequencing error and/or may incorporate a variation as compared to the reference thus preventing a match from being made. Longer seeds further have the disadvantage of being more likely to hit the end of the read and/or the end of the chromosome. Hence, where a seed is only 20-100 nucleotides in length, there may be several matches within the hash table, however, where the seed is 1,000 or more nucleotides in length there may be much fewer matches, but there may be no matches at all.

There are some methods for helping to minimize these issues. One method is to ensure there is appropriate over-sampling generated in the DNA processing steps prior to sequencing. For instance, as it is known that there is typically at least one variation within every 1,000 base pairs, the seed length may be chosen to maximize matches, while at the same time minimizing non-matches due to the incorporation of errors and/or variants. Additionally, the use of oversampling, such as in the pre-sequencing and/or sequencing steps, can be employed as a further method for minimizing various problems that are inherent to using seeds, such as within a hash function.

As indicated above, oversampling produces pileups. Pileups are those collections of reads that map in an overlapping fashion generally to the same place in the genome. For the majority of sample reads, such pileups may not be necessary, such as where the reads, and/or seeds generated therefrom, do not include a variant and/or do not map to multiple positions in the hash table (e.g., are not exactly duplicated in the genome). However, for those reads and/or seeds that may include a variant and/or an error and/or other mismatch between the seed and/or read and the reference genome, the production of pileups for any given region of the genome may be useful. For instance, even though only one exact hit between a seed generated from a read of the sample genome is necessary so as to be able to map the sample read to the reference genome, however, the fact that there may be a machine error or a true variant in the sample DNA sequence that could prevent such an exact match between the read and the reference from occurring, often times makes the production of overlapping pileups in the pre-sequencing and sequencing steps useful.

For example, for those instances where a sample seed does in fact contain a variant or an error, the production of read pileups may be useful in distinguishing between actual variance and machine and/or chemistry errors. In such an instance, a pileup can be employed to determine whether an apparent variation is in fact a real variation. For instance, if 95% of the reads in the pileup indicate that there is a "C" in a certain position, then odds are that is the correct call, even if the reference genome has a "T" at that location. In such an instance, the mismatch may be due to a SNP, e.g., a substitution of a "C" for a "T" in that position in the genome, where the genetic code for the individual actually varies from that of the reference. In such an instance, the depth of the pileup may be employed so as to compare the overlapping portions of the reads of the pileup at a position where there is variance, and based on the percentage of reads in the pileup having the variance, it can be determined whether the variance is in fact due to an actual variation in the sample sequence. Accordingly, the actual sequence of the reads that best fits the genomic sequence may in part be determined based on what is reflected in the pileup depths. The disadvantage of using pileups, however, is that it requires more processing time to process all the excess reads and/or seeds generated thereby.

Another method for minimizing the issues inherent in short or long reads is to employ a secondary hash table along with or in conjunction with the first, e.g., primary hash table. For instance, a second hash table and/or hash function may be employed for those seeds that do not have any hits in the primary hash table, or for those seeds that have multiple hits in the primary hash table. For example, when comparing one seed with another there are several outcomes that may result. In one instance, a no hit, e.g., a no match anywhere between the two sequences, may result, in which case this suggests a possible error or variation such as in the seed of a read of the subject as compared against a seed derived from the reference genome. Or there may be one or a plurality of matches found. If a large number of matches are found, however, this could be problematic.

For instance, with respect to the primary hash table, if each seed in the reference being hashed appears only a few times, e.g., once, twice, or three times, etc. then there may not be a need for a secondary hash table and/or hash function. However, if one or more of the seeds occurs a greater number of times, e.g., 5, 10, 15, 20, 25, 50, 100, 1,000, or more times, this could be problematic. For example, there are known regions in the sequence of the human genome that have been determined to be mathematically significant in that they are repeated a multiplicity of times. Consequently, any seed mapping to one of these positions, may in fact inadvertently map to a multiplicity of these positions, such as where the seed comprises the nucleotides of the overlapping sequences. In such an instance, determining which out of all the possibilities the seed actually aligns to may be difficult. However, as these repeating regions are known, and/or become known, any seed that would typically map to one or more of these regions may be demarcated to be allocated to a secondary hash table for processing by the first or a secondary hash function, so as to not waste time and processing power trying to use a primary hashing function to determine something that is likely to be indeterminable.

More particularly, when comparing the seeds of the genomic reference to the seeds generated from the subject's genomic reads, anywhere from 1 to hundreds or even thousands of match positions may result. The present system, however, may be configured to handle a certain number of duplicative matches, such as without the need for further processing steps, such as where the number of matches is below about 50, or below about 40, or below about 30, such as below about 25 or about 20, such as below about 16 matches or below about 10 or about 5 matches. However, if there are more matches of viable hits than this that are returned, then the system can be configured to implement a secondary hash function, e.g., using a secondary hash table.

Accordingly, rather than placing such seeds known to have an increased likelihood of redundancy in the primary hash table, such seeds can be placed in a secondary hash table, or a secondary region in the first hash table. Additionally, in some instances, a record that doesn't communicate anything about the multiplicity of potential map positions for that seed, but rather communicates a command to access a secondary hash table, e.g., an extend record, can be placed in the primary hash table. For example, the extend record can be an instruction, such as an instruction to extend the primary, e.g. non unique or duplicative, seed length to a longer, more unique seed length, such as by adding on one or more additional bases next to it, e.g., on the end(s) of the seed, to make it a longer seed sequence that can then get hashed and looked up, such as in the secondary table.

The record can be configured such that it informs or otherwise instructs how much to extend the known redundant seed by a given amount, and may also instruct as to where and/or how to extend the seed. For instance, because the hash table is usually precomputed, e.g., originally constructed from the seeds generated from the reference genome(s), it may be known prior to constructing the table, which, if any, of the seeds generated from the reference genome are going to occur a multiplicity of times. Hence, in various instances, it may be predetermined which seeds are going to need to be shifted over to the secondary hash table. For example, when constructing the hash table index, the characteristics of the reference seed sequences being input into the hash table as an index are known, so for every potential seed it may be determined whether it's a case that is going to give a multiplicity of hits, e.g., from 10-10,000 hits.

More particularly, in various instances, an algorithm can be performed to determine all the predicted matches a given seed derived from the reference and/or the subject's reads may have. If it is determined that for any particular seed that it is likely to return a multiplicity of matches, a flag, e.g., a record, may be generated, such as within a cell of the hash table, indicating that this particular seed is a high frequency hit. In such an instance, the record can further instruct that the primary hashing of this seed, and such seeds like it, should be skipped over because it is not practical to perform the number, e.g., 20-10,000 or more evaluations on such a seed needed to accurately determine where the seed actually maps. In such an instance, the primary hash function may not be able to accurately determine which position out of all the possible positions to where the seed may match, is the one to where the read actually aligns, and thus for practical purposes, because the seed cannot accurately be mapped at this stage, the primary hash function may not be likely to return a useable result, such as a result indicating accurately where the seed actually matches in the genome.

In such an instance, the hash function algorithm may be configured to calculate what would need to be done to make the redundant seed more unique. For example, the secondary hash function may determine by how many bases the seed needs to be extended, and in what order, and in what location, so as to ensure that the seed is no longer redundant, but rather suitably unique so as to be hashed. Accordingly, the record may also include an instruction to extend the redundant seed, e.g., extend by two, by four, by six, etc., on one or both ends of the seed so as to achieve a predetermined level of uniqueness. In such a manner as this, seeds that at first appear to be identical can be determined to be non-identical.

For example, in some instances, a typical record can instruct that the duplicative seed be extended by up to X number of odd or even bases, but in some instances, extended by an even number of bases, such as from about 2 to 4 to about 8 to 16 to about 32 or about 64 or more bases, such as equally on each side. For instance, where the extension is to be by 64 bases, the record could instruct that 32 bases be added on each side of the seed. The number of bases by which the seed is to be extended is configurable and may be any suitable number dependent on how the system is constructed. In certain instances, the secondary hash function may be employed to determine by how many bases the seed should be extended so as to get a more reasonable number of match results back. Therefore, the extension may be to the point of relative uniqueness, such as to where there is only 1, 2, 3, or even up to 16 or 25 or 50 match positions where the pattern shows up. In various instances, extending the seed equally from both ends may be useful such as to avoid problems with reverse reads, but in various instances the seed may be extended by the addition of one or more bases unequally to both sides.

More particularly, such as in one example, if the seed includes 28 bases, and an extend record, such as an extend record positioned within a cell in the primary hash table, instructs the hash function to extend the seed, such as by 64 bases, then the record may further direct the hash function as to how to extend the seed, such as by adding 32 bases on each side of the seed. However, the extension can take place at any suitable position on the read and may be done in a symmetrical or asymmetrical fashion. In certain instances, the record may instruct the hash function to extend the seed symmetrically because in certain instances such a symmetrical extension may work better, such as with reverse complements, discussed herein. In such an instance, the same number of bases will be added such as to the opposite sides of the seed when extending. Although in other instances extension may be performed by adding an even or an odd number of bases in a non-symmetrical format, and hence, it is not necessary to extend the seed by same number of bases on each side. Typically, the primary hash table is configured such that it is not completely full. For example it is desirable to configure it not to exceed 80% or 90% of its capacity. This is to maintain high performance of the lookup rate. When there are a high number of collisions in hashing seeds to the same location when constructing the table, the storing mechanism will create a chain of references to other locations so that the lookup mechanism will be able to find the one assigned to the overflowed seed. The denser the table, the higher the number of collisions and the longer the chains to be followed to find the actual match.

In various instances, such as where the initial, redundant seed is 28 bases long, and the record instructs for it to be extended, such as from 18 to 32 to 64 bases, such as on each opposed side of the seed, the digital representation of the seed may be about 64 bases×2 bits per base=128 bits. Accordingly, dependent on how the mapping module is set up, this may be too big for the primary hash table to process. Hence, in certain instances, to deal with the need for such extensive processing, in certain embodiments, the secondary hashing module can be configured to store the information associated with larger seeds. Since the number of seeds requiring extension is a fraction of the total number of seeds, the secondary hash table may be smaller than the primary hash table. However, in other instances, such as to reduce the processing requirements of the module, e.g., to save bits, the known redundant portion of the sequence, e.g., the primary sequence, may be replaced by a preselected variable such as of a predetermined sequence length. In such an instance, since the redundant sequence is already known and identified, it does not need to be digitally represented in its entirety. Rather, in various instances, all that is really needed to be done is to substitute the known, redundant sequence with a known variable sequence, and all that really needs to be looked up are the extension portions, e.g., wings, that have been added to either side of the variable sequence, since those are the only portions of the initial sequence that are non-redundant and new. Hence, in certain instances, the primary sequence may be replaced by a shorter unique identifier code (such as a 24 bit proxy instead of 56 bit representation) and then the extension bases can be added to the proxy, such as a 36 bit extension (e.g., totaling 60 bits) that can then be put into the extend record in the primary table. In a manner such as this, the disadvantages of having too short and/or too long of reads can be minimized and the benefit of having only one or a few look ups in the hash table can be maintained.

As indicated above, the implementation of the above described hash function may be executed in software and/or hardware. An advantage of implementing the hash module in hardware is that the processes may be accelerated and therefore performed in a much faster manner. For instance, where software may include various instructions for performing one or more of these various functions, the implementation of such instructions often requires data and instructions to be stored and/or fetched and/or read and/or interpreted, such as prior to execution. As indicated above, however, and described in greater detail herein below, a chip can be hardwired to perform these functions without having to fetch, interpret, and/or perform one or more of a sequence of instructions. Rather, the chip may be wired to perform such functions directly. Accordingly, in various aspects, the disclosure is directed to a custom hardwired machine that may be configured such that portions or all of the above described hashing module may be implemented by one or more network circuits, such as integrated circuits hardwired on a chip, such as an FPGA, ASIC or Structured ASIC.

For instance, in various instances, the hash table index may be constructed and the hash function may be performed on a chip, and in other instances, the hash table index may be generated off of the chip, such as via software run by a host CPU, but once generated it is loaded onto and employed by the chip, such as in running the hash module. In certain instances, the chip may include any suitable number of gigabytes, such as 8 gigabytes, such as 16 gigabytes, such as 32 gigabytes, such as 64 gigabytes, such as about 128 gigabytes. In various instances, the chip may be configurable such that the various processes of the hash module are performed employing only a portion or all the memory resources. For example, where a custom reference genome may be built, a large portion of the memory may be dedicated to storing the hash reference index and/or for storing reads and/or for reserving space for other functional modules to use, such as where 16 gigabytes are dedicated to storing the reads, 8 gigabytes may be dedicated to storing the hash index and another 8 gigabytes may be dedicated to other processing functions. In another example, where 32 gigabytes are dedicated to storing reads, 26 gigabytes may be dedicated for storing the primary hash table, 2.5 gigabytes may be dedicated for storing the secondary table, and 1.5 gigabytes may be dedicated for the reference genome.

In certain embodiments, the secondary hash table may be constructed so as to have a digital presence that is larger than the primary hash table. For instance, in various instances, the primary hash table can be configured to store hash records of 8 bytes each with 8 records per hash bucket totaling 64 bytes per bucket, and the secondary hash table can be configured to store 16 hash records totaling 128 bytes per bucket. For each hash record containing overflow hash bits matching the same bits of the hash key a possible matching position in the reference genome is reported. For the primary hash table therefore, up to 8 positions may be reported. For the secondary hash table up to 16 positions may be reported.

Regardless of being implemented in hardware or software, in many instances, it may be useful to structure the hash table to avoid collisions. For instance, there may be multiple seeds that, because of various system artifacts will want to be inserted into the hash table at the same place regardless of whether there is a match there or not. Such instances are termed collisions. Often times, collisions can be avoided, in part, by the way the hash table is structured. Accordingly, in various instances the hash table may be structured so as to avoid collisions, and therefore may be configured to include one or more virtual hash buckets.

In various instances, the hash table can be structured such that it is represented in an 8 byte, 16 byte, 32 byte, 64 byte, 128 byte format, or the like. But in various exemplary embodiments it may be useful to represent the hash table in a 64 byte format. This may be useful, for instance, where the hash function is to make use of accessing a memory, such as a DRAM, e.g., in a standard DIMM or SODIMM form factor, such as where the minimum burst size is typically 64 bytes. In such an instance, the design of the processor for accessing a given memory will be such that the number of bytes needed to form a bucket in the hash table is also 64, and therefore a maximized efficiency may be realized. However, if the table were to be structured in a 32 byte format, this would be inefficient because about half the bytes delivered in a burst would contain information not needed by the processor. That would cut the effective byte delivery rate in half. Conversely, if the number of bytes used to form a bucket in the hash table is a multiple of the minimum burst size, e.g., 128, there is no performance penalty as long as the processor actually needs all of the information returned in a single access. Therefore, in instances where the optimal burst size of the memory access is at a given size, e.g., 64 bytes, the hash table can be structured so burst size of the memory is optimally exploited, such as where the bytes allocated for representing bins in the hash table and processed by the mapping function, e.g., 64 bytes, are coincident with the burst size of the memory. Consequently, where the memory bandwidth is a constraint, the hash table can be structured so as to optimally exploit such constraints.

Further, it is to be noted, that although a record may be crammed into 8 bytes, the hash function can be constructed such that it is not the case that 8 bytes from the table are read so as to process one record, as this could be inefficient. Rather, all 8 records in a bucket can be read at once, or some sub-portion thereof. This may be useful in optimizing the processing speed of the system as, given the architecture described above, it would cost the same time at the same speed to process all 8 records as it would for simply processing 1 record. Accordingly, in certain instances, the mapping module may include a hash table that itself may include one or more subsections, e.g., virtual sections or buckets, wherein each bucket may have 1 or more slots, such as 8 slots, such that one or more different records can be inserted therein such as to manage collisions. However, in certain circumstances, one or more of such buckets may fill up with records, so a means may be provided for storing additional records in other buckets and recording information in the original bucket indicating that the hash table lookup mechanism needs to look further to find a match.

Hence, in certain instances it may also be useful to employ one or more additional methods such as for managing collisions, one such method may include one or more of linear probing and/or hash chaining. For instance, if it is not known what exactly is being searched in the hash table or a portion thereof, such as in one bucket of the hash table, and the particular bucket is full, then the hash lookup function can be configured such that if one bucket is full and is searched and the desired record not found, then the function can be directed to step to the next bucket, e.g., the +1 bucket, and that bucket can then be checked. In such a manner, all buckets can be searched when looking for a particular record. Such searching, therefore, can be performed sequentially looking through one bucket to another until what is being looked for is found or it becomes clear that it is not going to be found, such as where an empty slot in at least one of the buckets is found. Particularly, where each bucket is filled sequentially, and each bucket is searched according to the sequence of filling, if an empty slot is found, such as when searching sequentially through buckets looking for a particular record, then the empty slot could be indicative of the record not existing, because if it did exist, it would at least have been positioned in the empty slot, if not in the preceding buckets.

More particularly, where 64 bytes are designated for storing the information in a hash bucket wherein 8 records are contained, upon receiving a fetched bucket, the mapping processor can operate on all 8 records simultaneously to determine which are matches and which are not. For instance, when performing a look up such as of a seed from a read obtained from the sequenced sample DNA against a seed generated from the reference genome, the digital representation of the sample seed can be compared against the reference seeds in all, e.g., 8, records so as to find a match. In such an instance, several outcomes may result. A direct match may be found. A sample seed may go into the hash table and, in some instances, no match is found, e.g., because it is just not exactly the same as any corresponding seed in the reference, such as because there was a machine or sequencing error with respect to that seed or the read from which it is generated, or because the person has a genetic sequence that is different from the reference genome. Or a the seed may go into the hash table and a plurality of matches may be returned, such where the sample seed matches to 2, 3, 5, 10, 15, 20, or more places in the table. In such an instance, multiple records may be returned all pointing to various different locations in the reference genome where that particular seed matches, the records for these matches may either be in the same bucket, or a multiplicity of buckets may have to be probed to return all of the significant, e.g., match, results.

In certain instances, such as where space may become a limiting factor in the hash table, e.g., in the hash table buckets, an additional mechanism for resolving collisions and/or for saving space may implemented. For instance, when space becomes limited, such as when more than 8 records need to be stored in a bucket, or when for other instances it is desirable, a hash chaining function may be performed. Hash chaining can involve, for example, replacing a record containing a specific position location in the genomic sequence with a record containing a chain pointer that instead of pointing to a location in the genome points to some other address, e.g., a second bucket in the current hash table e.g. a primary or a secondary hash table. This has the advantage over the linear probing method of enabling the hash lookup mechanism to directly access the bucket containing the desired record rather than checking buckets sequentially in order.

Such a process may be useful given the system architecture. For instance, the primary seeds being hashed, such as in a primary lookup, are positioned at a given location in the table, e.g., their original position, whereas the seeds being chained are being put in a position that may be different from their original bucket. Hence, as indicated above, a first portion of the digitally represented seed, e.g., about 26 to about 29 bits, can be hashed and may be looked up in a first step. And, in a second step, the remaining about 27 to about 30 bits can be inserted into the hash table, such as in a hash chain, as a means for confirming the first pass. Accordingly, for any seed, its original address bits may be hashed in a first step, and the secondary address bits may be used in a second, confirmation step. Hence, the first portion of the seeds can be inserted into primary record location, and the second portion may be fit into the table in secondary record chain location. And, as indicated above, in various instances, these two different record locations may be positionally separated, such as by a chain format record. Therefore, in any destination bucket of chaining a chain format record may positionally separate the entries/records that are for local primary first bucket accesses and probing and those records that are for the chain.

Such hash chains can be continued for a multiplicity of lengths. An advantage of such chaining is that where one or more of the buckets include one or more, e.g., 2, 3, 4, 5, 6, or more empty record slots, these empty slots can be used to store the hash chain data. Accordingly, in certain instances, hash chaining may involve starting with an empty slot in one bucket and chaining that slot to another slot in another bucket, where the two buckets may be at remote locations in the hash table. Additional care may be taken to avoid confusion between records placed in a remote bucket as part of a hash chain, and "native" records that hash directly into the same bucket. As usual, the remaining about 27 to about 30 bits of the secondary access key are checked against corresponding about 27 to 30 bits stored in the records placed remotely in the chained bucket, but due to the distant placement of the chained bucket from the original hash bucket, confirming these about 27 to 30 bits would not be enough to guarantee that a matching hash record corresponds to the original seed reaching this bucket by chaining, as opposed to some other seed reaching the same bucket by direct access. (e.g., confirming the about 27 to 30 bits may be a full verification when the about 26 to 29 bits used for hash table addressing are implicitly checked by proximity to the initial hash bucket accessed.)

To prevent retrieving a wrong hash record without needing to store entire hash keys in the records, a positional system may be used in a chained bucket. Accordingly, a chained bucket must contain a chain continuation format record, which contains a further chain pointer to continue the bucket chain if required; this chain continuation record must appear in a slot of the bucket after all "native" records corresponding to direct hash access, and before all remote records belonging to the chain. During queries, before following any chain pointer, any records appearing after a chain continuation record should be ignored, and after following any chain pointer, any records appearing before a chain continuation record should be ignored.

For example, where the buckets are about 75%-85% full, 8 buckets may be scanned and only 15-25 slots may be found that can be used, whereas with hash chaining these slots may be found over 2 or 3 or 4 buckets. In such an instance, the number of probe or chain steps required to store a hash record matters because it influences the speed of the system. At run time, if probing is necessary to find the record, a multiplicity of hash look up accesses, e.g., a 64 byte bucket read, may need to be performed which slows the system down. Hash chaining helps to minimize the average number of accesses that have to be performed, because more excess hash records can generally be populated per chained bucket, which can be selected from a wide region, than per probing bucket, which must be sequentially next. Therefore, a given number of excess hash records can typically be populated into a shorter sequence of chained buckets than the necessary sequence of probing buckets, which likewise limits the number of accesses required to locate those excess records in a query. Nevertheless, probing remains valuable for smaller quantities of excess hash records, because probing does not require a bucket slot to be sacrificed for a chain pointer.

For example, after it has been determined where all the possible matches are for the seeds against the reference genome, it must be determined which out of all the possible locations a given read may match to is in fact the correct position to which it aligns. Hence, after mapping there may be a multiplicity of positions that one or more reads appear to match in the reference genome. Consequently, there may be a plurality of seeds that appear to be indicating the exact same thing, e.g., they may match to the exact same position on the reference, if you take into account the position of the seed in the read.

The actual alignment, therefore, must be determined for each given read. This determination may be made in several different ways. In one instance, all the reads may be evaluated so as to determine their correct alignment with respect to the reference genome based on the positions indicated by every seed from the read that returned position information during the hash lookup process. However, in various instances, prior to performing an alignment, a seed chain filtering function may be performed on one or more of the seeds.

For instance, in certain instances, the seeds associated with a given read that appear to map to the same general place as against the reference genome may be aggregated into a single chain that references the same region. All of the seeds associated with one read may be grouped into one or more seed chains such that each seed is a member of only one chain. It is such chain(s) that then cause the read to be aligned to each indicated position in the reference genome. Specifically, in various instances, all the seeds that have the same supporting evidence indicating that they all belong to the same general location(s) in the reference may be gathered together to form one or more chains. The seeds that group together, therefore, or at least appear as they are going to be near one another in the reference genome, e.g., within a certain band, will be grouped into a chain of seeds, and those that are outside of this band will be made into a different chain of seeds.

Once these various seeds have been aggregated into one or more various seed chains, it may be determined which of the chains actually represents the correct chain to be aligned. This may be done, at least in part, by use of a filtering algorithm that is a heuristic designed to eliminate weak seed chains which are highly unlikely to be the correct one. Generally, longer seed chains, in terms of length spanned within the read, are more likely to be correct, and furthermore, seed chains with more contributing seeds are more likely to be correct. In one example, a heuristic may be applied wherein a relatively strong "superior" seed chain, e.g. long or having many seeds, filters out a relatively weak "inferior" seed chain, e.g. short or having few seeds.

In one variation, the length of an inferior chain determines a threshold length, e.g. twice as long, such that a superior chain of at least the threshold length can filter it out. In another variation, the seed count of an inferior chain determines a threshold seed count, e.g. five times as many seeds, such that a superior chain of at least the threshold seed count can filter it out. In another variation, the length of an inferior chain determines a threshold seed count, e.g. two times the seed count minus the seed length, such that a superior chain of at least the threshold seed count can filter it out. In some variations, such as when chimeric alignments of reads are desired, only superior seed chains substantially overlapping inferior seed chains within the read may filter them out.

This process weeds out those seeds that have a low probability of having identified a region of the reference genome where a high quality alignment of the read can be found. It, therefore, may be useful because it reduces the number of alignments that need to be performed for each read thereby accelerating the processing speed and saving time. Accordingly, this process may be employed, in part, as a tuning feature, whereby when greater speed is desired, e.g., high speed mode, more detailed seed chain filtering is performed, and where greater overall accuracy is desired, e.g., enhanced accuracy mode, less seed chain filtering is performed, e.g., all the seed chains are evaluated.

In various embodiments, seed editing may be performed, such as prior to a seed chain filtering step. For instance, for each read, if all of the seeds of that read are subjected to a mapping function and none of them returned a hit, then there may be a high probability that there was one or more errors in the read, for instance, an error that the sequencer made. In such an instance, an editing function, such as a one-change editing process, e.g., an SNP editing process, can be performed on each seed, such as where a no match outcome was returned. For example, at position X, a one change edit function may instruct that the designated nucleotide be substituted for one of the other 3 nucleotides and it is determined whether a hit, e.g., a match, is obtained by making that change, e.g., a SNP substitution. This one-change editing may be performed in the same manner on every position in the seed and/or on every seed of the read, e.g., substituting each alternative base for each position in the seed. Additionally, where one change is made in one seed, the effects that change would have on every other overlapping seed may be determined in view of that one change.

Such editing may also be performed for inserts, such as where one of the four nucleotides is added at a given insert position, X, and it is determined if a hit was obtained by making the substitution. This may be done for all four nucleotides and/or for all positions (X, X+1, X+2, X+3, etc.) in the seed and/or all the seeds in the reads. Such editing may also be performed for deletions, such as where one of the four nucleotides is deleted at a given position, X, in the seed, and it is determined if a hit was obtained by making the deletion. This may then be repeated for all positions X+1, X+2, X+3, etc. Such editing, however, can result in a lot of extra processing work and time, such as by requiring a multiplicity of additional lookups, such as 2, or 3, or 4, or 5, or 10, or 50, or 100, or 200, etc. Nevertheless, such extra processing and time may be useful if by such editing an actual hit can be determined, e.g., a match made, where before there was no match. In such an instance, it can then typically be determined that an error was made and further that it was corrected, thereby salvaging the read.

Additionally, a further heuristic may be employed so as to determine whether an editing function should be performed or not, whereby the algorithm performs a calculation to determine the probability that a hit will be obtained if such editing were to be performed. If a certain threshold probability is met, such as 85% likelihood, then such seed chain editing may be performed. For instance, the system can generate various statistics on the seed chains, such as calculating how many high frequency hits are present and/or how many seed chains contain high frequency hits, and thereby determine if seed chain editing is likely to make a difference in determining matches. For example, if it is determined that there are a large proportion of high frequency hits, then, in such an instance, seed chain editing may be skipped because it is unlikely to make various of the sequences unique enough to give a hit within a reasonable number of hash table look ups, such as 100 or fewer, 50 or fewer, 40 or fewer, 30 or fewer, 20 or fewer, or 10 or fewer. Such statistics can be reviewed and it may then be determined whether to do seed editing or not. For instance, if the statistics show that for any one read, if half the positions show no match, and the others show high frequency matches, then it is probably worth doing seed editing, because where no matches are returned, there is probably an error, but if a lot of high frequency matches are returned it may simply not be worth performing seed editing.

The outcome from performing one or more of these mapping, filtering, and/or editing functions is a list of reads which includes for each read a list of all the possible locations to where the read may matchup with the reference genome. Hence, a mapping function may be performed so as to quickly determine where the reads of the FASTQ file obtained from the sequencer map to the reference genome, e.g., to where in the whole genome the various reads map. However, if there is an error in any of the reads or a genetic variation, you may not get an exact match to the reference and/or there may be several places one or more reads appear to match. It, therefore, must be determined where the various reads actually align with respect to the genome as a whole.

Accordingly, after mapping and/or filtering and/or editing, the location positions for a large number of reads have been determined, where for some of the individual reads a multiplicity of location positions have been determined, and it now needs to be determined which out of all the possible locations is in fact the true or most likely location to which the various reads align. Such aligning may be performed by one or more algorithms, such as a dynamic programming algorithm that matches the mapped reads to the reference genome and runs an alignment function thereon.

An exemplary aligning function compares one or more, e.g., all of the reads, to the reference, such as by placing them in a graphical relation to one another, e.g., such as in a table, e.g., a virtual array or matrix, where the sequence of one of the reference genome or the mapped reads is placed on one dimension or axis, e.g., the horizontal axis, and the other is placed on the opposed dimensions or axis, such as the vertical axis. A conceptual scoring wave front is then passed over the array so as to determine the alignment of the reads with the reference genome, such as by computing alignment scores for each cell in the matrix.

The scoring wave front represents one or more, e.g., all, the cells of the matrix, or a portion of those cells, which may be scored independently and/or simultaneously according to the rules of dynamic programming applicable in the alignment algorithm, such as Smith-Waterman, and/or Needleman-Wunsch, and/or related algorithms. For example, taking the origin of the matrix (corresponding to the beginning of the read and/or the beginning of a reference window or the conceptual scoring wave front) to be at the top-left corner, first only the top-left cell at coordinates (0,0) of the matrix may be scored, e.g., a 1-cell wave front; next, the two cells to the right and below at coordinates (0,1) and (1,0) may be scored, e.g., a 2-cell wave front; next the three cells at (0,2), (1,1), and (2,0) may be scored, e.g., a 3-cell wave front. These exemplary wave fronts may then extend diagonally in straight lines from bottom-left to top-right, and the motion of the wave front from step to step is diagonally from top-left to bottom-right through the matrix. Alignment scores may be computed sequentially or in other orders, such as by computing all the scores in the top row from left to right, followed by all the scores in the next row from left to right, etc. In this manner the diagonally sweeping diagonal wave front represents an optimal sequence of batches of scores computed simultaneously or in parallel in a series of wave front steps.

For instance, in one embodiment, a window of the reference genome containing the segment to which a read was mapped is placed on the horizontal axis, and the read is positioned on the vertical axis. In a manner such as this an array or matrix is generated, e.g., a virtual matrix, whereby the nucleotide at each position in the read may be compared with the nucleotide at each position in the reference window. As the wave front passes over the array, all potential ways of aligning the read to the reference window are considered, including if changes to one sequence would be required to make the read match the reference sequence, such as by changing one or more nucleotides of the read to other nucleotides, or inserting one or more new nucleotides into one sequence, or deleting one or more nucleotides from one sequence.

An alignment score, representing the extent of the changes that would be required to be made to achieve an exact alignment, is generated, wherein this score and/or other associated data may be stored in the given cells of the array. Each cell of the array corresponds to the possibility that the nucleotide at its position on the read axis aligns to the nucleotide at its position on the reference axis, and the score generated for each cell represents the partial alignment terminating with the cell's positions in the read and the reference window. The highest score generated in any cell represents the best overall alignment of the read to the reference window. In various instances, the alignment may be global, where the entire read must be aligned to some portion of the reference window, such as using a Needleman-Wunsch or similar algorithm; or in other instances, the alignment may be local, where only a portion of the read may be aligned to a portion of the reference window, such as by using a Smith-Waterman or similar algorithm.

The size of the reference window may be any suitable size. For instance, since a typical read may be from about 100 to about 1,000 nucleotides long, the length of the reference window accordingly, in some instances, may be from about 100 to 1,000 nucleotides long or longer. However, in some instances, the length of the reads may be greater, and/or the length of the reference window can be greater such as about 10,000, 25,000, 50,000, 75,000, 100,000, 200,000 nucleotides long or more. It may be advantageous for the reference window to be padded somewhat longer than the read, such as including 32 or 64 or 128 or 200 or even 500 extra nucleotides in the reference window beyond the extremes of the reference genome segment to which the read was mapped, such as to permit insertions and/or deletions near the ends of the read to be fully evaluated. For instance, if only a portion of the read was mapped to a segment of the reference, extra padding may be applied to the reference window corresponding to the unmapped portions of the read, or longer by some factor, such as 10% or 15% or 20% or 25% or even 50% or more, so as to allow the unmapped portions of the read space to fully align to the reference window. In some instances, however, the length of the reference window may be selected to be shorter than the length of the reads, such as where a long portion of the read is not mapped to the reference, such as more or less than 1000 nucleotides at one end of the read, such as in order to focus the alignment on the mapped portion.

The alignment wave front may be of unlimited length, or limited to any suitable fixed length, or of variable length. For instance, all cells along the entire diagonal line of each wave front step extending fully from one axis to the other axis may be scored. Alternatively, a limited length, such as 64 cells wide, may be scored on each wave front step, such as by tracing a diagonally 64-cell wide band of scored cells through the matrix, and leaving cells outside of this band unscored. In some instances, it may be unnecessary to calculate scores far from a band around the true alignment path, and substantial work may be saved by computing scores only in a limited bandwidth, using a fixed length scoring wave front, as herein described.

Accordingly, in various instances, an alignment function may be performed, such as on the data obtained from the mapping module. Hence, in various instances, an alignment function may form a module, such as an alignment module, that may form part of a system, e.g., a pipeline, that is used, such as in addition with a mapping module, in a process for determining the actual entire genomic sequence, or a portion thereof, of an individual. For instance, the output returned from the performance of the mapping function, such as from a mapping module, e.g., the list of possibilities as to where one or more or all of the reads maps to one or more positions in one or more reference genomes, may be employed by the alignment function so as to determine the actual sequence alignment of the subject's sequenced DNA.

Such an alignment function may at times be useful because, as described above, often times, for a variety of different reasons, the sequenced reads do not always match exactly to the reference genome. For instance, there may be an SNP (single nucleotide polymorphism) in one or more of the reads, e.g., a substitution of one nucleotide for another at a single position; there may be an "indel," insertion or deletion of one or more bases along one or more of the read sequences, which insertion or deletion is not present in the reference genome; and/or there may be a sequencing error (e.g., errors in sample prep and/or sequencer read and/or sequencer output, etc.) causing one or more of these apparent variations. Accordingly, when a read varies from the reference, such as by an SNP or indel, this may be because the reference differs from the true DNA sequence sampled, or because the read differs from the true DNA sequence sampled. The problem is to figure out how to correctly align the reads to the reference genome given the fact that in all likelihood the two sequences are going to vary from one another in a multiplicity of different ways.

Accordingly, in various instances, the input into an alignment function, such as from a mapping function, such as a prefix/suffix tree, or a Burrows/Wheeler transform, or a hash table and/or hash function, may be a list of possibilities as to where one or more reads may match to one or more positions of one or more reference sequences. For instance, for any given read, it may match any number of positions in the reference genome, such as at 1 location or 16, or 32, or 64, or 100, or 500, or 1,000 or more locations where a given read maps to in the genome. However, any individual read was derived, e.g., sequenced, from only one specific portion of the genome. Hence, in order to find the true location from where a given particular read was derived, an alignment function may be performed, e.g., a Smith-Waterman gapped alignment, a Needleman-Wunsch alignment, etc., so as to determine where in the genome one or more of the reads was actually derived, such as by comparing all of the possible locations where a match occurs and determining which of all the possibilities is the most likely location in the genome from which the read was sequenced, on the basis of which location's alignment score is greatest.

As indicated, typically, an algorithm is used to perform such an alignment function. For example, a Smith-Waterman and/or a Needleman-Wunsch alignment algorithm may be employed to align two or more sequences against one another. In this instance, they may be employed in a manner so as to determine the probabilities that for any given position where the read maps to the reference genome that the mapping is in fact the position from where the read originated. Typically these algorithms are configured so as to be performed by software, however, in various instances, such as herein presented, one or more of these algorithms can be configured so as to be executed in hardware, as described in greater detail herein below.

In particular, the alignment function operates, at least in part, to align one or more, e.g., all, of the reads to the reference genome despite the presence of one or more portions of mismatches, e.g., SNPs, insertions, deletions, structural artifacts, etc. so as to determine where the reads are likely to fit in the genome correctly. For instance, the one or more reads are compared against the reference genome, and the best possible fit for the read against the genome is determined, while accounting for substitutions and/or indels and/or structural variants. However, to better determine which of the modified versions of the read best fits against the reference genome, the proposed changes must be accounted for, and as such a scoring function may also be performed.

For instance, a scoring function may be performed, e.g., as part of an overall alignment function, whereby as the alignment module performs its function and introduces one or more changes into a sequence being compared to another, e.g., so as to achieve a better or best fit between the two, for each change that is made so as to achieve the better alignment, a number is detracted from a starting score, e.g., either a perfect score, or a zero starting score, in a manner such that as the alignment is performed the score for the alignment is also determined, such as where matches are detected the score is increased, and for each change introduced a penalty is incurred, and thus, the best fit for the possible alignments can be determined, for example, by figuring out which of all the possible modified reads fits to the genome with the highest score. Accordingly, in various instances, the alignment function may be configured to determine the best combination of changes that need to be made to the read(s) to achieve the highest scoring alignment, which alignment may then be determined to be the correct or most likely alignment.

In view of the above, there are, therefore, at least two goals that may be achieved from performing an alignment function. One is a report of the best alignment, including position in the reference genome and a description of what changes are necessary to make the read match the reference segment at that position, and the other is the alignment quality score. For instance, in various instances, the output from a the alignment module may be a Compact Idiosyncratic Gapped Alignment Report, e.g., a CIGAR string, wherein the CIGAR string output is a report detailing all the changes that were made to the reads so as to achieve their best fit alignment, e.g., detailed alignment instructions indicating how the query actually aligns with the reference. Such a CIGAR string readout may be useful in further stages of processing so as to better determine that for the given subject's genomic nucleotide sequence, the predicted variations as compared against a reference genome are in fact true variations, and not just due to machine, software, or human error.

As set forth above, in various embodiments, alignment is typically performed in a sequential manner, wherein the algorithm receives read sequence data, such as from a mapping module, pertaining to a read and one or more possible locations where the read may potentially map to the one or more reference genomes, and further receives genomic sequence data, such as from one or more memories, pertaining to the one or more positions in the one or more reference genomes to which the read may map. In particular, in various embodiments, the mapping module processes the reads, such as from a FASTQ file, and maps each of them to one or more positions in the reference genome to where they may possibly align. The aligner then takes these predicted positions and uses them to align the reads to the reference genome, such as by building a virtual array by which the reads can be compared with the reference genome.

In performing this function the aligner evaluates each mapped position for each individual read and particularly evaluates those reads that map to multiple possible locations in the reference genome and scores the possibility that each position is the correct position. It then compares the best scores, e.g., the two best scores, and makes a decision as to where the particular read actually aligns. For instance, in comparing the first and second best alignment scores, the aligner looks at the difference between the scores, and if the difference between them is great, then the confidence score that the one with the bigger score is correct will be high. However, where the difference between them is small, e.g., zero, then the confidence score in being able to tell from which of the two positions the read actually is derived is low, and more processing may be useful in being able to clearly determine the true location in the reference genome from where the read is derived. Hence, the aligner in part is looking for the biggest difference between the first and second best confidence scores in making its call that a given read maps to a given location in the reference genome. Ideally, the score of the best possible choice of alignment is significantly greater than the score for the second best alignment for that sequence.

There are many different ways an alignment scoring methodology may be implemented, for instance, each cell of the array may be scored or a sub-portion of cells may be scored, such as in accordance with the methods disclosed herein. Typically, each alignment match, corresponding to a diagonal step in the alignment matrix, contributes a positive score, such as +1, if the corresponding read and reference nucleotides match; and a negative score, such as −4, if the two nucleotides mismatch. Further, each deletion from the reference, corresponding to a horizontal step in the alignment matrix, contributes a negative score, such as −7, and each insertion into the reference, corresponding to a vertical step in the alignment matrix, contributes a negative score, such as −7.

In various instances, scoring parameters for nucleotide matches, nucleotide mismatches, insertions, and deletions may have any various positive or negative or zero values. In various instances, these scoring parameters may be modified based on available information. For instance, in certain instances, alignment gaps (insertions or deletions) are penalized by an affine function of the gap length, for example −7 for the first deleted (resp. inserted) nucleotide, but only −1 for each additional deleted (resp. inserted) nucleotide in continuous sequence. In various implementations, affine gap penalties may be achieved by splitting gap (insertion or deletion) penalties into two components, such as a gap open penalty, e.g. −6, applied to the first step in a gap; and a gap extend penalty, e.g. −1, applied to every or further steps in the gap. Affine gap penalties may yield more accurate alignments, such as by letting alignments containing long insertions or deletions achieve appropriately high scores. Further, each lateral move may have the same or different costs, such as the same cost per step, and/or where gaps occur, such gaps can come at a higher or lower costs, such that the cost for lateral movements of the aligner may be less expensive than the costs for gaps. Accordingly, in various embodiments, affine gap scoring may be implemented, however, this can be expensive in software and/or hardware, because it typically requires a plurality, e.g., 3 scores, for each cell to be scored, and hence, in various embodiments affine gap scoring is not implemented.

In various instances, scoring parameters may also be sensitive to "base quality scores" corresponding to nucleotides in the read. Some sequenced DNA read data, in formats such as FASTQ, may include a base quality score associated with each nucleotide, indicating an estimated probability that the nucleotide is incorrect, e.g. due to a sequencing error. In some read data, base quality scores may indicate the likelihood that an insertion and/or deletion sequencing error is present in or adjacent to each position, or additional quality scores may provide this information separately. More accurate alignments, therefore, may be achieved by making scoring parameters, including any or all of nucleotide match scores, nucleotide mismatch scores, gap (insertion and/or deletion) penalties, gap open penalties, and/or gap extend penalties, vary according to a base quality score associated with the current read nucleotide or position. For example, score bonuses and/or penalties could be made smaller when a base quality score indicates a high probability a sequencing or other error being present. Base quality sensitive scoring may be implemented, for example, using a fixed or configurable lookup-table, accessed using a base quality score, which returns corresponding scoring parameters.

In a hardware implementation in an integrated circuit, such as an FPGA, ASIC or Structured ASIC, a scoring wave front may be implemented as a linear array of scoring cells, such as 16 cells, or 32 cells, or 64 cells, or 128 cells or the like. Each of the scoring cells may be built of digital logic elements in a wired configuration to compute alignment scores. Hence, for each step of the wave front, for instance, each clock cycle, or some other fixed or variable unit of time, each of the scoring cells, or a portion of the cells, computes the score or scores required for a new cell in the virtual alignment matrix. Notionally, the various scoring cells are considered to be in various positions in the alignment matrix, corresponding to a scoring wave front as discussed herein, e.g., along a straight line extending from bottom-left to top-right in the matrix. As is well understood in the field of digital logic design, the physical scoring cells and their comprised digital logic need not be physically arranged in like manner on the integrated circuit.

Accordingly, as the wave front takes steps to sweep through the virtual alignment matrix, the notional positions of the scoring cells correspondingly update each cell, for example, notionally "moving" a step to the right, or for example, a step downward in the alignment matrix. All scoring cells make the same relative notional movement, keeping the diagonal wave front arrangement intact. Each time the wave front moves to a new position, e.g., with a vertical downward step, or a horizontal rightward step in the matrix, the scoring cells arrive in new notional positions, and compute alignment scores for the virtual alignment matrix cells they have entered.

In such an implementation, neighboring scoring cells in the linear array are coupled to communicate query (read) nucleotides, reference nucleotides, and previously calculated alignment scores. The nucleotides of the reference window may be fed sequentially into one end of the wave front, e.g., the top-right scoring cell in the linear array, and may shift from there sequentially down the length of the wave front, so that at any given time, a segment of reference nucleotides equal in length to the number of scoring cells is present within the cells, one successive nucleotide in each successive scoring cell.

Accordingly, each time the wave front steps horizontally, another reference nucleotide is fed into the top-right cell, and other reference nucleotides shift down-left through the wave front. This shifting of reference nucleotides may be the underlying reality of the notional movement of the wave front of scoring cells rightward through the alignment matrix. Hence, the nucleotides of the read may be fed sequentially into the opposite end of the wave front, e.g. the bottom-left scoring cell in the linear array, and shift from there sequentially up the length of the wave front, so that at any given time, a segment of query nucleotides equal in length to the number of scoring cells is present within the cells, one successive nucleotide in each successive scoring cell.

Likewise, each time the wave front steps vertically, another query nucleotide is fed into the bottom-left cell, and other query nucleotides shift up-right through the wave front. This shifting of query nucleotides is the underlying reality of the notional movement of the wave front of scoring cells downward through the alignment matrix. Accordingly, by commanding a shift of reference nucleotides, the wave front may be moved a step horizontally, and by commanding a shift of query nucleotides, the wave front may be moved a step vertically. Accordingly, to produce generally diagonal wave front movement, such as to follow a typical alignment of query and reference sequences without insertions or deletions, wave front steps may be commanded in alternating vertical and horizontal directions.

Accordingly, neighboring scoring cells in the linear array may be coupled to communicate previously calculated alignment scores. In various alignment scoring algorithms, such as a Smith-Waterman or Needleman-Wunsch, or such variant, the alignment score(s) in each cell of the virtual alignment matrix may be calculated using previously calculated scores in other cells of the matrix, such as the three cells positioned immediately to the left of the current cell, above the current cell, and diagonally up-left of the current cell. When a scoring cell calculates new score(s) for another matrix position it has entered, it must retrieve such previously calculated scores corresponding to such other matrix positions. These previously calculated scores may be obtained from storage of previously calculated scores within the same cell, and/or from storage of previously calculated scores in the one or two neighboring scoring cells in the linear array. This is because the three contributing score positions in the virtual alignment matrix (immediately left, above, and diagonally up-left) would have been scored either by the current scoring cell, or by one of its neighboring scoring cells in the linear array.

For instance, the cell immediately to the left in the matrix would have been scored by the current scoring cell, if the most recent wave front step was horizontal (rightward), or would have been scored by the neighboring cell down-left in the linear array, if the most recent wave front step was vertical (downward). Similarly, the cell immediately above in the matrix would have been scored by the current scoring cell, if the most recent wave front step was vertical (downward), or would have been scored by the neighboring cell up-right in the linear array, if the most recent wave front step was horizontal (rightward). Similarly, the cell diagonally up-left in the matrix would have been scored by the current scoring cell, if the most recent two wave front steps were in different directions, e.g., down then right, or right then down, or would have been scored by the neighboring cell up-right in the linear array, if the most recent two wave front steps were both horizontal (rightward), or would have been scored by the neighboring cell down-left in the linear array, if the most recent two wave front steps were both vertical (downward).

Accordingly, by considering information on the last one or two wave front step directions, a scoring cell may select the appropriate previously calculated scores, accessing them within itself, and/or within neighboring scoring cells, utilizing the coupling between neighboring cells. In a variation, scoring cells at the two ends of the wave front may have their outward score inputs hard-wired to invalid, or zero, or minimum-value scores, so that they will not affect new score calculations in these extreme cells.

A wave front being thus implemented in a linear array of scoring cells, with such coupling for shifting reference and query nucleotides through the array in opposing directions, in order to notionally move the wave front in vertical and horizontal steps, and coupling for accessing scores previously computed by neighboring cells in order to compute alignment score(s) in new virtual matrix cell positions entered by the wave front, it is accordingly possible to score a band of cells in the virtual matrix, the width of the wave front, such as by commanding successive steps of the wave front to sweep it through the matrix. For a new read and reference window to be aligned, therefore, the wave front may begin positioned inside the scoring matrix, or, advantageously, may gradually enter the scoring matrix from outside, beginning e.g., to the left, or above, or diagonally left and above the top-left corner of the matrix.

For instance, the wave front may begin with its top-left scoring cell positioned just left of the top-left cell of the virtual matrix, and the wave front may then sweep rightward into the matrix by a series of horizontal steps, scoring a horizontal band of cells in the top-left region of the matrix. When the wave front reaches a predicted alignment relationship between the reference and query, or when matching is detected from increasing alignment scores, the wave front may begin to sweep diagonally down-right, by alternating vertical and horizontal steps, scoring a diagonal band of cells through the middle of the matrix. When the bottom-left wave front scoring cell reaches the bottom of the alignment matrix, the wave front may begin sweeping rightward again by successive horizontal steps, until some or all wave front cells sweep out of the boundaries of the alignment matrix, scoring a horizontal band of cells in the bottom-right region of the matrix.

In a variation, increased efficiency may be obtained from the alignment wave front by sharing its scoring cells between two successive alignment operations. A next alignment matrix having been established in advance, as the top-right portion of the wave front exits the bottom-right region of the current alignment matrix, it may enter, immediately, or after crossing a minimum gap such as one cell or three cells, the top-right region of the next alignment matrix. In this manner, the horizontal wave front sweep out of one alignment matrix can be the same motion as the horizontal wave front sweep into the next alignment matrix. Doing this may include the reference and query bases of the next alignment to be fed into those scoring cells crossing into the next alignment matrix, and can reduce the average time consumed per alignment by the time to execute a number of wave front steps almost equal to the number of alignment cells in the wave front, e.g., such as 64 or 63 or 61 steps, which may take e.g. 64 or 63 or 61 clock cycles.

The number of scoring cells in an implementation of an alignment wave front may be selected to balance various factors, including alignment accuracy, maximum insertion and deletion length, area, cost, and power consumption of the digital logic, clock frequency of the aligner logic, and performance of the overall integrated circuit. A long wave front is desirable for good alignment accuracy, especially because a wave front of N cells can align across indels approximately N nucleotides long, or slightly shorter. But a longer wave front costs more logic, which consumes more power. Further, a longer wave front can increase wire routing complexity and delays on the integrated circuit, leading to lower maximum clock frequencies, reducing net aligner performance. Further still, if an integrated circuit has a limited size or power consumption, using a longer wave front may require less logic to be implemented on the IC elsewhere, such as replicating fewer entire wave fronts, or other aligner or mapper logic components, this decreasing net performance of the IC. In one particular embodiment, 64 scoring cells in the wave front may give an acceptable balance of these factors.

Accordingly, where the wave front is X, e.g., 64 scoring cells wide, the scored band in the alignment matrix will likewise be 64 cells wide (measured diagonally). The matrix cells outside of this band do not necessarily need to be processed nor their scores calculated, provided that the optimal (best-scoring) alignment path through the matrix stays within the scored band. In a relatively small matrix, therefore, used to align relatively short reads, e.g., 100 nucleotide or 250 nucleotide reads, this may be a safe assumption, such as if the wave front sweeps a perfect diagonal along the predicted aligned position of the read.

However, in some instances, such as in a large alignment matrix used to align long reads, e.g., 1000 or 10,000 or 100,000 nucleotides, there may be a substantial risk of accumulated indels causing the true alignment to deviate from a perfect diagonal, sufficiently far in aggregate that it may escape the scored band. In such instances, it may be useful to steer the wave front so that the highest set of scores will be near the center of the wave front. Consequently, as the wave front performs its sweep, if the highest scores start to move one way or the other, e.g., left to right, the wave front is shifted over to track this move. For instance, if the highest scores are observed in scoring cells substantially up-right from the center of the wave front, the wave front may be steered some distance straight rightward by successive horizontal steps, until the highest scores return near the center of the wave front.

Accordingly, an automatic steering mechanism may be implemented in the wave front control logic, to determine a steering target position within the length of the wave front, based on current and past scores observed in the wave front scoring cells, and to steer the wave front toward this target if it is off-center. More particularly, the position of the maximum score in the most recently scored wave front position may be used as a steering target. This is an effective method in some instances. In some instances, however, the maximum score position may be a poor steering target. For instance, with some combinations of alignment scoring parameters, when a long indel commences, and scores accordingly begin to decline, a pattern of two higher-score peaks with a lower-score valley between them can form along the wave front, the two peaks drifting apart as the indel continues.

Because it cannot be easily determined whether the event in progress is an insertion or a deletion, it is important for the wave front to track diagonally until successful matching commences again, either some distance to the right for a deletion, or some distance downward for an insertion. But if two spreading score peaks form, one of them is likely to be slightly higher than the other, and could pull the automatic steering in that direction, causing the wave front to lose the alignment if the actual indel was in the other direction. A more robust method, therefore, may be to subtract a delta value from the maximum observed wave front score to determine a threshold score, identify the two extreme scoring cells at least equal to this threshold score, and use the midpoint between these extreme cells as the steering target. This will tend to guide diagonally between a two-peak score pattern. Other steering criteria can readily be applied, however, which serve to keep higher scores near the center of the wave front. If there is a delayed reaction between obtaining scores from wave front scoring cells and making a corresponding steering decision, hysteresis can advantageously be applied to compensate for steering decisions made in the intervening time, to avoid oscillating patterns of automatic wave front steering.

One or more of such alignment procedures may be performed by any suitable alignment algorithm, such as a Needleman-Wunsch alignment algorithm and/or a Smith-Waterman alignment algorithm that may have been modified to accommodate the functionality herein described. In general both of these algorithms and those like them basically perform, in some instances, in a similar manner. For instance, as set forth above, these alignment algorithms typically build the virtual array in a similar manner such that, in various instances, the horizontal top boundary may be configured to represent the genomic reference sequence, which may be laid out across the top row of the array according to its base pair composition. Likewise, the vertical boundary may be configured to represent the sequenced and mapped query sequences that have been positioned in order, downwards along the first column, such that their nucleotide sequence order is generally matched to the nucleotide sequence of the reference to which they mapped. The intervening cells may then be populated with scores as to the probability that the relevant base of the query at a given position is positioned at that location relative to the reference. In performing this function, a swath may be moved diagonally across the matrix populating scores within the intervening cells and the probability for each base of the query being in the indicated position may be determined.

With respect to a Needleman-Wunsch alignment function, which generates optimal global (or semi-global) alignments, aligning the entire read sequence to some segment of the reference genome, the wave front steering may be configured such that it typically sweeps all the way from the top edge of the alignment matrix to the bottom edge. When the wave front sweep is complete, the maximum score on the bottom edge of the alignment matrix (corresponding to the end of the read) is selected, and the alignment is back-traced to a cell on the top edge of the matrix (corresponding to the beginning of the read). In various of the instances disclosed herein, the reads can be any length long, can be any size, and there need not be extensive read parameters as to how the alignment is performed, e.g., in various instances, the read can be as long as a chromosome. In such an instance, however, the memory size and chromosome length may be limiting factor.

With respect to a Smith-Waterman algorithm, which generates optimal local alignments, aligning the entire read sequence or part of the read sequence to some segment of the reference genome, this algorithm may be configured for finding the best scoring possible based on a full or partial alignment of the read. Hence, in various instances, the wave front-scored band may not extend to the top and/or bottom edges of the alignment matrix, such as if a very long read had only seeds in its middle mapping to the reference genome, but commonly the wave front may still score from top to bottom of the matrix. Local alignment is typically achieved by two adjustments. First, alignment scores are never allowed to fall below zero (or some other floor), and if a cell score otherwise calculated would be negative, a zero score is substituted, representing the start of a new alignment. Second, the maximum alignment score produced in any cell in the matrix, not necessarily along the bottom edge, is used as the terminus of the alignment. The alignment is backtraced from this maximum score up and left through the matrix to a zero score, which is used as the start position of the local alignment, even if it is not on the top row of the matrix.

In view of the above, there are several different possible pathways through the virtual array. In various embodiments, the wave front starts from the upper left corner of the virtual array, and moves downwards towards identifiers of the maximum score. For instance, the results of all possible aligns can be gathered, processed, correlated, and scored to determine the maximum score. When the end of a boundary or the end of the array has been reached and/or a computation leading to the highest score for all of the processed cells is determined (e.g., the overall highest score identified)

then a backtrace may be performed so as to find the pathway that was taken to achieve that highest score.

For example, a pathway that leads to a predicted maximum score may be identified, and once identified an audit may be performed so as to determine how that maximum score was derived, for instance, by moving backwards following the best score alignment arrows retracing the pathway that led to achieving the identified maximum score, such as calculated by the wave front scoring cells. This backwards reconstruction or backtrace involves starting from a determined maximum score, and working backward through the previous cells navigating the path of cells having the scores that led to achieving the maximum score all the way up the table and back to an initial boundary, such as the beginning of the array, or a zero score in the case of local alignment.

During a backtrace, having reached a particular cell in the alignment matrix, the next backtrace step is to the neighboring cell, immediately leftward, or above, or diagonally up-left, which contributed the best score that was selected to construct the score in the current cell. In this manner, the evolution of the maximum score may be determined, thereby figuring out how the maximum score was achieved. The backtrace may end at a corner, or an edge, or a boundary, or may end at a zero score, such as in the upper left hand corner of the array. Accordingly, it is such a back trace that identifies the proper alignment and thereby produces the CIGAR strand readout, e.g., 3M, 2D, 8M, 41, 16M, etc., that represents how the sample genomic sequence derived from the individual, or a portion thereof, matches to, or otherwise aligns with, the genomic sequence of the reference DNA.

Accordingly, once it has been determined where each read is mapped, and further determined where each read is aligned, e.g., each relevant read has been given a position and a quality score reflecting the probability that the position is the correct alignment, such that the nucleotide sequence for the subject's DNA is known, then the order of the various reads and/or genomic nucleic acid sequence of the subject may be verified, such as by performing a back trace function moving backwards up through the array so as to determine the identity of every nucleic acid in its proper order in the sample genomic sequence. Consequently, in some aspects, the present disclosure is directed to a back trace function, such as is part of an alignment module that performs both an alignment and a back trace function, such as a module that may be part of a pipeline of modules, such as a pipeline that is directed at taking raw sequence read data, such as form a genomic sample form an individual, and mapping and/or aligning that data, which data may then be sorted.

To facilitate the backtrace operation, it is useful to store a scoring vector for each scored cell in the alignment matrix, encoding the score-selection decision. For classical Smith-Waterman and/or Needleman-Wunsch scoring with linear gap penalties, the scoring vector can encode four possibilities, which may optionally be stored as a 2-bit integer from 0 to 3, for example: 0=new alignment (null score selected); 1=vertical alignment (score from the cell above selected, modified by gap penalty); 2=horizontal alignment (score from the cell to the left selected, modified by gap penalty); 3=diagonal alignment (score from the cell up and left selected, modified by nucleotide match or mismatch score). Optionally, the computed score(s) for each scored matrix cell may also be stored (in addition to the maximum achieved alignment score which is standardly stored), but this is not generally necessary for backtrace, and can consume large amounts of memory. Performing backtrace then becomes a matter of following the scoring vectors; when the backtrace has reached a given cell in the matrix, the next backtrace step is determined by the stored scoring vector for that cell, e.g.: 0=terminate backtrace; 1=backtrace upward; 2=backtrace leftward; 3=backtrace diagonally up-left.

Such scoring vectors may be stored in a two-dimensional table arranged according to the dimensions of the alignment matrix, wherein only entries corresponding to cells scored by the wave front are populated. Alternatively, to conserve memory, more easily record scoring vectors as they are generated, and more easily accommodate alignment matrices of various sizes, scoring vectors may be stored in a table with each row sized to store scoring vectors from a single wave front of scoring cells, e.g. 128 bits to store 64 2-bit scoring vectors from a 64-cell wave front, and a number of rows equal to the maximum number of wave front steps in an alignment operation.

Additionally, for this option, a record may be kept of the directions of the various wavefront steps, e.g., storing an extra, e.g., 129th, bit in each table row, encoding e.g., 0 for vertical wavefront step preceding this wavefront position, and 1 for horizontal wavefront step preceding this wavefront position. This extra bit can be used during backtrace to keep track of which virtual scoring matrix positions the scoring vectors in each table row correspond to, so that the proper scoring vector can be retrieved after each successive backtrace step. When a backtrace step is vertical or horizontal, the next scoring vector should be retrieved from the previous table row, but when a backtrace step is diagonal, the next scoring vector should be retrieved from two rows previous, because the wavefront had to take two steps to move from scoring any one cell to scoring the cell diagonally right-down from it.

In the case of affine gap scoring, scoring vector information may be extended, e.g. to 4 bits per scored cell. In addition to the e.g. 2-bit score-choice direction indicator, two 1-bit flags may be added, a vertical extend flag, and a horizontal extend flag. According to the methods of affine gap scoring extensions to Smith-Waterman or Needleman-Wunsch or similar alignment algorithms, for each cell, in addition to the primary alignment score representing the best-scoring alignment terminating in that cell, a 'vertical score' should be generated, corresponding to the maximum alignment score reaching that cell with a final vertical step, and a 'horizontal score' should be generated, corresponding to the maximum alignment score reaching that cell with a final horizontal step; and when computing any of the three scores, a vertical step into the cell may be computed either using the primary score from the cell above minus a gap-open penalty, or using the vertical score from the cell above minus a gap-extend penalty, whichever is greater; and a horizontal step into the cell may be computed either using the primary score from the cell to the left minus a gap-open penalty, or using the horizontal score from the cell to the left minus a gap-extend penalty, whichever is greater. In cases where the vertical score minus a gap extend penalty is selected, the vertical extend flag in the scoring vector should be set, e.g. '1', and otherwise it should be unset, e.g. '0'. In cases when the horizontal score minus a gap extend penalty is selected, the horizontal extend flag in the scoring vector should be set, e.g. '1', and otherwise it should be unset, e.g. '0'. During backtrace for affine gap scoring, any time backtrace takes a vertical step upward from a given cell, if that cell's scoring vector's vertical extend flag is set, the following backtrace step must also be vertical, regardless of the scoring vector for the cell above. Likewise, any time backtrace takes a horizontal step leftward from a given cell, if that cell's scoring vector's horizontal extend flag is set, the following backtrace step must also be horizontal, regardless of the scoring vector for the cell to the left.

Accordingly, such a table of scoring vectors, e.g. 129 bits per row for 64 cells using linear gap scoring, or 257 bits per row for 64 cells using affine gap scoring, with some number NR of rows, is adequate to support backtrace after concluding alignment scoring where the scoring wavefront took NR steps or fewer. For example, when aligning 300-nucleotide reads, the number of wavefront steps required may always be less than 1024, so the table may be $257 \times 1024$ bits, or approximately 32 kilobytes, which in many cases may be a reasonable local memory inside the IC. But if very long reads are to be aligned, e.g. 100,000 nucleotides, the memory requirements for scoring vectors may be quite large, e.g. 8 megabytes, which may be very costly to include as local memory inside the IC. For such support, scoring vector information may be recorded to bulk memory outside the IC, e.g. DRAM, but then the bandwidth requirements, e.g. 257 bits per clock cycle per aligner module, may be excessive, which may bottleneck and dramatically reduce aligner performance.

Accordingly, it is desirable to have a method for disposing of scoring vectors before completing alignment, so their storage requirements can be kept bounded, e.g. to perform incremental backtraces, generating incremental partial CIGAR strings for example, from early portions of an alignment's scoring vector history, so that such early portions of the scoring vectors may then be discarded. The challenge is that the backtrace is supposed to begin in the alignment's terminal, maximum scoring cell, which unknown until the alignment scoring completes, so any backtrace begun before alignment completes may begin from the wrong cell, not along the eventual final optimal alignment path.

Accordingly, a method is given for performing incremental backtrace from partial alignment information, e.g. comprising partial scoring vector information for alignment matrix cells scored so far. From a currently completed alignment boundary, e.g., a particular scored wave front position, backtrace is initiated from all cell positions on the boundary. Such backtrace from all boundary cells may be performed sequentially, or advantageously, especially in a hardware implementation, all the backtraces may be performed together. It is not necessary to extract alignment notations, e.g., CIGAR strings, from these multiple backtraces; only to determine what alignment matrix positions they pass through during the backtrace. In an implementation of simultaneous backtrace from a scoring boundary, a number of 1-bit registers may be utilized, corresponding to the number of alignment cells, initialized e.g., all to '1's, representing whether any of the backtraces pass through a corresponding position. For each step of simultaneous backtrace, scoring vectors corresponding to all the current '1's in these registers, e.g. from one row of the scoring vector table, can be examined, to determine a next backtrace step corresponding to each '1' in the registers, leading to a following position for each '1' in the registers, for the next simultaneous backtrace step.

Importantly, it is easily possible for multiple '1's in the registers to merge into common positions, corresponding to multiple of the simultaneous backtraces merging together onto common backtrace paths. Once two or more of the simultaneous backtraces merge together, they remain merged indefinitely, because henceforth they will utilize scoring vector information from the same cell. It has been observed, empirically and for theoretical reasons, that with high probability, all of the simultaneous backtraces merge into a singular backtrace path, in a relatively small number of backtrace steps, which e.g. may be a small multiple, e.g. 8, times the number of scoring cells in the wavefront. For example, with a 64-cell wavefront, with high probability, all backtraces from a given wavefront boundary merge into a single backtrace path within 512 backtrace steps. Alternatively, it is also possible, and not uncommon, for all backtraces to terminate within the number, e.g. 512, of backtrace steps.

Accordingly, the multiple simultaneous backtraces may be performed from a scoring boundary, e.g. a scored wavefront position, far enough back that they all either terminate or merge into a single backtrace path, e.g. in 512 backtrace steps or fewer. If they all merge together into a singular backtrace path, then from the location in the scoring matrix where they merge, or any distance further back along the singular backtrace path, an incremental backtrace from partial alignment information is possible. Further backtrace from the merge point, or any distance further back, is commenced, by normal singular backtrace methods, including recording the corresponding alignment notation, e.g., a partial CIGAR string. This incremental backtrace, and e.g. partial CIGAR string, must be part of any possible final backtrace, and e.g. full CIGAR string, that would result after alignment completes, unless such final backtrace would terminate before reaching the scoring boundary where simultaneous backtrace began, because if it reaches the scoring boundary, it must follow one of the simultaneous backtrace paths, and merge into the singular backtrace path, now incrementally extracted.

Therefore, all scoring vectors for the matrix regions corresponding to the incrementally extracted backtrace, e.g., in all table rows for wave front positions preceding the start of the extracted singular backtrace, may be safely discarded. When the final backtrace is performed from a maximum scoring cell, if it terminates before reaching the scoring boundary (or alternatively, if it terminates before reaching the start of the extracted singular backtrace), the incremental alignment notation, e.g. partial CIGAR string, may be discarded. If the final backtrace continues to the start of the extracted singular backtrace, its alignment notation, e.g., CIGAR string, may then be grafted onto the incremental alignment notation, e.g., partial CIGAR string.

Furthermore, in a very long alignment, the process of performing a simultaneous backtrace from a scoring boundary, e.g., scored wave front position, until all backtraces terminate or merge, followed by a singular backtrace with alignment notation extraction, may be repeated multiple times, from various successive scoring boundaries. The incremental alignment notation, e.g. partial CIGAR string, from each successive incremental backtrace may then be grafted onto the accumulated previous alignment notations, unless the new simultaneous backtrace or singular backtrace terminates early, in which case accumulated previous alignment notations may be discarded. The eventual final backtrace likewise grafts its alignment notation onto the most recent accumulated alignment notations, for a complete backtrace description, e.g. CIGAR string.

Accordingly, in this manner, the memory to store scoring vectors may be kept bounded, assuming simultaneous backtraces always merge together in a bounded number of steps, e.g. 512 steps. In rare cases where simultaneous backtraces fail to merge or terminate in the bounded number of steps, various exceptional actions may be taken, including failing the current alignment, or repeating it with a higher bound or with no bound, perhaps by a different or traditional method, such as storing all scoring vectors for the complete alignment, such as in external DRAM. In a variation, it may be reasonable to fail such an alignment, because it is extremely rare, and even rarer that such a failed alignment would have been a best-scoring alignment to be used in alignment reporting.

In an optional variation, scoring vector storage may be divided, physically or logically, into a number of distinct blocks, e.g. 512 rows each, and the final row in each block may be used as a scoring boundary to commence a simultaneous backtrace. Optionally, a simultaneous backtrace may be required to terminate or merge within the single block, e.g. 512 steps. Optionally, if simultaneous backtraces merge in fewer steps, the merged backtrace may nevertheless be continued through the whole block, before commencing an extraction of a singular backtrace in the previous block. Accordingly, after scoring vectors are fully written to block N, and begin writing to block N+1, a simultaneous backtrace may commence in block N, followed by a singular backtrace and alignment notation extraction in block N−1. If the speed of the simultaneous backtrace, the singular backtrace, and alignment scoring are all similar or identical, and can be performed simultaneously, e.g., in parallel hardware in an IC, then the singular backtrace in block N−1 may be simultaneous with scoring vectors filling block N+2, and when block N+3 is to be filled, block N−1 may be released and recycled.

Thus, in such an implementation, a minimum of 4 scoring vector blocks may be employed, and may be utilized cyclically. Hence, the total scoring vector storage for an aligner module may be 4 blocks of 257×512 bits each, for example, or approximately 64 kilobytes. In a variation, if the current maximum alignment score corresponds to an earlier block than the current wavefront position, this block and the previous block may be preserved rather than recycled, so that a final backtrace may commence from this position if it remains the maximum score; having an extra 2 blocks to keep preserved in this manner brings the minimum, e.g., to 6 blocks. In another variation, to support overlapped alignments, the scoring wave front crossing gradually from one alignment matrix to the next as described above, additional blocks, e.g. 1 or 2 additional blocks, may be utilized, e.g., 8 blocks total, e.g., approximately 128 kilobytes. Accordingly, if such a limited number of blocks, e.g., 4 blocks or 8 blocks, is used cyclically, alignment and backtrace of arbitrarily long reads is possible, e.g., 100,000 nucleotides, or an entire chromosome, without the use of external memory for scoring vectors.

As described above, certain regions of DNA are genes, which encode for proteins or functional RNA. Each gene exists on a single strand of the double-stranded DNA double-helix, often as a series of exons (coding segments) separated by introns (non-coding segments). Some genes have only a single exon, but most have several exons (separated by introns), and some have hundreds of exons or thousands of exons. Exons are commonly a few hundred nucleotides long, but may be as short as a single nucleotide or as long as tens or hundreds of thousands. Introns are commonly thousands of nucleotides long, and some exceed a million nucleotides.

A gene may be transcribed by RNA polymerase enzymes into messenger RNA (mRNA) or other types of RNA. The immediate RNA transcript is a single-stranded copy of the gene, except that DNA thymine (T) bases are transcribed into RNA Uracil (U) bases. But immediately after this copy is produced, the intron-copies are usually spliced out by spliceosomes, leaving the exon-copies concatenated together at "splice junctions" (which are not thereafter directly evident). RNA splicing does not always occur in the same way. Sometimes one or more exons are spliced out, and sometimes splice junctions do not fall on the most common intron/exon boundaries. Thus, a single gene can produce multiple different transcribed RNA segments, a process sometimes known as alternative splicing.

Spliced mRNA is transported (in eukaryotes) out of the cellular nucleus to a ribosome, which decodes it into a protein, each group of three RNA nucleotides (codon) coding for one amino acid. In this manner, genes in DNA serve as original instructions for the manufacture of proteins.

RNA splicing tends to occur at consistent exon/intron boundaries, which are characterized by typical sequence content, especially near the ends of the introns. In particular, the first two and last two bases of an intron, called an intron motif, follow one of only 3 sequences, the "canonical" intron motifs, the vast majority of the time (roughly 99.9%). The most common canonical intron motif is "GT/AG", meaning the first two bases of the intron are 'G', 'T', and the last two bases are 'A', 'G'. The GT/AG motif occurs roughly 98.8% of the time. The other canonical intron motifs are GC/AG, occurring roughly 1.0% of the time, and AT/AC, occurring roughly 0.1% of the time. These canonical motifs and their prevalence rates are reasonably consistent across species, but may not be universal.

Not all genes are transcribed, and those which are may be transcribed at different rates. Many factors can influence whether a given gene is transcribed into RNA, and how often. Some of these factors are inherited, some vary by cell specialization from one tissue to another, and some vary over time with environmental conditions or diseases. Therefore, two cells with exactly the same DNA may produce quite different types and quantities of proteins and functional RNA. Because of this, sequencing (reading) the RNA present in one or more cells provides different information from sequencing the DNA. A more complete picture of cellular condition and activity is provided by combining DNA sequencing and RNA sequencing.

Whole-transcriptome RNA sequencing is commonly performed by first selecting the target RNA, such as protein-coding RNA, then using reverse-transcriptase enzymes to convert the RNA segments back into strands of complementary DNA (cDNA). This DNA can be amplified with polymerase chain reaction (PCR) and/or fragmented into a desired distribution of sequence lengths. Then, the DNA fragments are sequenced with a DNA sequencer, such as a "shotgun" next-generation sequencer.

The resulting DNA reads are either reverse-complemented or forward copies of the original RNA strands, except that 'U's are replaced again with 'T's. With some library preparation and sequencing protocols, the orientation of the sequenced DNA strands relative to the original RNA may be maintained or flagged; but in common protocols, approximately 50% of the sequenced DNA will be reverse-complemented relative to the original RNA, with no direct indication of orientation (although there are indirect indications).

The DNA reads from RNA-seq protocols are different from whole-genome or whole-exome DNA sequencing in other ways. First, aside from contaminants, only transcribed RNA gets sequenced, so non-coding DNA and inactive genes do not generally appear. Second, the quantity of sequenced reads corresponding to various genes is related to the biological transcription rates of those genes. Third, due to intron splicing, the RNA-seq reads tend to skip over intron (non-coding) segments within genes.

RNA-seq reads are usually processed quite differently from DNA reads. Although both types of reads are typically mapped and aligned to a reference genome, the techniques of DNA and RNA mapping and alignment differ (see next section). After mapping and alignment, reads are commonly sorted by their mapped reference positions, for both DNA and RNA. Duplicate marking, which is optional for DNA processing, is not commonly used for RNA-seq data.

After this, DNA reads are commonly processed by a variant caller, to identify differences between the sampled DNA and the reference genome. RNA-seq reads are not commonly used for variant calling, although this is occasionally done. More commonly, aligned and sorted RNA reads are analyzed to determine which genes were expressed in what relative quantities, or which of various alternatively-spliced transcripts were produced in what relative quantities. This analysis commonly involves counting how many reads align to various genes, exons, etc., and may also involve transcript assembly (reference-based or de novo) to infer from relatively short RNA-seq reads how the longer RNA transcripts were likely spiced from the DNA.

Gene, exon, or transcript expression analysis is often extended to differential expression analysis, in which RNA-seq data from multiple samples, often from two or more different classes (sub-populations or phenotypes), is compared to quantify to what extent the genes, exon, or transcripts were expressed differently in different classes. This can include calculating the likelihood of a "null hypothesis" that corresponding expression levels were the same in the different classes, as well as estimating the "fold change" in expression between the samples, e.g. an 8- or 10- or more fold difference.

For many applications of DNA or RNA sequencing, an early processing stage is mapping and aligning reads to a reference genome. Normally, a DNA-oriented reference genome is used for both DNA and RNA sequencing, with 'T's not 'U's present, especially considering RNA-seq usually involved reverse-transcription into cDNA before sequencing. In the case of RNA-seq, as with whole-exome sequencing for that matter, the reference genome could conceivably be restricted to known coding regions, or to regions near coding DNA. However, it is common practice to map and align to a whole reference genome for the sampled organism.

The biggest difference required in an RNA-capable mapper/aligner is the ability to handle splice junctions. Because RNA-seq reads correspond to segments of transcribed and spliced RNA, commonly a read crosses one or more splice junctions. With respect to the DNA-oriented reference genome, this means a first portion of the read came from, and should map to, a first exon, a second portion of the read should map to a second exon, and so forth. For example, in a 100-base read, the first 40 bases may come from an exon at Chromosome 3 offset 2,345,000, and the remaining 60 bases may come from another exon 100,000 bases away, starting at chromosome offset 2,445,040. The alignment for such a read may be represented with mapping position Chr3: 2345000, and alignment CIGAR string "40M100000N60M", in which the "40M" and "60M" represent the portions aligned to respective exons, and the "100000N" represents a 100,000 base intron, these 100,000 reference bases being skipped by the read alignment. (Abstractly, this CIGAR string can be seen as equivalent to "40M100000D60M", where "100000D" represents a 100,000 base deletion from the reference, but it is customary to represent assumed spliced-out introns with 'N' versus deletions from assumed mutations or sequencing errors with 'D'.)

A practical difference between 'N' (intron) and 'D' (deletion) CIGAR events relates to their typical lengths. Deletion events are only rarely longer than 50 bases, and as such are usefully discovered and precisely positioned using Smith-Waterman or similar sequence alignment algorithms. Introns are often many thousands of bases long, or even a million bases or more, and it is not practical to use Smith-Waterman type aligners to detect such long alignment gaps. Therefore, the initial discovery of splice junctions is more the purview of "mapping", rather than "aligning".

The mapping problem is that each read may be partitioned into exon segments at unknown boundaries, and the various exon segments are likely to map to widely separated genomic locations, which need to be individually discovered. Techniques to map exon segments to their corresponding reference locations can be similar to techniques to map a whole read to one reference segment, but spliced mapping (the former) is more challenging because each exon may be significantly shorter than the whole read, and therefore contains much less information to guide the mapper. Indeed, a single exon may be as short as one (1) base, such as "G", and without additional information it is not practical to determine where in the million-base potential intron range that single base should map to.

In addition to discovering the mappings of two consecutive exon segments of a read, the splice junction between them needs to be precisely positioned, for at least some applications. Even though it may be clear that the first roughly 40 bases last roughly 60 bases of a 100-base read map to locations exactly 100,000 bases apart in Chromosome 3, it is often much less clear exactly how many read bases map to each of these two locations, or exactly where the splice junction, the boundary between the two exon segments, falls in the read. The correct CIGAR may plausibly be not just "40M100000N60M", for example, but "39M100000N61M" or "42M100000N58M". Precise positioning of splice junctions is more of an "aligning" operation, rather than "mapping".

An RNA-capable mapper may also usefully infer which of the two DNA strands the read sequence was transcribed from. In typical non-directional RNA-seq protocols, a given read may align either forward or reverse-complemented to the reference (with or without splice junctions). In paired-end RNA-seq protocols, commonly the two mate reads are oriented "FR" (forward/reverse), such that the mate mapping earlier in the reference genome is oriented forward, and the other mate is reverse-complemented. But in typical non-directional RNA-seq protocols, these mapping orientations do not determine which DNA strand carried the gene from which the RNA for this read was transcribed, in part because both orientations are produced when cDNA is amplified by PCR.

Finally, an RNA-capable mapper can usefully leverage an input database of "annotated" known splice junctions. All common human genes have been studied in detail, for example, and the splice junctions of most common and less common RNA transcripts annotated in genomic databases. This information is not 100% comprehensive; any individual sample is likely to exhibit some "novel" splicing not recorded in databases. But still, annotated splice junctions can serve as useful guides to enhance the accuracy of RNA-seq mapping and alignment. After mapping/aligning RNA-seq reads with or without annotated splice junctions, an advanced method is to detect the set of splice junctions observed in the aligned reads, with some criteria such as minimum number of alignments covering a splice junction, and use this set of empirically detected splice junctions as the annotated splice junctions for a second pass of RNA mapping/aligning. This can enhance sensitivity, by using splice junctions found in some reads to guide mapping of other reads.

Initial seed mapping for RNA-seq reads proceeds similarly to for DNA reads. A primary seed length K is chosen, ideally somewhat longer than the base-4 logarithm of the reference genome size to make seeds map fairly uniquely, such as K=18 or K=21 for a whole human genome reference. A hash table is constructed, populated with some or all seeds from the reference genome, the hash record in the hash table for each populated seed indicating its position and orientation in the reference. The hash table is loaded into memory accessible to the mapper engine hardware, such as DRAM modules on an FPGA board wired to pins on the FPGA instantiating the mapper engine hardware.

The mapper engine receives RNA reads originating from an RNA or DNA sequencer (often having been reverse-transcribed into cDNA before sequencing). From each read, the mapper extracts seeds of length K, ideally a sliding window of multiple overlapping K-base seeds, chosen with some pattern, such as starting at each base position, or starting at every even-numbered position. The mapper accesses the hash table in memory for each seed, obtaining a list of zero, one, or more positions in the reference genome where the seed matches. As with DNA mapping, seeds may be dynamically extended, accessing the hash table repeatedly with successively longer seeds when necessary to reduce a large set of matching positions to a reasonably small set, such as 16 or fewer matches. Seed matches are aggregated into seed chains, comprising seeds matching with the same orientation (forward or reverse-complemented with respect to the reference) along similar alignment diagonals.

For RNA-seq reads, an additional step by the mapper engine to refine initial seed mapping with anchored short seed mapping may be advantageous. For instance, as can be seen with respect to FIG. 1, RNA reads often cross one or more splice junctions, and a seed crossing a read's splice junction usually fails to map because its true image in the reference is split between two locations. When a read contains an exon shorter than the initial seed length K, or the read overlaps a longer exon by fewer bases than K, then seed mapping may fail to locate the corresponding reference position for that exon. Even when a whole or partial exon is somewhat longer than K bases, but shorter than the whole read, it can be vulnerable to seed mapping failure when it contains at least one edit (difference) from the reference, such as a single nucleotide polymorphism (SNP) or insertion or deletion (indel) from a mutation in the sample relative to the reference or from a sequencing error. For example, as can be seen with respect to FIG. 1, an example of a failure to map all exon segments with long (K-base) seeds is shown. For this reason, for good seed mapping sensitivity, it is desirable to query shorter seeds, which can fit in short exons or short read-overhangs of exons, or between edits.

It may be somewhat impractical to query a whole-genome hash table for seeds much shorter than a minimum length related to the base-4 logarithm of the reference genome size, because shorter seeds will tend to match very large numbers of locations. For example, with a whole human genome reference of size approximately 3.1 billion bases, the base 4 logarithm is approximately 15.8, and a minimum practical seed length to query may be K=16 or 18, with perhaps K=21 being a desirable setting; it is not practical to query K=11 base seeds, because each 11-base pattern will match an average of more than 700 reference locations.

However, after initial seed mapping with e.g. K=21 base seeds, it is possible to refine seed mapping with anchored seeds of a shorter length, such as L=11 bases. For anchored seed mapping, an anchored-seed hash table (which can be the same as the primary the same hash table, or a separate one) is populated with L-base seeds from the reference, which are keyed to specific regions of the reference, such as bins of some size, such as $2^{16}=65,536$ bases. Each reference region or bin is given a unique ID, such as its starting position in the reference genome divided by the bin size. L-base seeds within each reference bin are populated into the anchored-seed hash table, using a hash key formed from the L seed bases and the bin ID.

Figure 2:
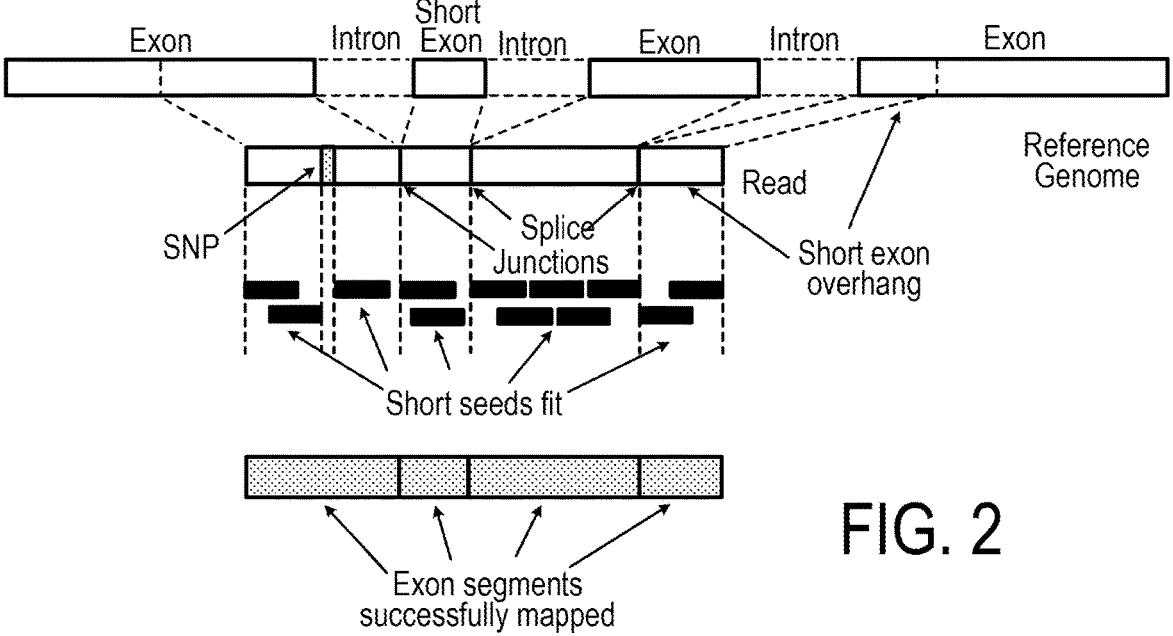
FIG. 2 depicts another exemplary RNA read, illustrating that short (L-base) seeds can be configured to more easily fit into short exons, and accommodate short exon overhangs, or exon segments cut by edits such as SNPs.

The mapper engine may query the anchored-seed hash table for any given L-base seed within any given bin, using a query hash key formed in the same manner from the L seed bases and the bin ID. Only L-base seed matches within that specific reference bin will be located by this query. Since the bin is much smaller than the whole reference genome, the short L-base seed has enough information to often map uniquely. For example, the base-4 logarithm of bin size 65,536 is 8, so L=11 (or 10, 12, etc.) is a practical anchored seed length to populate and query. As can be seen with respect to FIG. 2, short (L-base) seeds more easily fit into short exons, short exon overhangs, or exon segments cut by edits such as SNPs.

A key to make anchored seed mapping work is that mapper engine queries to the anchored-seed hash table are guided by the results of initial seed mapping. Initial matches with e.g. K=21 base seeds may not successfully map all exon segments of a read, but they are very likely to map at least one exon segment of each read, or of its paired end mate read. Given at least one K-base match within at least one exon segment in an RNA read or its mate, any other exon segments in the read which were not successfully mapped by K-base seeds are very likely to match relatively nearby in the reference genome.

For example, roughly 99% of human introns are shorter than 65,536 bases, so if one exon segment maps with K-base seeds to a given reference position, then other unmapped exon segments are likely to match within the same 65,536-base reference bin, or an adjacent bin. As can be seen with respect to FIG. 3, a search range can be defined, e.g. the bin size, or ½ or ¼ the bin size, or twice the bin size, and one or more reference bins within the search range of successfully-mapped K-base seeds can be queried in the anchored-seed hash table using L-base seeds. Thus, K-base seed matches serve as anchors for local searches with shorter L-base seeds. This is likely to find additional matches to previously unmapped exon segments of the read. In this manner, seed mapping sensitivity is improved for RNA reads.

Additionally, there are various ways that the mapper engine can utilize anchored short seed mapping. In one embodiment, after the mapper queries K-base initial seeds in the hash table and aggregates matches into seed chains, the mapper then extracts L-base seeds from the read, and queries these in nearby reference bins (within the selected search radius of current seed chains) to find additional matches to shorter L-base seeds, which the mapper engine then aggregates into additional seed chains, or adds to existing seed chains with similar alignment diagonals. In such an embodiment, it is advantageous for the anchored-seed hash table to be the same as the primary hash table, or for distinct primary and anchored-seed hash tables to reside in accessible memory simultaneously. In either case, to fit the hash table(s) with both K-base and L-base seeds in memory, roughly twice as much memory may be used, such as 64 GB of DRAM rather than 32 GB of DRAM, or alternatively, roughly half as many reference seeds of each length may be populated, such as 50% populated seed density rather than 100% populated seed density. To limit the number of anchored-seed hash table queries required, only the more promising initial seed chains may be used as anchors, and/or L-base seeds may be extracted from the read only from certain regions, such as regions where K-base seeds did not successfully map.

In another embodiment, mapping and/or alignment for a set of reads may be taken to completion in a first pass using K-base seeds only. The mapping/alignment results for each read may then be examined, such as by software outside the mapper engine, to determine which reads require refined mapping using anchored short seeds. One indication that may trigger anchored seed refinement is that first-pass alignments are clipped, especially with clipping near or greater than the short seed length L. Another indication triggering anchored seed refinement may be a substantial amount of mismatching observed within the first-pass alignments. Another indication triggering anchored seed refinement may be that paired-end mates did not both map successfully, or mapped far away from each other or in unexpected relative orientations. Advantageously, if one read is selected for short seed refinement, its paired-end mate is also selected. Advantageously, only a fraction of first-pass alignments may require short-seed refinement, such as 15% or 30%.

Figure 3:
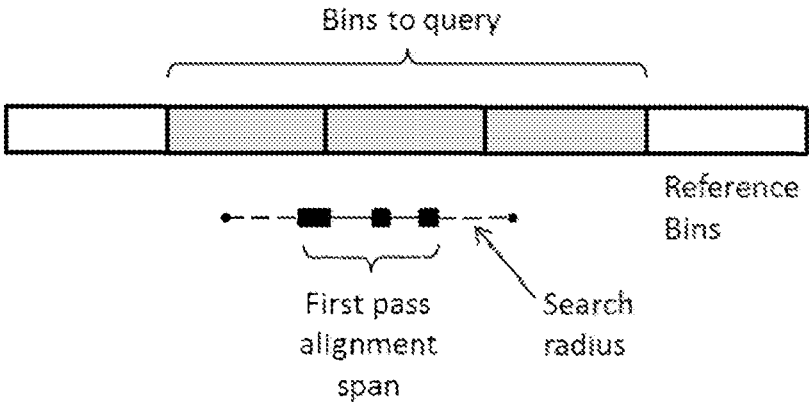
FIG. 3 depicts an exemplary reference bins that are within the search range of successfully-mapped K-base seeds that can be queried in the anchored-seed hash table, such as using L-base seeds.

For each read in the subset employing short-seed refinement, one or more reference bins to search may be selected, such as bins overlapping a search radius around first-pass alignment results for the read and/or its mate (See FIG. 3). Then a second mapping/alignment pass may be made over the subset of reads chosen for refinement. In the second pass, L-base seeds from each read may be queried in the anchored-seed hash table, keyed to the one or more selected reference bins for each read. Typically, for at least some of the reads selected for the second pass, improved mappings/alignments result, such as with higher alignment scores; the second-pass results can be retained in such cases when they are improved, or the first-pass results retained in other cases. Optionally, the primary hash table may be loaded into engine-accessible memory before the first mapping pass, and the anchored-seed hash table may be loaded before the second mapping pass, eliminating the need to fit both hash tables (or a single combined hash table) in memory at once, albeit both may be loaded at the same time, or to reduce reference seed population density to make both fit at once.

In some embodiments, the reference bins have configurable size, the search radius is configurable, and both the initial seed length (K) and anchored seed length (L) are configurable. In other embodiments, the reference bin size is a power of two. Exemplary preferred settings for human whole-transcriptome RNA-seq processing are K=21, L=11, reference bin size 2^16=65,536, and search radius 2^14=16, 384.

If annotated splice junctions are provided to the mapper engine, they can be leveraged to improve mapping sensitivity. The list of annotated junctions is loaded into memory accessible by the mapper engine. Advantageously, the annotated junctions may be formatted into a table easily accessed by the mapper engine, such as a table with an entry for each e.g. 1024-base bin of the reference, which either contains information about an intron with at least one endpoint in that bin, or points to a list (in space allocated after the initial table) of multiple intron descriptors. Each intron descriptor indicates the reference positions of both endpoints of an associated intron, and may also carry additional information such as which DNA strand the intron's gene is on, the intron's motif, and a measure of how frequently the splice junction occurs.

After seed mapping (initial seeds and/or anchored short seeds) and seed chain formation, the annotated junction table is accessed, at rows corresponding to the reference regions spanned by each seed chain, or regions near the ends of long seed chains. A list of introns with at least one endpoint nearby is obtained, and is compared with at least the seed chain for which the access was made. Each intron is discarded if it is not a possible or likely splice junction from the seed chain. In particular, by comparing the intron endpoint location in the reference with the seed chain endpoint in the reference and in the read, an effective location of the splice junction in the read is calculated. If this effective location is outside the bounds of the read, or overlaps the seed chain substantially (e.g. more than maxSpliceOlap=16 inside the seed chain's endpoint), or is too far outside the extents of the seed chain in the read (e.g. more than maxSpliceGap=150 bases outside the seed chain), then the annotated junction is discarded as unlikely to be relevant.

Each remaining intron descriptor is considered as a possible splice junction from one end of the associated seed chain. This information is utilized in two ways. First, the opposite end of the intron in the reference is taken as a likely location that an adjacent portion of the read should map to, even if that location was not discovered by seed mapping. Indeed, the most likely alignment diagonal at the opposite end of the intron is calculated exactly by adding or subtracting (depending on orientations) the intron length from the alignment diagonal at the corresponding end of the current seed chain. If that reference location and alignment diagonal are not consistent with any existing seed chain, then a new (pseudo) seed chain is fabricated starting at the reference location at the opposite end of the intron, and starting in the read at the corresponding position implied by the calculated alignment diagonal. In this manner, likely mapping locations of exon segments of the read are discovered without seeds mapping inside of them, by inferring their locations across introns from existing seed chains.

Second, annotated intron information is used to establish a known link between two seed chains, which represent adjacent exon segments in the read. Link information is recorded in one or both seed chain descriptors, identifying the other chain that it links to via an annotated splice junction. Furthermore, the precise position of the splice junction is known (assuming the annotated junction is correct), calculated by differences between annotated intron endpoints and seed chain alignment diagonals. This precise splice junction positioning is also recorded in one or both seed chain descriptors.

If multiple annotated splice junctions are discovered linking from the same seed chain, the link and splice junction position information can be recorded in various ways. For instance, each link between two chains may need to be recorded in only one of the two chains, so there may be no conflict if, for example, it is always recorded at the "destination" end of a link. One seed chain descriptor can have room to store multiple links, or have dynamic space for link information. Additionally, copies of existing seed chain descriptors can be made to hold alternate link information.

Annotated splice junction lookup may advantageously be iterated. Starting from one seed chain covering, for example, the first ⅓ of a read, an annotated splice junction may be discovered, linking to a previously undetected reference location, which is fabricated into a new seed chain. The annotated junction table may be accessed again for the newly fabricated seed chain, perhaps discovering that after a second ⅓ of the read, there is another known junction to another undiscovered reference location. Advantageously, the annotated junction table entries can indicate the distance (continuing in the same direction as the junction annotated) before the nearest other annotated junction is reached, within transcripts of the same gene, or in general. When this distance, measured after the calculated splice junction location in the read, extends beyond the end of the read, there is no need to access the annotated junction table again, because nothing will be found.

Within the mapper engine, seed matches with same orientation (forward or reverse-complement with respect to the reference) and similar alignment diagonals are aggregated into seed chains, with the intent that a single gapless or gapped alignment operation may later examine and score the alignment between the read and the reference for each seed chain. An alignment diagonal can be imagined as the diagonally-oriented alignment path covered by a matching seed, in the alignment rectangle formed with the read sequence on one axis and the reference sequence on the other axis; one representation as an integer may be calculated for forward alignments by subtracting a seed's position in the read from its position in the reference, and for reverse-complemented alignments by adding the seed's read position to its reference position.

When a read matches a segment of the reference exactly, such as positions 0 to 100 in the read matching positions 1,200,000 to 1,200,100 in the reference, all seeds normally match on the same diagonal, e.g. 1,200,000−0=1,200,100−100=1,200,000; a particular 21-base seed from bases 30 to 50 in the read would match bases 1,200,030 to 1,200,050 in the reference, also on the same diagonal 1,200,030−30=1,200,000. Seed matches with the same orientation and diagonal are normally included in the same seed chain, but also seeds on slightly different alignment diagonals may be included in the same seed chain, such as seeds whose diagonals differ by no more than 20 or no more than 50, or some more complex rule. Allowing some such tolerance for diagonal differences is useful because reads sometimes contain indels (insertions or deletions) with respect to the reference, and gapped alignment such as Smith-Waterman alignment in the aligner engine can resolve and score such indels for a single seed chain, as long as the indels are not too large, such as no more than 50 bases inserted or deleted.

But RNA-seq reads often cross splice junctions, at which a step from one read base to the next read base skips over a whole intron in the reference, which may be thousands of bases long, or even more than a million bases long. In such cases, seeds from one side of the splice junction in the read will map to the reference with dramatically different alignment diagonals from those on the other side of the splice junction; the diagonal-integer difference being equal to the length of the intron skipped, possibly thousands or more than a million. Such seeds may not be admitted to the same seed chain, because a gapped aligner cannot directly resolve such a long gap in the reference.

So, for RNA mapping, unlike for DNA, it is to be expected that the true alignment of a given read may comprise multiple seed chains, each seed chain corresponding to a different exon segment in the read. Each candidate alignment, therefore, may comprise a sequence of several seed chains. A next stage in the mapper engine is determining such candidate sequences of seed chains, known herein as scaffolds.

Each scaffold, as a sequence of one or more seed chains, has a physical interpretation as a piece-wise alignment of consecutive exon segments of the read to corresponding exon segments in the reference genome. As such, each seed chain in one scaffold should typically cover only a portion of the read, these portions progressing from the beginning of the read toward the end of the read along the sequence of seed chains; and the seed chains' corresponding reference segments should progress in a fixed direction through the reference, with intervening gaps corresponding to expected intron lengths. Each scaffold will be passed to the aligner engine, to resolve precise alignments and score them, and select the most likely candidate. But obtaining the list of scaffolds from the raw list of seed chains is challenging.

In practice, a seed mapping for a single RNA-seq read may yield from a small number of seed chains to dozens or more than a hundred seed chains. Given more than a hundred seed chains, the number of potential seed-chain sequences is astronomical. There is a problem, therefore, both of obtaining a reasonably short list of scaffolds for consideration in the aligner engine, and of determining that list of scaffolds from a given list of seed chains in a reasonable amount of time, so as not to slow down the mapper engine. A recursive method is presented for doing this efficiently.

First, it is very useful to sort seed chains in order of their covered positions in the read, such as in increasing order of the seed chains' start positions in the read. Seed chains may naturally be constructed in such an order, by querying seeds in the hash table in order from the beginning of the read to the end, and forming them into seed chains in that same order. But if this is not the case, or if the order is disturbed by subsequently modifying the list of seed chains with anchored-seed mapping or lookups of annotated splice junctions, then the seed chains should be sorted before scaffolding, such as using a "quicksort" or other sorting algorithm.

Next, rules are established under which one seed chain (B) is allowed to immediately follow another seed chain (A) in the same scaffold, establishing a seed-chain link from A to B. There is considerably flexibility in rules that can work well, but the rules should permit likely seed-chain links in a true-alignment scaffold, while excluding as many unlikely seed-chain links as possible. Here is a well-working set of rules, with various named parameters and good default values.

Criteria for seed chain B to follow seed chain A in a scaffold:
A & B have same orientation
(Gap between A & B in the read)=: gap-≤maxSpliceGap=150
(Overlap between A & B in the read)=: olap≤maxSpliceOlap=16
(Gap between A start and B start in the read)=: head>olap+(olapAdj=4)
(Gap between A end and B end in the read)=: tail≥olap+(olapAdj=4)
(A/B reference gap minus A/B read gap)=: intronLen≥minIntronLen=20
(A/B reference gap minus A/B read gap)=: intronLen-≤maxIntronLen=1,000,000
When annotated splice junctions are used, and an annotated link has been recorded between seed chains A and B, then they are always allowed to follow each other.

Here is a recursive algorithm to form multiple scaffolds:
Sort N seed chains by start position in the read, if necessary
Loop c0=0 to N−1
Skip c0 if already used inside any scaffold
Initialize last=0, scaf[0]=c0, start=c0+1, stack[0]=1, stack[1]=0, stackPos=0
Loop while last≥0
Loop c=start to N−1
If chain c can follow chain scaf[last]:
scaf[++last]=c
stack[last]=0 if stack[last]=c
Else if last>stackPos and chain c can follow chain scaf[last−1]:
stack[last]=c
Output scaffold scaf[0 . . . last]
Set stackPos=maximum in (0 . . . last) with stack[stackPos]>0
Set start=scaf[stackPos]+1
Set last=stackPos−1
Term and variable meanings in the algorithm:
"chain": index 0 . . . N−1 of a seed chain
scaf[ ]=scaffold under construction, each slot getting a chain 0 . . . N−1
c0=first chain in scaffold (slot 0)
last=end slot #(so far) in scaffold
start=first chain in search loop
stack[i]=highest-numbered alternative chain for scaf[i], or 0 if none. This represents the endpoint of the search for alternatives for scaf[i] after recursion backup.
stackPos=the target scaffold slot to replace via recursion backup. Observe that when the backup occurs, stack[stackPos] is baked in, and will not be updated until it is cleared.

This recursive search is implemented in physical logic within the mapper engine. There can be time available to execute this algorithm without significantly slowing down the engine, using standard methods of hardware parallelism. Specifically, a batch of seed chains for a given read can be buffered for scaffolding logic to process downstream in a processing pipeline, in parallel with seed mapping and chaining logic processing the next read.

Recursion may occasionally get carried away in practice, so it is necessary to limit it. A useful way to limit recursion while also limiting the set of scaffolds produced is to filter inferior scaffolds as they are produced. A useful scaffold filtering method is presented. For each scaffold, calculate its net coverage of the read, as a count of read bases covered by one or more seed chains in the scaffold. Higher coverage scaffolds are more likely to represent the true alignment. In particular, if the maximum read-coverage among all scaffolds formed (so far) is tracked, then scaffolds with a large coverage delta behind the maximum coverage are less likely to represent the true alignment.

Also, for each scaffold, calculate its net span in the reference genome, the distance between the outermost bases in the reference of the first and last seed chains in the scaffold. Scaffolds with very large reference spans are less likely to represent the true alignment. Combining these two measurements as follows is especially powerful for scaffold filtering: filter_metric=(max_coverage−coverage)+floor$(25*(\log_2(\text{ref\_span}+2^{13})-13)$. The constants 25 and 13 should be configurable parameters: rna-filt-ratio=25, and rna-span-log-min=13. Filter out all multi-chain scaffolds where this metric exceeds a configurable threshold, rna-max-covg-gap=150 for example. A threshold of 200 makes the filter considerably looser, and 100 considerably tighter.

This filter can be applied to a complete or incomplete set of finished scaffolds produced from the list of seed chains for a given read, by tracking or calculating the maximum coverage among all the scaffolds, and scanning the list of scaffolds, discarding those with filter_metric>rna-max-covg-gap.

Such a filter can also be applied as recursion pruning in the middle of scaffold formation. As each new seed chain is added to a scaffold, an updated reference span is noted, and also a potential coverage, calculated by subtracting coverage gaps within and preceding this seed chain from the read length. Using this partial span and potential coverage, if the metric would trigger filtering, then any longer scaffold using the current partial scaffold as a prefix would likewise be filtered, because reference span will only increase and potential coverage will only decrease. Therefore, all recursion retaining the current partial scaffold as a prefix can be skipped. Pruning recursion with the scaffold filter in this manner can significantly reduce the length of recursion to form a set of scaffolds from a long list of seed chains.

Performance of the recursive scaffold search can also be optimized. The recursive loops repeatedly scan the portions of the list of seed chains, and speed of the algorithm is therefore much better when the list of seed chains is shorter. But it is not actually necessary to execute the recursive algorithm on the entire list of seed chains, when some seed chains cannot possibly scaffold with other seed chains. One way to optimize is to detect "isolated" seed chains, which are located farther than maxIntronLen (e.g. 1,000,000 bases) from any other seed chain in the reference. Isolated seed chains can be emitted automatically as single-chain scaffolds, and removed from the list of seed chains before further scaffolding, thus shortening the list of seed chains scanned during recursion. Likewise, well-separated subsets of seed chains could be detected, such the subsets within each chromosome, or subsets separated by more than maxIntronLen in the reference, and the recursive scaffolding algorithm can be executed separately on each such subset, resulting in significantly reduced total execution time.

A first aligner engine step for each scaffold is to precisely position each splice junction, the boundary between two exon segments (represented by two corresponding seed chains in the scaffold). This is called "stitching" the exon segments together, or stitching the splice junctions. More precise stitching is still needed after seed mapping and scaffolding, because two successive seed chains by themselves may not make clear where the true boundary between them lies. For example, successive seed chains may be separated by some distance in the read, if seeds were unable to map immediately on one or both sides of the splice junction; or successive seed chains may overlap each other in the read, especially if the read sequence at the end of one exon matches the sequence at the beginning of the next exon. Even if successive seed chains abut with no gap or overlap, it is not guaranteed that the boundary between them lies at the true position of the splice junction.

Splice junction stitching is thus primarily an analysis to select the best stitching position between successive exon segments in the read, corresponding to the most likely splice junction position. Two factors are useful in determining this. The first factor is comparison of the read sequence with the left and right reference sequences, at the two exon-segment mapping locations in the reference genome. A given stitching position implies that read bases left of the stitch map to the left reference region, and reads bases right of the stitch map to the right reference region. As a potential stitch position is moved from left to right in the read, read bases switch their mapping as they are crossed, from the right reference region to the left one.

Figure 4:
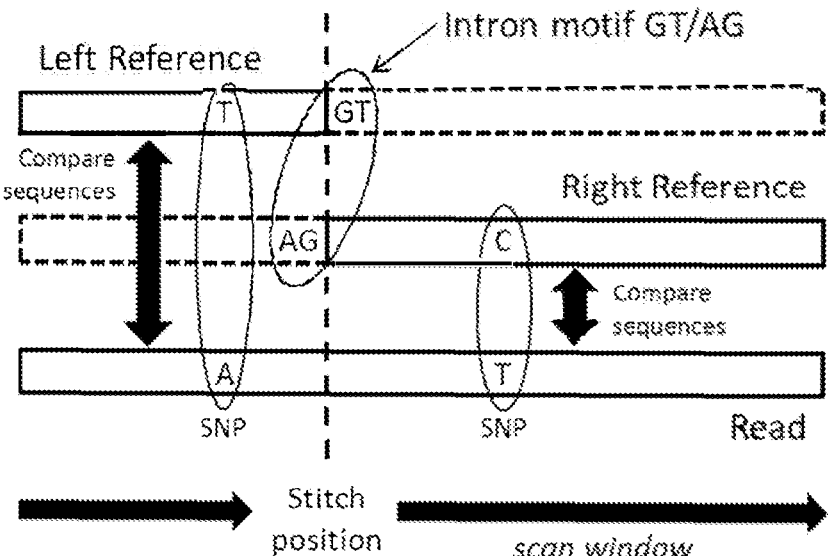
FIG. 4 depicts a comparison of read portions left and right of a stitch position.

As can be seen with respect to FIG. 4, the true splice junction position is likely to have good matching between the leftward portion of the read and the left reference region, and between the rightward portion of the read and the right reference region. The total number of mismatches (or SNPs) can be counted on both sides of a potential stitch position, by comparison with the corresponding reference region; and stitch positions with smaller SNP counts are more likely to be true. The comparison of read portions left and right of each stitch position is illustrated in FIG. 4.

This SNP counting is modeled efficiently by scanning stitch positions through a window of possible positions in the read, such as overlapping each of the two seed chains at most some distance, such as 48 bases. This scanning runs in the hardware aligner engine, for example, at a speed of one position per clock cycle. Each time the scan moves one step, such as from left to right, only one read base switches its mapping, from the right reference region to the left reference region. Therefore, the left sequence comparison either gains one SNP or remains the same, and the right sequence comparison either loses one SNP or remains the same; and thus the net SNP count changes by −1, 0, or +1. This incremental SNP count change for each step can be calculated by comparing one read base (the one crossed by the stitch position step) with two reference bases. If this incremental SNP count change is summed as steps are taken from left to right, then the current sum can be taken as a relative score, where the minimum score is best. Equivalently, each matching base can be given a positive match score, and each mismatching base a negative mismatching penalty; and the sum of incremental score changes should be maximized for the best stitch position.

Another factor is the intron motif implied by each stitch position. The intron motif is defined as the first two bases and last two bases of the skipped reference segment, or intron. Equivalently, the motif for any potential stitch position is formed from the first two bases after the left reference region and the last two bases before the right reference region, as shown in FIG. 4. This implied intron motif is dependent on the stitch position, and usually varies as the stitch position scans across the window of possible stitch positions. Certain "canonical" intron motifs occur much more commonly than others in natural RNA splicing. A stitch position that corresponds to a canonical intron motif is more likely to be the true splice junction position, especially if it is one of the more common canonical motifs.

A table of three canonical intron motifs in human RNA is shown in TABLE I. For each motif, its reverse-complement is also shown, because in most RNA-seq protocols the reads may map either forward or reverse-complemented with respect to the transcribed gene strand, so although only the "forward" canonical motif occurs in the original transcribed gene strand, its reverse-complement can appear in RNA-seq reads. For each canonical motif, and for the remaining class of non-canonical motifs, an approximate frequency in human RNA splicing is shown, along with a sample score penalty, which may be used, for example, with base matches scoring +1 and base mismatches scoring −4.

TABLE I

| Intron Motif | Reverse-Complement | Approx. Frequency | Score Penalty |
|---|---|---|---|
| GT/AG | CT/AC | 98.73% | 0 |
| GC/AG | CT/GC | 1.03% | 10 |

TABLE I-continued

| Intron Motif | Reverse-Complement | Approx. Frequency | Score Penalty |
|---|---|---|---|
| AT/AC | GT/AT | 0.11% | 15 |
| 250 non-canonical motifs | | 0.13% | 25 |

The splice stitching module accordingly scans a potential stitch position across a window of possible stitch locations, such as from left to right, summing incremental score changes due to bases switching which reference region they map to, and also subtracting at each potential stitch position an intron motif penalty according to the intron motif observed just after the left reference region and just before the right reference region, and chooses the maximum scoring position to stitch.

Additionally, certain special outcomes may be considered and scored. Stitching at the left edge or right edge of the window of possible stitch positions may be considered failure to stitch, and is likely to arise when one of the two reference regions is not a true mapping position for a read exon segment, such as when an annotated splice junction was followed, but turns out not to be true for this read. Left or right edge stitching can advantageously be given a scoring bonus, such as 25 in the same exemplary scoring scale, so that significant evidence of a true splice junction must appear for stitching to succeed.

Also, if an annotated splice junction was identified linking the two seed chains being stitched, the annotated junction is at a known position within the window of possible stitch positions. As one option, the stitching operation can be skipped, simply accepting the annotated junction's known position. As another option, the stitching operation can be performed, but the known position of the annotated junction may be given a score bonus, and/or may automatically be given the best available intron motif penalty, or a zero penalty. As another option, in lieu of an intron motif penalty, the known position of the annotated junction may be given a score bonus or penalty associated with the observed commonality or rarity of that splice junction as noted in annotation databases. If the annotated splice junction's known position is selected for stitching, then the stitched junction may be flagged as in agreement with an annotated junction, so this fact can be reported if this splice junction appears in the read's output alignment.

Selected stitch positions can be annotated into scaffolds in various manners. In a preferred embodiment, the constituent seed chains of a scaffold are edited to begin and end immediately adjacent to selected stitch positions.

Additionally, it is advantageous for the aligner engine to make larger scaffold edits in some circumstances, based on stitching results. If stitching fails, then the scaffold may be truncated, or split into two scaffolds at the failure point. Also, stitching may be attempted between non-adjacent seed chains in the scaffold, such as skipping a single seed chain. For example, for a scaffold containing seed chains 1, 2, 3, and 4, splice junction stitching should naturally be performed between the chains pairs (1,2), (2,3), and (3,4); but in addition, stitching may be attempted between chain pairs (1,3) and (2,4). If stitching from 1 to 3 scores better than stitching from 1 to 2 followed by 2 to 3, then seed chain 2 may be dropped from the scaffold.

Having determined precise splice junction positions in candidate scaffolds by stitching, corresponding complete alignments and alignment scores can be determined for each scaffold by use of a gapless aligner or gapped aligner (such as Smith-Waterman) module. For a scaffold with only a single seed chain, this is not significantly different than alignment for DNA reads, and the same hardware modules and methods can be used. For a scaffold with multiple seed chains, some further method is needed to obtain a complete, possibly spliced (containing intron operations) alignment.

One method by which complete spliced alignments can be determined is to separately align each exon segment the read, corresponding to each seed chain in the scaffold, to its corresponding reference segment, with a gapless and/or gapped aligner. This has disadvantages in when local (i.e. possibly clipped) alignments are desired. If individual exon segment alignments are produced without clipping, then they are not easily assembled together into a complete spliced alignment. If individual exon segment alignments are produced without clipping, then their alignment scores can be examined to determine if the best overall local alignment would clip off one or more entire exon segments, but appropriate clipping at arbitrary locations within the exon segments is not easily determined. It may therefore be expensive to produce both clipped and unclipped versions of each exon segment alignment to resolve these difficulties.

One method for determining complete spliced alignments for a multi-chain scaffold involves concatenating exon segments together before aligning. Each aligner module-gapless or gapped—may be fed two nucleotide sequences to align, a query (read) sequence and a reference sequence. The concatenated query sequence may be simply the entire read, which is the concatenation of its exon segments, with optional clipping of the beginning or end of the read if the first or last exon segment does not extend to the read beginning or end.

The concatenated reference sequence is obtained by fetching the reference genome segment that is the mapped image of each exon-segment seed chain, and concatenating these reference segments together. Note that for a given exon segment (seed chain), its reference segment may be a different length than its segment of the read, in a case where the leftmost seeds in the seed chain fell on a somewhat different alignment diagonal than the rightmost seeds; e.g., the seeds in the seed chain imply the presence of an indel. In such a case, a gapped aligner should be used.

Furthermore, for gapped alignment, the first and last exon segments of the reference sequence may be extended outward, for example extending the first exon segment with 50 preceding reference bases and the last exon segment with 50 following reference bases, to provide room for deletions within the first and last exon segments.

By concatenating the scaffold's exon segments from the read and reference, a single concatenated query sequence and a single concatenated reference sequence can be fed to the aligner module, which can therefore function in much the same manner for spliced RNA alignments as for unspliced (RNA or DNA) alignments. However, some further modifications are advantageous. First, to determine appropriate clipping of local alignments at any position within any exon segment, score penalties (or bonuses) may be applied at each splice junction the alignment crosses. In one embodiment, a score penalty for each splice junction is related to its intron motif and annotated splice junction status, and may be the same score penalty used in splice junction stitching.

Accordingly, an unannotated splice junction with rare or non-canonical intron motif may have a large associated score penalty, and one or more whole exon segments become more likely to get clipped from the spliced alignment in order to exclude such an unlikely splice junction, unless enough sequence matching occurs on both sides of the splice junction to serve as convincing evidence the splice junction is really present by overcoming its score penalty. In a preferred embodiment, the concatenated query and reference sequences each have a dummy base inserted between successive exon segments, and the appropriate score penalty for each splice junction is attached to its corresponding dummy base. This allows the splice junction score penalties to be included without specialized logic, and provides room for possible alignment clipping on either side of the splice junction dummy base.

Additionally, in various instances, for gapped alignment such as Smith-Waterman, it can be advantageous to force alignment paths to pass through the predetermined splice junctions. In other words, no alignment path should cross from one query exon segment to the next without simultaneously crossing from the corresponding reference exon segment to the next. One reason for this restriction is that only the properly synchronized splice junction will score properly, based on the intron motif determined during splice junction stitching.

Another reason is that the concatenated reference sequence has been formed using the precise reference exon segment boundaries corresponding to the selected stitch positions of each splice junction, so there are not additional reference bases for the gapped aligner to adjust splice junctions freely. Furthermore, to avoid difficult-to-interpret alignments (such as CIGAR strings with 'I' or 'D' operations adjacent to 'N' operations), it is desirable to require at least one query and reference base before each included splice junction to be "diagonally" aligned (query base aligned to reference base, as in a CIGAR 'M' operation), and at least one query and reference base after each included splice junction to be "diagonally" aligned.

To enforce these restrictions, the concatenated reference and query sequences are divided into zones, which are assigned identifiers or zone IDs, such as integer values. In one embodiment, one zone ID is assigned to each dummy base between exon segments, another zone ID to the last base of each exon segment preceding a splice junction (but not the final base of the concatenated sequence), and another zone ID to all the remaining bases of each exon segment.

For example, for a scaffold with three exon segments (seed chains) each 20 bases long, there could be 4 zone IDs: zone 1 for bases 1-19 of the first exon segment, zone 2 for base 20 of the first exon segment, zone 3 for the dummy base between the first and second exon segments, zone 4 for bases 1-19 of the second exon segment, zone 5 for base 20 of the second exon segment, zone 6 for the dummy base between the second and third exon segments, and zone 7 for bases 1-20 of the third exon segment. The same zone mapping applies to the both the concatenated query sequence and the concatenated reference sequence, bearing in mind that corresponding multi-base query and reference zones with the same zone ID may have different lengths due to indels in the seed chains. Then, in the gapless aligner, a scoring cell is modified to only allow a valid alignment score at the intersection between identical zone IDs, i.e. where the query zone ID matches the reference zone ID.

Accordingly, in various instances, the disclosure is directed to devices and methods for employing the same for the mapping and aligning of both DNA and/or RNA. As such, in particular instances, a hardwired digital logic circuit, e.g., an integrated circuit, is provided wherein the IC includes a configuration, such as a hardwired and/or pre-configured configuration, that is adapted for performing one or more steps in a DNA and/or RNA mapping and/or aligning operation. More particularly, the devices herein disclosed may be configured for performing various analysis on RNA, such as RNA analyses performed by one or more hardwired processing engines, or a subset of the same.

For instance, in some embodiments, a device and/or system for executing a DNA and/or sequence analysis pipeline on DNA and/or RNA sequence data, such as on a read of RNA-derived genomic data, is provided. In such an instance, a system may include one or more of: a memory, such as for storing one or more of a DNA and/or RNA reference sequence, e.g., RNA-derived genomic reference data, an index of the one or more DNA and/or RNA reference sequences, and a plurality of reads of genomic data, such as where each of the DNA and/or RNA reference sequences and the plurality of reads of sequence data include a sequence of nucleotides; and an integrated circuit, as disclosed herein. Particularly, the integrated circuit may be formed of a set of hardwired digital logic circuits that may be interconnected by a plurality of physical electrical interconnects. In such an instance, the one or more of the plurality of physical electrical interconnects may include a memory interface for the integrated circuit to access the memory. Further, the hardwired digital logic circuits may be arranged as a set of processing engines, such as where one or more of the processing engines are formed of a subset of the hardwired digital logic circuit, and are configured to perform at least one step in the DNA and/or RNA genomic sequence analysis pipeline on the plurality of reads of sequence data. It is to be noted that, in various instances, a read of RNA-derived genomic data, may indicate a read that has been obtained by sequencing sample RNA directly, or by sequencing some further product derived from sample RNA, such as reverse-transcribed cDNA, and the like, and may be referenced herein by an "RNA read" or "read of RNA data", which includes generality as to the source of the RNA data obtained.

More particularly, the set of processing engines may include a DNA and/or RNA mapping module, alignment module, sorting module, and/or a variant calling module, which may include an HMM module and/or a Smith-Waterman (SW) module. For instance, in a first configuration, a hardwired digital logic circuit, as herein disclosed, may be configured to access in the memory, via the memory interface, at least some of the DNA and/or RNA sequence of nucleotides in a selected read of the plurality of reads and the index of the one or more DNA and/or RNA reference sequences, and to map the selected RNA and/or DNA read to one or more segments of the one or more genetic reference sequences based on the index to produce a mapped read. In particular instances, such as with respect to RNA mapping, the RNA mapping module may be configured for performing one or more of anchored short seed mapping, annotated splice junction lookup, and/or seed chain scaffolding, and/or the like with respect to RNA mapping steps.

Likewise, in a second configuration of the hardwired digital logic circuits, an alignment module may be provided, wherein the alignment module is configured for accessing the one or more DNA and/or RNA reference sequences from the memory via the memory interface so as to align the mapped DNA and/or RNA reads, e.g., from the mapping module, to one or more positions in the one or more segments of the one or more DNA and/or RNA reference sequences to produce an aligned read. In particular instances, such as with respect to RNA alignment, the RNA alignment module may be configured for performing one or more of splice junction stitching, and/or spliced read alignment, and/or the like with respect to RNA alignment steps.

Accordingly, in various instances, a hardwired digital logic circuit may be provided wherein the digital logic circuit, or a subset thereof, includes a mapping and/or aligning module that may be adapted to include a set of configured, e.g., preconfigured, processing engines for performing one or more steps in an RNA analysis pipeline, such as where the one or more steps may include anchored short seed mapping, annotated splice junction lookup, seed chain scaffolding, splice junction stitching, spliced read alignment, and/or one or more other associated steps with performing mapping and/or aligning operations, such as in a genetic analysis pipeline.

Additionally, in some instances, a variant calling module may be provided, wherein the variant calling (VC) module is configured, such as in a third configuration of the hardwired digital logic circuits, to access the aligned DNA and/or RNA read and at least one of the reference sequences and perform one or more of the following steps. For instance, the VC module may be configured to compare the sequence of nucleotides in the aligned DNA and/or RNA reads to the sequence of nucleotides of the at least one genetic reference sequence, so as to determine one or more differences between the sequence of nucleotides in the aligned DNA/RNA read and the DNA/RNA sequence of nucleotides in the at least one genetic reference sequence, and to generate one or more variant calls representing the one or more differences. Further, with respect to the disclosed IC, one or more of the plurality of physical electrical interconnects may also include an output from the integrated circuit for communicating result data from the mapping module and/or the alignment module and/or variant calling module.

More particularly, an integrated circuit of the disclosure may include one or more sets of the hardwired digital logic circuits and/or subsets thereof, such as including first, second, third, or more subsets of configured, e.g., pre-configured, hardwired digital logic circuits that are configured as one or more processing engines for performing one or more discrete steps in a DNA and/or RNA sequence analysis pipeline. For instance, the hardwired digital logic circuit may include a first subset of digital logic circuits that is configured as a processing engine so as to receive a read of DNA and/or RNA data via one or more physical electrical interconnects. Additionally, a second subset of the hardwired digital logic circuits may be provided, where the subset is configured as a processing engine to extract a portion of the DNA or RNA read to generate a seed, such as where the seed represents a subset of the sequence of DNA or RNA nucleotides represented by the read, such as for performing one or more of anchored short seed mapping. One or more additional subsets of the digital logic circuits may be included such as a processing engine for annotated splice junction look up and/or for performing seed chain mapping. Further, subsets of the digital logic circuits may be included and configured as a processing engine such as for performing one or more alignment functions on RNA data, including a subset of digital logic circuits for performing a splice junction stitching operation and/or a spliced read alignment.

Accordingly, an integrated circuit of the disclosure may include one or more digital logic circuits, or a subset of the same, for performing one or more steps in anchored short seed mapping. As described herein in detail, short seed mapping may be performed for improving the sensitivity of database, e.g., hash-table based, seed mapping, such as by using longer-seed matches as anchors to guide localized searches with shorter seeds. It is useful for making hash-table based mapping work well for RNA reads, but is also useful for enhancing sensitivity with respect to DNA mapping. Particularly, initial seed mapping may use one or more K-base seeds derived from the read of genomic DNA and/or RNA data to query a first index, e.g., a hash-table based index, of the reference DNA and/or RNA genome. In such an instance, subsequent anchored short seed mapping may be performed such as by using L-base seeds (L<K) to query a second hash-table based index of a plurality of reference bins, for instance, where each of the plurality of reference bins may be a complete or an incomplete subset of the reference genome. This may also be useful where each K and/or L-base seed is used to separately query the first and/or second index, e.g., hash-table based index, so as to thereby target each of one or more anchor bins selected from the plurality of reference bins.

In such an instance, one or more data structures, e.g., a single or multiple data structure, may be provided wherein the data structure(s) may include a first index, e.g., hash-table based index, and may further include a second index, e.g., a second hash-table based index. Additionally, where one or more anchor bins are provided, the targeting of the one or more anchor bins may be included as a step in the processes. Consequently, such targeting may involve the inclusion of an identifier of each anchor bin in a hash key, such as a hash key used to query the first and/or second hash-table based indices. In some instances, the one or more anchor bins, such as for L-base seed queries, may be selected, e.g., inside the mapping engine, based on the matches found by the K-base seed queries. Accordingly, the mapping engine may be configured for performing an anchored short seed mapping operation before or after the outputting of match locations, such as where one or more of the anchor bins for L-base seed queries are selected inside or outside of the mapping engine based on match locations output by the mapping engine. In certain instances, the mapping engine may perform an anchored short seed mapping, where in a secondary mapping procedure may pass over at least a subset of the input reads.

Additionally, with respect to performing an alignment, the one or more anchor bins for K-base or L-base seed queries may be selected inside or outside the mapping engine, and may be based on alignments output by the aligning module, either in software or hardware, such as where the alignment engine receives match locations from the mapping engine. In such an instance, a subset of the input reads may be selected to include or exclude reads with sufficiently clipped alignments. In some instances, the subset of the input reads may be selected to include or exclude reads with sufficiently low scoring alignments. And in various other instances, the input reads may be paired-end reads, and the subset of the input reads may be selected to include or exclude pairs of reads lacking alignments in properly paired configurations.

Further, the mapping module for performing an RNA sequence analysis may include one or more processing engines that are configured for performing one or more annotated splice junction lookups. A splice junction lookup may be employed for improving the sensitivity of RNA specific read mapping. For instance, after mapping portions of the RNA read using an RNA reference index, e.g., which may or may not be a hash-table based index, a "database," or any other suitable form of data structure, such as in the same memory as the reference and/or index thereof, may be generated and/or queried. Specifically, the "database" may be generated based on the known and/or determined RNA splice junctions for the subject species, and may be accessed based on the mapped positions. It is to be noted that each known splice junction may represent a possibly long "intron" (up to 1 Mbp or longer) segment in the reference, such as where read alignments would commonly "jump" from one endpoint of the intron to the other.

Accordingly, the database may be accessed in such a manner as to retrieve known splice junctions that have one endpoint in, or near, each of the reference segments along portions of the read already mapped, but which may have another portion of the read that extends beyond the near intron endpoint. In such instances, this other portion of the read may then be tentatively assumed to continue matching the reference after jumping over the intron, even though prior mapping efforts may not have detected any such matching in that region. Later spliced alignment and scoring can then measure how well the read actually matches aligning over this splice junction. This method, therefore, may enhance the ability of the integrated circuit to detect likely spliced mappings of a read, in spite of obstacles, such as short exons, short exon overhangs, and/or edits (SNPs, etc.) blocking matching in a medium-length exon segment.

Consequently, a memory connectable to the integrated circuit may be provided where the memory contains an index of the reference genome and a list of annotated splice junctions within that reference genome. The mapping engine, therefore, may map a first portion of a read of RNA-derived genomic data to a matching location in the reference genome, such as by accessing the index of the reference using the first portion of the read. The mapping engine may then access the list of annotated splice junctions, and retrieve an intron descriptor, such as where the intron descriptor includes a first endpoint and a second endpoint in the reference genome, for instance, where the first endpoint is within a limited distance of the matching location in the reference genome.

The mapping engine may then map a second portion of the read of RNA-derived genomic data to an inferred location in the reference genome, such as where the inferred location in the reference genome may be adjacent to the second endpoint in the reference genome of the intron descriptor. The mapper will then output the mapped locations of the read of RNA-derived genomic data, such as where the mapped RNA-derived genomic data includes at least the matching location in the reference genome and the inferred location in the reference genome. Accordingly, in various instances, a list of annotated splice junctions may be provided, wherein the list may be formulated as a table containing an entry for one or more, e.g., each, of the multiplicity of reference bins thereby forming a partition of the reference genome. This list of annotated splice junctions may then be accessed in a manner that involves determining at least one reference bin within a limited distance of the matching location in the reference genome, and accessing the table entries that correspond to the at least one reference bin.

In such an instance, an effective splice junction location in the read may be determined such as by using a first portion of the read, e.g., matching a location in the reference genome, by using an intron descriptor's first endpoint and a second endpoint in the reference genome. Further, in some instances, a limited distance may be determined to at least require that the effective splice junction location in the read not be outside the bounds of the read. Accordingly, a first seed chain may be determined, e.g., using at least the first portion of the read of RNA-derived genomic data, and a matching location in the reference genome. A second seed chain may then be determined, such as by using at least a second portion of the read of RNA-derived genomic data, and the inferred location in the reference genome. A link between the first seed chain and the second seed chain may then be established, and the output may be mapped to locations of the read of RNA-derived genomic data that include descriptions of the first seed chain, the second seed chain, and the link between them.

Further still, the mapping module for performing an RNA sequence analysis may include one or more processing engines that are configured for performing a seed chain scaffolding operation. It is to be noted, however, that although a "seed" chain is herein referenced, such "seed" chains are not limited to the context of hash-table based seed mapping, this concept may be extended to any mapping of a portion of a read to a segment of a reference genome. Such scaffolding operations are useful for translating a list of seed chains into a list of scaffolds, such as where each scaffold is a sequence of one or more seed chains that represents a plausible spliced alignment of the read.

In various instances, successive portions of the read may map to successive segments of a single chromosome of the reference, such as in consistent orientation and order. Accordingly, the method of forming the set of scaffolds may be selective, since for a substantial list of seed chains, the number of conceivable sequences of those seed chains may be very high. Hence, a list of scaffolds may be generated so as to be comprehensive enough to include the true spliced alignment of the read with high confidence, such as without generating too many spurious scaffolds. In such an instance, each scaffold can later be scored, e.g., by spliced alignment.

Accordingly, a mapping engine of the disclosure may be configured to determine a list of seed chains, where each seed chain of the list of seed chains represent a match between a corresponding portion of the read of RNA-derived genomic data and a corresponding segment of the reference genome. By examination of the list of seed chains, the mapper may then produce a list of scaffolds, such as where each scaffold may include a sequence of one or more distinct seed chains from the list of seed chains, and/or the scaffold implies a corresponding read-portion sequence of the one or more corresponding portions of the read of RNA-derived genomic data. In such an instance, the read-portion sequence may progress in a uniform direction through the read of RNA-derived genomic data. Likewise, the scaffold may further imply a corresponding reference-segment sequence of the one or more corresponding segments of the reference genome, where the reference-segment sequence progresses in a uniform direction through the reference genome.

Further, the production of the list of scaffolds may additionally involve sorting the list of seed chains in increasing or decreasing order of the corresponding segments of the reference genome, such as where the list of scaffolds is produced in conformance to a set of rules, where the set of rules determines when one seed chain may follow another seed chain within a scaffold. Such a set of rules may include a minimum and/or a maximum allowed gap and/or a minimum and/or maximum allowed overlap between successive read portions in the read-portion sequence. In certain instances, the read-portion sequence and the reference-segment sequence may imply an intron-length sequence of calculated alignment diagonal shifts from each read portion and corresponding reference segment to the next read portion. Further still, the set of rules may include a minimum allowed intron length and a maximum allowed intron length for the intron-length sequence.

Furthermore, in various instances, the producing of the list of scaffolds may involve producing an initial scaffold portion having a partial sequence of one or more distinct seed chains, and may additionally include producing at least two distinct scaffolds in the list of scaffolds, where one or all of the at least two distinct scaffolds may be extensions of the initial scaffold portion to longer scaffolds. Such production of the list of scaffolds may involve filtering out scaffolds that are inferior, such as inferior according to a calculated filtering metric, such as a filtering metric that is calculated using the difference between each scaffold's net coverage of the read of RNA-derived genomic data, and/or a maximum net coverage of the read of RNA-derived genomic data, e.g., the maximum net coverage being calculated over the list of scaffolds. In some instances, the filtering metric may be calculated using each scaffold's net span in the reference genome.

As indicated, in various instances, a hardwired digital logic circuit may be provided wherein the digital logic circuit, or a subset of logic circuits, includes an aligning module that may be adapted to include a set of processing engines for performing one or more aligning steps in an RNA analysis pipeline, such as where the one or more steps may include splice junction stitching and/or spliced read alignment. Specifically, the alignment module for performing an RNA sequence analysis may include one or more processing engines that are configured for performing one or more splice junction stitching operations and/or one or more spliced read alignments.

Particularly, in various instances, a pair of partial mappings, e.g., seed chains, such as of two consecutive seed chains in a scaffold, for an RNA read may be generated and/or otherwise provided. In various instances, the partially mapped seed chains may represent two exon segments of a spliced mapping candidate that skips a possible intron in the reference. In such an instance, a processing engine of the alignment module may be configured for performing a splice junction stitching operation that is adapted for accurately, e.g., precisely, determining more or less precisely the most likely position in the read where the intron was jumped. The result is a stitching position between two bases of the read, such that bases left of the stitching point align to the first exon segment, and bases right of the stitching point align to the second exon segment. This may be done by 1) testing many possible stitching positions, and 2) scoring the test results. Such scoring may be based on a number of different criteria, such as on the number of base mismatches observed, and/or the absence or presence and type of canonical intron motif observed at the two ends of the implied intron span in the reference, e.g., corresponding to a given stitching position.

This splice stitching operation may be configured as a pre-processing procedure for spliced alignments that would otherwise be resource intensive and/or expensive to implement if the operation had to be performed in a manner that considers all possible stitching positions. Accordingly, an aligner engine may receive a spliced mapping for a read of RNA-derived genomic data, where the spliced mapping includes at least a first portion and a second portion of the read of RNA-derived genomic data, and at least a first segment and a second segment of the reference genome.

Further, the aligner engine may be configured for performing a splice stitching operation in a manner so as to determine a best stitching position within the read of RNA-derived genomic data. Such a best stitching position may be performed by optimizing multiple stitching factors that pertain to each considered stitching position. The stitching factors may include the degree of matching between the first portion of the read, e.g., length-adjusted to end at the considered stitching position, and the first segment of the reference genome, length-adjusted identically. The stitching factors may further include the degree of matching between the second portion of the read, length-adjusted to begin at the considered stitching position, and the second segment of the reference genome, length-adjusted identically. In this instance, the stitching factors may further include the likelihood of an intron motif corresponding to the considered stitching position, such as where the intron motif includes at least two reference bases adjacent to the length-adjusted first segment of the reference, and at least two reference bases adjacent to the length-adjusted second segment of the reference.

In various instances, the stitching factors may be combined into a score, and a considered stitching position, with the numerically best score, may be determined as the best stitching position. In certain instances, a transition may be made from a first considered stitching position to a second considered stitching position across at least one intervening nucleotide in the read of RNA-derived genomic data. In such an instance, the score for the second considered stitching position may be calculated in part by adjusting the score for the first considered stitching position to account for any difference between how well the at least one intervening nucleotide matches the first segment of the reference genome and how well the at least one intervening nucleotide matches the second segment of the reference genome. In certain instances, the best stitching position may be communicated to a gapless alignment module, and the gapless alignment module may be configured to determine a best gapless alignment of read of RNA-derived genomic data to the concatenation of the at least two length-adjusted segments of the reference genome. The best stitching position may then be communicated to a gapped alignment module, and the gapped alignment module may then determine a best gapped or gapless alignment of read of RNA-derived genomic data to the concatenation of the at least two length-adjusted segments of the reference genome.

The aligner module may further include an engine configured for performing a spliced read alignment. For instance, in performing a spliced read alignment, a sequence of multiple partial mappings, e.g. seed chains, such as consecutive seed chains in a scaffold, for an RNA read may be generated. The multiple partial mappings may represent multiple exon segments of spliced mapping candidates, which candidates may skip one or more possible introns in a reference sequence (such as having undergone splice junction stitching for each intron). In such instances, a spliced alignment operation may be performed by aligning the read(s) against a concatenation of the multiple exon segments in the reference.

Specifically, an aligner engine may be provided and configured to receive a spliced mapping for one or more reads of RNA-derived genomic data. The spliced mapping may include determining a sequence of multiple abutting portions between reads of RNA-derived genomic data and one or more corresponding sequences having one or more, e.g., multiple, segments of the reference genome. The aligner engine may then perform a spliced alignment operation on these sequences to determine a best spliced alignment of the read of RNA-derived genomic data to the sequence of multiple segments of the reference genome. For instance, the spliced alignment operation may include concatenating the multiple segments of the reference genome into an aggregate reference sequence having each of the multiple segments of the reference genome joined at concatenation junctions. Further, a read sequence having at least the multiple abutting portions of the read of RNA-derived genomic data may be generated and joined at such concatenation junctions.

A best sequence alignment of the read sequence may be calculated with respect to the aggregate reference sequence, such as where the best sequence alignment is constrained so that concatenation junctions in the read sequence align to corresponding concatenation junctions in the aggregate reference sequence. The sequence alignment may be edited into a spliced alignment, which editing may include inserting intron descriptors at alignment positions corresponding to the concatenation junctions, such as where the intron descriptors encode intron lengths that may be equal to the corresponding distances between the segments of the reference genome. The aligner engine may then output the spliced alignment.

In such an instance, the best sequence alignment may be determined as an alignment with a numerically best score among calculated scores for all candidate alignments, where each candidate alignment score is calculated to include a mismatch penalty for each nucleotide of the read sequence failing to match an aligned nucleotide of the aggregate reference sequence. The candidate alignment score may further be calculated to include one or more other penalties, such as an indel penalty for each insertion or deletion in the candidate alignment and/or a splicing penalty for each concatenation junction included in the candidate alignment, such as where the splicing penalty is determined at least in part according to an intron motif associated with adjoining segments of the reference genome. In various instances, the aggregate reference sequence may be configured to include dummy bases, such as at the concatenation junctions, which dummy bases may be utilized to carry associated splicing penalty values.

In these instances, the calculating of a best sequence alignment may involve dynamic programming to calculate cell scores for a two-dimensional matrix of scoring cells, the two dimensions corresponding to the read sequence and the aggregate reference sequence. In such instances, each of the multiple abutting portions of the read may be assigned a zone ID; and additionally, each of the multiple segments of the reference genome may also be assigned a zone ID. Such zone IDs may be configured so as to be equal for each corresponding portion of the read and segment of the reference, such as where each scoring cell in the matrix of scoring cells has a cell read zone ID that is equal to the zone ID of the corresponding portion of the read. Additionally, a cell reference zone ID may be configured so as to be equal to the zone ID of the corresponding segment of the reference, and the best sequence alignment may be constrained to pass only though scoring cells whose cell read zone IDs are equal to their cell reference zone IDs.

Figure 5:
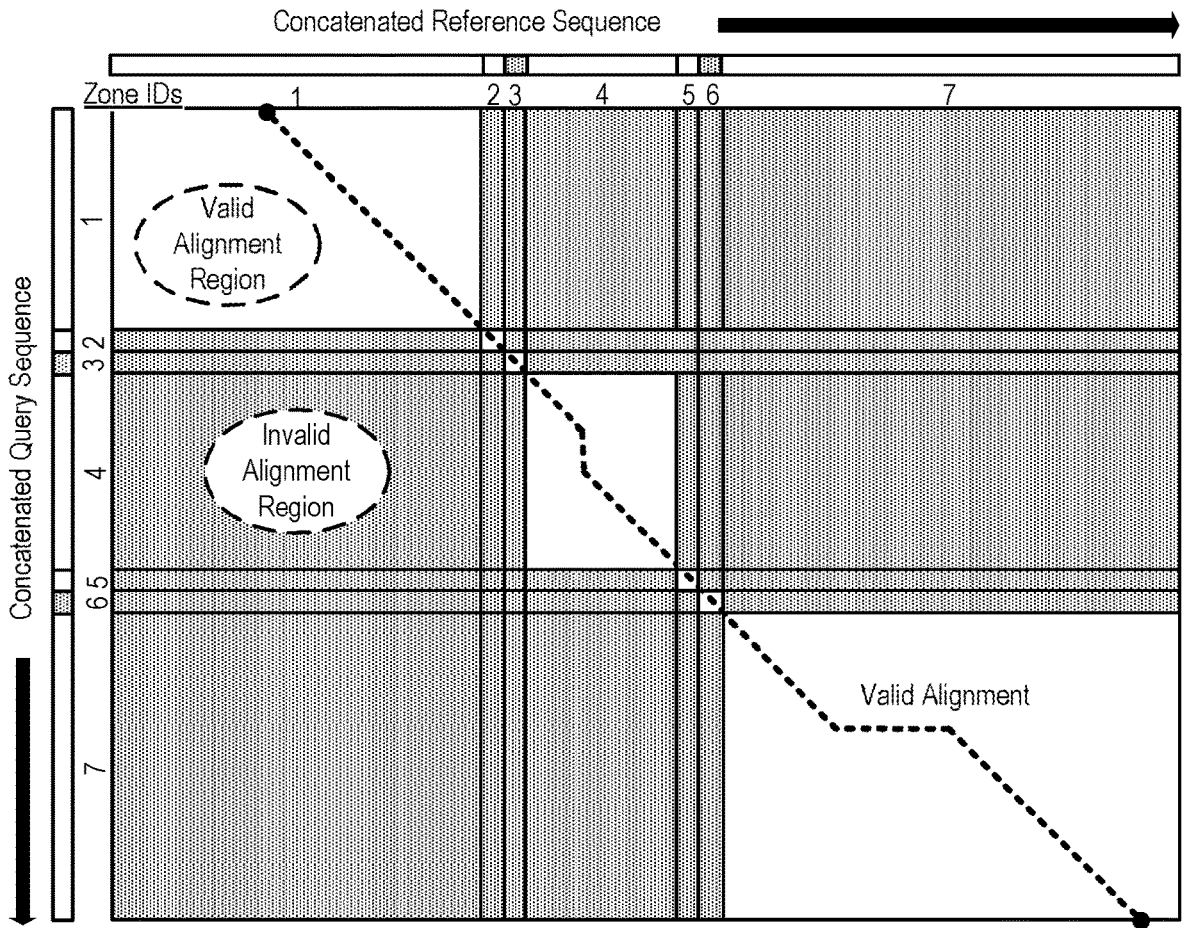
FIG. 5 depicts an abstract alignment rectangle, with concatenated query sequence on the vertical axis and concatenated reference sequence on the horizontal axis.

FIG. 5 shows an abstract alignment rectangle, with a concatenated query sequence on the vertical axis and a concatenated reference sequence on the horizontal axis. Dummy bases of each concatenated sequence are shaded (zones 3 and 6). A grid overlays the alignment rectangle to show the boundaries between zones on each axis. Sub-rectangles with matching zone ID are valid alignment regions, and other (shaded) sub-rectangles are invalid alignment regions. A valid exemplary alignment is shown, which is end-to-end in the query sequence, and contains an insertion (vertical segment) in the second exon segment (zone 4), and a deletion (horizontal segment) in the third exon segment (zone 7). The valid alignment passes diagonally through the splice junctions (zones 3 and 6).

Gapless or gapped alignment using concatenated query and reference sequences produces a correct alignment score, but the alignment trace (e.g. CIGAR string) requires editing, because it does not yet contain intron ('N') operations. For example, a spliced alignment of a 100-base read without indels may emerge from alignment with CIGAR "101M", meaning 101 bases aligned diagonally without indels. There are two adjustments needed in this CIGAR. First, the dummy base between exon segments is counted in the CIGAR, and should not be. Second, the intron operation, e.g. 895 bases long, needs to be inserted at the position of the dummy base. The correct CIGAR may be "40M895N60M", for example.

Given the scaffold with comprising seed chains defining the endpoints of the exon segments as stitched, it is straightforward arithmetic to locate the position of each splice junction in the CIGAR, remove "1M" for the dummy base, and replace it with an intron operation of the proper length. For local alignments, this process must account for the possibility that one or more whole exon segments were clipped from the alignment. The same process of arithmetic can calculate the correct start and end positions of the alignment in the reference genome.

Having obtained alignment scores, start and end positions, and CIGAR strings for each aligned scaffold, processing to select and output the best possibly-spliced alignment is similar to DNA processing. Paired end alignment candidates are examined to find properly positioned and oriented alignment pairs. Alignment candidate pairs, including non-properly-paired candidates, are given score penalties for being unpaired or having improbably empirical insert lengths; pair scores are formed by combining (such as adding) alignment scores from each mate and a pairing penalty; and the best scoring pair of alignments is chosen and output from the aligner engine.

Apparent insert length, usually measured as the span in the reference covered by the two mate read alignments, can appear extremely long due to introns within either or both mates, or unobserved introns in the gap between the mates. (Physical inserts are potentially much shorter, being the lengths of the sequenced RNA or cDNA molecule, where the introns are spliced out.) Therefore, much longer apparent insert lengths must be considered properly paired and given zero or small pairing penalties; this can be done according to a known intron length distribution in the sampled species, and/or the observed apparent insert distribution in the RNA-seq data being processed.

In one embodiment, for each read processed, the alignment score, start position, and encoded CIGAR string are output from the aligner module. In addition, in another embodiment, for each splice junction in the alignment, its intron motif and annotation status are output. A mapping quality or confidence, such as a phred-scale "MAPQ" parameter, may also be estimated and output. In a preferred embodiment, MAPQ is estimated primarily in proportion to the difference between the best pair score and the second-best pair score with a different alignment for the current read. Additional alignment candidates, or secondary alignments, may also be output for each read, such as a limited number of other candidates scoring within a defined or configured score difference threshold.

It is to be understood, such as with reference to the above, that although a mapping function may in some instances have been described, such as with reference to a mapper, and/or an alignment function may have in some instances been described, such as with reference to an aligner, these different functions may be performed sequentially by the same architecture, which has commonly been referenced in the art as an aligner. Accordingly, in various instances, both the mapping function and the aligning function, as herein described may be performed by a common architecture that may be understood to be an aligner, especially in those instances wherein to perform an alignment function, a mapping function need first be performed.

The output from the alignment module is a SAM (Text) or BAM (e.g., binary version of a SAM) file along with a mapping quality score (MAPQ), which quality score reflects the confidence that the predicted and aligned location of the read to the reference is actually where the read is derived. Accordingly, once it has been determined where each read is mapped, and further determined where each read is aligned, e.g., each relevant read has been given a position and a quality score reflecting the probability that the position is the correct alignment, such that the nucleotide sequence for the subject's DNA is known as well as how the subject's DNA differs from that of the reference (e.g., the CIGAR string has been determined), then the various reads representing the genomic nucleic acid sequence of the subject may be sorted by chromosome location, so that the exact location of the read on the chromosomes may be determined. Consequently, in some aspects, the present disclosure is directed to a sorting function, such as may be performed by a sorting module, which sorting module may be part of a pipeline of modules, such as a pipeline that is directed at taking raw sequence read data, such as form a genomic sample form an individual, and mapping and/or aligning that data, which data may then be sorted.

More particularly, once the reads have been assigned a position, such as relative to the reference genome, which may include identifying to which chromosome the read belongs and/or its offset from the beginning of that chromosome, the reads may be sorted by position. Sorting may be useful, such as in downstream analyses, whereby all of the reads that overlap a given position in the genome may be formed into a pile up so as to be adjacent to one another, such as after being processed through the sorting module, whereby it can be readily determined if the majority of the reads agree with the reference value or not. Hence, where the majority of reads do not agree with the reference value a variant call can be flagged. Sorting, therefore, may involve one or more of sorting the reads that align to the relatively same position, such as the same chromosome position, so as to produce a pileup, such that all the reads that cover the same location are physically grouped together; and may further involve analyzing the reads of the pileup to determine where the reads may indicate an actual variant in the genome, as compared to the reference genome, which variant may be distinguishable, such as by the consensus of the pileup, from an error, such as a machine read error or error an error in the sequencing methods which may be exhibited by a small minority of the reads.

Once the data has been obtained there are one or more other modules that may be run so as to clean up the data. For instance, one module that may be included, for example, in a sequence analysis pipeline, such as for determining the genomic sequence of an individual, may be a local realignment module. For example, it is often difficult to determine insertions and deletions that occur at the end of the read. This is because the Smith-Waterman or equivalent alignment process lacks enough context beyond the indel to allow the scoring to detect its presence. Consequently, the actual indel may be reported as one or more SNPs. In such an instance, the accuracy of the predicted location for any given read may be enhanced by performing a local realignment on the mapped and/or aligned and/or sorted read data.

In such instances, pileups may be used to help clarify the proper alignment, such as where a position in question is at the end of any given read, that same position is likely to be at the middle of some other read in the pileup. Accordingly, in performing a local realignment the various reads in a pileup may be analyzed so as to determine if some of the reads in the pile up indicate that there was an insertion or a deletion at a given position where an other read does not include the indel, or rather includes a substitution, at that position, then the indel may be inserted, such as into the reference, where it is not present, and the reads in the local pileup that overlap that region may be realigned to see if collectively a better score is achieved then when the insertion and/or deletion was not there. Accordingly, if there is an improvement, the whole set of reads in the pileup may be reviewed and if the score of the overall set has improved then it is clear to make the call that there really was an indel at that position. In a manner such as this, the fact that there is not enough context to more accurately align a read at the end of a chromosome, for any individual read, may be compensated for. Hence, when performing a local realignment, one or more pileups where one or more indels may be positioned are examined, and it is determined if by adding an indel at any given position the overall alignment score may be enhanced.

Another module that may be included, for example, in a sequence analysis pipeline, such as for determining the genomic sequence of an individual, may be a duplicate marking module. For instance, a duplicate marking function may be performed so as to compensate for chemistry errors that may occur during the sequencing phase. For example, as described above, during some sequencing procedures nucleic acid sequences are attached to beads and built up from there using labeled nucleotide bases. Ideally there will be only one read per bead. However, sometimes multiple reads become attached to a single bead and this results in an excessive number of copies of the attached read. This phenomenon is known as read duplication.

Such read duplication may throw off the statistics and create a statistical bias because instead of having an equal representation of all reads, various reads have been duplicated, such as because of the duplicate template sequences attached to more than one bead are over represented. Accordingly, these may be determined because any read that aligns to the exact same position, and has the exact same length, is likely a duplicate. Once this is identified by the system, only one read need be subjected to further processing and the others may be marked as duplicates and, therefore, can be discarded or ignored. A typical situation where this occurs is where there is not enough genetic material to process from the very beginning and the system attempts to overcompensate for that.

Another module that may be included, for example, in a sequence analysis pipeline, such as for determining the genomic sequence of an individual, may be a base quality score recalibrater. For instance, every base of every read has a Phred score that indicates the probability that the called base at that position is incorrect. For example, the Phred score for any base is due in part to the nature of the base that precedes it and the error profile will be different depending on which base precedes the base in question. Further, there is a greater likelihood of an error occurring at the ends of a read, e.g., such as where at the ends of the reads the chemistry is starting to lose its performance. A base quality score recalibration is a covariant analysis that may go back and measures the empirical quality of the base quality score as a function of all those things by which it varies.

In various instances, it involves two passes, the first gathers all the actual, empirical measured data and statistics on the error rate observed as a function of all the variables, and the second pass involves the actual recalibration of the scores by flowing all the reads through a filter modifying the quality scores for every single base as a function of the variables based on what was actually empirically measured in the data set. This compensates for all the differences in the data due to the various variables and cleans up that data and score. The purpose of all this cleanup is to ensure the best possible variant calling is achieved. Many variant callers base their decisions in part on the reported quality of each of the nucleotides that pile up at each position in the genome. If the quality scores are not accurate, there could easily result a wrong call.

Another module that may be included, for example, in a sequence analysis pipeline, such as for determining the genomic sequence of an individual, may be a compression module, which executes a compression function. As indicated above, it may be useful at some point to take the generated and processed data and transmit it to a remote location, such as the cloud, and hence, the data may need to be compressed at a particular stage of processing, whereby once compressed it may be transmitted and/or otherwise uploaded, such as on to the cloud or to a server farm, etc., for instance, for the performance of the variant calling module. The results once obtained may then be decompressed and/or stored in the memory, on a data base on the cloud, such as an electronic health and/or research database, and the like, which in turn, can be made available for tertiary processing, etc.

Particularly, once the genetic data has been generated and/or processed, e.g., in one or more primary and/or secondary processing protocols, such as by being mapped, aligned, and/or sorted, such as to produce one or more variant call files, for instance, to determine how the genetic sequence data from a subject differs from one or more reference sequences, a further aspect of the disclosure may be directed to performing one or more other analytical functions on the generated and/or processed genetic data such as for further, e.g., tertiary, processing. For example, the system may be configured for further processing of the generated and/or secondarily processed data, such as by running it through one or more tertiary processing pipelines, such as one or more of a genome pipeline, an epigenome pipeline, metagenome pipeline, joint genotyping, a MuTect2 pipeline, or other tertiary processing pipeline, such as by the devices and methods disclosed herein. For instance, in various instances, an additional layer of processing may be provided, such as for disease diagnostics, therapeutic treatment, and/or prophylactic prevention, such as including NIPT, NICU, Cancer, LDT, AgBio, and other such disease diagnostics, prophylaxis, and/or treatments employing the data generated by one or more of the present primary and/or secondary and/or tertiary pipelines. Hence, the devices and methods herein disclosed may be used to generate genetic sequence data, which data may then be used to generate one or more variant call files and/or other associated data that may further be subject to the execution of other tertiary processing pipelines in accordance with the devices and methods disclosed herein, such as for particular and/or general disease diagnostics as well as for prophylactic and/or therapeutic treatment and/or developmental modalities.

Accordingly, as set forth herein above, in various aspects, this present disclosure is directed to systems, apparatuses, and methods for implementing genomics and/or bioinformatic protocols such as, in various instances, for performing one or more functions for analyzing genetic data on an integrated circuit, such as implemented in a hardware processing platform. For example, in one aspect, a bioinformatics system is provided, wherein the system may involve the performance of various bioanalytical functions that have been optimized so as to be performed faster and/or with increased accuracy in a hardware implementation. Accordingly, in various instances, the methods and systems herein described may include the performance of one or more algorithms for executing these functions, wherein the algorithms may be implemented in a hardware solution, such as where the algorithm has been optimized so as to be implemented by an integrated circuit formed of one or more hardwired digital logic circuits. In such an instance, the hardwired digital logic circuits may be interconnected, such as by one or a plurality of physical electrical interconnects, and may be arranged to function as one or more processing engines. In various instances, a plurality of hardwired digital logic circuits are provided, which hardwired digital logic circuits are configured as a set of processing engines, wherein each processing engine is capable of performing one or more steps in the bioinformatics genetic analysis protocol.

More particularly, in one instance, a system for executing a sequence analysis pipeline such as on genetic sequence data is provided. The system may include one or more of an electronic data source, a memory, and an integrated circuit. For instance, in one embodiment, an electronic data source is included, where in the electronic data source may be configured for providing one or more digital signals, such as a digital signal representing one or more reads of genetic data, for example, where each read of genomic data includes a sequence of nucleotides. Further, the memory may be configured for storing one or more genetic reference sequences, and may further be configured for storing an index, such as an index of the one or more genetic reference sequences.

Further still, in various instances, one or more of the plurality of physical electrical interconnects may include an input, such as to the integrated circuit, and may further be connected with the electronic data source, so as to be able to receive the one or more reads of genomic data. In various embodiments, the hardwired digital logic circuits may be arranged as a set of processing engines, such as where each processing engine is formed of a subset of the hardwired digital logic circuits, and is configured so as to perform one or more steps in the sequence analysis pipeline, such as on digitized genetic data, e.g., on the plurality of reads of genomic data. In such instances, each subset of the hardwired digital logic circuits may be in a wired configuration so as to perform the one or more steps in the sequence analysis pipeline, such as where the one or more steps may include performing one or more of: a base calling and/or error correction operation, such as on the digitized genetic data, and/or may include one or more of performing a mapping, an alignment, and/or a sorting function on the genetic data. In certain instances, the pipeline may include performing one or more of a realignment, a deduplication, a base quality score recalibration, a reduction and/or compression, and/or a decompression on the digitized genetic data. In certain instances the pipeline may include performing a variant calling operation on the genetic data.

Accordingly, in various embodiments, the systems, apparatuses, and methods for implementing genomics and/or bioinformatic protocols, as herein described, may involve taking processes that may have typically been performed on software, and embedding those functions into an integrated circuit, such as on a chip 100, for instance as part of a circuit board 105, such as where the functions have been optimized to enhance its performance on the chip. Hence, in one embodiment, as can be seen with respect to FIGS. 6 and 7 a chip 100 is provided wherein the chip 100 has been designed so as to efficiently perform the functions of the pipeline. In various particular embodiments the chip 100 may be a field programmable gate array (FPGA), an application specific integrated circuit (ASIC), or a structured application specific integrated circuit (sASIC), or the like.

For instance, the functioning of one or more of these algorithms may be embedded onto a chip, such as into an FPGA or ASIC or structured ASIC chip, and may be optimized so as to perform more efficiently because of their implementation in such hardware. Accordingly, in one embodiment a FPGA chip is provided wherein the chip is capable of being configurable, e.g., its programming may be changed, so as to be more adaptable in meeting a given user's needs with respect to performing the various genomic functions detailed herein. In such an instance, the user can change and/or modify the algorithms employed dependent on the key parameters desired to be emphasized in the overall system, such as to give additional functionality or change out what was first presented on the chip, e.g., such as re-configuring the chip to employ a different algorithm.

Further, in another embodiment an FPGA or structured ASIC chip is provided wherein the chip is capable of being configurable such as fully or to a limited extent, e.g., some of its programming may be changed, so as to be more adaptable in meeting a given user's needs with respect to performing the various genomic functions detailed herein. In accordance with another embodiment an ASIC is provided, such as where the FPGA or sASIC is converted to an ASIC chip where its functionality may be locked down into the chip. In such an instance, various parameters, such as various parameters regarding the function of one or more of the algorithms set forth herein, may be user selected, for instance, governing how the various modules are supposed to function, but the way those modules actually function is locked in.

Figure 6:
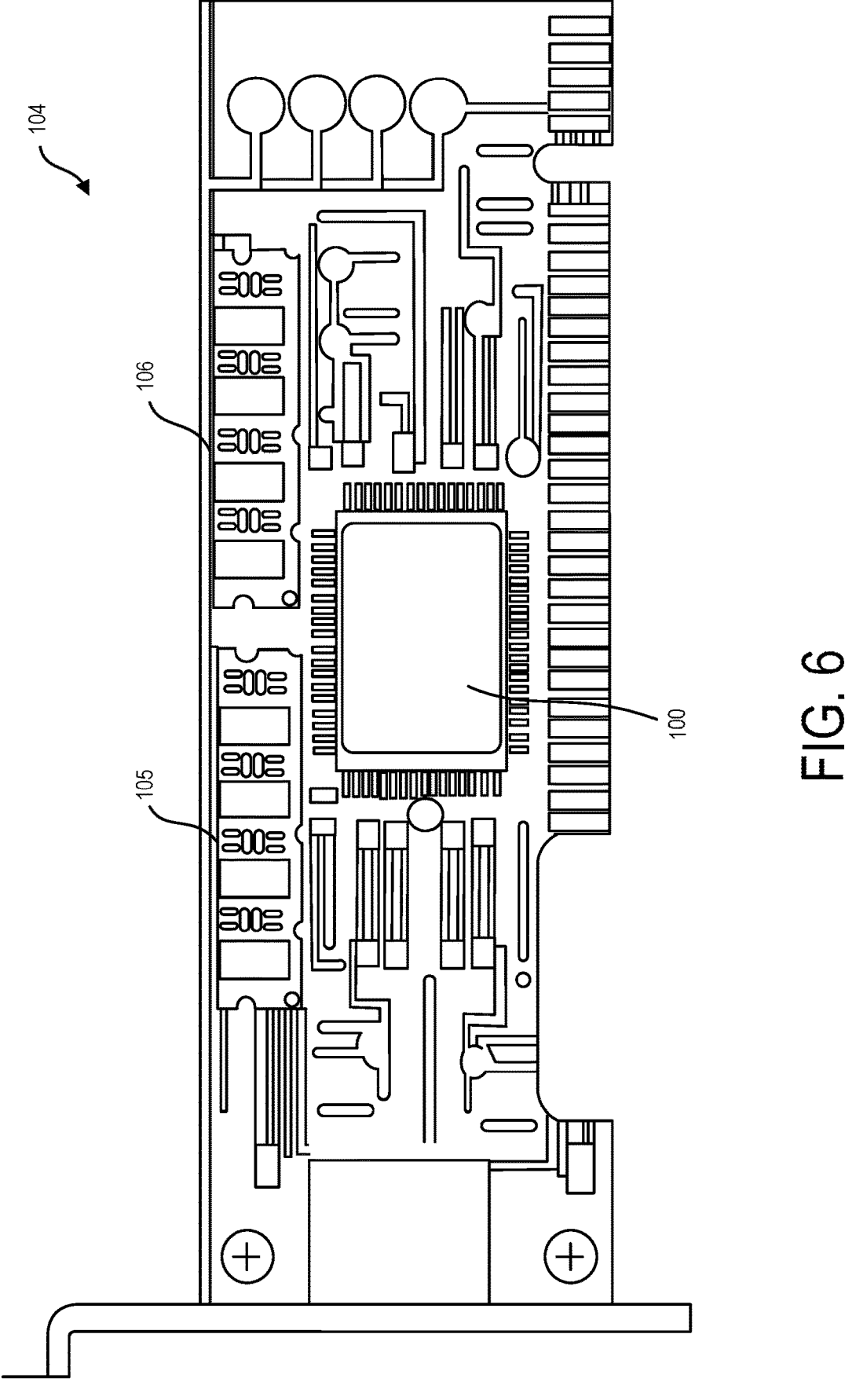
FIG. 6 illustrates an apparatus in accordance with an implementation of the disclosure.
Figure 7:
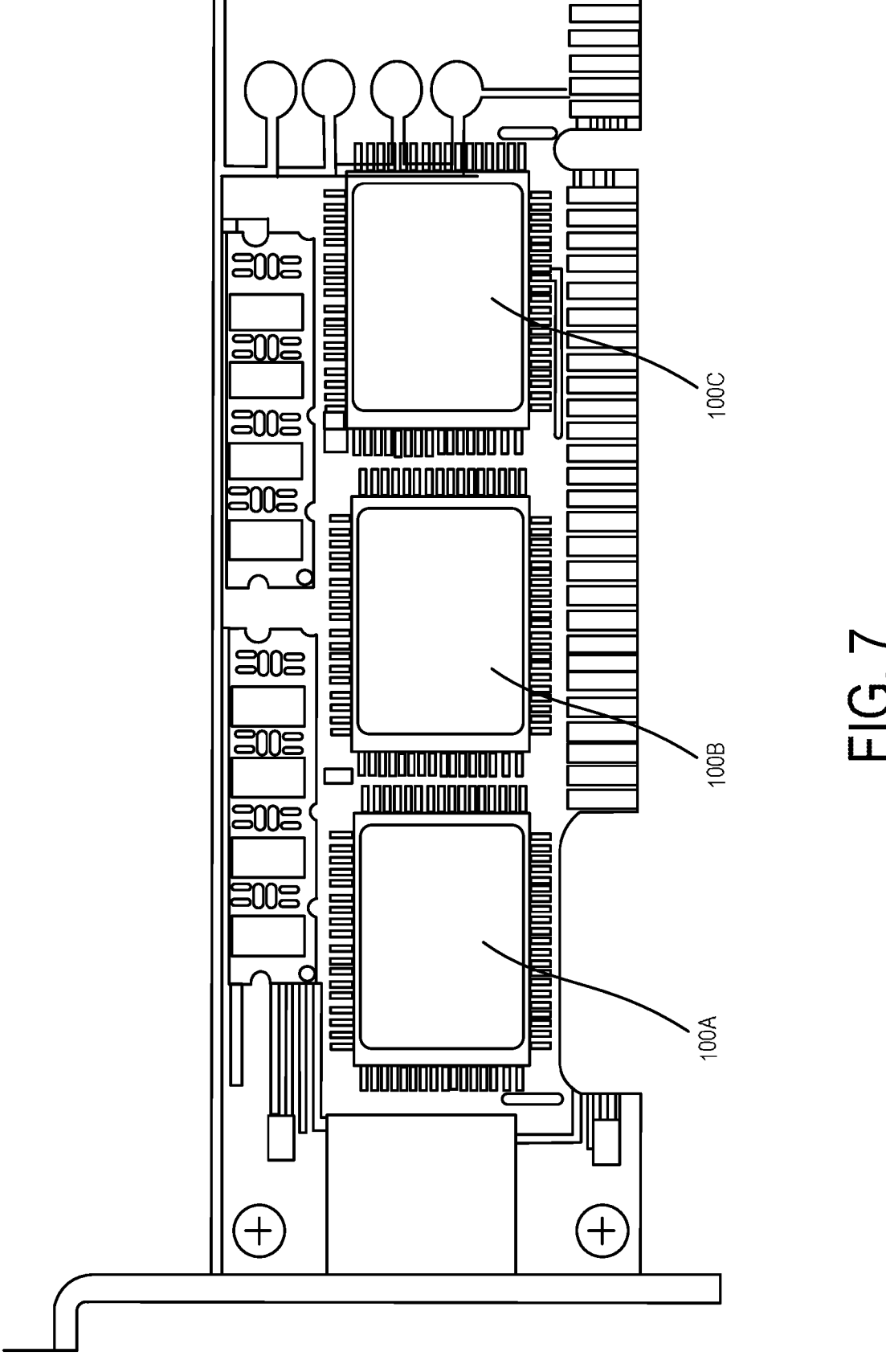
FIG. 7 illustrates another apparatus in accordance with an alternative implementation of the disclosure.

In various embodiments, as seen with respect to FIGS. 6 and 7 the chip 100 may be part of a circuit board, such as part of an expansion card 104, for instance, a peripheral component interconnect (PCI) card, including a PCIe card, which in various embodiments may be associated, such as, communicably coupled, e.g., electrically connected, with an automated sequencer device so as to function part and parcel with the sequencer, such as where the data files, e.g., FASTQ files, generated by the sequencer is transferred directly over to the chip, such as for secondary genomic processing, such as immediately subsequent to the FASTQ file generation and/or primary processing, e.g., immediately after the sequencing function has been performed.

Accordingly, in certain instances, a PCI 104 card is provided wherein the PCI card may include a chip with a PCIe bus 105, where the card 102 and/or chip 100 may include one or more of: a configuration manager, such as a configuration control (Cent-Com); a direct memory access engine (e.g., a driver); an API; a client level interface (CLI), a library; a memory, such as a random access memory (RAM) or a dynamic random access memory (DRAM); and/or a chip level interconnect, such as a DDR3. For instance, in various instances a configuration manager may be included wherein the configuration manager is driven, such as by a parameter file. In such an instance the configuration manager may be adapted so as to configure the various modules of the pipeline. In various instances, it may be user editable, and thereby allow a user to determine which modules of the pipeline are going to be used, e.g., from all of them to a subset of less than all of them, such as for a particular dataset, such as a particular set of FASTQ files.

For example, in various embodiments, the functioning of the pipeline is very configurable such that one or more of the modules, such as structured into the chip, may be run or not run, as desired. Further, each module in use can also be configured so as to run in accordance with one or more preselected parameters, which the user may have control over, such as regarding how the module is going to perform and behave. Hence, there may be two different sets of configuration files, such as one that controls the basic operations of the system as a whole, and may be hidden from the user, and another that is capable of being manipulated by the user, thereby allowing the user to select various of the parameters by which one or more of the subsystems, e.g., modules, of the chip 100 and/or PCI card 104 will be run.

Accordingly, various of the above described modules may be hardwired into the chip, or may be external to the chip, but positioned in a coupling relationship therewith, such as on a PCI board 104, or they may be located remotely from the chip, such as on a different PCI board, or even on a different server, such as on a server that may be accessed via the cloud 30. For instance, in certain implementations, one or more of the above described modules may be hardwired onto a chip 100 and the chip installed onto the circuit board 104 of a stand-alone device 300, or coupled to a sequencer, whereby the user configures and runs the system directly by themselves according to their own preselected parameters. Alternatively, as indicated herein, one or more of the above described modules may be present on a system that is accessible via the cloud 30, wherein the directing of the functioning of the pipeline, and/or the modules thereof, may include the user logging on to a server, e.g., a remote server, and transmitting data to and therefrom, and thereby selects which modules to be run on the data set. In certain instances, one or more of the modules may be performed remotely, such as via the cloud accessed server.

In various instances, in configuring the system, the chip, e.g., the chip 100 on an expansion card 104, such as a PCI card, may be included in a server 300, whereby the server runs the various applications of the system. In certain instances, the server 300 may have a terminal connectable there with, whereby a windows interface may be presentable to the user such that the user may select the modules to be run and the parameters by which they are to be run, such as by selecting a box from a menu of boxes. In other instances, however, the parameter file may be a text file detailing categories by module under file names that the user can then edit, so as to select which modules will be run in accordance with which parameters. For instance, in various embodiments, each chip may include all or a selection of the modules, such as one or more of: a base calling, error correcting, a mapping, an alignment, a sorting, a local realignment, a duplicate marking, a recalibration, a variant calling, a compression, and/or a decompression module, from which the user may select which modules will run, when, and to various extents how it will run, without changing the functioning of the underlying algorithms by which the individual modules are operated.

Additionally, in various instances, a direct memory access (DMA) engine in the chip, and a DMA driver, may be included wherein the DMA driver includes code that runs in the kernel. Accordingly, the DMA driver may be the foundation of the overall operating system. For instance, where the kernel runs in a literal addressing space, layered above that may be a virtual user space. This operating system software, therefore operates in between these layers managing the mapping from the virtual to the physical space. More particularly, the kernel represents the lowest level of code that gives the platform access to the PCI 104, e.g., PCIe, bus 105, to which the chip 100 is coupled. Accordingly, since, in various embodiments, the chip 100 may be configured as an expansion card 104 with a PCIe expansion bus 105, which expansion card 104 may be coupled with various hardware of a device, such as a sequencer, the DMA driver may function so as to communicate with the hardware of the sequencer, and may further be configured for running at the kernel level on the CPU 100, so as to also communicate with the DMA engine in the chip 100, and/or be configured for operating in the virtual user space so as to receive instructions from the user.

To facilitate this communication within the chip and/or between the chip and one or more cards, every single configurable parameter of a module may be assigned to a register address. In such an instance, the card may have its own address space, which address space may be different from the address space for one or more memories, such as 64 gigabytes of memory, and/or additionally every module may have registers and local memory associated with it, each with its own address space. Accordingly, the driver knows where everything is, all the addresses, and knows how to communicate between the chip 100, the PCI card 104, and/or the hardware of the server. Further, knowing where all the addresses are and communicating with an API the driver can read the parameter file that a user generates, and can look up for that parameter where the file is actually located in the host computer system and will read and interpret the value in the file and will deliver that value in the right register in the right place in the chip. Hence, the driver may handle delivering the selected parameter instructions, such as with respect to various user selected configurations, and ships that data to the chip via the DMA engine to configure any of its processing functions.

Particularly, once the genetic data has been generated and/or processed, e.g., in one or more primary and/or secondary processing protocols, such as by being mapped, aligned, and/or sorted, such as to produce one or more variant call files, for instance, to determine how the genetic sequence data from a subject differs from one or more reference sequences, a further aspect of the disclosure may be directed to performing one or more other analytical functions on the generated and/or processed genetic data such as for further, e.g., tertiary, processing. For example, the system, as presented in FIGS. 8-11, may be configured for further processing of the generated and/or secondarily processed data, such as by running it through one or more tertiary processing pipelines 700, such as one or more of a genome pipeline, an epigenome pipeline, metagenome pipeline, joint genotyping, a MuTect2 pipeline, or other tertiary processing pipeline, such as by the devices and methods disclosed herein. For instance, in various instances, an additional layer of processing 122 may be provided, such as for disease diagnostics, therapeutic treatment, and/or prophylactic prevention, such as including NIPT, NICU, Cancer, LDT, AgBio, and other such disease diagnostics, prophylaxis, and/or treatments employing the data generated by one or more of the present primary and/or secondary and/or tertiary pipelines.

Hence, the devices and methods herein disclosed may be used to generate genetic sequence data, which data may then be used to generate one or more variant call files and/or other associated data that may further be subject to the execution of other tertiary processing pipelines in accordance with the devices and methods disclosed herein, such as for particular and/or general disease diagnostics as well as for prophylactic and/or therapeutic treatment and/or developmental modalities.

Further, in various instances, an API may be included wherein the API is configured so as to include a list of function calls that the user can make, so as to configure and operate the system. For instance, an API may be defined in a header file that describes the functionality and determines how to call a function, such as the parameters that are passed, the inputs and outputs, what comes in, what goes out, and what gets returned. For example, in various embodiments, one or more of the elements of the pipeline may be configurable such as by instructions entered by a user and/or one or more third party applications. These instructions may be communicated to the chip via the API which communicates with the driver, instructing the driver as to which parts of the chip, e.g., which modules are to be activated, when, and in what order, given a preselected parameter configuration.

As indicated above, the DMA driver runs at the kernel level, and has its own very low level, basic API that provides access to the hardware and functions so as to access applicable registers and modules. On top of this layer is built a virtual layer of service functions, that form the building blocks that are used for a multiplicity of functions that send files down to the kernel and gets results back, and further performs more higher level functions. On top of that layer is an additional layer that uses those service functions, which is the API level that a user will interface with and it functions primarily for configuration, downloading files, and uploading results. Such configuration may include communicating with registers and also performing function calls.

For example, as described herein above, one function call may be to generate the hash table via the hashing algorithm. Specifically, because in certain embodiments this function may be based on a reference genome, once for every reference genome, the hash tables that are used in the mapper may need to be constructed, based on the reference, there is therefore a function call that performs this function, which function call will accept a file name of where the reference file is stored and it will then generate one or more data files that contain the hash table and the reference. Another function call may be to load the hash table that was generated via the hashing algorithm and transfer that down to the memory on the chip 100, and/or put it at the right spot where the hardware is expecting them to be. Of course, the reference itself will need to be downloaded onto the chip 100, as well for the performance of the alignment function, and the configuration manager can perform that function such as by loading everything that needs to be there in order for the modules of the chip 100 to perform their functions into a memory on to the chip or attached to the chip 100.

Additionally, the API may be configured to allow the chip 100 to interface with the circuit board of the sequencer, when included therewith, so as to receive the FASTQ sequencing files directly from the sequencer such as immediately once they have been generated and then transfers that information to the configuration manager which then directs that information to the appropriate memory banks in the hardware 100 that makes that information available to the pertinent modules of the hardware so that they can perform their designated functions on that information so as to call bases, map, align, sort, etc. the sample DNA with respect to the reference genome.

Further still, a client level interface (CLI) may be included wherein the CLI may allow the user to call one or more of these functions directly. In various embodiments, the CLI may be a software application that is adapted to configure the use of the hardware. The CLI, therefore, may be a program that accepts instructions, e.g., arguments, and makes functionality available simply by calling an application program. As indicated above, the CLI can be command line based or GUI (graphical user interface) based. The line based commands happen at a level below the GUI, where the GUI includes a windows based file manager with click on function boxes that delineate which modules will be used and the parameters of their use. For example, in operation, if instructed, the CLI will locate the reference, will determine if a hash table and/or index needs to be generated, or if already generated locate where it is stored, and direct the uploading of the generated hash table and/or index, etc. These type of instructions may appear as user options at the GUI that the user can select the chip to perform.

Furthermore, a library may be included wherein the library may include pre-existing, editable, configuration files, such as files orientated to the typical user selected functioning of the hardware, such as with respect to a portion or whole genome analysis, for instance, for ancestry analysis, or disease diagnostics, or drug discovery, or protein profiling, etc. These types of preset parameters, such as for performing such analyses, may be stored in the library. For example, if the platform herein described is employed such as for oncology research, the preset parameters may be configured differently than if the platform were directed simply to researching a genealogy.

More particularly, for oncology, accuracy may be an important factor, therefore, the parameters of the system may be set to ensure increased accuracy albeit in exchange for possibly a decrease in speed. However, for other genomics applications, speed may be the key determinant and therefore the parameters of the system may be set to maximize speed, which however may sacrifice some accuracy. Accordingly, in various embodiments, often used parameter settings for performing different tasks can be preset into the library to facilitate ease of use. Such parameter settings may also include the necessary software applications employed in running the system. For instance, the library may contain the code that executes the API, and may further include sample files, scripts, and any other ancillary information necessary for running the system. Hence, the library may be configured for compiling software for running the API as well as various executables.

In various instances, the PCI 104 and/or chip 100 may also include a memory, such as a Random Access Memory (RAM) or a Dynamic Rapid Access Memory with e.g. a DDR3 interface, such as a memory that may be used for facilitating the performance of the various modules described herein, for instance, the mapper, aligner, and/or sorter. For example, the DRAM may be where the reference, the hash table, and/or the hash table index, and/or reads may be stored. Further, as seen with respect to FIG. 9, the memory may be used for facilitating the performance of various other modules, e.g., 114, described herein, for instance, the deduper, local realigner, base quality score recalibrator, variant caller, compressor, and/or decompressor. For example, the DRAM may be where sorted reads, annotated reads, compressed reads, and/or variant calls may be stored. Further, the memory may be configured so as to include a separate interface for each of the various memory modules employed by the aligner and/or any other module, such as where each memory may include a file layer and logical layer. As indicated above, because there may be multiple memories and/or multiple modules, a chip level interconnect may be included so as to facilitate communication through the chip 100.

Accordingly, in various instances, an apparatus of the disclosure may include a chip 100, wherein the chip includes an integrated circuit that is formed of a set of hardwired digital logic circuits that may be interconnected by one or more physical electrical interconnects. In various embodiments, the one or more physical electrical interconnects include an input to the integrated circuit that may be connected with an electronic data source for receiving data. Further, in certain embodiments, the hardwired digital logic circuits may be arranged as a set of processing engines, such as wherein each processing engine may be formed of a subset of the hardwired digital logic circuits, which are configured to perform one or more of the steps in the sequence analysis pipeline. More particularly, each subset of the hardwired digital logic circuits may be in a wired configuration so as to perform the one or more steps in the sequence analysis pipeline.

In various instances, the set of processing engines may include one or more of a mapping module 112, an alignment module 113, and/or a sorting module 114a, such as where the one or more of these modules are in the wired configuration. For instance, a mapping module may be included, where in the wired configuration, the mapping module may access an index, such as of one or more genetic reference sequences, e.g., from a memory, such as via one or more of the plurality of physical electronic interconnects, so as to map the plurality of reads to one or more segments of the one or more genetic reference sequences. Further, in various instances, an alignment module may be included, wherein the wired configuration, the alignment module may access the one or more genetic reference sequences, e.g., from the memory, such as via one or more of the plurality of physical electronic interconnects, so to align the plurality of reads to the one or more segments of the one or more genetic reference sequences. Further still, in various instances, a sorting module may be included, wherein the wired configuration, the sorting module may access the one or more aligned sequences, e.g., from the memory, such as via one or more of the plurality of physical electronic interconnects, so to sort the plurality of reads to a chromosome, such as from the one or more genetic reference sequences. In like manner, in various instances, one or more of local realignment, duplicate marking, base quality score recalibration, and/or variant calling modules may be included in the chip, such as in the wired configuration consistent as with the modules described above, so as to perform their respective functions.

As indicated above, in various instances one or more integrated circuits of the disclosure may be configured as one or more chips such as one or more of an ASIC, a FPGA, and/or a structured ASIC chip. For instance, an integrated circuit is characteristically a set of electronic circuits on a small wafer or "chip" of semiconductor material, such as silicon. Typically integrated circuits include circuit elements that may be inseparably associated and electrically interconnected. A prototypical digital integrated circuit includes a variety of circuit elements such as one or more of logic gates, flip-flops, multiplexers, and other various circuit elements that are configured and/or configurable for functioning in circuit such as a microprocessor, or other microcontroller, such as for binary processing of "zero" and "one" signals, for instance, in the performance of one or more of the operations of the disclosure.

More particularly, one or more mask-programmable logic gates may be configured or programmed for performing a logical operation, such as implementing a Boolean function, on one or more logical inputs so as to produce a single logical output. Such logic gates may be configured using one or more diodes or transistors in such a manner that the gate operates as an electronic switch. In various instances, logic gates can be cascaded in a manner akin to the way that Boolean functions can be composed, thereby allowing the construction of a physical model of all of Boolean logic and, therefore, all of the algorithms and mathematics that can be described with Boolean logic, such as those described herein, may be implemented in the logic gates of the integrated circuits of the present disclosure. In various embodiments, a collection of gates may be present on the wafer in such a manner as to form a gate array, such as a gate array circuit.

In various instances, an integrated circuit may also include one or more flip-flops. A flip-flop may be a circuit, or at least a part thereof, that is configured as a latch. Typically, a flip-flop has two stable states and can change from one to the other such as by signals applied to one or more control inputs, and, therefore, a flip-flop will have one or two outputs. In use, flip-flops are employed to store state information, and consequently, may be deployed as a basic storage element, such as in sequential logic operations. The integrated may also include a multiplexer. A multiplexer may be configured for selecting one of several input signals, such as digital (or analog) input signals, and further may be configured for forwarding the selected input to an output. In this manner, a multiplexer may be used to increase the amount of data that can be sent over a network within a certain amount of time and bandwidth.

In certain instances, as recited herein, a typical integrated circuit can include anywhere from one to millions of such circuit elements configured for performing operations, such as those operations presently disclosed, wherein the various circuit elements occupy only a few square millimeters of space. The small size of these circuits allows high speed, low power dissipation, and reduced manufacturing cost.

Such integrated circuits may be fabricated using a variety of different technologies but, in general, are usually constructed as a monolithic integrated circuit. For instance, a typical integrated circuit, e.g., a semiconductor, may be fabricated in a layer process, such as a layer process that includes about three main process steps, such as imaging, deposition and etching. In various instances, one or more of these process steps may be supplemented by further processing steps such as doping, cleaning, and the like. For example, in a typical fabrication procedure, a wafer, such as a mono-crystal silicon wafer may be provided for use as a substrate upon which the integrated circuit is to be constructed, e.g., printed. Photolithography may then be employed to print on the wafer so as to mark different areas of the substrate that may then be doped and/or printed with tracks, such as with a metal insulator such as aluminum.

Typically, an integrated circuit is composed of one or a plurality of overlapping layers, such as where each layer is defined by photolithography. Some layers may form diffusion layers, marking where various dopants have diffused into the substrate, and other layers define where additional ions may be implanted. Additional layers may define the conductors (e.g., polysilicon, metal layers, and the like) as well as the connection layers between the conducting layers. For instance, a transistor may be formed wherever the gate layer (polysilicon or metal) crosses a diffusion layer, and in various instances, meandering stripes may be used to form on-chip resistors. Exemplary integrated circuits may include: an ASIC, an FGPA, and/or a Structured ASIC.

Often times, integrated circuits are fabricated for general use. However, in various instances, such as some of those described herein, an integrated circuit may be customized, such as to form an application-specific integrated circuit or "ASIC." An ASIC, generally referred to as a "standard cell ASIC," is an integrated circuit that has been customized for a particular use, rather than for a general-purpose use. Typically an ASIC may have a large number of logic gates, such as in some instances, over 100 million gates, which gates can be configured for preforming a multiplicity of different operations such as being configured as microprocessors and/or memory blocks, including ROM, RAM, EEPROM, flash memory, and other large building blocks, such as for the purpose of performing the operations herein disclosed. A unique feature of an ASIC is that because it is a chip that is constructed for performing a specific set of applications, the chip may be fabricated in such a manner as to be customizable, such as by employing a gate-array design protocol.

For instance, a gate array or uncommitted logic array (ULA) may be used in the design and manufacture of application-specific integrated circuits (ASICs). In such an instance, an ASIC may be manufactured from a prefabricated chip that has active devices like gates, e.g., NAND-gates, which at first may be unconnected, but may at a later time be interconnected, such as according to the gate-array design protocol, for example, by adding metal layers, such as in the factory. Accordingly, with respect to producing an ASIC, a gate array circuit may be prefabricated on a silicon chip circuit that upon production has no particular function, but does include one or more of transistors, standard NAND or NOR logic gates, and may have further other active devices that may be placed at predefined positions and manufactured on the wafer, which wafer in this instance may be termed a "master slice." Hence, the creation of a circuit having the determined specified functions may be accomplished by adding a final surface layer or layers of metal interconnects to the chips on the master slice late in the manufacturing process, and joining these elements to allow the function of the chip to be customized as desired, e.g., in accordance with the design protocol.

More particularly, a gate-array design protocol employs a manufacturing method where the various diffused layers, e.g., transistors and other active circuit elements, such as those described above, are predefined and constructed on general use wafers but are stored prior to metallization such that various of the circuit elements remain unconnected. In such an instance, the chip may then, at a later point in time, be customized in accordance with various specific use parameters such as by a physical design process that defines the interconnections of the final device. For instance, gate array master slices are usually prefabricated and stockpiled in large quantities waiting for customization. An application circuit must be built on the gate array in such a manner that the circuit has enough gates, wiring and I/O pins so as to perform the desired functions.

Since requirements vary, gate array wafers often come in standard families, including larger members having more, e.g., all, resources, but being correspondingly more expensive, and somewhat smaller members having a limited selection of resources, but also being less expensive. The right wafer standard should be chosen based on the number of resources required to perform the selected functions. The amount of resources to be deployed may fairly easily be determined, such as by counting how many gates and I/Os pins are needed, however, the amount of routing tracks needed may vary considerably and should therefore be selected carefully. However, because the master slice is somewhat prefabricated, the design and fabrication, according to the individual design protocol specifications, may be finished in a shorter time compared with standard cell or full custom (FPGA) design. In a manner such as this, the gate array approach reduces the mask costs, since fewer custom masks need to be produced. In addition manufacturing test tooling lead time and costs are also reduced, since the same test fixtures may be used for all gate array products manufactured on the same die size.

In such an instance, the manufacture of such a standard cell chip, e.g., ASIC, may include anywhere from two to nine, or ten, or twelve, or more deposition layers, such as where one or more, e.g., all, of the subsequent metal layers run perpendicular to the one below it. Such fabrication methods are useful because they provide for a somewhat customized chip design in a relatively short construction time period because the final metallization process can be performed quickly. However, such gate-array chips, e.g., ASICs, are often a compromise as mapping a given design onto a "stock" wafer does not typically give 100% utilization. Another disadvantage with respect to an ASIC is the non-recurring engineering (NRE) cost that can run into the millions of dollars. Nevertheless, the per unit production cost of an ASIC can be quite low, comparatively.

An alternative to a standard cell ASIC for the production of customizable chips is a field-programmable gated array or "FPGA." An FPGA employs programmable logic blocks and interconnects that are re-writeable thereby allowing the same FPGA to be designed and at least partially re-designed so as to be used in many different applications, or the same applications in a multiplicity of different ways over time. More specifically, a field-programmable gate array is an integrated circuit that is designed to be configured one or a multiplicity of times, such as by a customer or a designer, e.g., after manufacturing.

Typically, FPGAs have large resources of logic gates and/or memory, e.g., RAM, blocks that can be configured to implement complex digital computations. For instance, FPGAs contain programmable logic components called "logic blocks", as well as a multiplicity, e.g., a hierarchy, of reconfigurable interconnects that allow the blocks to be "wired together." More particularly, FGPAs may have a multiplicity of changeable logic gates that can be inter-wired in a variety of different configurations, so as to form logic blocks that can be configured to perform a wide variety of complex combinational functions, such as those with respect to performing the operations herein detailed. In various instances, the logic blocks of an FPGA may be configured to include memory elements such as simple flip-flops or more complete memory blocks such as ROM or RAM. As FPGA designs employ very fast I/Os and bidirectional data buses it may, in certain instances, be difficult to verify the correct timing of valid data within setup and hold times. Accordingly, in some instances, the appropriate floor planning may enable resource allocations within an FPGA to meet these time constraints. FPGAs, therefore, may be used to implement any logical function that a standard cell ASIC could perform. However, the ability to update the functionality after shipping, partial re-configuration of a portion of the design, and the low non-recurring engineering costs relative to an ASIC design (notwithstanding the generally higher per unit cost), offer advantages for many applications.

In some instances, the coarse-grained architectural approach of a typical FPGA fabrication may be performed in such a manner as to combine the logic blocks and interconnects of traditional FPGAs with embedded microprocessors and related peripherals to form a complete "system on a programmable chip". In certain instances, an FPGA of the disclosure may have the ability to be reprogrammed at "run time," and may, in accordance with the methods disclosed herein, allow for reconfigurable computing or the production of reconfigurable systems, e.g., a CPU that can reconfigure itself to suit the operations disclosed herein. In some instances, software-configurable microprocessors may be employed to provide an array of processor cores and FPGA-like programmable cores that may be present on the same chip.

A common FPGA architecture may include an array of configurable logic blocks, I/O pads, and/or one or more routing channels. Typically, a logic block may include one or a plurality of logical cells, where a typical cell may include a 4-input LUT, a Full adder (FA), and/or flip-flop, and the like, which function to produce an output. In various instances, the output can be either synchronous or asynchronous. An application circuit may be mapped into an FPGA and the number of logic blocks, I/Os, and routing tracks to be included can be determined from the design, the number of which may vary. It is to be noted that since unused routing tracks may increase the cost and decrease the performance of the integrated circuit without providing any benefit, the number of routing tracks should be enough such that its processes fit in terms of lookup tables (LUTs) and I/Os to be routed without being in excess. Further, since clock signals are normally routed via special-purpose dedicated routing networks (e.g., global buffers) they and other such signals may be separately managed.

An FPGA, as herein disclosed, may also include higher level functionality fixed into the silicon, such as one or more multipliers, generic DSP blocks, embedded processors, high speed I/O logic, and/or embedded memories. Inclusion of these common functions embedded into the silicon wafer reduces the area required and gives those functions increased speed. It is to be noted that the disclosed FPGAs may be used for systems validation including pre-silicon validation, post-silicon validation, and firmware development, such as to validate the final design prior to the production of "for use" chips, such as standard cell ASIC or Structured ASIC chips, which may represent the final end product.

In the production of an exemplary integrated circuit, such as an FPGA, etc., having the requisite functionality as herein described, one or more of the following steps may be followed, in any logical sequence. First, a hardware description language (HDL) or a schematic design may be provided. An electronic design automation tool, e.g., a CAD, can then be employed to generate a technology-mapped netlist. The netlist can then be fitted to the actual FPGA architecture such as by using a process called place-and-route in accordance with the appropriate place-and-route software. Once the design and validation process is complete, the binary file generated may be used to (re) configure the FPGA.

In a typical design protocol flow, the design may be simulated at multiple stages throughout the design process. Initially the RTL description, such as in VHDL or Verilog, may be simulated by creating test benches to simulate the system and observe results. In certain instances, the synthesis engine may map the proposed design to the netlist, and after the synthesis engine has mapped the design to a netlist, the netlist may be translated to a gate level description. At this stage a simulation may be performed, e.g., again, to confirm the synthesis proceeded without errors. The design may then be laid out in the FPGA, at which point propagation delays may be added, and a simulation may be run, e.g., again, with these values back-annotated onto the netlist, such as prior to final validation and further fabrication, such as in the generation of one or more ASIC or structured ASIC based chips.

Accordingly, a hybrid between an ASIC and a FPGA is a structured ASIC, which falls between an FPGA and an ASIC. The traditional "standard cell ASIC", disclosed above, is typically expensive, e.g., extremely expensive, and time consuming to develop. For instance, in developing a standard cell ASIC a large set of photolithographic masks may be produced for each standard cell ASIC design. However, after this up-front investment in the initial development has been made, the typical production costs become very low, and the operating parameters with respect to power, frequency, and logic capacity can readily be optimized.

Alternatively, unlike Standard cell ASICs, the typical FPGA and/or CLPD, containing programmable logic, are relatively fast and cheap to develop, largely because the pre-existing devices are programmed electronically, and no photolithographic masks are required. However, with respect to operating parameters, such as power, frequency, and logic capacity, these are poor in comparison to a standard cell ASIC, and per-unit costs can be very high, particularly for large-capacity devices.

Structured ASICs, on the other hand, are a compromise between these two. Unlike gate arrays, structured ASICs tend to include predefined or configurable memories and/or analog blocks. Hence, development cost is much lower than for standard cell, because only a few photolithographic masks must be produced for each structured ASIC design, such as for configurable metal layers. And, although per-unit production costs are significantly higher than standard cell, they are still far lower than FPGA unit costs. With respect to power and frequency, these are a compromise between standard cell and FPGAs, but their logic capacity is similar to the largest FPGAs. Hence, in many instances, structured ASICs may be a technology that can reduce the up-front cost and time to develop a new custom integrated circuit.

With respect to design and fabrication of a structured ASIC, before a series of structured ASICs can be developed, a "master slice" may first be developed, such as by using standard cell ASIC methodology. As indicated above, the master slice may include most of the typical integrated circuit layers, such as one or more transistors, memories or memory cells, input/output cells, phase-locked loops, or other clock generators, and the like. Optionally a master slice may contain flip-flops, latches, and/or multi-transistor combinational gates. Some amount of local wiring between components may be included in the master slice, but much of the wiring to implement a full logic design may be omitted, such as to be added later. Note that a master slice can theoretically be constructed to include any logic suitable for standard cell ASICs, potentially including large complex modules, and operating parameters (power, frequency, logic capacity) of master slice logic are optimal, just as for standard cell ASICs. Photolithographic masks may be produced for master slice content, the mask set being similar or somewhat smaller than a standard cell ASIC mask set.

Accordingly, the master slice includes a set of digital logic circuits that may or may not yet be hardwired to function in a particular way.

Following construction of the master slice, a series of one or more complete structured ASICs may be implemented, such as by building upon the same master slice. Typically many structured ASIC designs utilize the same master slice, to amortize the cost of the master slice over many projects. Each individual structured ASIC design may be implemented by determining a set of new wired connections between components (transistors, etc.) in the master slice, which will effectively build the master slice components into higher level gates, flip flops, latches, memories, and large complex logic modules. Accordingly, these determined wired connections may be implemented in a small number of additional "configurable" metal layers 904A and 904B fabricated on top of the master slice, such as by connecting metal pads, or vias, in the master slice, for instance, by wires in the configurable metal layers. These additional metal layers are called "configurable" because they can be customized to each structured ASIC design project; however, they are fixed at fabrication time and cannot be rewired electronically except as the implemented logic design provides. There can be any number of configurable metal layers.

Most any conceivable logic design can thus be implemented using a master slice and appropriate wiring metal layers, as long as the master slice contains enough logic resources (transistors, memories, etc.) to form all the required logic design elements. The number of configurable metal layers varies from one structured ASIC design flow to another, but typically may be between 1 and 5 configurable metal layers more or less. A small additional set of photolithographic masks may be produced, corresponding to the configurable metal layers, and in device fabrication, the full mask set (master slice masks and configurable metal layer masks) may be used to build wafers of complete structured ASIC dice. Alternatively, master slice wafers might be pre-fabricated in bulk, and metal layers added in a later fabrication step to complete wafers of specific structured ASIC designs.

Advantageously, a structured ASIC master slice can be designed in one step, e.g., by a first designer, while specific structured ASIC logic designs based on that master slice may be designed, in a second step, such as by various other designers utilizing services of the structured ASIC designer. In particular, the various parties may typically be responsible for "front end" logic design specific to the desired integrated circuit functionality, such as RTL (register transfer logic) code development, simulation, emulation, regression testing, debugging, and the like; while the structured ASIC designer may typically be responsible for "back end" design flow, including synthesis, place and route, static timing analysis, test logic insertion, and/or tapeout. An additional party, e.g., a foundry, may be employed to produce physical photolithographic masks, fabricate wafers, and/or test and/or package the device dice. In various instances, a structured ASIC designer may also design custom master slices for a particular application class, such as to contain logic resource types or quantities customized to those applications.

Accordingly, by virtue of there being pre-defined metal layers (thus reducing manufacturing time) and pre-characterization of what is on the silicon wafer, e.g., master slice, (thus reducing design cycle time) the cycle time and design cycle time in the structured ASIC may be reduced as compared to typical ASIC manufacturing processes. For instance, in a cell based ASIC design or FPGA, e.g., gate-array, design the user may often have to design power, clock, and test structures themselves. However, in a structured ASIC these may be predefined which can save production time and expense as compared to cell based or gate-array profiles.

Particularly, the design task for structured ASIC's is to map the circuit into a fixed arrangement of known cells. More particularly, the comparative architecture of a structured ASIC typically may include two main levels, such as both structured elements and an array of structured elements. Such structured elements may include both combinational and sequential function blocks, which can function as either logical or storage elements. Additionally, with respect to arrays of structural elements, uniform or non-uniform array styles may be employed such as in a fixed arrangement of structured elements.

Consequently, in a structured ASIC design, the logic mask-layers of the device may be predefined. In such an instance, design differentiation and customization may be achieved such as by creating custom metal layers that create custom connections between predefined lower-layer logic elements. Likewise, the design tools used for structured ASIC can be substantially lower in cost and easier (faster) to use than cell-based tools, because they do not have to perform all the functions that cell-based tools do. More particularly, pre-existing standard cell-based CAD tools may be used in the design process. In some instances, however, CAD tools designed specifically for structured ASIC's may be used. Product specific placement tools may also be used. Further, as disclosed herein, new and improved algorithms have been developed so as to exploit the modularity of structured ASIC's, and better account for a more clock aware design. Additionally, the methods herein disclosed may be employed so as to enhance the evaluation and analysis processes, as discussed above.

In these manners the structured ASIC technology may act as a bridge filling the gap between field-programmable gate arrays and standard ASIC designs. More specifically, because only a small number of chip layers need be custom-produced, structured ASIC designs may have much smaller non-recurring expenditures (NRE) than "standard-cell" or "full-custom" chips, which require that a full mask set be produced for every design. Accordingly, a structured ASIC offers high performance (a characteristic of a typical ASIC), and low NRE cost (a characteristic of FPGA). Hence, a Structured ASIC fabrication process can be employed so as to allow the end product to be introduced quickly to market, to have lower cost, and to be more easily designed.

In some instances, however, a FPGA, may be advantageous in that the interconnects and logic blocks are programmable after fabrication. This offers a high flexibility of design and ease of debugging in prototyping. However, the capability of FPGAs to implement large circuits is sometimes limited, in both size and speed, which in some circumstances, may be due to the inherent complexity in programmable routing and/or significant space that may be occupied by the various included programming elements. On the other hand, ASICs also have some disadvantages, such as an expensive design flow, due in part to the fact that every different design typically needs a complete different set of masks. The structured ASIC, therefore, may be a solution between these two. It may basically have the same structure as a FPGA, but may be mask-programmable, such as in an ASIC, instead of being field-programmable, by configuring one or several via layers between metal layers. For instance, one or more, e.g., each SRAM configuration bit can be replaced by a choice of either including or not including a via or between various metal contacts.

For example, with respect to the architecture of a structured ASIC, a typical architecture may often times be fine-grained, medium grained, and/or hierarchical. A fine-grained architecture may include many connections in and out of a structured element, whereas higher granularities reduce connections to the structured element but may also decrease the functionality it can support. Each individual design will benefit differently at varying granularities. More particularly, in a fine-grained architecture, the architecture may include structured elements that contain unconnected discrete components, such as transistors, resistors, and other control elements that can later be connected. In a medium grained architecture, the architecture of the structured elements may include generic logic as well as gates, MUX's, LUT's and/or storage elements, such as flip-flops. Alternatively, in a hierarchical architecture, the architecture may include mini structured elements, for instance that contain gates, MUX's, and LUT's, but do not typically contain storage elements like flip-flops. In other instances, the mini element may be combined with registers or flip-flops.

With respect to implementing a structured ASIC the various fabrication steps may include one or more of register transfer level design (RTL); logical synthesis, so as to map the RTL into structured elements; design for test insertion, so as to improve testability and fault coverage; placement, so as to map each structured element onto an array element and to place each element into a fixed arrangement; physical synthesis in such a manner that improves the timing of the layout, and optimizes the placement of each element; clock synthesis in a manner that distributes the clock network and minimizes the clock skew and delay; as well as routing or otherwise inserting the wiring between the various elements. In various instances, these steps may be performed in any logical order and in a manner to make the design process, such as with respect to logical synthesis, less complex, as well as to help build up a more complete target structured ASIC library that enhances what specifically can be implemented from the design.

Furthermore, it has become common for some designers of processor cores to license the processor design to various customers so as to embed in their own silicon devices. Such embedded cores may include ARM, PowerPC, Krait, etc. as general-purpose processors, and may also include more specialized processors such as graphics processors (GPUs) or vector processors. Embedded processor cores may be large, complex logic modules, pipelined to run at high operating frequencies such as about 1 or 2 GHz to about 3 to 6 GHz, or more. In order to achieve such high frequencies, careful physical layout and routing may be used for processor cores and associated cache memory; and as a result, embedded processor technology may often be supplied as a "hard macro" (such as for defining precise placement and routing of the subcomponents) for a particular silicon fabrication process.

However, such an embedded processor core may be a suboptimal candidate for implementation in a structured ASIC using configurable metal layers. Hard macros do not generally apply to structured ASIC configurable layers, and even if an embedded processor were implemented as closely as possible to its hard macro in the configurable metal layers, it would likely be frequency limited (e.g. 30% or 50% of nominal operating frequency), and would likely consume very large portions of the available master slice resources. The relative area inefficiency of structured ASIC fabric as compared to standard cell could cause the embedded processor to cover a significantly larger physical silicon area, and in combination with reduced operating frequency, the performance to area (or cost) ratio could be much lower than a standard cell implementation of the same embedded core.

However, it is practical to implement embedded one or more processor cores efficiently in a structured ASIC master slice, such as by using a standard cell design methodology, as disclosed herein, including the use of hard macros. These would retain full operating frequency and performance, and consume only normal silicon area. The processor core and/or cache input and output wires could be connected to other resources in the master slice, or advantageously, exposed to configurable metal layer routing, to enable the embedded cores to be connected to any infrastructure and logic modules implemented in each particular structured ASIC design. In a manner such as this, the embedded processor cores become master slice resources available to many various structured ASIC designs later implemented using the master slice.

Embedded processor cores in a structured ASIC can be connected to logic infrastructure so that software (firmware) running on the cores can share and access various memory and other resources, on-chip and off-chip, and to communicate with any or all other logic modules on the chip, via memory and/or directly. In this manner, the processor cores can operate in parallel with other logic modules, and/or cooperate with other logic modules to complete joint work, such as by the processor cores requesting tasks to be performed by other modules, or other modules requesting tasks to be performed by the processor cores, or both.

When Bio-IT acceleration modules (such as to perform mapping, alignment, sorting, duplicate marking, base quality score recalibration, local re-alignment, variant calling, compression, decompression, etc. as described herein) are implemented in an FPGA and/or a structured ASIC along with embedded processor cores, the resulting system on a chip (SOC) has important advantages, especially in a combination of speed and flexibility. Extreme speed may be achieved by the hardware acceleration modules, and extreme flexibility may be achieved by the full programmability of the processor cores. By reprogramming the processor cores, the bio-IT algorithms executed can be easily modified, but these algorithms can run orders of magnitude faster than in traditional CPUs because computationally intensive operations may be offloaded to hardware accelerators. Communication and memory organization can be optimized for cooperative processor-accelerator work. Additional software algorithm acceleration can be obtained by additional hardware modules designed to pre-process or post-process data used by the processor cores, such as organizing reads overlapping a reference genome locus into a pileup data structure, for presentation to the processor cores. In some processor architectures, instruction sets can be extended to utilize connected hardware resources; in the Bio-IT SOC environment, new processor instructions can be defined to access Bio-IT hardware acceleration functions.

As summarized in Table II, below, a structured ASIC, therefore, has several prefabricated advantages, such as over an ASIC or FPGA. For instance, the various components may be "almost" connected, such as in a variety of predefined configurations, and multiple global and local clocks may be prefabricated. This means, therefore, that signal integrity and timing issues should inherently be addressed. Additionally, only a few metal layers may be needed for fabrication. Further, unlike standard FPGAs, the structured ASIC should have a capacity, performance, and power consumption closer to that of a standard cell ASIC. This should allow for easier and faster design processes and times as well as reduced NRE costs than in standard cell ASIC's, and should drastically reduce turnaround time. Further still, no skew problems should need to be addressed.

TABLE II

| | FPGA | Structured ASIC | Standard Cell ASIC |
|---|---|---|---|
| Silicon area | Very high | Low | Very low |
| Power utilization | High | Low | Very low |
| Operating frequency | Low | High | High |
| Logic capacity | Medium | Medium | High |
| Development cost | Very low | Low | High |
| Per-unit cost | Very high | Low | Very low |

A structured ASIC, therefore, has several different beneficial properties, including one or more of: low NRE cost, lower requirements for implementation engineering efforts, lower mask tooling charges, such as over an ASIC, with the additional benefits of high performance, low power consumption, fewer fabrication layers, less complexity, in a pre-made cell block configuration that is available for placing circuit elements, together which leads to a quicker production time. There are, however, some disadvantages to structured ASICs, for instance, there are sometimes a lack of adequate design tools, which tools and processing may be expensive and need to be altered from traditional ASIC tools. Further, these new architectures are still being subjected to formal evaluations and comparative analyses. And, there may be tradeoffs between 3-, 4-, and 5-input LUT's, and/or between sizes of distributed RAM.

Accordingly, in view of the above, there are both advantages and disadvantages to ASICs, FPGAs, and Structured ASICs. For instance, standard cell ASICs may be difficult to design, need a long development time, have a high NRE cost. However, an ASIC may also support large designs, support complex designs, have a high performance at a low power consumption, which therefore could result in a low or lower Per-Unit Cost (at high volume). On the other hand, FPGAs may be easy to design, involve a short development time, and a low NRE cost. However, FPGAs may have a limited design size and/or complexity, may have limited performance, and a high power consumption, which may result in a high or higher Per-Unit Cost. In many instances, a structured ASIC may be designed to maximize these benefits and minimize these disadvantages. For instance, generally speaking there may be about a 100:33:1 ratio between the number of gates in a given area for standard cell ASIC's, structured ASIC's, and FPGA's; a 100:75:15 ratio for performance (based on clock frequency); and a 1:3:12 ratio for power, respectively.

As indicated above, in various instances a chip 100 of the disclosure may be configured as an expansion card, such as where the chip includes a PCIe bus and is positioned so as to be in communication with one or more memories, such as being surrounding by memories, such as being substantially surrounded by memories, such as being entirely surrounded by memories. In various embodiments, the chip may be a dense and/or fast FPGA chip that in various instances, may be convertible to an ASIC or an sASIC. In various instances, the chip may be a structured ASIC that is convertible into an ASIC. In some instances, the chip may be an ASIC.

As indicated above, the modules herein disclosed may be implemented in the hardware of the chip, such as by being hardwired therein, and in such instances their implementation may be such that their functioning may take place at a faster speed as compared to when implemented in software, such as where there are minimal instructions to be fetched, read, and/or executed. Hence, given the unique hardware implementation, the modules of the disclosure may function directly in accordance with their operations parameters, such as without needing to fetch, read, and/or execute instructions. Additionally, memory requirements and processing times may be reduced, such as where the communications within chip is via files rather than through accessing a memory. Of course, in some instances, the chip and/or card may be sized so as to include more memory, such as more on board memory, so as to enhance parallel processing capabilities, thereby resulting in even faster processing speeds. For instance, in certain embodiments, a chip of the disclosure may include an embedded DRAM, so that the chip does not have to rely on external memory, which would therefore result in a further increase in processing speed, such as where a Burrows-Wheeler algorithm may be employed, instead of a hash table and hash function, which may in various instances, rely on external, e.g., host memory. In such instances, the running of the entire pipeline can be accomplished in 6 minutes or less, such as from start to finish.

Figure 8:
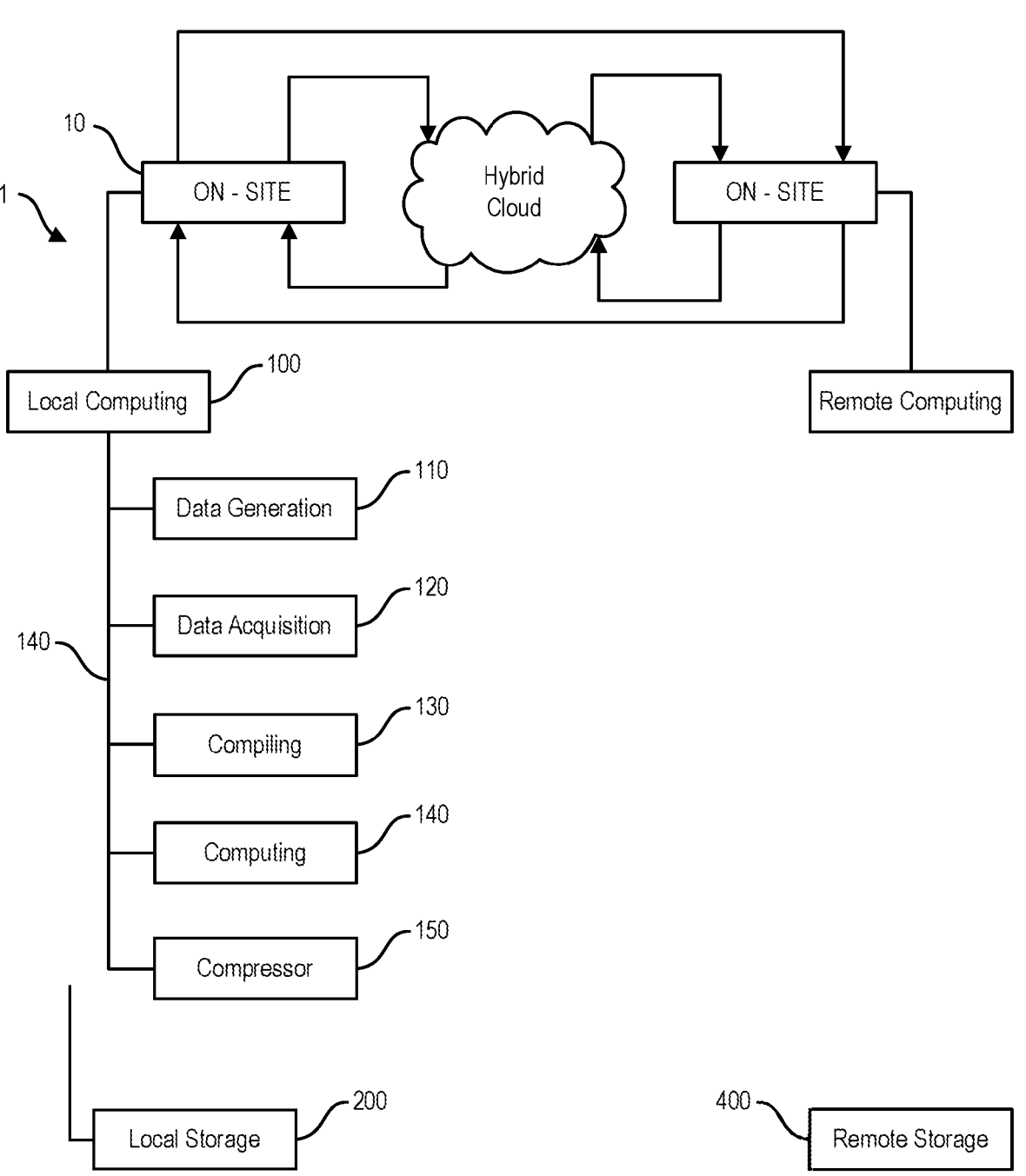
FIG. 8 depicts a block diagram for a genomic infrastructure for onsite and/or cloud based genomics processing and analysis.

As indicated above, and as seen at FIG. 8, there are various different points where any given module can be positioned on the hardware, or be positioned remotely therefrom, such as on a server accessible on the cloud. Where a given module is positioned on the chip, e.g., hardwired into the chip, its function may be performed by the hardware, however, where desired, the module may be positioned remotely from the chip, at which point the platform may include the necessary instrumentality for sending the relevant data to a remote location, such as a server accessible via the cloud, so that the particular module's functionality may be engaged for further processing of the data, in accordance with the user selected desired protocols. Accordingly, part of the platform may include a web-based interface for the performance of one or more tasks pursuant to the functioning of one or more of the modules disclosed herein. For instance, where mapping 112, alignment 113, and/or sorting 114a are all modules that may occur on the chip, in various instances, one or more of local realignment 114d, duplicate marking 114b, base quality core recalibration 114c, and/or variant calling 115 may take place on the cloud.

Particularly, once the genetic data has been generated and/or processed, e.g., in one or more primary and/or secondary processing protocols, such as by being mapped, aligned, and/or sorted, such as to produce one or more variant call files, for instance, to determine how the genetic sequence data from a subject differs from one or more reference sequences, a further aspect of the disclosure may be directed to performing one or more other analytical functions on the generated and/or processed genetic data such as for further, e.g., tertiary, processing, as depicted in FIGS. 8-11. For example, the system may be configured for further processing of the generated and/or secondarily processed data, such as by running it through one or more tertiary processing pipelines 700 and 122, such as one or more of a genome pipeline, an epigenome pipeline, metagenome pipeline, joint genotyping, a MuTect2 pipeline, or other tertiary processing pipeline, such as by the devices and methods disclosed herein. For instance, in various instances, an additional layer of processing 800 may be provided, such as for disease diagnostics, therapeutic treatment, and/or prophylactic prevention, such as including NIPT, NICU, Cancer, LDT, AgBio, and other such disease diagnostics, prophylaxis, and/or treatments employing the data generated by one or more of the present primary and/or secondary and/or tertiary pipelines. Hence, the devices and methods herein disclosed may be used to generate genetic sequence data, which data may then be used to generate one or more variant call files and/or other associated data that may further be subject to the execution of other tertiary processing pipelines in accordance with the devices and methods disclosed herein, such as for particular and/or general disease diagnostics as well as for prophylactic and/or therapeutic treatment and/or developmental modalities.

As described above, the system 1 herein presented may include the generating, such as by the sequencer on a chip technology disclosed herein, or the otherwise acquiring of genetic sequence data, and may include the performance of one or more secondary processing protocols, such as including one or more of mapping, aligning, and sorting of the generated genetic sequence data, such as to produce one or more variant call files, for instance, so as to determine how the genetic sequence data from a subject differs from one or more reference sequences or genomes. A further aspect of the disclosure may be directed to performing one or more other analytical functions on the generated and/or processed genetic data such as for further, e.g., tertiary, processing, which processing may be performed on or in association with the same chip or chipset as that hosting the aforementioned sequencer technology.

In a first instance, such as with respect to the generation, acquisition, and/or transmission of genetic sequence data, as set forth in FIG. 8, such data may be produced either locally or remotely and/or the results thereof may then be directly processed, such as by a local computing resource 100, or may be transmitted to a remote location, such as to a remote computing resource 300, for further processing. For instance, the generated genetic sequence data may be processed locally, and directly, such as where the sequencing and secondary processing functionalities are housed on the same chipset and/or within the same device. Likewise, the generated genetic sequence data may be processed locally, and indirectly, such as where the sequencing and secondary processing functionalities occur separately by distinct apparatuses that share the same facility or location but may be separated by a space albeit communicably connected, such as via a local network 100. In a further instance, the genetic sequence data may be derived remotely, such as by a NGS, and the resultant data may be transmitted over a cloud based network 50 to a remote location, such as separated geographically from the sequencer.

Specifically, as illustrated in FIGS. 8-11, in various embodiments, a nucleotide sequencer may be provided on site, such as by a sequencer on a chip or by an NGS, wherein the sequencer is associated with a local computing resource 100 either directly or indirectly such as by a local network connection 10. The local computing resource 100 may include or otherwise be associated with one or more of a data generation 110 and/or a data acquisition 120 mechanism(s). Such mechanisms may be any mechanism configured for either generating and/or otherwise acquiring data, such as analog, digital, and/or electromagnetic data related to one or more genetic sequences of a subject or group of subjects.

For example, such a data generating mechanism 110 may be a primary processor such as a sequencer, such as a NGS, a sequencer on a chip, or other like mechanism for generating genetic sequence information. Further, such data acquisition mechanisms 120 may be any mechanism configured for receiving data, such as generated genetic sequence information, and/or together with the data generator 110 and/or computing resource 150 capable of subjecting the same to one or more secondary processing protocols, such as a secondary processing pipeline apparatus configured for running a mapper, aligner, sorter, and/or variant caller protocol on the generated and/or acquired sequence data as herein described. In various instances, the data generating 110 and/or data acquisition 120 apparatuses may be networked together such as over a local network 10, such as for local storage 200, or may be networked together over a cloud based network 30, such as for transmitting and/or receiving data, such as digital data related to the primary and/or secondary processing of genetic sequence information, such as to or from a remote location 30 such as for remote processing 300 and/or storage 400. In various embodiments, one or more of these components may be communicably coupled together by a hybrid network as herein described.

The local computing resource 100 may also include or otherwise be associated with a compiler 130 and/or a processor 150, such as a compiler 130 configured for compiling the generated and/or acquired data and/or data associated therewith, and a processor 150 configured for processing the generated and/or acquired and/or compiled data and/or controlling the system 1 and its components as herein described. Further, the local computing resource 100 may include a compressor unit 160 configured for compressing data, such as generated and/or acquired primary and/or secondary processed data, which data may be compressed, such as prior to transfer over a local 10 and/or cloud 30 and/or hybrid cloud based 50 network.

Figure 11:
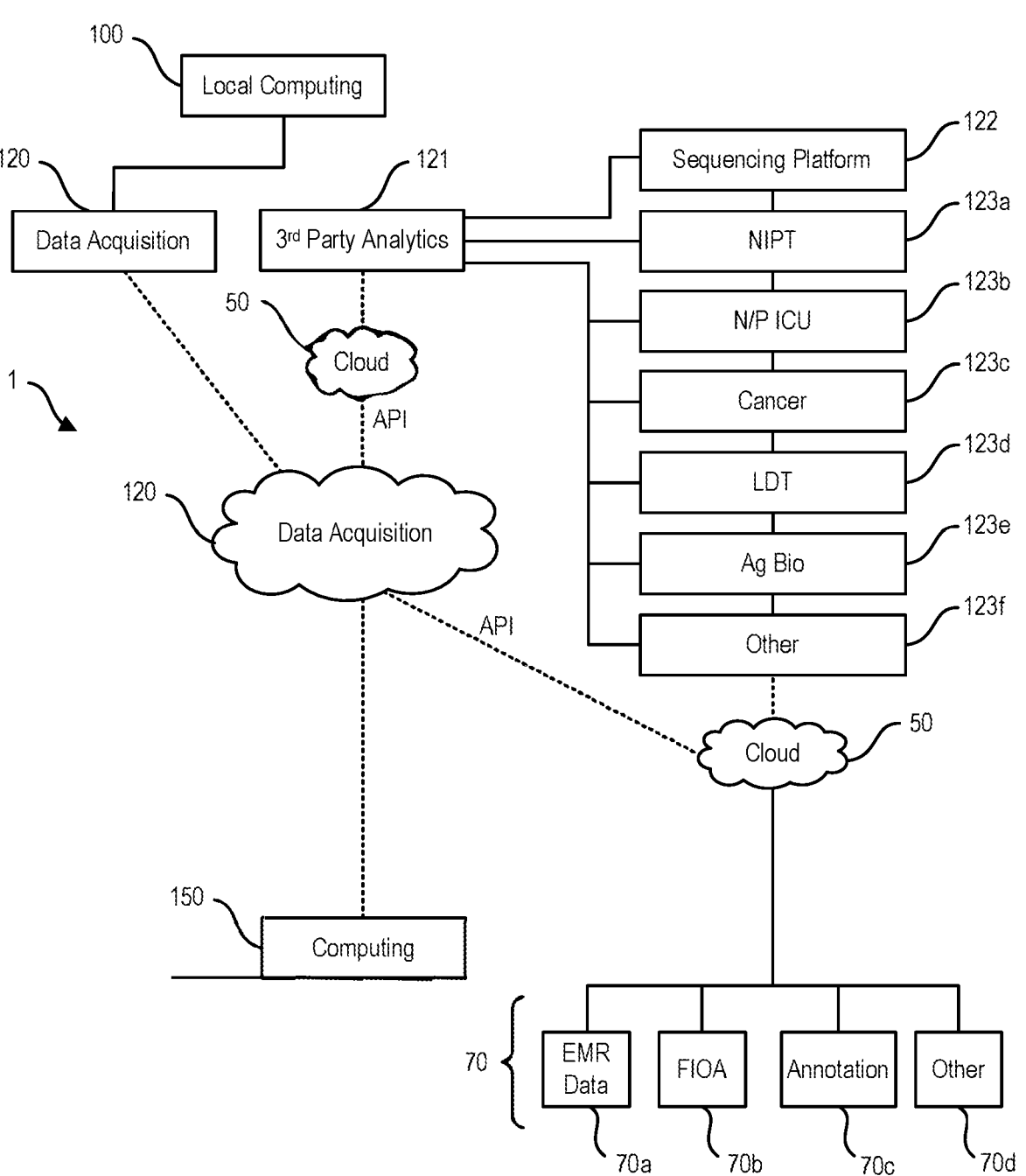
FIG. 11 depicts the block diagram of FIG. 8 illustrating greater detail regarding the $3^{rd}$-Party analytics function for a genomic infrastructure for onsite and/or cloud based genomics processing and analysis.

In particular instances, as can be seen with respect to FIGS. 8 and 11, the system 1 may be configured for subjecting the generated and/or secondarily processed data to further processing, e.g., via a local 100 and/or a remote 300 computing resource, such as by running it through one or more tertiary processing pipelines, such as one or more of a genome pipeline, an epigenome pipeline, metagenome pipeline, joint genotyping, a MuTect2 pipeline, or other tertiary processing pipeline. Such data may then be compressed and/or stored locally 200 and/or be transferred so as to be stored remotely.

In additional instances, the system 1 may include a further tier of processing modules, such as configured for rendering additional processing such as for diagnosis, disease and/or therapeutic discovery, and/or prophylaxis thereof. For instance, in various instances, an additional layer of processing may be provided, such as for disease diagnostics, therapeutic treatment, and/or prophylactic prevention, such as including NIPT, NICU, Cancer, LDT, AgBio, and other such disease diagnostics, prophylaxis, and/or treatments employing the data generated by one or more of the present primary and/or secondary and/or tertiary pipelines.

Accordingly, herein presented is a system 1 for producing and using a global hybrid cloud network 50. For instance, presently, the cloud 30 is used primarily for storage, such as at a remote storage location 400. In such an instance, the computing of data is performed locally 100 by a local computing resource 150, and where storage needs are extensive, the cloud 30 is accessed so as to store the data generated by the local computing resource 150, such as by use of a remote storage resource 400. Hence, generated data is typically either wholly managed on site locally 100, or it is totally managed off site 300, on the cloud 30.

Particularly, in a general implementation of a bioinformatics analysis platform, the computing 150 and/or storage 200 functions are maintained locally on site, and where storage needs exceed local storage capacity, or where there is a need for stored data to be made available to other remote users, such data may be transferred via internet 30 to the cloud for remote storage 400 thereby. In such an instance, where the computing resources 150 required for performance of the computing functions are minimal, but the storage requirements extensive, the computing function 150 may be maintained locally 100, while the storage function 400 may be maintained remotely, with the fully processed data being transferred back and forth between the processing function 150, such as for local processing only, and the storage function 400, such as for the remote storage 400 of the processed data.

For instance, this may be exemplified with respect to the sequencing function, such as with a typical NGS, where the computing resource 150 is configured for performing the functions required for the sequencing of the genetic material so as to produce genetic sequenced data, e.g., reads, which data is produced onsite 100. These reads, once generated, such as by the onsite NGS, may then be transferred such as over the cloud network 30, such as for storage 400 at a remote location 300 in a manner so as to be recalled from the cloud 30 when necessary such as for further processing, such as for the performance of one or more of secondary and/or tertiary processing functions, that is at a location remote from the storage facility 400, e.g., locally. In such an instance, the local storage resource 150 serves merely as a storage cache where data is placed while waiting transfer to or from the cloud 30, such as to or from the remote storage facility 400.

Likewise, where the computing function is extensive, such as requiring one or more remote computer cluster cores 300 for processing the data, and where the storage demands for storing the processed data 200 are relatively minimal, as compared to the computing resources 300 required to process the data, the data to be processed may be sent, such as over the cloud 30, so as to be processed by a remote computing resource 300, which resource may include one or more cores or clusters of computing resources, e.g., one or more super computing resources. In such an instance, once the data has been processed by the cloud based computer core 300, the processed data may then be transferred over the cloud network 30 so as to be stored local 200 and readily available for use by the local computing resource 150, such as for local analysis and/or diagnostics.

This may be exemplified with respect to a typical secondary processing function, such as where the pre-processed sequenced, e.g., read, data that is stored locally 200 is accessed, such as by the local computing resource 100, and transmitted over the cloud internet 30 to a remote computing facility 300 so as to be further processed thereby, e.g., in a secondary processing function, to obtain processed results data that may then be sent back to the local facility 100 for storage 200 thereby. This may be the case where a local practitioner generates sequenced read data using a local data generating resource 100, e.g., automated sequencer, and then sends that data over the network 30 to a remote computing facility 300, which then runs one or more functions on that data, such as a Burrows-Wheeler transform or Needlemen-Wunsch and/or Smith-Waterman alignment function on that sequence data, so as to generate results data that may then be transmitted over the internet 30 to the local computing resource 100 so as to be examined thereby in one or more local administered processing protocols and/or stored locally 200.

What is needed, however, is a seamless integration between the engagement between local 100 and remote 300 computer processing as well as between local 200 and remote 400 storage, such as in the hybrid cloud 50 based system presented herein. In such an instance, the system can be configured such that local 100 and remote 300 computing resources are configured so as to run seamlessly together, such that data to be processed thereby can be allocated real time to either the local 200 or the remote 300 computing resource without paying an extensive penalty due to transfer rate and/or in operational efficiency. This may be the case, for instance, where the software and/or hardware to be deployed or otherwise run by the computing resources are configured so as to correspond to one another and/or are the same or functionally similar, e.g., the hardware and/or software is configured in the same manner so as to run the same algorithms in the same manner on the generated and/or received data.

Figure 9:
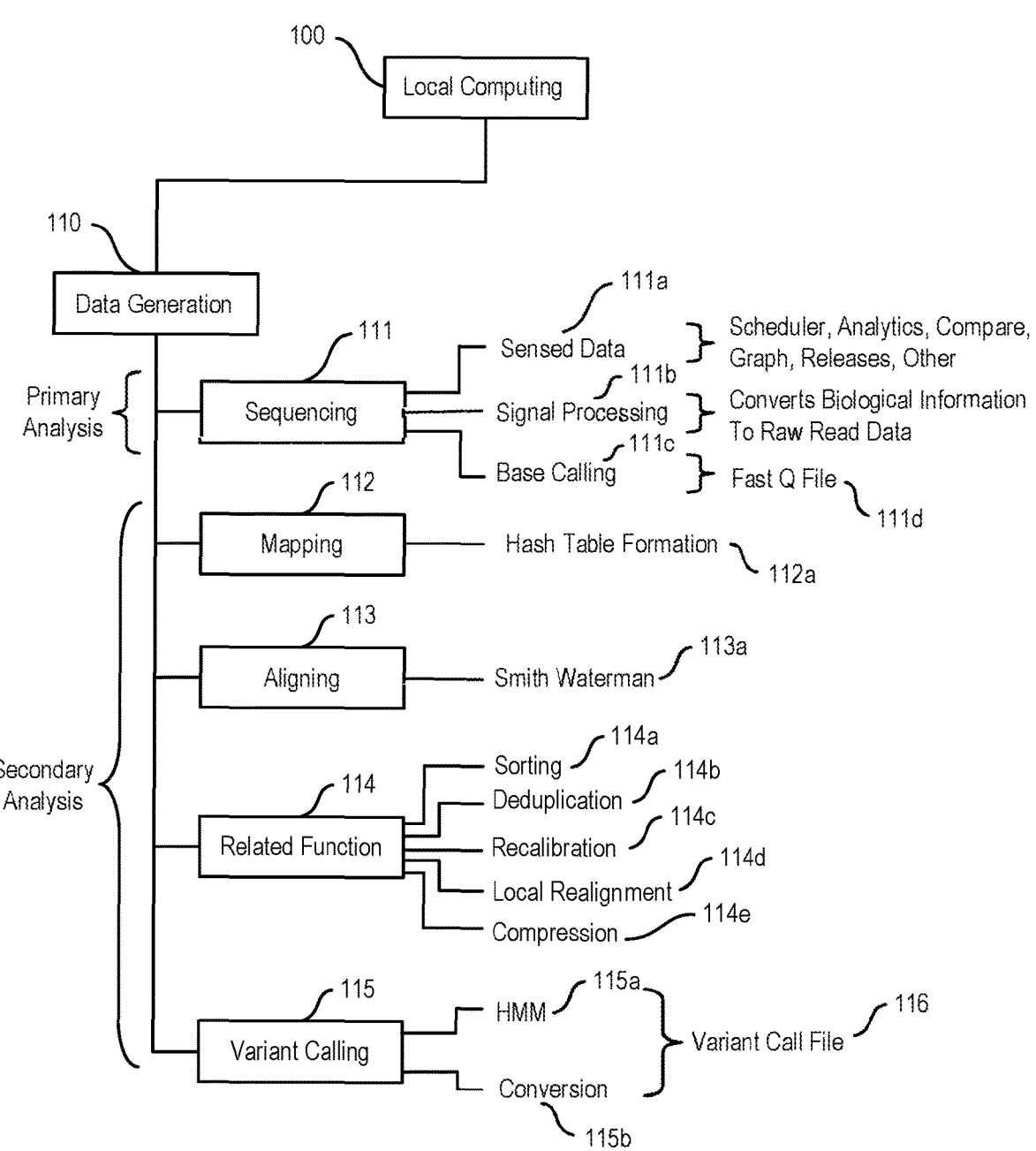
FIG. 9 depicts a block diagram of a local and/or cloud based computing function of FIG. 8 for a genomic infrastructure for onsite and/or cloud based genomics processing and analysis.

For instance, as can be seen with respect to FIGS. 8-9 a local computing resource 100 may be configured for generating data, and therefore may include a data generating mechanism 110, such as for primary data generation and/or analysis, e.g., so as to produce a FASTQ sequence file. This data generating mechanism 110 may be a local computer, as described herein throughout, having a processor that may be configured to run one or more software applications and/or may be hardwired so as to perform one or more algorithms such as in a wired configuration on the generated and/or acquired data. For example, the data generating mechanism 110 may be configured for one or more of generating data, such as sequencing data 111, which data may be sensed data 111a, such as data that is detectable as a change in voltage, ion concentration, electromagnetic radiation, and the like; and/or the data generating mechanism 110 may be configured for generating and/or processing signal, e.g., analog or digital signal data, such as data representing one or more nucleotide identities in a sequence or chain of associated nucleotides. In such an instance, the data generating mechanism 110, e.g., sequencer 111, may further be configured for preliminarily processing the generated data so as to perform one or more base call operations 111c, such as on the data so as to produce sequence identity data, e.g., a FASTQ file.

It is to be noted, that in this instance, the data 111 so generated may be generated locally, such as by a local data generating and/or computing resource 150, e.g., a sequencer on a chip; or it may be produced remotely, e.g., by a remote computing and/or generating resource, such as a remote NGS 300, but be transferred over the cloud 30/50 to the local computing resource 100 such as for secondary processing 150 and/or storage thereby in a local storage resource 200, such as while awaiting further local processing 150. In such an instance, where the data generation resource 300 is remote from the local processing 100 and/or storage 200 resources, the corresponding resources may be configured such that the remote and/or local storage, remote and local processing, and/or communicating protocols employed by each resource may be adapted to smoothly and/or seamlessly integrate with one another, e.g., by running the same, similar, and/or equivalent software and/or by having the same, similar, and/or equivalent hardware configurations, and/or employing the same communications and/or transfer protocols, which, in some instances, may have been implemented at the time of manufacture or later thereto.

Particularly, these functions may be implemented in a hardwired configuration such as where the sequencing function and the secondary processing function are maintained upon the same or associated chip or chipset, e.g., such as where the sequencer and secondary processor are directly interconnected on a chip, as herein described, or may be implemented via software that has been optimized to allow the two remote devices to communicate seamlessly with one another. A combination of optimized hardware and software implementations for performing the recited functions may also be employed, as described herein. In various embodiments, the data generating resource, such as the sequencer 111, whether implemented in software and/or in hardware or a combination of the same, may further be configured to include an initial tier of processors 500 such as a scheduler, various analytics, comparers, graphers, releasers, and the like, so as to assist the data generator 111, e.g., sequencer, in converting biological information into raw read data, such as in a FASTQ file format 111d.

Likewise, the same may be true with respect to the performance of the other functions that may be deployed by the local 100 and/or remote 300 computing resources. For example, the local computing resource 100 may include hardware and/or software configured for performing one or more secondary tier 700 of processing functions 112-115 on remotely and/or locally generated data, such as genetic sequence data, in a manner that the processing and results thereof may be seamlessly shared with one another and/or stored thereby. Particularly, the local computing function 100 and/or the remote computing function 300 may be configured for generating and/or receiving primary data, such as genetic sequence data, e.g., in a FASTQ or other like file format, and running one or more secondary processing protocols 600 on that generated and/or acquired data, which protocols may be implemented in a software, hardware, or combinational format. For instance, the data generating and/or processing resource 110 may be configured for performing one or more of a mapping operation 112, an alignment operation 113, or other related function 114 on the acquired or generated data.

More particularly, the data generating resource 110 may include a mapping engine 112, as herein described, or may otherwise include programming for running a mapping algorithm on the genetic sequence data, such as for performing a Burrows-Wheeler transform and/or other algorithms for building a hash table and/or running a hash function 112a on said data, such as for hash seed mapping, so as to generate mapped sequence data. The data generating resource 110 may also include an alignment engine 113, as herein described, or may otherwise include programming for running an alignment algorithm on the genetic sequence data, e.g., mapped sequenced data, such as for performing a gapped and/or gapless Smith-Waterman alignment, and/or Needleman-Wunsch, or other like scoring algorithm 113a on said data, so as to generate aligned sequence data. The data generating resource 110 may also be configured to include one or more other modules 114 adapted to perform one or more other processing functions on the genetic sequence data, such as on the mapped and/or aligned sequence data, and thus may include a suitably configured engine 114 or otherwise include programming for running the one or more other processing functions such as a sorting 114a, deduplication 114b, recalibration 114c, local realignment 114d, duplicate marking 114f, Base Quality Score Recalibration 114g function(s) and/or a compression function (such as to produce a BAM, Reduced BAM, and/or a CRAM compression and/or decompression file) 114e, in accordance with the methods herein described, which processing functions may be configured as one or more pipelines of the system 1. Likewise, the system 1 may be configured to include a module 115 adapted for processing the data, e.g., the sequenced, mapped, aligned, and/or sorted data in a manner such as to produce a variant call file 116, such as in a hardware and/or software based processing functionality.

More particularly, the system 1 may include a variant call module 115 for running one or more variant call functions, such as a Hidden Markov Model (HMM) and/or GATK function 115a such as in a wired configuration and/or via one or more software applications, e.g., either locally or remotely, and/or a converter 115b for the same.

In particular embodiments, as set forth in FIGS. 8 and 10, the system 1 may include a local computing function 100 that may be configured for employing a computer processing resource 150 for performing one or more further computer processing functions on data generated by the system generator 110 or acquired by the system acquisition mechanism 120 (as described below), such as by being transferred thereto, for instance, by a third party 121, such as via a cloud 30 or hybrid cloud network 50. For instance, a third party analyzer 121 may deploy a remote computing resource 300 so as to generate relevant data in need of further processing, such as genetic sequence data or the like, which data may be communicated to the system 1 over the network 30/50 so as to be further processed. This may be useful, for instance, where the remote computing resource 300 is a NGS, configured for taking raw biological data and converting it to a digital representation thereof, such as in the form of one or more FASTQ files containing reads of genetic sequence data, and where further processing is desired, such as to determine how the generated sequence of an individual differs from that of one or more reference sequences, as herein described, and/or it is desired to subject the results thereof to furthered, e.g., tertiary, processing.

In such an instance, the system 1 may be adapted so as to allow one or more parties, e.g., a primary and/or secondary and/or third party user, to access the associated local processing resources 100, and/or a suitably configured remote processing resource 300 associated therewith, in a manner so as to allow the user to perform one or more quantitative and/or qualitative processing functions 152 on the generated and/or acquired data. For instance, in one configuration, the system 1 may include, e.g., in addition to primary 600 and/or secondary 600 processing pipelines, a third tier of processing modules 700, which processing modules may be configured for performing one or more processing functions on the generated and/or acquired primary and/or secondary processed data.

Particularly, in one embodiment, the system 1 may be configured for generating and/or receiving processed genetic sequence data 111 that has been either remotely or locally mapped 112, aligned 113, sorted 114a, and/or further processed 114 so as to generate a variant call file 116, which variant call file may then be subjected to further processing such as within the system 1, such as in response to a second and/or third party analytics requests 121. More particularly, the system 1 may be configured to receive processing requests from a third party 121, and further be configured for performing such requested tertiary processing 700 on the generated and/or acquired data. Specifically, the system 1 may be configured for producing and/or acquiring genetic sequence data 111, may be configured for taking that genetic sequence data and mapping 112, aligning 113, and/or sorting 114a it to produce one or more variant call files (VCFs) 116, and additionally the system 1 may be configured for performing a tertiary processing function 700 on the data, e.g., with respect to the one or more VCFs. The system 1 may be configured so as to perform any form of tertiary processing 700 on the generated and/or acquired data, such as by subjecting it to one or more pipeline processing functions 700 such as to generate genome data 122a, epigenome data 122b, metagenome data 122c, and the like, including joint genotyping 122d, GATK 122e and/or MuTect2 122f analysis pipelines. Further, the system 1 may be configured for performing an additional tier of processing on the generated and/or processed data, such as including one or more of non-invasive prenatal testing (NIPT) 123a, N/P ICU 123b, cancer related diagnostics and/or therapeutic modalities 123c, various laboratory developed tests (LDT) 123d, agricultural biological (Ag Bio) applications 123e, or other such health care related 123f processing function.

Hence, in various embodiments, where a primary user may access and/or configure the system 1 and its various components directly, such as through direct access therewith, such as through the local computing resource 100, as presented herein, the system 1 may also be adapted for being accessed by a secondary party, such as is connected to the system 1 via a local network or intranet connection 10 so as to configure and run the system 1 within the local environment. Additionally, in certain embodiments, as presented in FIG. 2B, the system may be adapted for being accessed and/or configured by a third party 121, such as over an associated hybrid-cloud network 50 connecting the third party 121 to the system 1, such as through an application program interface (API), accessible as through one or more graphical user interface (GUI) components. Such a GUI may be configured to allow the third party user to access the system 1, and using the API configure the various components of the system, the modules, associated pipelines, and other associated data generating and/or processing functionalities so as to run only those system components necessary and/or useful to the third party and/or requested or desired to be run thereby.

Accordingly, in various instances, the system 1 as herein presented may be adapted so as to be configurable by a primary, secondary, or tertiary user of the system. In such an instance, the system 1 may be adapted to allow the user to configure the system 1 and thereby to arrange its components in such a manner as to deploy one, all, or a selection of the analytical system resources, e.g., 152, to be run on data that is either generated, acquired, or otherwise transferred to the system, e.g., by the primary, secondary, or third party user, such that the system 1 runs only those portions of the system necessary or useful for running the analytics requested by the user to obtain the desired results thereof. For example, for these and other such purposes, an API may be included within the system 1 wherein the API is configured so as to include or otherwise be operably associated with a graphical user interface (GUI) including an operable menu and/or a related list of system function calls from which the user can select and/or otherwise make so as to configure and operate the system and its components as desired.

In such an instance, the GUI menu and/or system function calls may direct the user selectable operations of one or more of a first tier of operations 600 including: sequencing 111, mapping 112, aligning 113, sorting 114a, variant calling 115, and/or other associated functions 114 in accordance with the teachings herein, such as with relation to the primary and/or secondary processing functions herein described. Further, where desired the GUI menu and/or system function calls may direct the operations of one or more of a second tier of operations 700 including: a genome pipeline 122a, epigenome pipeline 122b, metagenome pipeline 122c, a joint genotyping pipeline 122d, GATK 122e and/or MuTect2 122f analysis pipelines. Furthermore, where desired the GUI menu and system function calls may direct the user selectable operations of one or more of a third tier of operations 800 including: non-invasive prenatal testing (NIPT) 123a, N/P ICU 123*b*, cancer related diagnostics and/or therapeutic modalities 123*c*, various laboratory developed tests (LDT) 123*d*, agricultural biological (Ag Bio) applications 123*e*, or other such health care related 123*f* processing functions.

Accordingly, the menu and system function calls may include one or more primary, secondary, and/or tertiary processing functions, so as to allow the system and/or its component parts to be configured such as with respect to performing one or more data analysis pipelines as selected and configured by the user. In such an instance, the local computing resource 100 may be configured to correspond to and/or mirror the remote computing resource 300, and/or likewise the local storage resource 200 may be configured to correspond and/or mirror the remote storage resource 400 so that the various components of the system may be run and/or the data generated thereby may be stored either locally or remotely in a seamless distributed manner as chosen by the use of the system 1. Additionally, in particular embodiments, the system 1 may be made accessible to third parties, for running proprietary analysis protocols 121*a* on the generated and/or processed data, such as by running through an artificial intelligence interface designed to find correlations there between.

The system 1 may be configured so as to perform any form of tertiary processing on the generated and/or acquired data. Hence, in various embodiments, a primary, secondary, or tertiary user may access and/or configure any level of the system 1 and its various components either directly, such as through direct access with the computing resource 100, indirectly, such as via a local network connection 10, or over an associated hybrid-cloud network 50 connecting the party to the system 1, such as through an appropriately configured API having the appropriate permissions. In such an instance, the system components may be presented as a menu, such as a GUI selectable menu, where the user can select from all the various processing and storage options desired to be run on the user presented data. Further, in various instances, the user may upload their own system protocols so as to be adopted and run by the system so as to process various data in a manner designed and selected for by the user. In such an instance, the GUI and associated API will allow the user to access the system 1 and using the API add to and configure the various components of the system, the modules, associated pipelines, and other associated data generating and/or processing functionalities so as to run only those system components necessary and/or useful to the party and/or requested or desired to be run thereby.

Where the above with respect to FIGS. 8 and 9 are directed to data generation 110 such as local data generation 100, employing a local computing resource 150; as indicated above, and with respect to FIG. 9, one or more of the above demarcated modules, and their respective functions and/or associated resources, may be configured for being performed remotely, such as by a remote computing resource 300, and further be adapted to be transmitted to the system 1, such as in a seamless transfer protocol over a cloud based internet connection 30/50, such as via a suitably configured data acquisition mechanism 120.

Accordingly, in such an instance, the local computing resource 100 may include a data acquisition mechanism 120, such as configured for transmitting and/or receiving such acquired data and/or associated information. For instance, the system 1 may include a data acquisition mechanism 120 that is configured in a manner so as to allow the continued processing and/or storage of data to take place in a seamless and steady manner, such as over a cloud or hybrid based network 30/50 where the processing functions are distributed both locally 100 and/or remotely 300, and likewise where one or more of the results of such processing may be stored locally 200 and/or remotely 400, such that the system seamlessly allocates to which local or remote resource a given job is to be sent for processing and/or storage regardless of where the resource is physically positioned. Such distributed processing, transferring, and acquisition may include one or more of sequencing 111, mapping 112, aligning 113, sorting 114*a*, duplicate marking 114*c*, deduplication, recalibration 114*d*, local realignment 114*e*, Base Quality Score Recalibration 114*f* function(s) and/or a compression function 114*g*, as well as a variant call function 116, as herein described. Where stored locally 200 or remotely 400, the processed data, in whatever state it is in in the process may be made available to either the local 100 or remote processing 300 resources, such as for further processing prior to re-transmission and/or re-storage.

Specifically, the system 1 may be configured for producing and/or acquiring genetic sequence data 111, may be configured for taking that genetic sequence data 111 and processing it locally 150, or transferring the data over a suitably configured cloud 30 or hybrid cloud 50 network such as to a remote processing facility for remote processing 300. Further, once processed the system 1 may be configured for storing the processed data remotely 400 or transferring it back for local storage 200. Accordingly, the system 1 may be configured for either local or remote generation and/or processing of data, such as where the generation and/or processing steps may be from a first tier of primary and/or secondary processing functions 600, which tier may include one or more of: sequencing 111, mapping 112, aligning 113, and/or sorting 114*a* so as to produce one or more variant call files (VCFs) 116. Likewise, the system 1 may be configured for either local or remote generation and/or processing of data, such as where the generation and/or processing steps may be from a second tier of tertiary processing functions 700, which tier may include one or more of generating and/or acquiring data pursuant to a genome pipeline 122*a*, epigenome pipeline 122*b*, metagenome pipeline 122*c*, a joint genotyping pipeline 122*d*, GATK 122*e* and/or MuTect2 122*f* analysis pipeline. Additionally, the system 1 may be configured for either local or remote generation and/or processing of data, such as where the generation and/or processing steps may be from a third tier of tertiary processing functions as shown in FIG. 11, which tier may include one or more of generating and/or acquiring data related to and including: non-invasive prenatal testing (NIPT) 123*a*, N/P ICU 123*b*, cancer related diagnostics and/or therapeutic modalities 123*c*, various laboratory developed tests (LDT) 123*d*, agricultural biological (Ag Bio) applications 123*e*, or other such health care related 123*f* processing functions.

Figure 10:
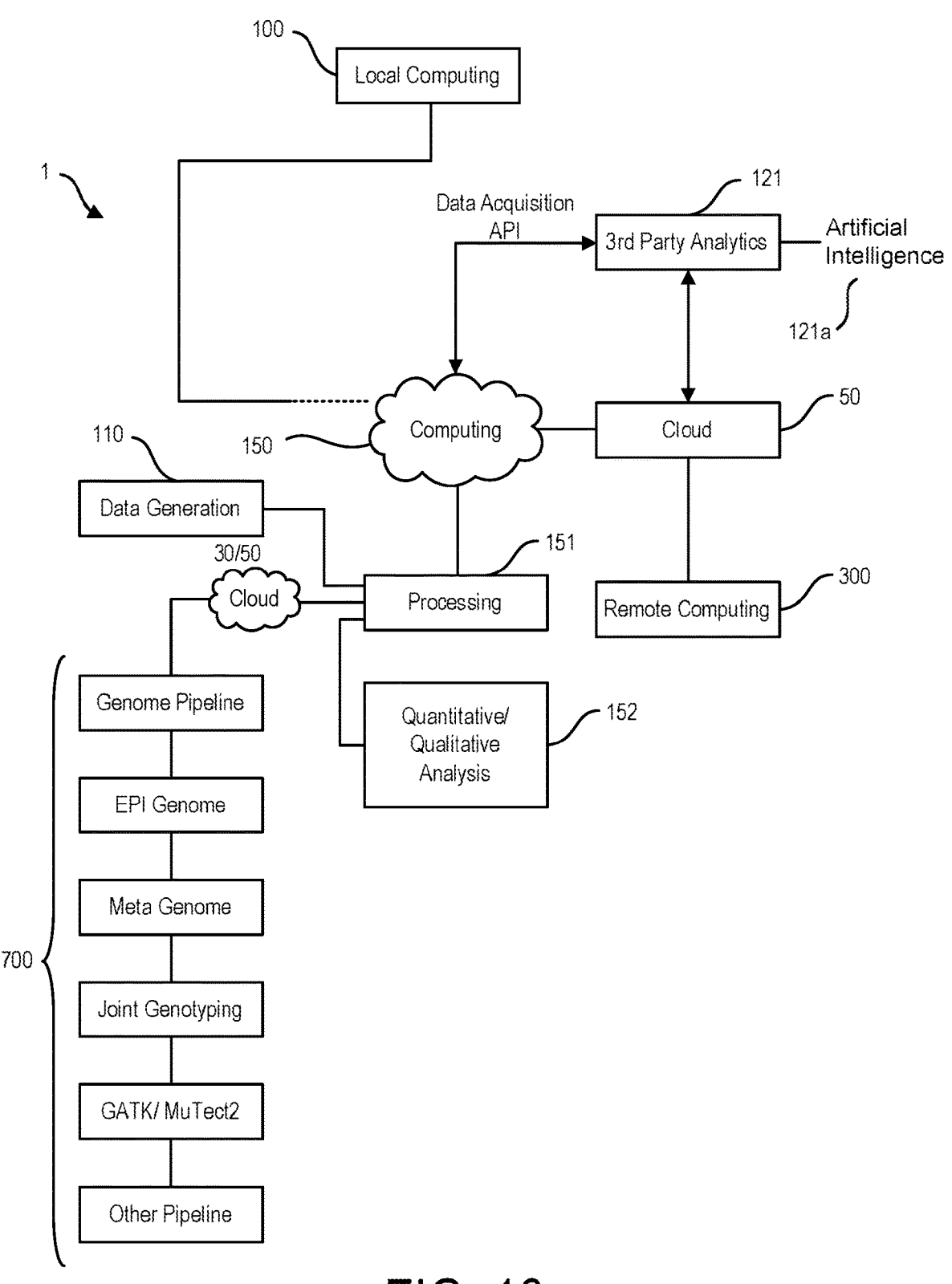
FIG. 10 depicts the block diagram of FIG. 9 illustrating greater detail regarding the computing function for a genomic infrastructure for onsite and/or cloud based genomics processing and analysis.

In particular embodiments, as set forth in FIGS. 8, 9, and 10, the system 1 may further be configured for allowing one or more parties to access the system and transfer information to or from the associated local processing 100 and/or remote 300 processing resources as well as to store information either locally 200 or remotely 400 in a manner that allows the user to choose what information get processed and/or stored where on the system 1. In such an instance, a user can not only decide what primary, secondary, and/or tertiary processing functions get performed on generated and/or acquired data, but also how those resources get deployed, and/or where the results of such processing gets stored. For instance, in one configuration, the user may select whether data is generated either locally or remotely, or a combination thereof, whether it is subjected to secondary processing, and if so, which modules of secondary processing it is subjected to, and/or which resource runs which of those processes, and further may determine whether the then generated or acquired data is further subjected to tertiary processing, and if so, which modules and/or which tiers of tertiary processing 700 it is subjected to, and/or which resource runs which of those processes, and likewise, where the results of those processes are stored for each step of the operations.

Particularly, in one embodiment, the user may configure the system 1 so that the generating of genetic sequence data 111 takes place remotely, such as by an NGS, but the secondary processing 600 of the data occurs locally 100. In such an instance, the user can then determine which of the secondary processing functions occur locally 100, such as by selecting the processing functions, such as mapping 112, aligning 113, sorting 111, and/or producing a VCF 116, from a menu of available processing options. The user may then select whether the locally processed data is subjected to tertiary processing, and if so which modules are activated so as to further process the data, and whether such tertiary processing occurs locally 100 or remotely 300. Likewise, the user can select various options for the various tiers of tertiary processing options, and where any generated and/or acquired data is to be stored, either locally 200 or remotely 400, at any given step or time of operation.

More particularly, a primary user may configure the system to receive processing requests from a third party, where the third party may configure the system so as for performing such requested primary, secondary, and/or tertiary processing on generated and/or acquired data. Specifically, the user or second or third party may configure the system 1 for producing and/or acquiring genetic sequence data, either locally 100 or remotely 200, may configure the system 1 for taking that genetic sequence data and mapping, aligning, and/or sorting it, either locally or remotely, so as to produce one or more variant call files (VCFs), and additionally may configure the system for performing a tertiary processing function on the data, e.g., with respect to the one or more VCFs, either locally or remotely. More particular still, the user or other party may configure the system 1 so as to perform any form of tertiary processing on the generated and/or acquired data, and where that processing is to occur in the system. Hence, in various embodiments, the first, second, and/or third party 121 user may access and/or configure the system 1 and its various components directly such as by directly accessing the local computing function 100, via a local network connection 10, or over an associated hybrid-cloud network 50 connecting the party 121 to the system 1, such as through an application program interface (API), accessible as through one or more graphical user interface (GUI) components. In such an instance, the third party user may access the system 1 and use the API to configure the various components of the system, the modules, associated pipelines, and other associated data generating and/or processing functionalities so as to run only those system components necessary and/or useful to the third party and/or requested or desired to be run thereby, and further allocate which computing resources will provide the requested processing, and where the results data will be stored.

Accordingly, in various instances, the system 1 may be configurable by a primary, secondary, or tertiary user of the system who can configure the system 1 so as to arrange its components in such a manner as to deploy one, all, or a selection of the analytical system resources to be run on data that the user either directly generates, causes to be generated by the system 1, or causes to be transferred to the system 1, such as over a network associated therewith, such as via the data acquisition mechanism 120. In such a manner, the system 1 is configurable so as to only run those portions of the system necessary or useful for the analytics desired and/or requested by the requesting party. For example, for these and other such purposes, an API may be included wherein the API is configured so as to include a GUI operable menu and/or a related list of system function calls that from which the user can select so as to configure and operate the system as desired. Additionally, in particular embodiments, the system 1 may be made accessible to third parties, such as governmental regulators, such as the Federal Drug Administration (FDA) 70b, or allow third parties to collate, compile, and/or access a data base of genetic information derived or otherwise acquired and/or compiled by the system 1 so as to form an electronic medical records (EMR) database 70a and/or to allow governmental access and/or oversight of the system, such as the FDA for Drug Development Evaluation. The system 1 may also be set up to conglomerate, compile, and/or annotate the data 70c and/or allow other high level users access thereto.

Figure 13:
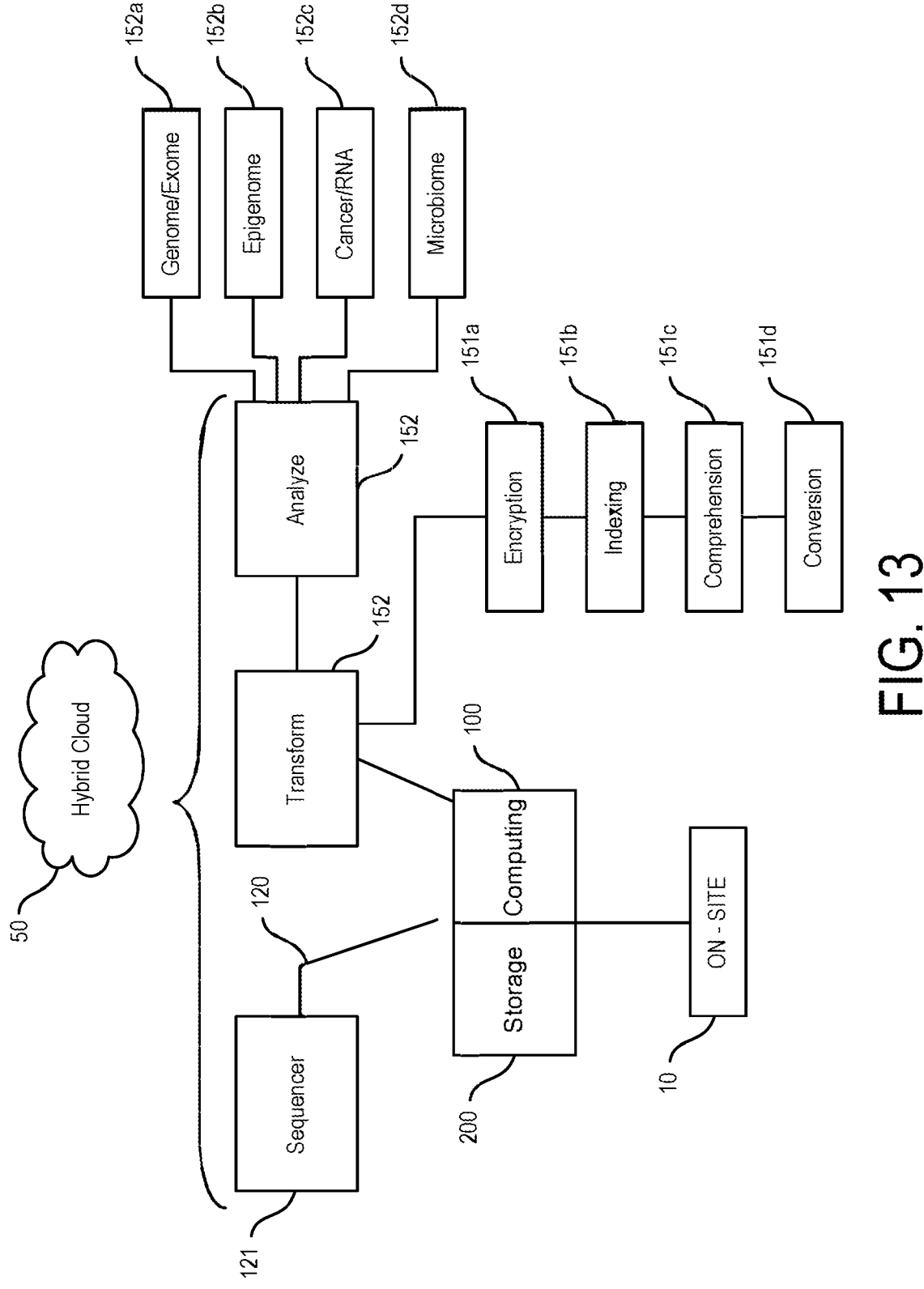
FIG. 13 depicts the block diagram of FIG. 12 in greater detail, illustrating a hybrid cloud configuration.

Accordingly, in various embodiments, as can be seen with respect to FIG. 13, a hybrid cloud 50 is provided wherein the hybrid cloud is configured for connecting a local computing 100 and/or storage resource 200 with a remote computing 300 and/or storage 400 resource, such as where the local and remote resources are separated one from the other distally, spatially, geographically, and the like. In such an instance, the local and distal resources may be configured for communicating with one another in a manner so as to share information, such as digital data, seamlessly between the two. Particularly, the local resources may be configured for performing one or more types of processing on the data, such as prior to transmission across the hybrid network 50, and the remote resources may be configured for performing one or more types of further processing of the data.

For instance, in one particular configuration, the system 1 may be configured such that a generating and/or analyzing function 152 is configured for being performed locally 100 by a local computing resource, such as for the purpose of performing a primary and/or secondary processing function, so as to generate and/or process genetic sequence data, as herein described. Additionally, in various embodiments, the local resources may be configured for performing one or more tertiary processing functions on the data, such as one or more of genome, exome, and/or epigenome analysis, or a cancer, microbiome, and/or other DNA/RNA processing analysis. Further, where such processed data is meant to be transferred, such as to a remote computing 300 and/or storage 400 resource, the data may be transformed such as by a suitably configured transformer 151, which transformer 151 may be configured for indexing, converting, compressing, and/or encrypting the data, such as prior to transfer over the hybrid network 50.

In particular instances, such as where the generated and processed data is transferred to a remote computing resource 300 for further processing, such processing may be of a global nature and may include receiving data from a plurality of local computing resources 100, collating such pluralities of data, annotating the data, and comparing the same, such as to interpret the data, determine trends thereof, analyzing the same for various biomarkers, and aiding in the development of diagnostics, therapeutics, and/or prophylactics. Accordingly, in various instances, the remote computing resource 300 may be configured as a data processing hub, such as where data from a variety of sources may be transferred, processed, and/or stored while waiting to be transformed and/or transferred, such as by being accessed by the local computing resource 100. More particularly, the remote processing hub 300 may be configured for receiving data from a plurality of resources 100, processing the same, and distributing the processed data back to the variety of local resources 100 so as to allow for collaboration amongst researchers and/or resources 100. Such collaboration may include various data sharing protocols, and may additionally include preparing the data to be transferred, such as by allowing a user of the system 1 to select amongst various security protocols and/or privacy settings so as to control how the data will be prepared for transfer.

In one particular instance, as presented in FIG. 11, a local computing 100 and/or storage 200 resource is provided, such as on-site at a user's location. The computing resource 100 and/or storage 200 resource may be coupled to a data generating resource 121, such as an NGS or sequencer on a chip, as herein described, such as over a direct or an intranet connection 10, where the sequencer 121 is configured for generating genetic sequencing data, such as FASTQ files. For instance, the sequencer 121 may be part of and/or housed in the same apparatus as that of the computing resource 100 and/or storage unit 200, so as to have a direct communicable and/or operable connection therewith, or the sequencer 121 and computing resource 100 and/or storage resource 200 may be part of separate apparatuses from one another, but housed in the same facility, and thus connected over a cabled or intranet 10 connection. In some instances, the sequencer 121 may be housed in a separate facility than that of the computing 100 and/or storage 200 resource and thus may be connected over an internet 30 or hybrid cloud connection 50.

In such instances, the genetic sequence data may be processed 100 and stored locally 200, prior to being transformed, by a suitably configured transformer 151, or the generated sequence data may be transmitted directly to one or more of the transformer 151 and/or analyzer 152, such as over a suitably configured local connection 10, intranet 30, or hybrid cloud connection 50, as described above such as prior to being processed locally. Particularly, like the data generating resource 121, the transformer 151 and/or analyzer 152 may be part of and/or housed in the same apparatus as that of the computing resource 100 and/or storage unit 200, so as to have a direct communicable and/or operable connection therewith, or the transformer 151 and/or analyzer 152 and computing resource 100 and/or storage resource 200 may be part of separate apparatuses from one another, but housed in the same facility, and thus connected over a cabled or intranet 10 connection. In some instances, the transformer 151 and/or analyzer 152 may be housed in a separate facility than that of the computing 100 and/or storage 200 resource and thus may be connected over an internet 30 or hybrid cloud connection 50.

In such instances, as seen with respect to FIG. 13, the transformer 151 may be configured for preparing the data to be transmitted either prior to analysis or post analysis, such as by a suitably configured computing resource 100 and/or analyzer 152. For instance, the analyzer 152 may perform a secondary and/or tertiary processing function on the data, as herein described, such as for analyzing the generated sequence data with respect to determining its genomic and/or exomic characteristics 152a, its epigenomic features 152b, any various DNA and/or RNA markers of interests and/or indicators of cancer 152c, and its relationships to one or more microbiomes 152d, as well as one or more other secondary and/or tertiary processes as described herein. As indicated, the generated and/or processed data may be transformed, such as by a suitably configured transformer 151 such as prior to transmission throughout the system 1 from one component thereof to another, such as over a direct, local 10, internet 30, or hybrid cloud 50 connection. Such transformation may include one or more of conversion 151d, such as where the data is converted from one form to another; comprehension 151c, including the coding, decoding, and/or otherwise taking data from an incomprehensible form and transforming it to a comprehensible form, or from one comprehensible form to another; indexing 151b, such as including compiling and/or collating the generated data from one or more resources, and making it locatable and/or searchable, such as via a generated index; and/or encryption 151a, such as creating a lockable and unlockable, password protected dataset, such as prior to transmission over an internet 30 and/or hybrid cloud 50.

Hence, in these and/or other such instances, the hybrid cloud 50 may be configured for allowing seamless and protected transmission of data throughout the components of the system, such as where the hybrid cloud 50 is adapted to allow the various users of the system to configure its component parts and/or the system itself so as to meet the research, diagnostic, therapeutic and/or prophylactic discovery and/or development needs of the user. Particularly, the hybrid cloud 50 and/or the various components of the system 1 may be operably connected with compatible and/or corresponding API interfaces that are adapted to allow a user to remotely configure the various components of the system 1 so as to deploy the resources desired in the manner desired, and further to do so either locally, remotely, or a combination of the same, such as based on the demands of the system and the particulars of the analyses being performed, all the while being enabled to communicate in a secured, encryptable environment. Another exemplary embodiment of the hybrid cloud system, as herein presented, is depicted in FIG. 12.

Figure 12:
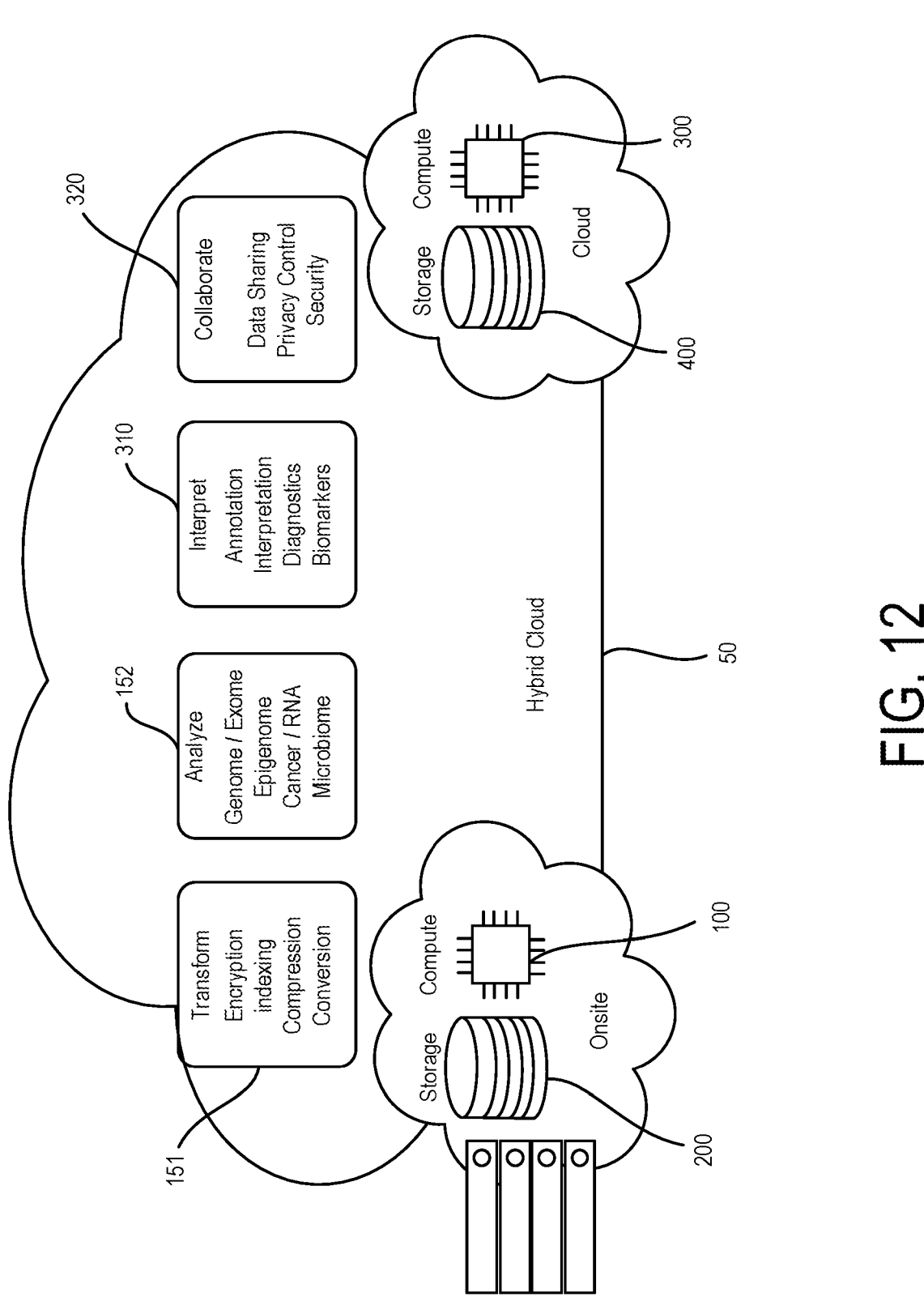
FIG. 12 depicts a block diagram illustrating a hybrid cloud configuration.
Figure 15:
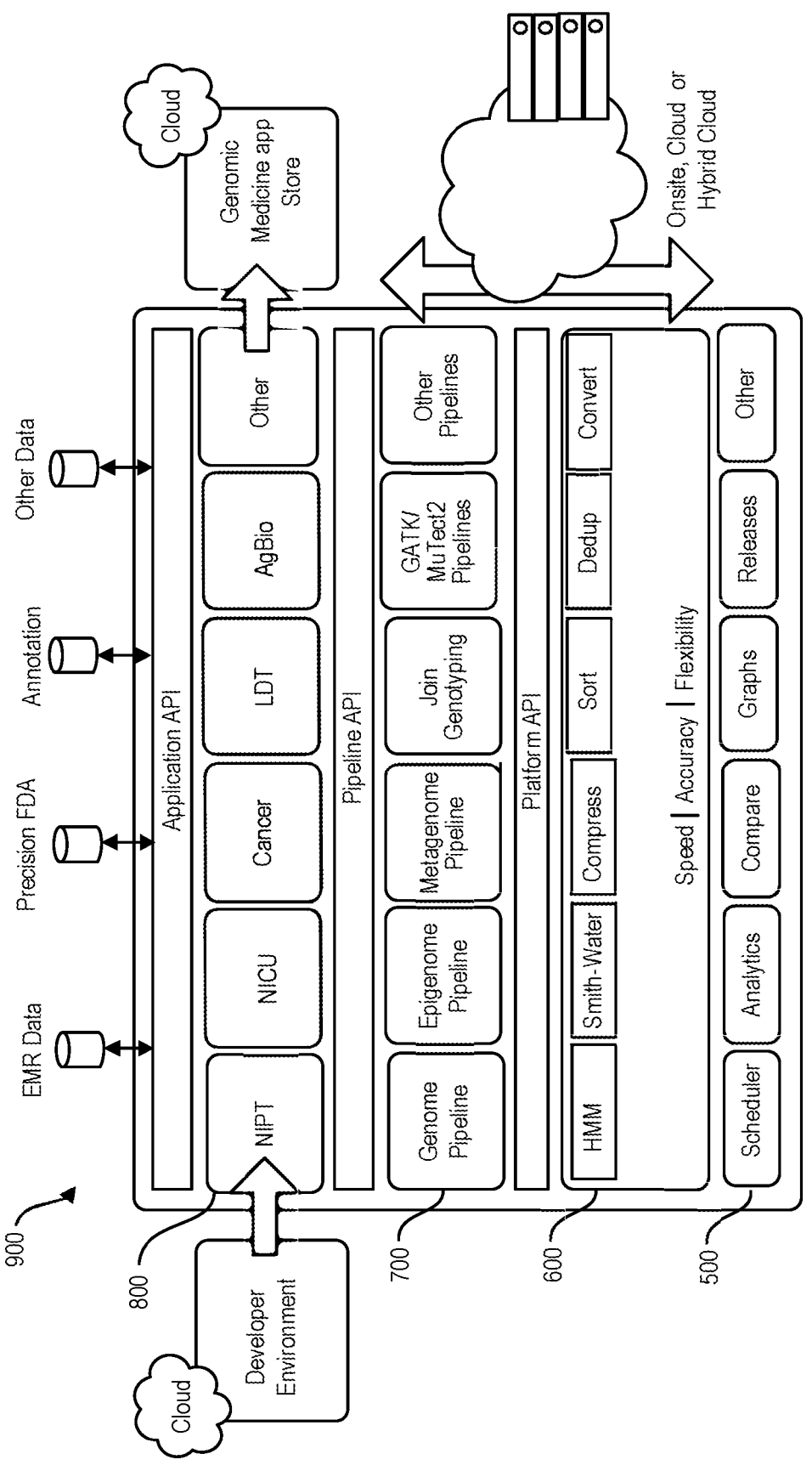
FIG. 15 depicts a block diagram illustrating a primary, secondary, and/or tertiary analysis pipeline as presented herein.

For instance, as can be seen with respect to FIGS. 10-12, and more specifically with respect to FIG. 15, the system 1 may be a multi-tiered and/or multiplexed bioanalytical processing platform that includes layers of processing units each having one or more processing pipelines that may be deployed in a systematic and/or concurrent and/or sequential manner so as to process genetic information from its primary processing stage 400/500, so as to produce genetic sequence data, such as in one or more FASTQ files; to its secondary processing stage 600, so as to produce one or more variant call files; and further to take the one or more variant call files, or other associated processed data, and perform one or more other operations thereon such as for the purposes of performing one or more diagnostics and/or prophylactic and/or therapeutic procedures there with, such as in response to a third party request 121 and/or in response to data submitted by the third party 121. Such further processing may include various pipeline protocols 700, such as configured so as to run analytics on the determined genetic variation data of one or more subjects, including genome, epigenome, metagenome, and/or genotyping analytics, such as in one tier, and/or various disease diagnostic and/or research protocols 800, which may include one or more of NIPT, NICU, cancer, LDT, biological, AgBio applications and the like. Particularly, the system 1 may further be adapted so as to receive and/or transmit various data 900 related to the procedures and processes herein such as related to electronic medical records (EMR) data, Federal Drug Administration testing and/or structuring data, data relevant to annotation, and the like. Such data may be useful so as to allow a user to make and/or allow access to generated medical, diagnostic, therapeutic, and/or prophylactic modalities developed through use of the system 1 and/or made accessible thereby.

Hence, one or more, e.g., all, of these functions therefore may be performed locally, e.g., on site 10, on the cloud 30, or via controlled access through the hybrid cloud 50. In such an instance, developer environment is created that allows the user to control the functionality of the system to meet his or her individual needs and/or to allow access thereto for others seeking the same or similar results. Consequently, the various components, processes, procedures, tools, tiers, and hierarchies of the system may be configurable such as via a GUI interface that allows the user to select which components to be run on which data at what time in what order in accordance with the user determined desires and protocols so as to generate relevant data and connections between data that may be securely communicated throughout the system whether locally or remotely. As indicated, these components can be made to communicate seamlessly together regardless of location and/or how connected, such as by being configurable so as to run the same or similar processes in the same or similar manner such as by employing corresponding API interfaces dispersed throughout the system the employment of which allows the various users to configure the various components to run the various procedures in like manner.

For instance, an API may be defined in a header file with respect to the processes to be run by each particular component of the system 1, wherein the header describes the functionality and determines how to call a function, such as the parameters that are passed, the inputs received and outputs transmitted, and the manner in which this occurs, what comes in and how, what goes out and how, and what gets returned, and in what manner. For example, in various embodiments, one or more of the components and/or elements thereof, which may form one or more pipelines of one or more tiers of the system may be configurable such as by instructions entered by a user and/or one or more second and/or third party applications. These instructions may be communicated to the system via the corresponding APIs which communicate with one or more of the various drivers of the system, instructing the driver(s) as to which parts of the system, e.g., which modules and/or which processes thereof are to be activated, when, and in what order, given a preselected parameter configuration, which may be determined by a user selectable interface, e.g., GUI.

As described above, the one or more DMA drivers of the system 1 may be configured to run in corresponding fashion, such as at the kernel level of each component and the system 1 as a whole. In such an instance, one or more of the provided kernel's may have their own very low level, basic API that provides access to the hardware and functions of the various components of the system 1 so as to access applicable registers and modules so as to configure and direct the processes and the manners in which they are run on the system 1. Particularly, on top of this layer, a virtual layer of service functions may be built so as to form the building blocks that are used for a multiplicity of functions that send files down to the kernel(s) and get results back, encodes, encrypts, and/or transmits the relevant data and further performs more higher level functions thereon. On top of that layer an additional layer may be built that uses those service functions, which may be an API level that a user may interface with, which may be adapted to function primarily for configuration of the system 1 as a whole or its component parts, downloading files, and uploading results, which files and/or results may be transmitted throughout the system either locally or globally.

Such configuration may include communicating with registers and also performing function calls. For example, as described herein above, one or more function calls necessary and/or useful to perform the steps, e.g., sequentially, to execute a mapping and/or aligning and/or sorting and/or variant call, or other secondary and/or tertiary function as herein described may be implemented in accordance with the hardware operations and/or related algorithms so as to generate the necessary processes and perform the required steps.

Specifically, because in certain embodiments one or more of these operations may be based on one or more structures, the various structures needed for implementing these operations may need to be constructed. There will therefore be a function call that performs this function, which function call will cause the requisite structure to be built for the performance of the operation, and because of this a call will accept a file name of where the structure parameter files are stored and will then generate one or more data files that contain and/or configure the requisite structure. Another function call may be to load the structure that was generated via the respective algorithm and transfer that down to the memory on the chip and/or system 1, and/or put it at the right spot where the hardware is expecting them to be. Of course, various data will need to be downloaded onto the chip and/or otherwise be transferred to the system generator, as well for the performance of the various other selected functions of the system 1, and the configuration manager can perform these functions, such as by loading everything that needs to be there in order for the modules of pipelines of the tiers of the platforms of the chip and/or system as a whole to perform their functions, into a memory on, attached, or otherwise associated with the chip and/or system.

Figure 16:
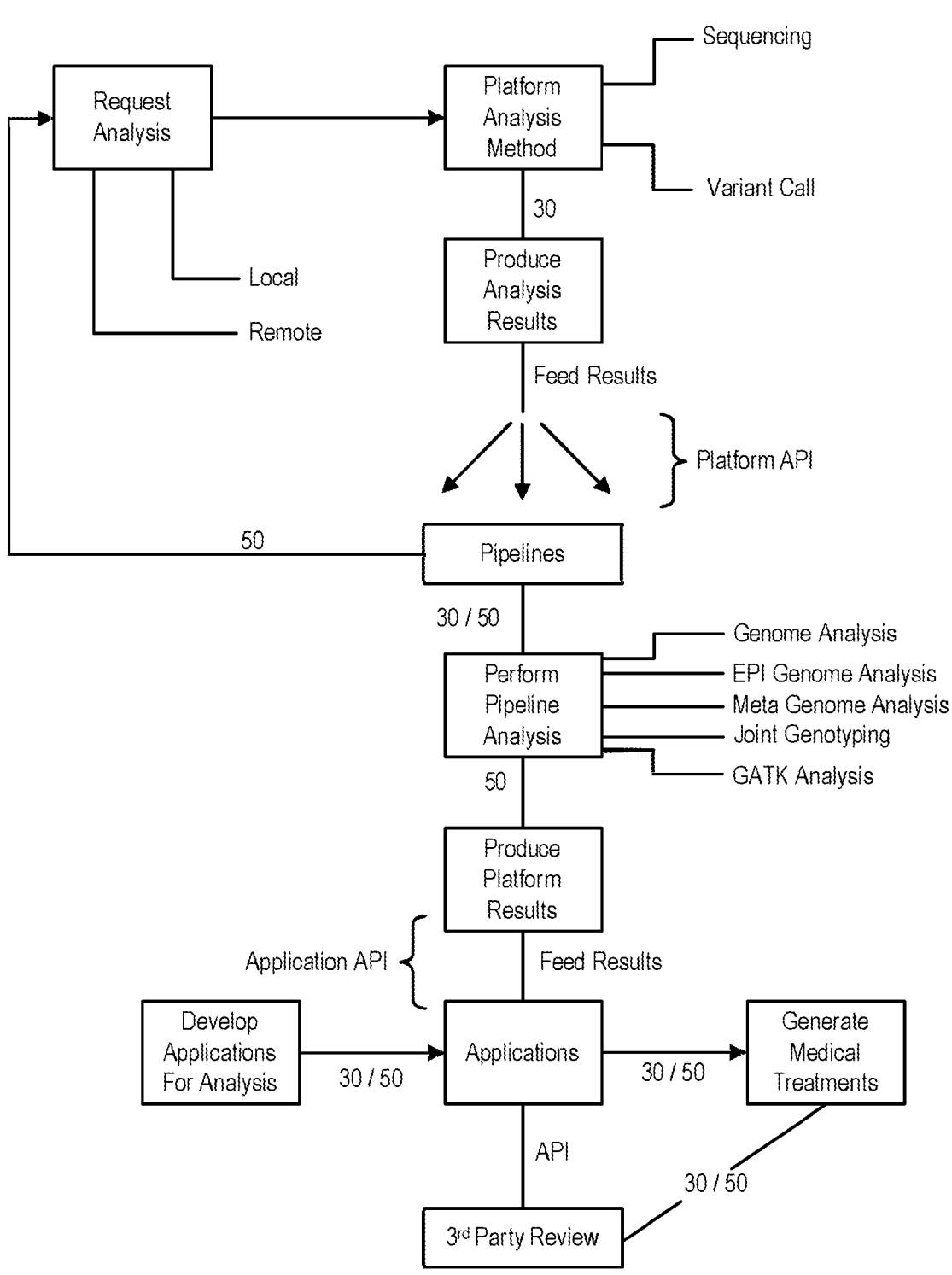
FIG. 16 depicts a flow diagram for an analysis pipeline of the disclosure.

Additionally, as can be seen with respect to FIG. 16, the API may be configured to allow one or more chips of the system 1 to interface with the circuit board of the sequencer 121, the computing resource 100/300, transformer 151, analyzer 152, interpreter 310, collaborator 320, or other system component, when included therewith, so as to receive the FASTQ and/or other generated and/or processed genetic sequencing files directly from the sequencer or other processing component such as immediately once they have been generated and/or processed and then transfers that information to the configuration manager which then directs that information to the appropriate memory banks in the hardware and/or software that makes that information available to the pertinent modules of the hardware, software, and/or system as a whole so that they can perform their designated functions on that information so as to call bases, map, align, sort, etc. the sample DNA/RNA with respect to the reference genome, and or to run associated secondary and/or tertiary processing operations thereon.

Accordingly, in various embodiments, a client level interface (CLI) may be included wherein the CLI may allow the user to call one or more of these functions directly. In various embodiments, the CLI may be a software application, e.g., having a GUI, that is adapted to configure the accessibility and/or use of the hardware and/or various other software applications of the system. The CLI, therefore, may be a program that accepts instructions, e.g., arguments, and makes functionality available simply by calling an application program. As indicated above, the CLI can be command line based or GUI (graphical user interface) based. The line based commands happen at a level below the GUI, where the GUI includes a windows based file manager with click on function boxes that delineate which modules, which pipelines, which tiers, of which platforms will be used and the parameters of their use. For example, in operation, if instructed, the CLI will locate the reference, will determine if a hash table and/or index needs to be generated, or if already generated locate where it is stored, and direct the uploading of the generated hash table and/or index, etc. These types of instructions may appear as user options at the GUI that the user can select the associated chip(s)/system 1 to perform.

Furthermore, a library may be included wherein the library may include pre-existing, editable, configuration files, such as files orientated to the typical user selected functioning of the hardware and/or associated software, such as with respect to a portion or whole genome and/or protein analysis, for instance, for various analyses, such as personal medical histories and ancestry analysis, or disease diagnostics, or drug discovery, therapeutics, and/or one or more of the other analytics, etc. These types of parameters may be preset, such as for performing such analyses, and may be stored in the library. For example, if the platform herein described is employed such as for NIPT, NICU, Cancer, LDT, AgBio, and related research on a collective level, the preset parameters may be configured differently than if the platform were directed simply to researching genomic and/or genealogy based research, such as on an individual level. See, for instance, FIG. 11.

More particularly, for specific diagnosis of an individual, accuracy may be an important factor, therefore, the parameters of the system may be set to ensure increased accuracy albeit in exchange for possibly a decrease in speed. However, for other genomics applications, speed may be the key determinant and therefore the parameters of the system may be set to maximize speed, which however may sacrifice some accuracy. Accordingly, in various embodiments, often used parameter settings for performing different tasks can be preset into the library to facilitate ease of use. Such parameter settings may also include the necessary software applications and/or hardware configurations employed in running the system 1. For instance, the library may contain the code that executes the API, and may further include sample files, scripts, and any other ancillary information necessary for running the system 1. Hence, the library may be configured for compiling software for running the API as well as various of the executables.

Figure 14:
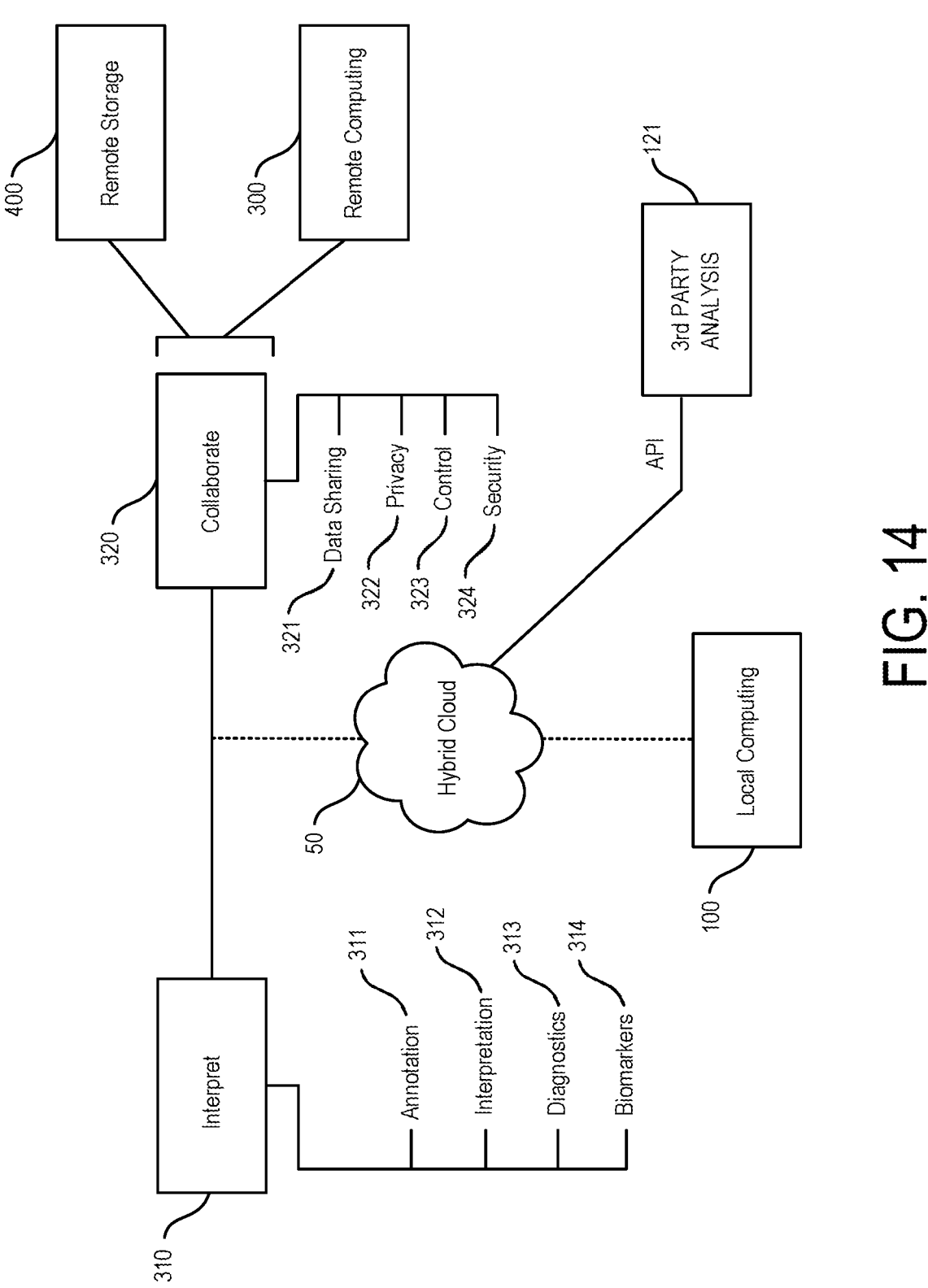
FIG. 14 depicts the block diagram of FIG. 13 in greater detail, illustrating a hybrid cloud configuration.

Additionally, as can be seen with respect to FIGS. 12-14, the system may be configured such that one or more of the system components may be performed remotely, such as where the system component is adapted to run one or more comparative functions on the data, such as an interpretive function 310 and/or collaborative function 320. For instance, where an interpretive protocol is employed on the data, the interpretive protocol 312 may be configured to analyze and draw conclusions about the data and/or determine various relationships with respect thereto, one or more other analytical protocols may also be performed and include annotating the data 311, performing a diagnostic 313 on the data, and/or analyzes the data, so as to determine the presence or absence of one or more biomarkers 314. Additionally, where a collaborative protocol is performed, the system 1 may be configured for providing an electronic forum where data sharing 321 may occur, which data sharing protocol may include user selectable security 324 and/or privacy 322 settings that allow the data to be encrypted and/or password protected, so that the identity and sources of the data may be hidden from a user of the system 1. In particular instances, the system 1 may be configured so as to allow a 3$^{rd}$ party analyzer 121 to run virtual simulations on the data. Further, one generated, the interpreted data and/or the data subjected to one or more collaborative analyses may be stored either remotely 400 or locally 200 so as to be made available to the remote 300 or local 100 computing resources, such as for further processing and/or analysis.

Accordingly, in view of the disclosures herein, in one aspect, a device for performing one or more of a multiplicity of operations in performing a genomics sequence analysis operation is provided. In certain instances, the device may be a "work bench" computing solution having a chip set associated with a PCIe card that itself may be inserted into the computing device and thereby associated with one or more internal CPUs, GPUs, and/or associated memories. Particularly, the computing device, processing units, associated memories, and/or associated PCIe card(s) having one or more of the FPGA/ASIC chipsets disclosed herein may be in communication with one another and provided within a housing such as in a box set manner that is typical within the art, which box set may be configured for work-bench use and/or provided and/or usable within a server rack. In other embodiments, the chip sets and/or associated interconnect express card(s) can be associated within a Next Gen sequencing device so as to form one unit there with.

However, in various instances, one or more of the integrated circuits disclosed herein may be provided and configured for being accessed via a cloud based interface, such as provided with respect to FIGS. 12-15. In some instances, the box set may be configured for being accessed remotely, such as where the box set configuration is made so as to be portable to the cloud. However, in other cases, one or more of the integrated circuits disclosed herein may be part of a server rack, such as where the server accessible system is configured specifically for being accessed remotely, such as via the cloud.

For instance, in one embodiment, a server having one or more, e.g., a multiplicity, of CPU and/or GPU cores and associated memories may be provided in conjunction with one or more of the FPGAs/ASICs disclosed herein. Particularly, in one implementation, an 18-24 CPU core box set/server having SSDs, 128×8 RAM, and one or more BioIT FPGA/ASIC system may be provided in a manner so as to be accessible remotely. In such an instance, the one or more FPGAs may be adapted for being reconfigured, such as partially reconfigured, between one or more of the various steps of the genomics analysis pipeline. In other instances, the server system may include up to about 36 CPU/GPU cores and about 972 GB of RAM, which may be associated with about 8 FPGAs, configurable as herein described.

More particularly, the provided FPGAs may be configured so as to be dedicated to performing one or more computationally intensive operations in the BioIT pipeline, such as where one FPGA is provided and dedicated to performing a mapping operation, and another FPGA is provided and configured for performing an alignment operation, although, in some instances, a single FPGA may be provided and configured for being at least partially reconfigured between performing both a mapping and an alignment operation. Other operations in the pipeline that may be performed by dedicated FPGAs may include performing an HMM operation, a local realignment, e.g., Smith-Waterman operation, and/or various other variant calling operations. Likewise, various of the pipeline operations may be configured for being performed by one or more of the associated CPUs/GPUs of the system. Such operations may be one or more less computationally intensive operations of the pipeline, such as for preforming a sorting, deduplication, and other variant calling operations. Hence, the system may be configured for performing a combination of operations part by CPU, and part by hardware, such as by an FPGA/ASIC of the system.

Accordingly, in various implementations of the system, various CPU and hardwired integrated circuit instances may be provided for performing dedicated functions of the genomic pipeline analysis provided herein. For instance, various FPGA instances may be provided for performing dedicated genomic analysis operations, such as an FPGA instance for performing mapping, another for performing aligning, another for performing local realignment and/or other Smith-Waterman operations, another for performing HMM operations, and the like. Likewise, various CPU/GPU instances may be provided for performing dedicated genomic analysis operations, such as CPU/GPU instance for performing sorting, deduplication, compression, various variant calling operations and the like. In such instances, an associated memory or memories may be provided, such as between the various computation steps of the pipeline, for receiving results data as it is computed, compiled, and processed throughout the system, such as between the various CPU and/or FPGA instances. Further, it is to be noted that the size of the various CPU and/or FPGA instances may vary dependent on the computational needs of the system, and may range from small to medium to large to very large, and the number of CPU/GPU and FPGA/ASIC instances may vary likewise.

Hence, the system may further include a workflow manager that is configured for scheduling and directing the movement of data through out the system and from one instance to another, from one memory to another. In some instances, the memory may be a dedicated memory that is instance specific, and in other instances the memory may be configured to be flexible and therefore capable of being switched from one instance to another, such as an elastic block storage memory. In yet other instances, the memory may be instance non-specific and therefore capable of being communicably coupled to a plurality of instances, such as for elastic file storage.

Additionally, the workflow manager may be a dedicated instance, such as a CPU/GPU core that is dedicated and/or configured for determining what jobs need to be performed and when and what resources will be utilized in the performance of those jobs, as well as for queuing up the jobs and directing them from resource to resource. The workflow manager may include or may otherwise be configured as a load estimator and/or form an elastic control node that is a dedicated instance that may be run by a processor, e.g. a C4 CPU core, or may be run without many cores. In various instances, the workflow manager may have a database connected to it, which may be configured for managing all the jobs that need to be, are being, or have been processed. Hence, the manager may be configured for detecting and managing how data flows throughout the system, determining how to allocate system resources, and when to bring more resources online.

As indicated above, in certain instances, a work bench solution may be provided where the system includes a plurality of X CPU core servers that feed into an FPGA with size of Z, where X, Y, and Z are numbers that may vary depending on the processing needs of the system, but should be selected and/or otherwise configured for being optimized. For instance, typical system configurations are not optimized for performing the BioIT operations of the system herein described. Specifically, certain system configurations have not been optimized so as to maximize the flow of data from various CPU/GPU instances to various integrated circuits, such as FPGAs, of the system. More specifically, the system architecture may be configured in such a manner that the CPU/FPGA hardware are run in an optimally efficient manner so as to keep both instance platforms busy during all run times.

Hence, although it is generally good to have large FPGA capabilities, it may not be efficient to have a great ability to process data, if there is not enough data needing to be processed being fed into the system. For instance, in various instances 4 CPU cores may be configured to feed data into a medium large, e.g., 2.5×, FPGA. However, where the CPU does not generate enough work to keep the FPGA busy and/or fully utilized, the configuration will be less than ideal. Such configurations where the CPU instance(s) don't produce enough work to keep the available FPGAs busy. Provided herein, therefore, is an architecture and a manner of implementing the same that is configured such that the system is run in a manner that the CPU/FPGA software/ hardware are run efficiently so as to ensure the present CPUs optimally feed the available FPGAs in such a manner to keep both instance platforms busy during all run times. Pursuantly, allowing such a system to be accessible from the cloud will ensure a plurality of data being provided to the system so as to be queued up by the workflow manager and directed to the specific CPU/FPGA resources that are configured and capable of receiving and processing the data in an optimally efficient manner, such as where the CPUs perform the less computationally intensive data, and the FPGAs handle the computationally intensive tasks, and the memories provide for the storing of data between the various steps of the procedure and/or between the various different instance types and instances, and thereby avoiding period of instance latency. Specifically, during mapping and aligning, very little of the CPU is utilized, because of the intensive nature of the computations, these tasks are configured for being performed by the hardware implementations. Likewise, during variant calling, the tasks may be split in such a way as to be roughly fairly distributed between the CPU/ FPGA instances in their tasks, such as where HMM and Smith-Waterman operations may be performed by the hardware, and various other operations may be performed by software run on one or more CPU/GPU instances.

Accordingly, the architectural parameters set forth herein are not necessarily limited to one-set architecture, but rather the system is configured so as to have more flexibility for organizing its implementations, and relying on the workflow manager to determine what instances are active when, how, and for how long, and directing which computations are performed on which instances. Specifically, the cloud based architectures set forth herein, such as provided in the appended figures, shows that various known deficiencies in previous architectural offerings may cause inefficiencies that can be overcome by flexibly allowing more CPU/GPU core instances to access various different hardware instances, e.g., of FPGAs, that have been organized in a more intentional manner so to be able to dedicate the right instance to performing the appropriate functions so as to be optimized by being implemented in that format, such that a greater proportion of available CPU instances can be full time busy producing results data that can be optimally fed into the available FPGA instances so as to keep the selected FPGA instances full time busy. Therefore, it is desirable to provide a structured architecture that is as efficient as possible and is full time busy. It is to be noted that configurations where too few CPUs feed into too many FPGAs such that one or more of the FPGAs are being underutilized is not efficient and should be avoided.

In one implementation, the architecture can be configured so as to virtually include several different layers, such as a first layer having X, e.g., from 4 to about 30 CPU cores, and a second level having from 1 to 12 FPGA instances, where the size may range from small to medium to large, etc. A third level of CPU cores and/or a fourth level of further FPGAs, and so on, may also be included. Hence, because there are many available instances in the cloud, such as instances that simply include CPUs or GPUs and/or FPGAs and/or combinations of them, such as in one or more levels described herein. Accordingly, in a manner such as this the architecture may be organized so that the most intensive, specific computing functions are performed by the hardware instances, and those functions that can be run through the CPUs, are directed to the appropriate CPU at the appropriate level for general processing purposes.

For example, the architecture can be configured to maximize efficiency and reduce latency by combining the various instances on various different virtual levels. Particularly, a plurality, e.g., a significant and/or all, of the Level 1 CPU instances can be configured to feed into the various Level 2, e.g., F12X, FPGA instances that have been specifically configured to perform specific functions, such as mapping, aligning, Smith-Waterman, HMM, variant calling, and the like. Hence, the Level 1 CPUs can be engaged to form a first level of a genomics analysis pipeline for performing general processing steps and queuing to prepare the data for pipeline analysis, which data once processed by one or a multiplicity of CPUs can be fed into a dedicated, e.g., F12X, FPGA instance at Level 2, such as where the F12X FPGA instance is configured for performing intensive computing functions such as mapping and/or aligning functions, etc.

In this manner, in a particular implementation, the CPU instances in the pipeline route their data, once prepared, to the one or two mapping and aligning FPGA instances. Once the mapping has been performed the result data may be stored in a memory and/or then fed into an aligning instance, where aligning may be performed, e.g., by at least one dedicated Level 2 FPGA instance. Likewise, the processed mapped and aligned data may then be stored in a memory and/or directed to a Level 3 CPU instance for further processing, which may be the same Level 1 or a different instance, such as for performing a less processing intense genomics analysis function, such as for performing a sorting function. Additionally, once the Level 3 CPUs have performed their processing, the resultant data may then be forwarded either back up to other Level 2 instances of the FPGAs or to a Level 4 FPGA instance, such as for further genomics processing intense functions, such as for performing a Smith-Waterman processing function, e.g., at a SW dedicated FPGA instance. Likewise, once the SW analysis has been performed, such as by an SW dedicated F12X FPGA, then the processed data may be sent to one or more associated memories and/or further down the processing pipeline, such as to another, e.g., Level 4 or 5, or back up to Level 1 or 3, CPU and/or FPGA instance, such as for performing HMM and/or Variant Calling analysis, such as in a dedicated FPGA and/or further layer of CPU processing core.

In a manner such as this latency and efficiency issues can be overcome by combining the various different instances, on one or more different levels, so as to provide a pipeline platform for genomics processing. Such a configuration may involve more than a scaling and/or combining instances, the instances may be configured so that they specialize in performing dedicated functions. In such an instance, the Mapping FPGA instance only performs mapping, and likewise the aligning FPGA only performs aligning, and so on, rather than a single instance performing end-to-end processing of the pipeline. Albeit, in other configurations, one or more of the FPGAs may be at least partially reconfigured, such as between performing pipeline tasks.

Hence, the pipeline manager may functions to manage the queue of genomic processing requests being formulated by the Level I CPU instances so as to be broken down into discrete jobs, aggregated, and be routed to the appropriate job specific CPU/F1 instances for processing, such as for mapping and/or aligning, which F1 data once processed can be sent backwards or forwards to the next level of CPU/FPGA processing of the results data, such as for the performance of various steps in the variant calling module. For instance, the variant calling function may be divided into a plurality of operations, which can be performed in software, then forwarded to HMM processing in one or more FPGA hardware instances, and then sent to a CPU for continued variant calling operations, such as where the entire platform is elastically sized and implemented to minimize cost of the expensive FPGA instances, while maximizing utilization, minimizing latency, and therefore optimizing operations. Accordingly, in this manner, less hardware instances are needed because of their pure processing capabilities and hardwired specificity, and therefore, the number of FPGAs to the number of CPUs may be minimized, and their use, e.g., of the FPGAs, may be maximized, and therefore, the system optimized so as to keep all instances full time busy. Such a configuration is optimally designed for genomics processing analysis, especially for mapping, aligning, and variant calling.

An additional structural element that may be added, e.g., as an attachment, to the pipeline architecture, disclosed herein, is one or more elastic memory modules, which may be configured to function for providing block storage of the data, e.g., results data, as it is transitioned throughout the pipeline. Accordingly, one or more Elastic Block Data Storage (EBDS) module may be inserted between one or more of the processing levels, e.g., between the different instances and/or instance levels, such that as data gets processed and results obtained, the processed results may be directed to the EBDS device for storage prior to being routed to the next level of processing, such as by a dedicated FPGA processing module. The same EBDS may be employed between all instances, or instance levels, or a multiplicity of EBDSs may be employed between the various instances and/or instance levels, such as for storing and/or compiling and/or for queuing of results data.

In this configuration, prior to sending data directly from one instance and/or one level of processing to another, the data may be routed to an EBDS, or other memory device or structure, for storage and thereafter routed to the appropriate hardwired-processing module. Specifically, a block storage module may be attached to the node for memory storage where data can be written to the BSD for storage at one level, and the BSD may be flipped to another node for routing the stored data to the next processing level. In this manner, one or more, e.g., multiple, BDS modules may be included in the pipeline and configured for being flipped from one node to another so as to participate in the transitioning of data throughout the pipeline. Further, as indicated above, a more flexible File Storage Device may be employed, such as a device that is capable of being coupled to one or more instances concurrently, such as without having to be switched from one to the other.

Accordingly, there are many steps in the processing pipeline, e.g., at its attendant nodes, as data is prepared for processing, e.g., preprocessing, which data once it is prepared is directed to an appropriate processing instance at one level where results data may be generated, then the result data may be stored, e.g., within an EDS device, queued and prepared for the next stage of processing by being flipped to the next node of instances and routed to the next instance for processing by the next order of FPGA and/or CPU processing instances, where further results data may be generated, and again once generated the results data may be directed either back to the same or forward to the next level of EDS for storage prior to being advanced to the next stage of processing.

Particularly, in one specific implementation, flow through the pipeline may look like the following: CPU: data prepared (queued and/or stored); FPGA: Mapping, temporary storage, FPGA: aligning, temporary storage, CPU: sorting, temporary storage, CPU: deduplication, temporary storage, FPGA: HMM, temporary storage, CPU: variant calling 1, temporary storage, FPGA: Smith-Waterman, temporary storage, CPU: variant calling 2, temporary storage, CPU: VCGF, temporary storage, and so on. It is noted, one or more of these steps may be performed in any logical order and may be implemented by any suitably configured resource such as implemented in software and/or hardware, in various different combinations. Further, one or more EDS or other suitably configured data and/or file storage devices may be attached to one or more of the various nodes, e.g., between the various levels of instances, such as for temporary storage between the various different processing steps. Accordingly, in a manner such as this, each level of processing instances may be elastically scaled on an as needed basis, such as between each of the different nodes or levels of nodes, such as for processing one or several genomes.

In another aspect, as can be seen with respect to FIG. 16, a method for using the system to generate one or more data files upon which one or more secondary and/or tertiary processing protocols may be run is provided. For instance, the method may include providing a genomic infrastructure such as for one or more of onsite, cloud-based, and/or hybrid genomic and/or bioinformatics generation and/or processing and/or analysis.

In such an instance, the genomic infrastructure may include a bioinformatics processing platform having one or more memories that are configured to store one or more configurable processing structures for configuring the system so as to be able to perform one or more analytical processing functions on data, such as data including a genomic sequence of interest or processed result data pertaining thereto. The memory may include the genomic sequence of interest to be processed, e.g., once generated and/or acquired, one or more genetic reference sequences, and/or may additionally include an index of the one or more genetic reference sequences and/or a list of splice junctions pertaining thereto. The system may also include an input having a platform application programming interface (API) for selecting from a list of options one or more of the configurable processing structures, such as for configuring the system, such as by selecting which processing functions of the system will be run on the data, e.g., the pre- or processed genomic sequences of interest. A graphical user interface (GUI) may also be present, such as operably associated with the API, so as to present a menu by which a user can select which of the available options he or she desires to be run on the data.

The system may be implemented on one or more integrated circuits that may be formed of one or more sets of configurable, e.g., preconfigured and/or hardwired, digital logic circuits that may be interconnected by a plurality of physical electrical interconnects. In such an instance, the integrated circuit may have an input, such as a memory interface, for receiving one or a plurality of the configurable structure protocols, e.g., from the memory, and may further be adapted for implementing the one or more structures on the integrated circuit in accordance with the configurable processing structure protocols. The memory interface of the input may also be configured for receiving the genomic sequence data, which may be in the form of a plurality of reads of genomic data. The interface may also be adapted for accessing the one or more genetic reference sequences and the index(es).

In various instances, the digital logic circuits may be arranged as a set of processing engines that are each formed of a subset of the digital logic circuits. The digital logic circuits and/or processing engines may be configured so as to perform one or more pre-configurable steps of a primary, secondary, and/or tertiary processing protocol so as to generate the plurality of reads of genomic sequence data, and/or for processing the plurality of reads of genomic data, such as according to the genetic reference sequence(s) or other genetic sequence derived information. The integrated circuit may further have an output so as to output result data from the primary, secondary, and/or tertiary processing, such as according to the platform application programming interface (API).

Particularly, in various embodiments, the digital logic circuits and/or the sets of processing engines may form a plurality of genomic processing pipelines, such as where each pipeline may have an input that is defined according to the platform application programming interface so as to receive the result data from the primary and/or secondary processing by the bioinformatics processing platform, and for performing one or more analytic processes thereon so as to produce result data. Additionally, the plurality of genomic processing pipelines may have a common pipeline API that defines a secondary and/or tertiary processing operation to be run on the result data from the primary and/or secondary processed data, such as where each of the plurality of genomic processing pipelines is configured to perform a subset of the secondary and/or tertiary processing operations and to output result data of the secondary and/or tertiary processing according to the pipeline API.

In such instances, a plurality of the genomic analysis applications may be stored in the memory and/or an associated searchable application repository, such as where each of the plurality of genomic analysis applications are accessible via an electronic medium by a computer such as for execution by a computer processor, so as to perform a targeted analysis of the genomic pre- or post processed data from the result data of the primary, secondary, and/or tertiary processing, such as by one or more of the plurality of genomic processing pipelines. In particular instances, each of the plurality of genomic analysis applications may be defined by the API and may be configured for receiving the result data of the primary, secondary, and/or tertiary processing, and/or for performing the target analysis of the pre- or post processed genomic data, and for outputting the result data from the targeted analysis to one of one or more genomic databases.

The method may additionally include, selecting, e.g., from the menu of the GUI, one or more genomic processing pipelines from a plurality of the available genomic processing pipelines of the system; selecting one or more genomic analysis applications from the plurality of genomic analysis applications that are stored in an application repository; and executing, using a computer processor, the one or more selected genomic analysis applications to perform a targeted analysis of genomic data from the result data of the primary, secondary, and/or tertiary processing.

Additionally, in various embodiments, all of mapping, aligning, and sorting, may take place on the chip, and local realignment, duplicate marking, base quality score recalibration may, and/or one or more of the tertiary processing protocols and/or pipelines, in various embodiments, also take place on the chip, and in various instances, various compression protocols, such as BAM and CRAM, may also take place on the chip. However, once the primary, secondary, and/or tertiary processed data has been produced, it may be compressed, such as prior to being transmitted, such as by being sent across the system, being sent up to the cloud, such as for the performance of the variant calling module, a secondary, tertiary, and/or other processing platform, such as including an interpretive and/or collaborative analysis protocol. This might be useful especially given the fact that variant calling, including the tertiary processing thereof, can be a moving target, e.g., there is not one standardized agreed upon algorithm that the industry uses.

Hence, different algorithms can be employed, such as by remote users, so as to achieve a different type of result, as desired, and as such having a cloud based module for the performance of this function may be useful for allowing the flexibility to select which algorithm is useful at any particular given moment, and also as for serial and/or parallel processing. Accordingly, any one of the modules disclosed herein can be implemented as either hardware, e.g., on the chip, or software, e.g., on the cloud, but in certain embodiments, all of the modules may be configured so that their function may be performed on the chip, or all of the modules may be configured so that their function may be performed remotely, such as on the cloud, or there will be a mixture of modules wherein some are positioned on one or more chips and some are positioned on the cloud. Further, as indicated, in various embodiments, the chip(s) itself may be configured so as to function in conjunction with, and in some embodiments, in immediate operation with a genetic sequencer, such as an NGS and/or sequencer on a chip.

More specifically, in various embodiments, an apparatus of the disclosure may be a chip, such as a chip that is configured for processing genomics data, such as by employing a pipeline of data analysis modules. According, as can be seen with respect to FIGS. 17-19, a genomics pipeline processor chip 100 is provided along with associated hardware of a genomics pipeline processor system 10. The chip 100 has one or more connections to external memory 102 (at "DDR3 Mem Controller"), and a connection 104 (e.g., "PCIe Interface") to the outside world, such as a host computer 106, for example. A crossbar 108 (e.g., switch) provides access to the memory interfaces to various requestors. DMA engines 110 transfer data at high speeds between the host and the processor chip's 100 external memories 102 (via the crossbar 108), and/or between the host and a central controller 112. The central controller 112 controls chip operations, especially coordinating the efforts of multiple processing engines. The processing engines are formed of a set of hardwired digital logic circuits that are interconnected by physical electrical interconnects, and are organized into engine clusters 114. In some implementations, the engines in one cluster share one crossbar port, via an arbiter. The central controller 112 has connections to each of the engine clusters. Each engine cluster 114 has a number of processing engines for processing genomic data, including a mapper 120 (or mapping module), an aligner 122 (or aligning module), and a sorter 124 (or sorting module). An engine cluster 114 can include other engines or modules, as well.

In accordance with one data flow model consistent with implementations described herein, the host sends commands and data via the DMA engines 110 to the central controller 112, which load-balances the data to the processing engines. The processing engines return processed data to the central controller 112, which streams it back to the host via the DMA engines 110. This data flow model is suited for mapping and alignment.

In accordance with an alternative data flow model consistent with implementations described herein, the host streams data into the external memory, either directly via DMA engines 110 and the crossbar 108, or via the central controller 112. The host sends commands to the central controller 112, which sends commands to the processing engines, which instruct the processing engines as to what data to process. The processing engines access input data from the external memory, process it, and write results back to the external memory, reporting status to the central controller 112. The central controller 112 either streams the result data back to the host from the external memory, or notifies the host to fetch the result data itself via the DMA engines 110.

Figure 17:
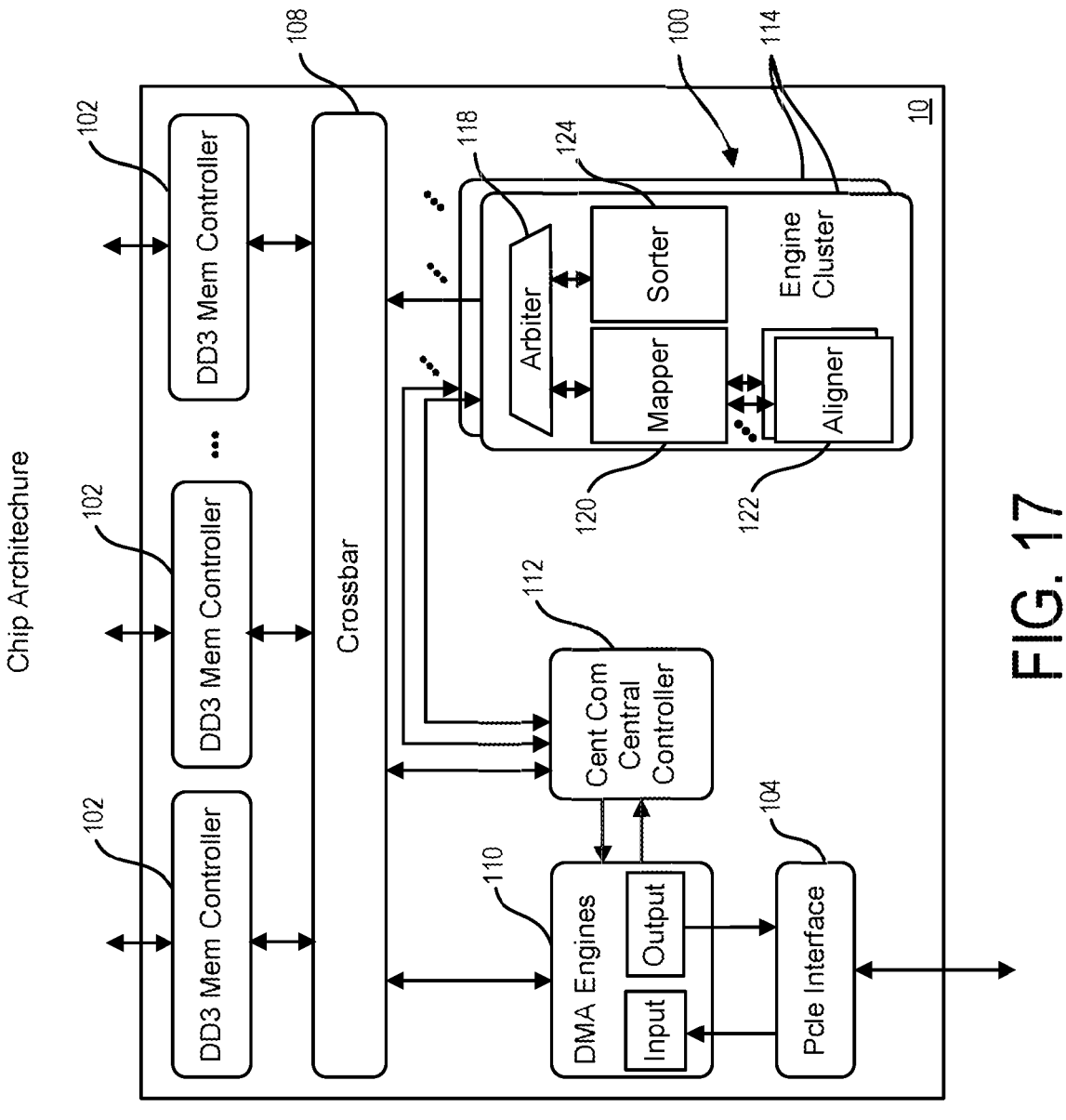
FIG. 17 illustrates an exemplary design and fabrication of an integrated circuit.
Figure 18:
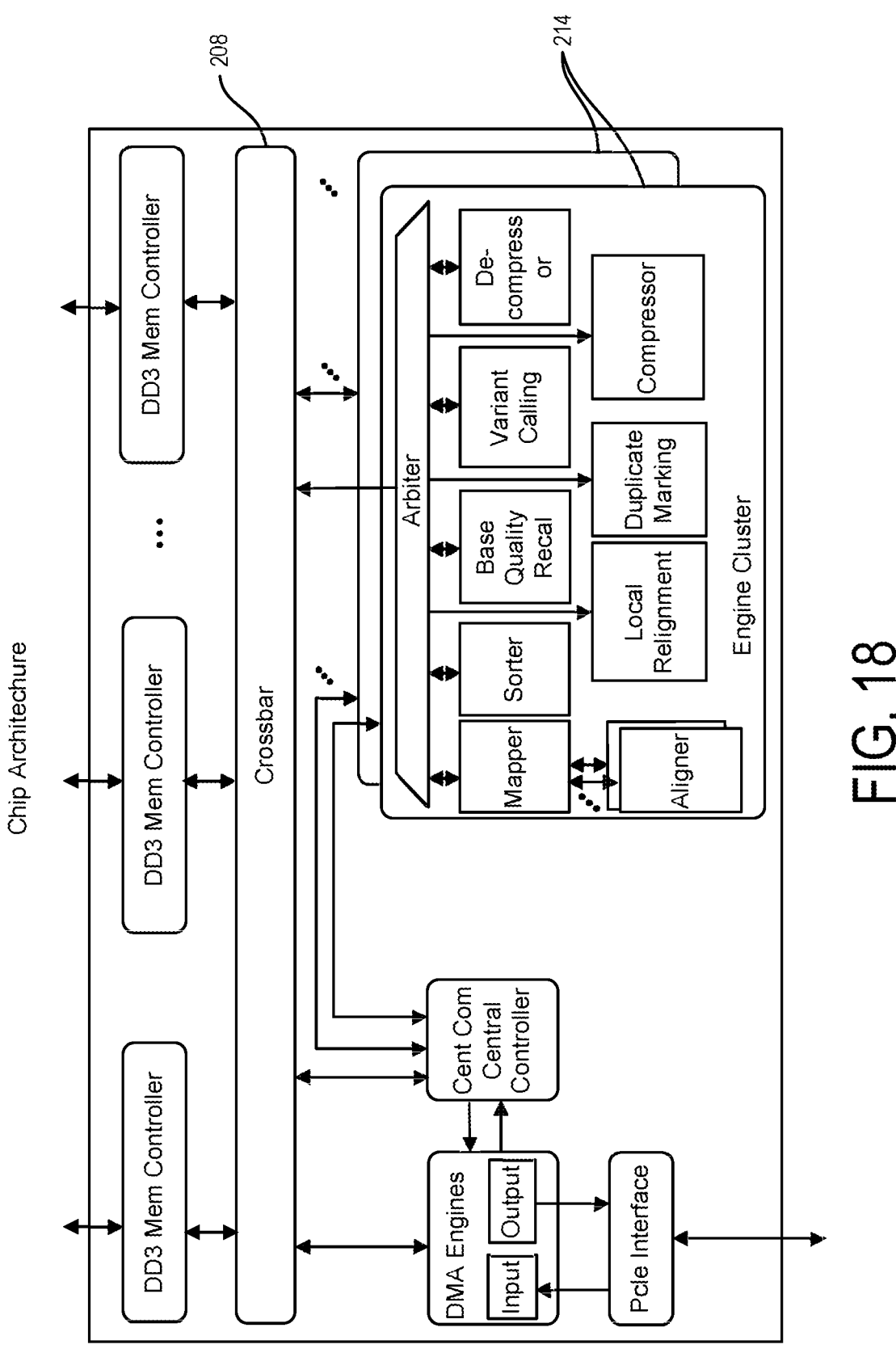
FIG. 18 is a block diagram of a hardware processor architecture in accordance with an implementation of the disclosure.

FIGS. 17 and 18 illustrate a genomics pipeline processor system, showing a full complement of processing engines inside an engine cluster 114/214. The pipeline processor system may include one or more engine clusters 114/214. In some implementations, the pipeline processor system 20 includes four our more engine clusters 114/214. The processing engines or processing engine types can include, without limitation, a mapper, an aligner, a sorter, a local realigner, a base quality recalibrater, a duplicate marker, a variant caller, a compressor and/or a decompressor. In some implementations, each engine cluster 114/214 has one of each processing engine type. Accordingly, all processing engines of the same type can access the crossbar 108 simultaneously, through different crossbar ports, because they are each in a different engine cluster 114/214. Not every processing engine type needs to be formed in every engine cluster 114/214. Processing engine types that require massive parallel processing or memory bandwidth, such as the mapper (and attached aligner(s)) and sorter, may appear in every engine cluster of the pipeline processor system. Other engine types may appear in only one or some of the engine clusters 114/214, as needed to satisfy their performance requirements or the performance requirements of the pipeline processor system.

Figure 19:
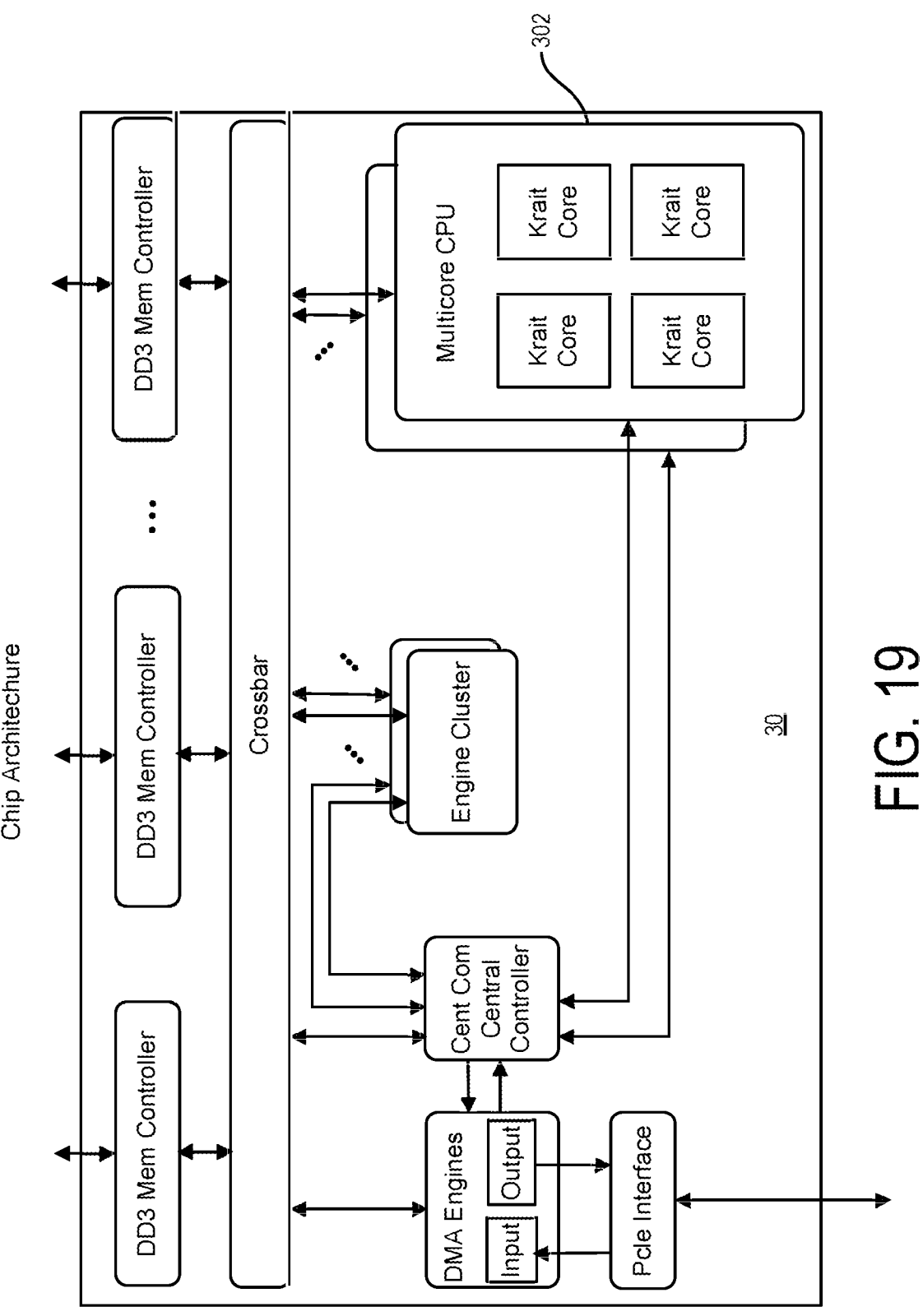
FIG. 19 is a block diagram of a hardware processor architecture in accordance with another implementation of the disclosure.

FIG. 19 illustrates a genomics pipeline processor system, showing, in addition to the engine clusters described above, one or more embedded central processing units (CPUs) 202. Examples of such embedded CPUs include Snapdragons® or standard ARM® cores. These CPUs execute fully programmable bio-IT algorithms, such as advanced variant calling. Such processing is accelerated by computing functions in the engine clusters, which can be called by the CPU cores 202 as needed. Furthermore, even engine-centric processing, such as mapping and alignment, can be managed by the CPU cores 202, giving them heightened programmability.

Figure 20:
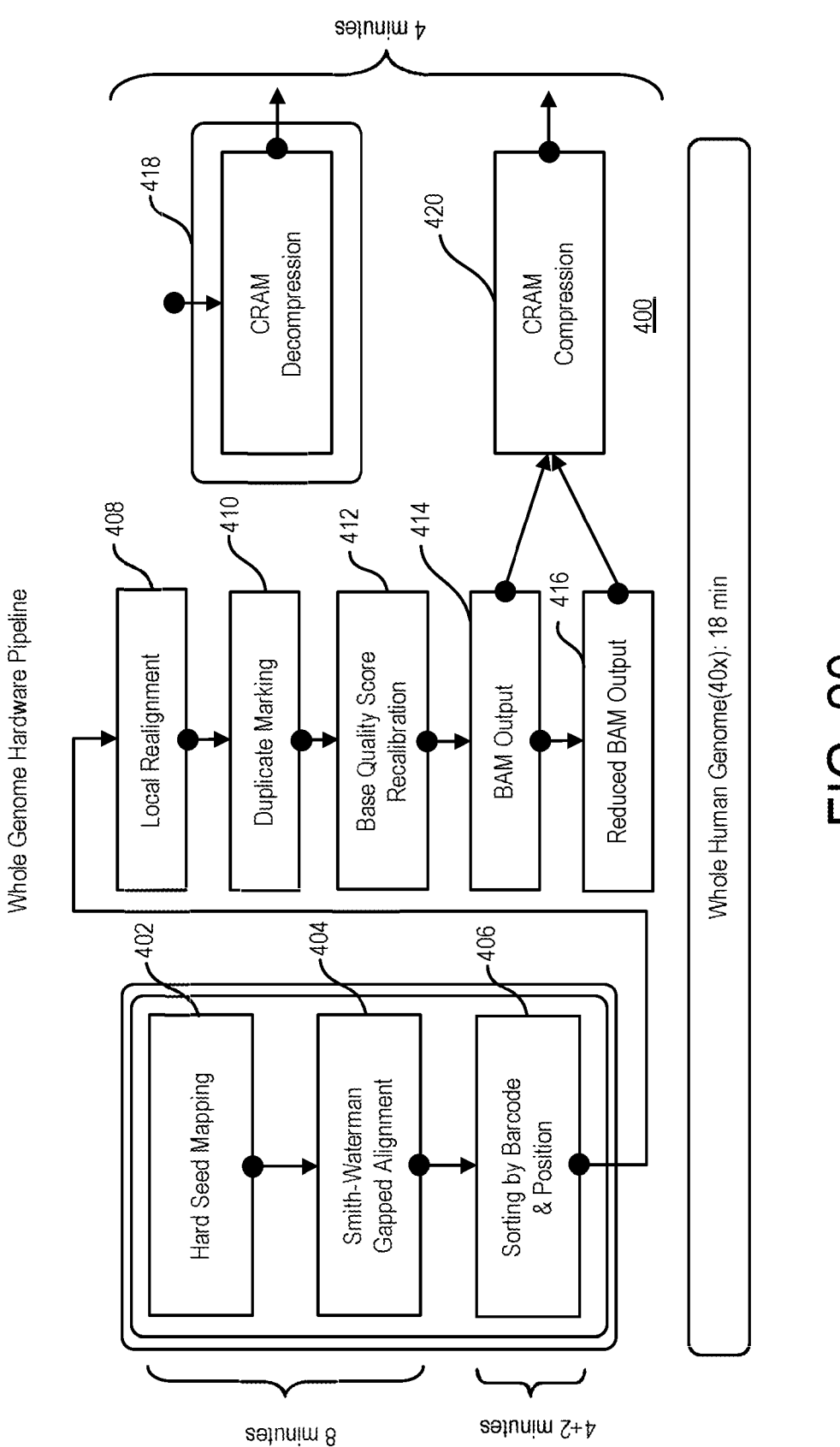
FIG. 20 illustrates a genetic sequence analysis pipeline.

FIG. 20 illustrates a processing flow for a genomics pipeline processor system and method. In some preferred implementations, there are three passes over the data. The first pass includes mapping 402 and alignment 404, with the full set of reads streamed through the engines. The second pass includes sorting 406, where one large block to be sorted (e.g., a substantial portion or all reads previously mapped to a single chromosome) is loaded into memory, sorted by the processing engines, and returned to the host. The third pass includes downstream stages (local realignment 408, duplicate marking 410, base quality score recalibration (BQSR) 412, BAM output 414, reduced BAM output 416, and/or CRAM compression 418). The steps and functions of the third pass may be done in any combination or subcombination, and in any order, in a single pass. A virtual pipeline architecture, such as described above, is used to stream reads from the host into circular buffers in memory, through one processing engine after another in sequence, and back out to the host. In some implementations, CRAM decompression can be a separate streaming function. In some implementations, the BAM output 414, reduced BAM output 416, and/or CRAM compression 418 can be replaced with variant calling, compression and decompression.

Figure 21:
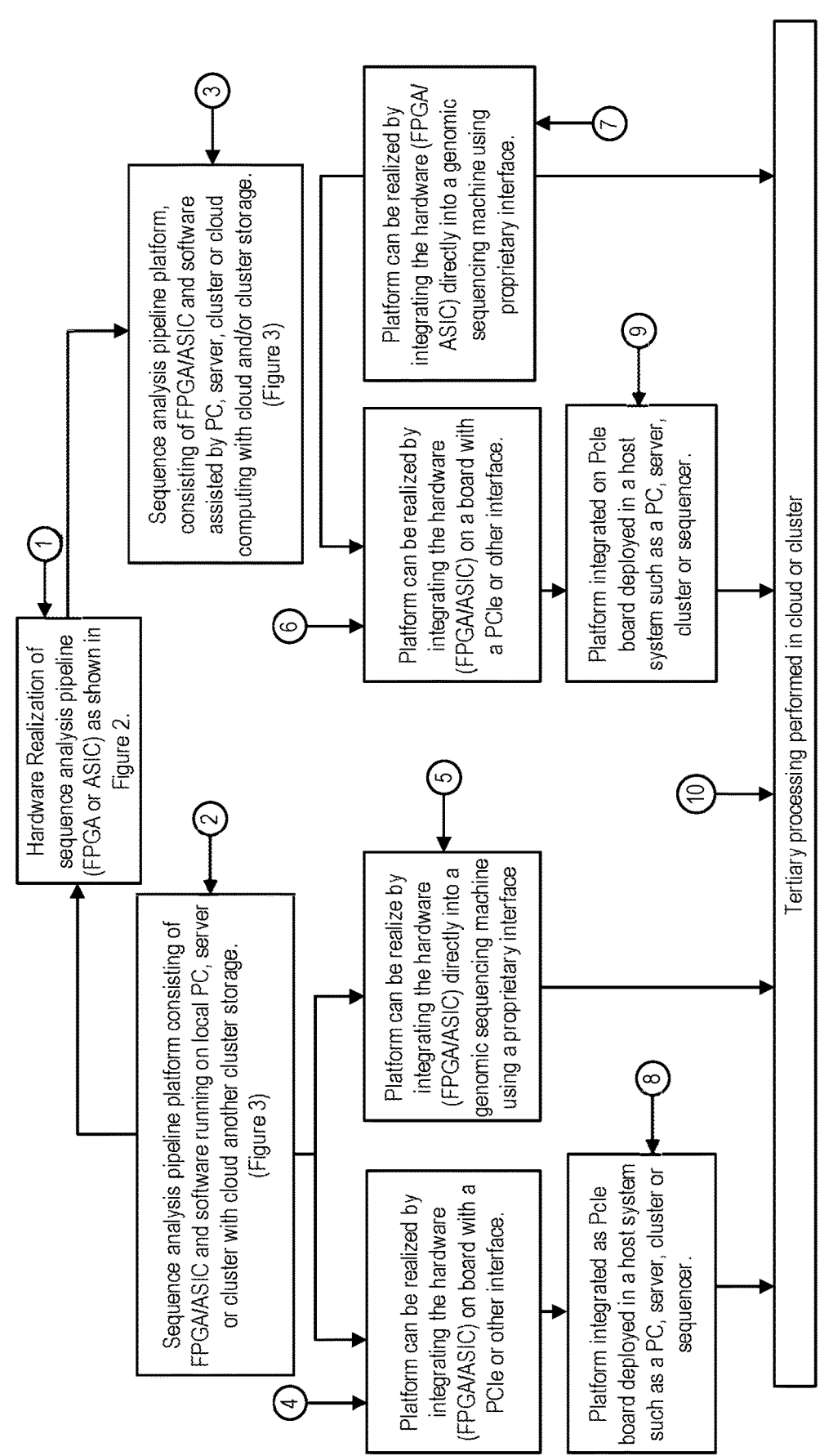
FIG. 21 illustrates processing steps using a genetic sequence analysis hardware platform.

In various instances, a hardware implementation of a sequence analysis pipeline is described. FIG. 21 shows a general block diagram of an implementation of the current disclosure. In Block 1 a hardware implementation of a sequence analysis pipeline is described. This can be done in a number of different ways such as an FPGA or ASIC or structured ASIC implementation. The functional blocks that are implemented by the FPGA or ASIC or structured ASIC are shown in FIGS. 6 and 7. FIGS. 6 and 7 includes a number of blocks or modules to do sequence analysis. The input to the hardware realization can be a FASTQ file, but is not limited to this format. In addition to the FASTQ file, the input to the FPGA or ASIC or structured ASIC consists of side information, such as Flow Space Information from technology such as the Ion Torrent. The blocks or modules in FIG. 21 illustrate the following blocks: Error Control, Mapping, Alignment, Sorting, Local Realignment, Duplicate Marking, Base Quality Recalibration, BAM and Side Information reduction and variant calling.

These blocks or modules can be present inside, or implemented by, the hardware, but some of these blocks may be omitted or other blocks added to achieve the purpose of realizing a sequence analysis pipeline. Blocks 2 and 3 describe two alternatives of a sequence analysis pipeline platform. The sequence analysis pipeline platform comprising an FPGA or ASIC or structured ASIC and software assisted by a host (i.e., PC, server, cluster or cloud computing) with cloud and/or cluster storage. Blocks 4-7 describe different interfaces that the sequence analysis pipeline can have. In Blocks 4 and 6 the interface can be a PCIe interface, but is not limited to a PCIe interface. In Blocks 5 and 7 the hardware (FPGA or ASIC or structured ASIC) can be directly integrated into a sequencing machine. Blocks 8 and 9 describe the integration of the hardware sequence analysis pipeline integrated into a host system such as a PC, server cluster or sequencer. Surrounding the hardware FPGA or ASIC or structured ASIC are lots of DDR3 memory elements and a PCIe interface. The board with the FPGA/ASIC/sASIC connects to a host computer, consisting of a host CPU, that could be either a low power CPU such as an ARM®, Snapdragon®, or any other processor. Block 10 illustrates a hardware sequence analysis pipeline API that can be accessed by third party applications to perform tertiary analysis.

Accordingly, in various embodiments, an apparatus of the disclosure may include a computing architecture, such as embedded in an FPGA or a silicon application specific integrated circuit (ASIC) 100 as seen in FIGS. 6 and 7. The integrated circuit 100 can be integrated into a printed circuit board (PCB) 104, such as a Peripheral Component Interface- Express (PCIe) card, that can be plugged into a computing platform. In various instances, as shown in FIG. 6, the PCIe card 104 may include a single FPGA or ASIC 100, which integrated circuit may be surrounded by local memories 105, however, in various embodiments, as seen with respect to FIG. 7, the PCIe card 104 may include a plurality of FPGAs and/or ASICs 100A, 100B and 100C. In various instances, the PCI card may also include a PCIe bus. This PCIe card 104 can be added to a computing platform to execute algorithms on extremely large data sets. Accordingly, in various instances, the overall work flow of genomic sequencing involving the integrated circuit may include the following: Sample preparation, Alignment (including mapping and alignment), Variant analysis, Biological Interpretation, and/or Specific Applications.

Hence, in various embodiments, an apparatus of the disclosure may include a computing architecture that achieves the high performance execution of algorithms, such as mapping and alignment algorithms, that operate on extremely large data sets, such as where the data sets exhibit poor locality of reference (LOR). These algorithms are designed to reconstruct a whole genome from millions of short read sequences, from modern so-called next generation sequencers, require multi-gigabyte data structures that are randomly accessed. Once reconstruction is achieved, as described herein above, further algorithms with similar characteristics are used to compare one genome to libraries of others, do gene function analysis, etc.

Currently, there are two major approaches in use, general purpose multicore CPUs and general purpose Graphic Processing Units (GPGPUs). In such an instance ach CPU in a multicore system may have a classical cache based architecture, wherein instructions and data are fetched from a level 1 cache (L1 cache) that is small but has extremely fast access. Multiple L1 caches may be connected to a larger but slower shared L2 cache. The L2 cache may be connected to a large but slower DRAM (Dynamic Random Access Memory) system memory, or may be connected to an even larger but slower L3 cache which may then connected to DRAM. An advantage of this arrangement may be that applications in which programs and data exhibit locality of reference behave nearly as if they are executing on a computer with a single memory as large as the DRAM but as fast as the L1 cache. Because full custom, highly optimized CPUs operate at very high clock rates, e.g., 2 to 4 GHz, this architecture may be essential to achieving good performance.

Further, GPGPUs may be employed to extend this architecture, such as by implementing very large numbers of small CPUs, each with their own small L1 cache, wherein each CPU executes the same instructions on different subsets of the data. This is a so called SIMD (Single Instruction stream, Multiple Data stream) architecture. Economy is gained by sharing the instruction fetch and decode logic across a large number of CPUs. Each cache has access to multiple large external DRAMs via an interconnection network. Assuming the computation to be performed is highly parallelizable, GPGPUs have a significant advantage over general purpose CPUs due to having large numbers of computing resources. Nevertheless, they still have a caching architecture and their performance is hurt by applications that do not have a high enough degree of locality of reference. That leads to a high cache miss rate and processors that are idle while waiting for data to arrive from the external DRAM.

For instance, in various instances, Dynamic RAMs may be used for system memory because they are more economical than Static RAMs (SRAM). The rule of thumb used to be that DRAMs had 4× the capacity for the same cost as SRAMs. However, due to declining demand for SRAMs in favor of DRAMs, that difference has increased considerably due to the economies of scale that favor DRAMs which are in high demand. Independent of cost, DRAMs are 4× as dense as SRAMs laid out in the same silicon area because they only require one transistor and capacitor per bit compared to 4 transistors per bit to implement the SRAM's flip-flop. The DRAM represents a single bit of information as the presence or absence of charge on a capacitor. A problem with this arrangement is that the charge decays over time, so it has to be refreshed periodically. The need to do this has led to architectures that organize the memory into independent blocks and access mechanisms that deliver multiple words of memory per request. This compensates for times when a given block is unavailable while being refreshed. The idea is to move a lot of data while a given block is available. This is in contrast to SRAMs in which any location in memory is available in a single access in a constant amount of time. This characteristic allows memory accesses to be single word oriented rather than block oriented. DRAMs work well in a caching architecture because each cache miss leads to a block of memory being read in from the DRAM. The theory of locality of reference is that if just accessed word N, then probably going to access words N+1, N+2, N+3 and so on.

FIG. 7 presents an alternative embodiment to FIG. 6, having a multiplicity of chips 100A, 100B, 100C, where each chip may include one or more of the various genomics and/or bioinformatics processing modules, e.g., of an exemplary pipeline analysis apparatus, as disclosed herein.

FIG. 17 illustrates a system 100 for executing a sequence analysis pipeline on genetic sequence data. The system 100 includes a configuration manager 102 that includes a computing system. The computing system of the configuration manager 102 can include a personal computer or other computer workstation, or can be implemented by a suite of networked computers. The configuration manager 102 can further include one or more third party applications connected with the computing system by one or more APIs, which, with one or more proprietary applications, generate a configuration for processing genomics data from a sequencer or other genomics data source. The configuration manager 102 further includes drivers that load the configuration to the genomics pipeline processor system 10. The genomics pipeline processor system 10 can output result data to, or be accessed via, the Web 50 or other network, for storage of the result data in an electronic health record 200 or other knowledge database 400.

As discussed in several paces herein above, the chip implementing the genomics pipeline processor can be connected or integrated in a sequencer. The chip can also be connected or integrated on an expansion card, e.g. PCIe, and the expansion card can by connected or integrated in a sequencer. In other implementations, the chip can be connected or integrated in a server computer that is connected to a sequencer, to transfer genomic reads from the sequencer to the server. In yet other implementations, the chip can be connected or integrated in a server in a cloud computing cluster of computers and servers. A system can include one or more sequencers connected (e.g. via Ethernet) to a server containing the chip, where genomic reads are generated by the multiple sequencers, transmitted to the server, and then mapped and aligned in the chip.

For instance, in general next generation DNA sequencer (NGS) data pipelines, the primary analysis stage processing is generally specific to a given sequencing technology. This primary analysis stage functions to translate physical signals detected inside the sequencer into "reads" of nucleotide sequences with associated quality (confidence) scores, e.g. FASTQ format files, or other formats containing sequence and usually quality information. After such a format is achieved, secondary analysis proceeds, as described herein, to determine the content of the sequenced sample DNA (or RNA etc.), such as by mapping and aligning reads to a reference genome, sorting, duplicate marking, base quality score recalibration, local re-alignment, and variant calling. Tertiary analysis may then follow, to extract medical or research implications from the determined DNA content.

However, primary analysis, as mentioned above, is often quite specific in nature to the sequencing technology employed. In various sequencers, nucleotides are detected by sensing electrical charges, electrical currents, or radiated light. Some primary analysis pipelines often include: Signal processing to amplify, filter, separate, and measure sensor output; Data reduction, such as by quantization, decimation, averaging, transformation, etc.; Image processing or numerical processing to identify and enhance meaningful signals, and associate them with specific reads and nucleotides (e.g. image offset calculation, cluster identification); Algorithmic processing and heuristics to compensate for sequencing technology artifacts (e.g. phasing estimates, cross-talk matrices); Bayesian probability calculations; Hidden Markov models; Base calling (selecting the most likely nucleotide at each position in the sequence); Base call quality (confidence) estimation, and the like.

Primary analysis can be extremely commutatively intensive, sometimes as intensive as secondary analysis. For instance, in existing sequencing technologies, primary analysis often utilizes FPGAs and/or GPUs to accelerate processing beyond CPU capabilities. But these accelerated functions can be performed much more efficiently in custom integrated circuitry, such as that described herein. For example, they can be implemented in a structured ASIC using the configurable metal layers, as they do not require as much physical layout precision as embedded processor cores; however, the massively parallel computation implemented in large FPGAs and GPUs may be difficult to fit in the configurable structured ASIC resources. An alternative is to implement primary processing acceleration logic in the master slice of a structured ASIC, taking advantage of the standard cell space efficiency in the master slice.

A reason that secondary processing functions may be implemented in a structured ASIC configurable metal layers is that secondary genomic data processing algorithms are still evolving via active research. It may be therefore beneficial to be able to inexpensively produce a freshly updated structured ASIC design periodically, such as every year or every two years, to utilize the latest algorithms. By contrast, primary analysis algorithms currently employed are more mature, the necessary processing having been researched and defined by the respective sequencer manufacturers. Even to the extent it is still subject to change, the algorithms are more generic signal and numerical processing than is the case in secondary analysis, so that appropriate configurability and micro-coding of primary processing acceleration modules can make them flexible enough to accommodate significant changes. If present, embedded processor cores increase this flexibility even further. For these reasons, it is reasonable to design primary processing acceleration modalities into an FPGA and/or structured ASIC master slice, as herein described.

It is also advantageous to integrate primary processing acceleration and secondary processing acceleration in a single integrated circuit FPGA or ASIC (standard cell or structured ASIC), with or without embedded processors. This may be beneficial because sequencers produce data requiring both primary and secondary analysis, and integrating them in a single device is most efficient in terms of cost, space, power, and resource sharing. If embedded processors are also present, they can be leveraged to increase the speed and flexibility of both primary and secondary processing.

These three components—primary accelerators, secondary accelerators, and embedded processors—can be implemented in an FPGA or structured ASIC master slice, and/or using configurable metal layers, in any combination. All three could be in the master slice, or all three could use configurable metal layers, or any one or two of them could be in the master slice, and the others use configurable metal layers. In any of these configurations, all three can communicate with each other, in any combination, directly and/or via memory, and cooperate in common tasks. One advantageous configuration is to implement primary acceleration and embedded processors in the master slice, and implement secondary acceleration using configurable metal layers.

Additionally, as indicated above, the chip, whether implemented as an ASIC, FPGA, or a structured ASIC, may include or otherwise be associated with one or more memory architectures. For instance, a memory architecture can consist of M memory modules that interface with the chip, such as with an ASIC. The ASIC may be implemented using many different technologies, including FPGAs (Field Programmable Gate Arrays) or structured ASIC, standard cells, or full custom logic. Within the ASIC are a Memory Subsystem (MSS) and Functional Processing Units (FPUs). The MSS contains M memory controllers (MCs) for the memory modules, N system memory interfaces (SMIs) for the FPUs, and an N×M crossbar that allows any SMI to access any MC. Arbitration is provided in the case of contention.

Each memory module is constructed from DRAM chips that are addressed by an AMM bit word and support data transfers $D_{MM}$ bits wide. The memory has $2^{A_{MM}}$ address locations. A key characteristic of DRAM is that it performs reads/writes in W word bursts using the supplied address as the base address, B, and fetching or storing locations B+1, B+2, . . . B+W−1 as well. A typical value for W is 8.

In the MSS of the ASIC, each memory controller supplies the required control signals and performs any necessary multiplexing/demultiplexing between the system word width, $D_{SYS}$, and the memory word width, $D_{MM}$, as well as handling the requirements for read/write bursts. It can contain extra buffering so that multiple memory requests can be queued up and processed in a pipelined fashion to maximize throughput. This compensates for multiple clock cycles of latency between presentation of an address and completion of a memory operation (read or write).

The MC may operate at the speed of the attached DRAM in a memory module. Assume its clock rate is $C_{MM}$. This is often several times faster than the core speed at which the majority of the logic in the ASIC operates which is $C_{SYS}$. Hence the multiplexing/demultiplexing logic is placed close to its associated interface pins to minimize signal distances. Demultiplexing is the first operation performed on incoming data and multiplexing is the last operation performed on outgoing data. The remainder of the MSS operates on $D_{SYS}$ width data which is wider than $D_{MM}$, enabling use of the slower $C_{SYS}$ clock speed.

Each system memory interface in the MSS presents an $A_{SYS}$ bit address bus and a $D_{SYS}$ bit data bus to any attached FPU. The SMI is designed to make it appear to an attached FPU that it has random access to a single large fast memory. The FPU has no awareness of the existence of separate memory modules. $A_{SYS}$ is large enough to allow access to any memory location in any attached memory module. The mapping from system address space to memory module address space is explained below.

The N system memory interfaces are cross connected to the M memory modules via an N×M crossbar. The crossbar provides min (M,N) simultaneous connections among the SMIs and MCs, provides arbitration for conflicts, and facilitates translation of system address space into memory module address space.

The organization of FPUs is highly flexible. One or more FPUs can share the same system memory interface. To maximize performance, FPUs that do not operate at the same time should share an SMI. Those that operate concurrently, should be attached to different SMIs. An FPU that operates on a data structure larger than $D_{SYS}$ can use multiple SMIs to access the whole data structure in a single memory operation. Hence this memory architecture supports a wide range of computation architectures. Each FPU may be identical and thus an array of them may be implemented in a two dimensional structure. This is illustrated where FPU (i,j) is the $j^{th}$ unit attached to SMI i, $0 \leq i \leq N$, $0 \leq j < k_i$. In this case, all the $k_i$ are the same size and $k_i$ may be as small as 1. This supports SIMD (single instruction stream, multiple data stream) and MIMD architectures (multiple instruction stream, multiple data stream) depending on whether the FPUs fetch instructions from the same or individual instruction memories.

In one particular aspect, the disclosure is directed to a system, such as to a system for executing a sequence analysis pipeline on genetic sequence data. In various instances, the system may include an electronic data source, such as a data source that provides digital signals, for instance, digital signals representing a plurality of reads of genomic data, where each of the plurality of reads of genomic data include a sequence of nucleotides. The system may include one or more of a memory, such as a memory storing one or more genetic reference sequences and/or an index of the one or more genetic reference sequences; and/or the system may include a chip, such as an ASIC, FPGA, or sASIC.

More particularly, in various particular embodiments, the system may include a structured application specific integrated circuit (ASIC), such as where the chip is formed of a set of mask-programmable, hardwired digital logic circuits that may be interconnected by a plurality of physical electrical interconnects. In various instances, one or more of the plurality of physical electrical interconnects include an input to the structured ASIC that is connected with the electronic data source, such as for receiving the plurality of reads of genomic data. In such an instance, one or more of the plurality of physical electrical interconnects may include a memory interface for the structured ASIC to access the memory. Accordingly, the hardwired digital logic circuits may be arranged as a set of processing engines, such as where each processing engine may be formed of a subset of the hardwired digital logic circuits so as to perform one or more steps in the sequence analysis pipeline on the plurality of reads of genomic data. In various embodiments, one or more, e.g., each, subset of the hardwired digital logic circuits may be in a wired configuration such as to perform the one or more steps in the sequence analysis pipeline. For instance, the set of processing engines may be configured to include one or more of a mapping module, an alignment module, and/or a sorting module.

For example, the set of processing engines may include a mapping module that is in the wired configuration, and is configured to access, according to at least some of the sequence of nucleotides in a read of the plurality of reads, the index of the one or more genetic reference sequences from the memory via the memory interface so as to map the read to one or more segments of the one or more genetic reference sequences based on the index. For instance, in certain embodiments, the index of the one or more genetic reference sequences may include a hash table, and/or the mapping module may apply a hash function to the at least some of the sequence of nucleotides to access the hash table of the index.

The processing engines may also or alternatively include an alignment module that is in the wired configuration, and is configured to access the one or more genetic reference sequences from the memory, e.g., via the memory interface, so as to align the read to one or more positions in the one or more segments of the one or more genetic reference sequences, such as obtained from the mapping module. The processing engines may also or alternatively include a sorting module that is in the wired configuration, and is configured to access the one or more aligned reads from the memory, e.g., via the memory interface, so as to sort the read to one or more positions, e.g., chromosomal positions, in the genetic reference sequences, such as obtained from the alignment module.

In various instances, the structured ASIC may include a master slice that incorporates at least some of the hardwired digital logic circuits, and in some instances, may include one or more configurable metal layers that are formed on the master slice, such as where each of the one or more configurable metal layers may have at least some of the plurality of physical electrical interconnects that interconnect the at least some of the hardwired digital logic circuits to form the set of processing engines. In certain embodiments, one or more of the plurality of physical electrical interconnects may include an output from the structured ASIC, such as for communicating result data from the mapping module and/or the alignment module and/or sorting module.

In various instances, the structured ASIC may include a master controller to establish the wired configuration for each subset of the hardwired digital logic circuits so as to perform the one or more steps in the sequence analysis pipeline. In various embodiments, the wired configuration is established upon manufacture of the integrated circuit and is non-volatile. In some embodiments, the structured ASIC and/or the memory are housed on an expansion card, such as a peripheral component interconnect (PCI) card. As indicated above, in various embodiments, the system may include a sequencer, such as where the sequencer includes the electronic data source that provides the digital signals representing the plurality of reads of genomic data. And in such an instance, the expansion card may be physically integrated with the sequencer.

Additionally, in various embodiments, a structured application-specific integrated circuit (ASIC) may be provided, such as for analyzing genetic sequence data, such as where the genetic sequence data is stored in a memory, such as a memory storing one or more genetic reference sequences associated with genomic data, and/or an index of the one or more genetic reference sequences. In such an instance, the structured ASIC may include a master slice that further includes a set of digital logic circuits, and may additionally include one or more configurable metal layers that are formed on the master slice, such as where each of the one or more configurable metal layers may have a set of wired connections arranged to interconnect a subset of the digital logic circuits to form a set of processing engines. In such an instance, the set of processing engines may include a mapping engine, an alignment engine, and/or a sorting engine. In various instances, a portion of the set of digital logic circuits in the master slice is hardwired as a base calling engine.

For instance, the set of processing engines may include a mapping engine to access, e.g., according to at least some of the sequence of nucleotides in a read of the plurality of reads, the index of the one or more genetic reference sequences stored in the memory, so as to map the read to one or more segments of the one or more genetic reference sequences, e.g., based on the index. Additionally or alternatively, the set of processing engines may include an alignment engine such as to access the one or more genetic reference sequences from the memory, e.g., via the memory interface, so as to align the read to one or more positions in the one or more segments of the one or more genetic reference sequences from the mapping module. Additionally, or alternatively the set of processing engines may include a sorting engine to sort each aligned read according to the one or more positions in the one or more genetic reference sequences.

In one embodiment, a system for executing a sequence analysis pipeline on genetic sequence data is provided where the system includes an electronic data source that provides digital signals representing a plurality of reads of genomic data, such as where each of the plurality of reads of genomic data include a sequence of nucleotides. The system may include one or more of a memory, e.g., for storing one or more genetic reference sequences and/or an index of the one or more genetic reference sequences; and/or the system may include an integrated circuit having a master slice, such as a master slice formed by a photolithographic mask that defines a set of digital logic circuits. In such an instance, the master slice may be configured for having one or more functions, as those described herein above, integrated therein. For instance, the master slice may have one or more configurable metal layers, such as where each of the one or more configurable metal layers has one or more conductive interconnects that connect a subset of the set of digital logic circuits in a wired configuration to perform the aforesaid functions.

In various aspects, a method of making a structured application-specific integrated circuit (ASIC) for analyzing genetic sequence data is provided. In certain embodiments, the method includes one or more of providing a plurality of photolithographic masks, such as masks that define a set of digital logic circuits of a master slice; forming the set of digital logic, such as by using the plurality of photolithographic masks to form the master slice; providing two or more different sets of design-specific configurable metal layer masks, such as masks that define corresponding two or more digital logic to implement a set of processing engines; forming two or more configurable metal layers, such as using two or more different sets of design-specific configurable metal layer masks, for instance, where each of the two more configurable metal layers have a set of wired connections that may be arranged according to a design of the configurable metal layer masks, for example, to interconnect a subset of the digital logic circuits to form a set of processing engines; and/or providing the two or more configurable metal layers onto the master slice to form the set of processing engines.

One or more aspects or features of the subject matter described herein can be realized in digital electronic circuitry, integrated circuitry, specially designed application specific integrated circuits (ASICs), field programmable gate arrays (FPGAs), or structured ASIC computer hardware, firmware, software, and/or combinations thereof.

These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT), a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A method for dynamic configuration and execution of a genomic data processing pipeline based on one or more user-selectable options presented via a graphical user interface (GUI) of a nucleic acid sequencing device, the method comprising:

obtaining, by one or more processors of the nucleic acid sequencing device executing an application programming interface (API) that provides an interface between the GUI of the nucleic acid sequencing device and a programmable logic device, first data representing a selection of one or more of the user-selectable options submitted via the GUI, wherein one of the user-selectable options identifies a particular reference sequence to be used by a genomic data processing pipeline;

configuring, by one or more processors of the nucleic acid sequencing device, one or more programmable hardware resources of the programmable logic device from a first state that does not include hardware resources configured as a genomic analysis pipeline that uses the particular reference sequence identified by the first data into a second state that includes hardware resources that have been configured as a genomic analysis pipeline that uses the particular reference sequence identified by the first data;

providing, to the programmable logic device and by one or more processors of the nucleic acid sequencing device using the API, second data representing a set of genomic data or a set of data derived from genomic data;

instructing, by one or more processors of the nucleic acid sequencing device, the configured genomic data processing pipeline to execute a genomic processing operation on the obtained second data to generate result data;

obtaining, by one or more processors of the nucleic acid sequencing device, the result data that is generated by execution of the configured genomic data processing pipeline on the obtained second data by the programmable logic device; and providing, by the one or more processors of the nucleic acid sequencing device, output data that is based on the result data.

2. The method of claim 1, wherein providing, by the one or more processors of the nucleic acid sequencing device, the output data that is based on the result data comprises:

providing, by the one or more processors of the nucleic acid sequencing device, output data that is based on the result data for display on a display of the nucleic acid sequencing device.

3. The method of claim 1, wherein providing, by the one or more processors of the nucleic acid sequencing device, the output data that is based on the result data comprises:

providing, by the one or more processors of the nucleic acid sequencing device, output data that is based on the result data for output by a device that is different from the nucleic acid sequencing device.

4. The method of claim 1, wherein the genomic processing operation includes one or more of a read mapping operation, a read alignment operation, a sorting operation, a variant calling operation, or a tertiary analysis operation.

5. The method of claim 1, wherein the method further comprises:

obtaining, by one or more processors of the nucleic acid sequencing device, data representing the particular reference sequence; and storing, by one or more processors of the nucleic acid sequencing device, the obtained data representing the particular reference sequence in a memory device that is accessible by the programmable logic device.

6. The method of claim 1, wherein providing, to the programmable logic device and by one or more processors of the nucleic acid sequencing device using the API, second data representing a set of genomic data or a set of data derived from genomic data comprises:

obtaining, by one or more processors of the nucleic acid sequencing device, at least a portion of a FASTQ file generated by the nucleic acid sequencing device; and storing, by one or more processors of the nucleic acid sequencing device and via the API, the obtained portion of the FASTQ file in a memory device that is accessible by the programmable logic device.

7. A system for dynamic configuration and execution of a genomic data processing pipeline based on one or more user-selectable options presented via a graphical user interface (GUI) of a nucleic acid sequencing device, the system comprising:

a nucleic acid sequencing device that includes one or more processors and one more memory devices storing instructions that, when executed by the one or more processors, cause the one or more processors to perform operations; and a second device that includes one or more programmable logic devices that can be configured to execute one or more operations on input data obtained by the second device;

wherein the system is configured to perform operations comprising:

obtaining, by the one or more processors of the nucleic acid sequencing device executing an application programming interface (API) that provides an interface between the GUI of the nucleic acid sequencing device and a programmable logic device, first data representing a selection of one or more of the user-selectable options submitted via the GUI, wherein one of the user-selectable options identifies a particular reference sequence to be used by a genomic data processing pipeline;

configuring, by the one or more processors of the nucleic acid sequencing device, one or more programmable hardware resources of the programmable logic device from a first state that does not include hardware resources configured as a genomic analysis pipeline that uses the particular reference sequence identified by the first data into a second state that includes hardware resources that have been configured as a genomic analysis pipeline that uses the particular reference sequence identified by the first data;

providing, to the programmable logic device and by one or more processors of the nucleic acid sequencing device using the API, second data representing a set of genomic data or a set of data derived from genomic data;

instructing, by the one or more processors of the nucleic acid sequencing device, the configured genomic data processing pipeline to execute a genomic processing operation on the obtained second data to generate result data;

obtaining, by the one or more processors of the nucleic acid sequencing device, the result data that is generated by execution of the configured genomic data processing pipeline on the obtained second data by the programmable logic device; and providing, by the one or more processors of the nucleic acid sequencing device executing one or more of the instructions, output data that is based on the result data.

8. The system of claim 7, wherein providing, by the one or more processors of the nucleic acid sequencing device, the output data that is based on the result data comprises:

providing, by the one or more processors of the nucleic acid sequencing device, output data that is based on the result data for display on a display of the one or more processors of the nucleic acid sequencing device.

9. The system of claim 7, wherein providing, by the one or more processors of the nucleic acid sequencing device, the output data that is based on the result data comprises:

providing, by the one or more processors of the nucleic acid sequencing device, output data that is based on the result data for output by a second user device that is different from the nucleic acid sequencing device.

10. The system of claim 7, wherein the genomic processing operation includes one or more of a read mapping operation, a read alignment operation, a sorting operation, a variant calling operation, or a tertiary analysis operation.

11. The system of claim 7, wherein the operations further comprise:

obtaining, by the one or more processors of the nucleic acid sequencing device, data representing the particular reference sequence; and storing, by the one or more processors of the nucleic acid sequencing device, the obtained data representing the particular reference sequence in a memory device that is accessible by the programmable logic device.

12. The system of claim 7, wherein providing, to the programmable logic device and by the one or more processors of the nucleic acid sequencing device using the API, second data representing a set of genomic data or a set of data derived from genomic data comprises:

obtaining, by the one or more processors of the nucleic acid sequencing device, at least a portion of a FASTQ file generated by the nucleic acid sequencing device; and storing, by the one or more processors of the nucleic acid sequencing device and via the API, the obtained portion of the FASTQ file in a memory device that is accessible by the programmable logic device.

13. One or non-transitory more computer readable storage media storing instructions that, when executed by a nucleic acid sequencing device, cause the nucleic acid sequencing device to perform operations for dynamic configuration and execution of a genomic data processing pipeline based on one or more user-selectable options presented via a graphical user interface (GUI) of the nucleic acid sequencing device, the operations comprising:

obtaining, by one or more processors of the nucleic acid sequencing device executing an application programming interface (API) that provides an interface between the GUI of the nucleic acid sequencing device and a programmable logic device, first data representing a selection of one or more of the user-selectable options submitted via the GUI, wherein one of the user-selectable options identify a particular reference sequence to be used by a genomic data processing pipeline;

configuring, by one or more processors of the nucleic acid sequencing device, one or more programmable hardware resources of the programmable logic device from a first state that does not include hardware resources configured as a genomic analysis pipeline that uses the particular reference sequence identified by the first data into a second state that includes hardware resources that have been configured as a genomic analysis pipeline that uses the particular reference sequence identified by the first data;

providing, by one or more processors of the nucleic acid sequencing device, second data representing a set of genomic data or a set of data derived from genomic data; and instructing, by one or more processors of the nucleic acid sequencing device, the configured genomic data processing pipeline to execute a genomic processing operation on the obtained second data to generate result data;

obtaining, by one or more processors of the nucleic acid sequencing device, the result data that is generated by execution of the configured genomic data processing pipeline on the obtained second data by the programmable logic device; and providing, by one or more processors of the nucleic acid sequencing device, output data that is based on the result data.

14. The one or more non-transitory computer readable storage media of claim 13, wherein providing, by one or more processors of the nucleic acid sequencing device, the output data that is based on the result data comprises:

providing, by one or more processors of the nucleic acid sequencing device, output data that is based on the result data for display on a display of the nucleic acid sequencing device.

15. The one or more non-transitory computer readable storage media of claim 13, wherein providing, by one or more processors of the nucleic acid sequencing device, the output data that is based on the result data comprises:

providing, by one or more processors of the nucleic acid sequencing device, output data that is based on the result data for output by a second user device that is different from the nucleic acid sequencing device.

16. The one or more non-transitory computer readable storage media of claim 13, wherein the genomic processing operation includes one or more of a read mapping operation, a read alignment operation, a sorting operation, a variant calling operation, or a tertiary analysis operation.

17. The one or more non-transitory computer readable storage media of claim 13, wherein the operations further comprise:

obtaining, by one or more processors of the nucleic acid sequencing device, data representing the particular reference sequence; and storing, by one or more processors of the nucleic acid sequencing device, the obtained data representing the particular reference sequence in a memory device that is accessible by the programmable logic device.

18. The one or more non-transitory computer readable storage media of claim 13, wherein obtaining, by one or more processors of the nucleic acid sequencing device, second data representing a set of genomic data or a set of data derived from genomic data comprises:

obtaining, by one or more processors of the nucleic acid sequencing device, at least a portion of a FASTQ file generated by the nucleic acid sequencing device; and storing, by one or more processors of the nucleic acid sequencing device, the obtained portion of the FASTQ file in a memory device that is accessible by the programmable logic device.

\* \* \* \* \*